United States Patent
Xie et al.

(10) Patent No.: US 10,927,124 B2
(45) Date of Patent: *Feb. 23, 2021

(54) COMPOUNDS AND COMPOSITIONS AND USES THEREOF

(71) Applicant: PGI Drug Discovery LLC, Paramus, NJ (US)

(72) Inventors: Linghong Xie, Southborough, MA (US); Michele L. R. Heffernan, Holliston, MA (US); Philip Glyn Jones, Marlborough, MA (US); Taleen G. Hanania, Valhalla, NY (US)

(73) Assignees: Sunovion Pharmaceuticals Inc., Marlborough, MA (US); PGI Drug Discovery LLC, Paramus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/214,985

(22) Filed: Dec. 10, 2018

(65) Prior Publication Data

US 2019/0308990 A1    Oct. 10, 2019

Related U.S. Application Data

(63) Continuation of application No. 15/663,688, filed on Jul. 28, 2017, now Pat. No. 10,196,403.

(60) Provisional application No. 62/368,526, filed on Jul. 29, 2016.

(51) Int. Cl.
| | | |
|---|---|---|
| C07D 493/04 | (2006.01) | |
| C07D 313/08 | (2006.01) | |
| C07D 307/87 | (2006.01) | |
| C07D 311/76 | (2006.01) | |

(52) U.S. Cl.
CPC ......... *C07D 493/04* (2013.01); *C07D 307/87* (2013.01); *C07D 311/76* (2013.01); *C07D 313/08* (2013.01)

(58) Field of Classification Search
CPC .. C07D 493/04; C07D 307/87; C07D 311/76; C07D 313/08
USPC ........................................................ 549/398
See application file for complete search history.

(56) References Cited

U.S. PATENT DOCUMENTS

| | | | |
|---|---|---|---|
| 3,438,995 A | 4/1969 | Faust et al. | |
| 3,470,179 A | 9/1969 | Ott | |
| 3,536,809 A | 10/1970 | Applezweig | |
| 3,549,624 A | 12/1970 | Conover et al. | |
| 3,551,427 A | 12/1970 | Sandoz | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,021,451 A | 5/1977 | Dobson et al. | |
| 4,021,452 A | 5/1977 | Floyd | |
| 4,036,842 A | 7/1977 | Dobson et al. | |
| 4,066,648 A | 1/1978 | Oka et al. | |
| 4,127,665 A | 11/1978 | Sarges et al. | |
| 4,337,343 A | 6/1982 | Maillard et al. | |
| 4,500,543 A | 2/1985 | Debernardis et al. | |
| 4,556,656 A | 12/1985 | McAll | |
| 4,904,300 A | 2/1990 | Lutz | |
| 4,963,568 A | 10/1990 | Schoenleber et al. | |
| 4,994,486 A | 2/1991 | Schoenleber et al. | |
| 4,999,359 A | 3/1991 | Vecchietti et al. | |
| 5,032,598 A | 7/1991 | Baldwin et al. | |
| 5,041,451 A | 8/1991 | Colle et al. | |
| 5,059,595 A | 10/1991 | Le Grazie | |
| 5,073,543 A | 12/1991 | Marshall et al. | |
| 5,109,008 A | 4/1992 | Scopes et al. | |
| 5,120,548 A | 6/1992 | McClelland et al. | |
| 5,134,127 A | 7/1992 | Stella et al. | |
| 5,288,749 A | 2/1994 | Meyer et al. | |
| 5,304,657 A | 4/1994 | Toki et al. | |
| 5,354,556 A | 10/1994 | Sparks et al. | |
| 5,391,556 A | 2/1995 | Heckel et al. | |
| 5,393,759 A | 2/1995 | Combourieu et al. | |
| 5,464,834 A | 11/1995 | Peligion et al. | |

(Continued)

FOREIGN PATENT DOCUMENTS

| | | |
|---|---|---|
| AU | 2010325925 A1 | 6/2011 |
| AU | 2016200448 A1 | 2/2016 |
| CA | 2031684 | 6/1991 |
| CA | 2323493 A1 | 9/1999 |
| CA | 2787416 A1 | 8/2011 |

(Continued)

OTHER PUBLICATIONS

Ahmad, I and Snieckus, V., "A Convenient Entro into the Rhoeadan Skelton. Total Synthesis of (±)-cis-alpinigenine", Canadian Journal of Chemistry, 60(12):2678-2686 (1982).

(Continued)

*Primary Examiner* — Daniel R Carcanague
(74) *Attorney, Agent, or Firm* — Heslin Rothenberg Farley & Mesiti P.C.

(57) ABSTRACT

Disclosed are compounds of formula (I):

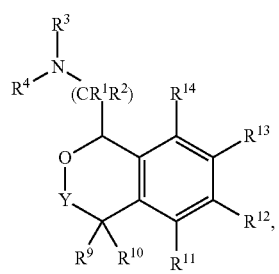

and pharmaceutical compositions containing such compounds. Methods of treating neurological or psychiatric disease and disorders in a subject in need are also disclosed.

26 Claims, 11 Drawing Sheets

(56) References Cited

U.S. PATENT DOCUMENTS

| | | |
|---|---|---|
| 5,532,203 A | 7/1996 | Fory et al. |
| 5,532,233 A | 7/1996 | Weber et al. |
| 5,591,767 A | 1/1997 | Mohr et al. |
| 5,621,133 A | 4/1997 | Deninno et al. |
| 5,639,476 A | 6/1997 | Oshlack et al. |
| 5,646,173 A | 7/1997 | Bos et al. |
| 5,656,658 A | 8/1997 | Hammarberg et al. |
| 5,674,533 A | 10/1997 | Santus et al. |
| 5,684,020 A | 11/1997 | Peligion et al. |
| 5,733,566 A | 3/1998 | Lewis |
| 6,031,099 A | 2/2000 | Moltzen et al. |
| 6,235,774 B1 | 5/2001 | Fagrig et al. |
| 6,262,044 B1 | 7/2001 | Møller et al. |
| 6,313,309 B1 | 11/2001 | Baxter et al. |
| 6,436,943 B1 | 8/2002 | Stoltefuss et al. |
| 6,503,913 B1 | 1/2003 | Goldmann et al. |
| 7,019,026 B1 | 3/2006 | Andersen et al. |
| 7,282,499 B2 | 10/2007 | Arjona et al. |
| 7,297,704 B2 | 11/2007 | Sabb et al. |
| 7,414,068 B2 | 8/2008 | Lim et al. |
| 7,544,717 B2 | 6/2009 | Hom et al. |
| 7,745,462 B2 | 6/2010 | Fairhurst et al. |
| 7,884,109 B2 | 2/2011 | Ohlmeyer et al. |
| 8,227,625 B2 | 7/2012 | Corbera-Arjona et al. |
| 8,710,245 B2 | 4/2014 | Shao et al. |
| 9,216,975 B2 | 12/2015 | Napoletano et al. |
| 10,196,403 B2 | 2/2019 | Hanania et al. |
| 10,336,732 B2 * | 7/2019 | Xie .................. C07D 405/04 |
| 2003/0073687 A1 | 4/2003 | Bebbington et al. |
| 2003/0149057 A1 | 8/2003 | Want et al. |
| 2004/0180883 A1 | 9/2004 | Gilmore |
| 2004/0220402 A1 | 11/2004 | Chow et al. |
| 2005/0032873 A1 | 2/2005 | Hatzenbuhler et al. |
| 2005/0075366 A1 | 4/2005 | Heidelbaug et al. |
| 2005/0187281 A1 | 8/2005 | Hinze et al. |
| 2005/0239832 A1 | 10/2005 | John et al. |
| 2005/0267199 A1 | 12/2005 | Hom et al. |
| 2006/0047127 A1 | 3/2006 | Arjona |
| 2006/0148872 A1 | 7/2006 | Chow et al. |
| 2006/0258714 A1 | 11/2006 | Heffernan et al. |
| 2007/0032481 A1 | 2/2007 | Dvorak et al. |
| 2007/0072926 A1 | 3/2007 | Chow et al. |
| 2007/0185144 A1 | 8/2007 | Zhong et al. |
| 2008/0081910 A1 | 4/2008 | Saab et al. |
| 2008/0113961 A1 | 5/2008 | Nishi et al. |
| 2008/0255239 A1 | 10/2008 | Chow et al. |
| 2008/0306082 A1 | 12/2008 | Dahnke et al. |
| 2009/0069305 A1 | 3/2009 | Gaul et al. |
| 2009/0118283 A1 | 5/2009 | Defert et al. |
| 2009/0318690 A1 | 12/2009 | Sasaki et al. |
| 2010/0035887 A1 | 2/2010 | Ricciardi |
| 2010/0178299 A1 | 7/2010 | Sitkovsky et al. |
| 2010/0197714 A1 | 8/2010 | Wunsch et al. |
| 2012/0171199 A1 | 7/2012 | Dobson et al. |
| 2012/0295881 A1 | 11/2012 | Lange et al. |
| 2013/0109677 A1 | 5/2013 | Shao et al. |
| 2014/0256712 A1 | 9/2014 | Shao et al. |
| 2015/0031709 A1 | 1/2015 | Campbell et al. |
| 2016/0083399 A1 | 3/2016 | Shao et al. |
| 2016/0264597 A1 | 9/2016 | Chytil et al. |
| 2017/0001987 A1 | 1/2017 | Xie et al. |
| 2018/0028492 A1 | 2/2018 | Powel et al. |
| 2018/0030064 A1 | 2/2018 | Xie et al. |
| 2018/0057506 A1 | 3/2018 | Chytil et al. |
| 2018/0093974 A1 | 4/2018 | Xie et al. |
| 2018/0118727 A1 | 5/2018 | Campbell et al. |
| 2019/0038594 A1 | 2/2019 | Bowen et al. |

FOREIGN PATENT DOCUMENTS

| | | |
|---|---|---|
| CN | 1300291 A | 6/2001 |
| CN | 101468986 | 7/2009 |
| CN | 101468987 | 7/2009 |
| CN | 101759710 | 6/2010 |
| CN | 102731574 | 10/2012 |
| CN | 104193761 A | 12/2014 |
| DE | 2624693 A | 7/1977 |
| DE | 3827727 | 2/1990 |
| DE | 4104257 | 8/1992 |
| EP | 0021940 A1 | 1/1981 |
| EP | 333427 A1 | 9/1989 |
| EP | 0358957 A1 | 3/1990 |
| EP | 366327 A1 | 5/1990 |
| EP | 368175 | 5/1990 |
| EP | 370732 A2 | 5/1990 |
| EP | 416740 | 3/1991 |
| EP | 0431421 | 6/1991 |
| EP | 431945 A2 | 6/1991 |
| EP | 483647 A1 | 5/1992 |
| EP | 0518805 A1 | 12/1992 |
| EP | 555824 A1 | 8/1993 |
| EP | 574313 A1 | 12/1993 |
| EP | 600836 A2 | 6/1994 |
| EP | 745598 A1 | 12/1996 |
| EP | 1634873 A1 | 3/2006 |
| EP | 1829869 A1 | 9/2007 |
| EP | 1982714 A1 | 10/2008 |
| EP | 1982987 A1 | 10/2008 |
| EP | 2377850 A1 | 10/2011 |
| FR | 2875230 A1 | 3/2006 |
| GB | 984365 | 2/1965 |
| GB | 1552004 A | 9/1979 |
| JP | S567772 A | 1/1981 |
| JP | 01006267 | 1/1989 |
| JP | H2243691 | 9/1990 |
| JP | H 03163068 B2 | 7/1991 |
| JP | H 03223277 B2 | 10/1991 |
| JP | 049367 | 1/1992 |
| JP | H0570453 A | 3/1993 |
| JP | 03223277 B2 | 10/2001 |
| JP | 2003261566 A | 9/2003 |
| JP | 2004269449 A | 9/2004 |
| JP | 2005145859 A | 6/2005 |
| JP | 2006117568 A | 5/2006 |
| JP | 2008540369 A | 11/2008 |
| JP | 2014214130 A | 11/2014 |
| JP | 2015227348 A | 12/2015 |
| MX | 2012006326 A | 10/2012 |
| RU | 2128649 C1 | 4/1999 |
| SG | 181498 A1 | 7/2012 |
| WO | WO 91/08205 A1 | 6/1991 |
| WO | WO 92/03434 | 3/1992 |
| WO | WO 92/14465 | 9/1992 |
| WO | WO 92/15592 A1 | 9/1992 |
| WO | WO 94/00441 A1 | 1/1994 |
| WO | WO 96/04287 A1 | 2/1996 |
| WO | WO 96/38435 | 12/1996 |
| WO | WO 99/01437 | 1/1999 |
| WO | WO 99/46237 A1 | 9/1999 |
| WO | WO 99/46267 A1 | 9/1999 |
| WO | WO 0000487 | 1/2000 |
| WO | WO 2000/023445 | 4/2000 |
| WO | WO 2000/035915 | 6/2000 |
| WO | WO 2000/043397 | 7/2000 |
| WO | WO 2000/068230 | 11/2000 |
| WO | WO 2000/078742 | 12/2000 |
| WO | WO 2001/017516 | 3/2001 |
| WO | WO 2001/19831 A1 | 3/2001 |
| WO | WO 01/32610 | 5/2001 |
| WO | WO 01/32655 | 5/2001 |
| WO | WO 2001/0132610 A1 | 5/2001 |
| WO | WO 2001/0132655 A2 | 5/2001 |
| WO | WO 01/62233 | 8/2001 |
| WO | WO 01/72745 | 10/2001 |
| WO | WO 2002/012189 | 2/2002 |
| WO | WO 2002/022614 | 3/2002 |
| WO | WO 2002/066443 A2 | 8/2002 |
| WO | WO 01/80893 | 10/2002 |
| WO | WO 02/083667 | 10/2002 |
| WO | WO 2002/102387 A1 | 12/2002 |
| WO | WO 2003/006455 A1 | 1/2003 |
| WO | WO 2003/035065 A1 | 5/2003 |
| WO | WO 2003/092374 | 11/2003 |
| WO | WO 2004/004726 A1 | 1/2004 |

(56) References Cited

FOREIGN PATENT DOCUMENTS

| | | |
|---|---|---|
| WO | WO 2004/035812 A2 | 4/2004 |
| WO | WO 2004/066912 A2 | 8/2004 |
| WO | WO 2004/078723 A1 | 9/2004 |
| WO | WO 2004/082687 A1 | 9/2004 |
| WO | WO 2004/087680 A1 | 10/2004 |
| WO | WO 2004/089913 | 10/2004 |
| WO | WO 2004/112719 A2 | 12/2004 |
| WO | WO 2005/035518 A1 | 4/2005 |
| WO | WO 2005/072412 A2 | 8/2005 |
| WO | WO 2005/073236 A2 | 8/2005 |
| WO | WO 2005/079800 A1 | 9/2005 |
| WO | WO 2005/087779 A1 | 9/2005 |
| WO | 2005111025 A1 | 11/2005 |
| WO | WO 2006/014135 A1 | 2/2006 |
| WO | WO 2006/014136 A1 | 2/2006 |
| WO | WO 2006/015259 A2 | 2/2006 |
| WO | WO 2006/030124 | 3/2006 |
| WO | WO 2006/053274 A2 | 5/2006 |
| WO | WO 2006/066172 | 6/2006 |
| WO | WO 2006/089053 | 8/2006 |
| WO | WO 2006/117305 | 11/2006 |
| WO | WO 2007/001939 A1 | 1/2007 |
| WO | WO 2007/002681 A2 | 1/2007 |
| WO | WO 2007/006546 A1 | 1/2007 |
| WO | WO 2007/095586 A2 | 8/2007 |
| WO | WO 2007/102999 A2 | 9/2007 |
| WO | WO 2007/120594 A1 | 10/2007 |
| WO | WO 2007/126041 A1 | 11/2007 |
| WO | WO 2008/011560 | 1/2008 |
| WO | WO 2008/042422 A2 | 4/2008 |
| WO | WO 2008/048981 A2 | 4/2008 |
| WO | WO 2008/058342 A1 | 5/2008 |
| WO | WO 2008/119689 A1 | 10/2008 |
| WO | WO 2008/125348 | 10/2008 |
| WO | WO 2008/155132 A1 | 12/2008 |
| WO | WO 2009/009550 A1 | 1/2009 |
| WO | WO 2009/057974 A2 | 5/2009 |
| WO | WO 2009/067202 A1 | 5/2009 |
| WO | WO 2009/068467 A1 | 6/2009 |
| WO | WO 2009/072621 A1 | 6/2009 |
| WO | WO 2009/085256 A1 | 7/2009 |
| WO | WO 2010/053583 A2 | 5/2010 |
| WO | WO 2010/090716 | 8/2010 |
| WO | WO 2010/092180 A1 | 8/2010 |
| WO | WO 2010/092181 A1 | 8/2010 |
| WO | WO 2011/017389 | 2/2011 |
| WO | WO 2011/036889 A1 | 3/2011 |
| WO | WO 2011/060035 A1 | 5/2011 |
| WO | WO 2011/060217 A1 | 5/2011 |
| WO | WO 2011/069063 A2 | 6/2011 |
| WO | WO 2011/081205 A1 | 7/2011 |
| WO | WO 2011/133729 A2 | 10/2011 |
| WO | WO 2012/020133 A1 | 2/2012 |
| WO | WO 2012/122340 A1 | 9/2012 |
| WO | WO 2013/010453 A1 | 1/2013 |
| WO | WO 2013/067248 A1 | 5/2013 |
| WO | WO 2013/119895 | 8/2013 |
| WO | WO 2013/192346 A1 | 12/2013 |
| WO | WO 2014/078454 | 5/2014 |
| WO | WO 2014/106238 A1 | 7/2014 |
| WO | WO 2006/066950 A2 | 6/2016 |
| WO | WO 2018/023072 | 2/2018 |
| WO | WO 2011/094740 | 8/2018 |
| ZA | 9102744 A | 2/1992 |

OTHER PUBLICATIONS

Adaa.org [online], "Treatment," Jan. 29, 2009, [retrieved on Mar. 16, 2019] retreived from URL <https://adaa.org/understanding-anxiety/depression/treatment>, 5 pages.
Akdemir et al., "Identification of novel a7 nicotinic receptor ligands by in silico screening against the crystal structure of a chimeric a7 receptor ligand binding domain," Bioorganic and Medicinal Chemistry, 2012, 20: 5992-6002.
American Chemical Society, STN Database RN 63463-05-8 entered Nov. 16, 1984.
Answer Summary, from the search of CAPLUS, Apr. 21, 2016. {Total 29 pages.).
Antoz, F.J., et al., "The Structure and Chemistry of Actinobolin", Journal of American Chemical Society, 92(16):4933-4942 (1970).
AU Application No. 2013216935, Examination Report No. 2 dated Aug. 1, 2017.
Bakshi, et al., "Antagonism of Phencyclidine-Induced Deficits in Prepulse Inhibition by the Putative Atypical Antipsychotic Olanzapine," Psychopharamcology, 122(2):198-201, 1995.
Berardi, et al., "4-(Tetralin-l-yl)-and-4-(Naphthalen-lyl)akyl] Derivatives of 1-Cyclohexylpiperazine as σ Receptor Ligands with Agonists $\sigma_2$ Activity", Journal of Medicinal Chemistry, American Chemical Society, 47(9):2308-23-17 (2004).
Berardi, et al., "A Multireceptorial Binding Reinvestigation on an Extended Class of σ Ligands: N-[ω-(Indan-l-yl and Tetralin-l-yl)alkyl] Derivatives of 3,3-Dimethylpiperdine Reveal High Affinities Towards $\sigma_1$ and EBP Sites", Bioorganic & Medicinal Chemistry, 9(5):1325-1335 (2001).
Berardi, et al., "Novel Potent σ Ligands: N-[ω-(Tetralin-l-yl)alkyl] piperdine Derivatives", Journal of Medicinal Chemistry, American Chemical Society, 38(21):4255-4260 (1996).
Berge, S.M., et al., "Pharmaceutical Salts", Journal of Pharmaceutical Sciences, 66(1):1-19 (1977).
Bianchi, D.A., et al., "Model Studies towards Stephaoxocanes: Construction of the 2-oxo-4azaphenalene Core of Stephaoxocanidine and Eletefine", European Journal of Organic Chemistry, 24:4731-4736 (2003).
Boger, D.L., et al., "Thermal Cycloaddition of 1,3,5-Triazine with Enamines: Regiospecific Pyrimidine Annulation", Journal of Organic Chemistry, 47:2673-2675 (1982).
Böhme, H. and Hitzel, V., "Homoisochroman-Derivative mit basischer Seitenkette in 1-Stellung", Archiv der Pharmazie 306:948-953 (1973) No English Translation.
Böhme, H. and Ziegler, F., "The Aminomethylation of 1-cyano-isochromane and 1-cyano-isothiochromane", Arch Pharm (Weinheim), 307(4):287-290 (1974) with English Translation.
CAPULUS Search Results of Apr. 6, 2016; 102 pages.
CAS Database Registry 444792-99-8 (XP-002742897) Aug. 24, 2002; 1 page.
CAS Database Registry 444793-00-4 (XP-002742898) Aug. 24, 2002; 1 page.
CAS Database Registry 444796-01-5 (XP-002742896) Aug. 24, 2002; 1 page.
CAS Database Registry 46490-93-1 (XP-002742899) Nov. 16, 1984; 1 page.
CAS Database Registry 738532-48-4 (XP-002742900) Sep. 3, 2004; 1 page.
CAS Database Registry Accession No. 1022058-43-0, May 23, 2008.
CAS Database Registry Accession No. 1022339-80-5, May 25, 2008.
CAS Database Registry Accession No. 1022468-83-2, May 25, 2008.
CAS Database Registry Accession No. 1022813-67-7, May 27, 2008.
CAS Database Registry Accession No. 1023480-64-9, May 29, 2008.
CAS Database Registry Accession No. 1024262-27-8 Jun. 1, 2008.
CAS Database Registry Accession No. 3549452-84-9, Sep. 28, 2001.
CAS Database Registry Accession No. 3594552-83-8, Sep. 28, 2001.
CAS Database Registry Accession Nos. 131022-75-8, 1310059-007-4, 1310059-06-3, 1310059-08-5 and 1310059-09-6 as cited in the Japanese Office Action dated Mar. 14, 2017 for Japanese Application No. 2014-556702.
CAS Database Registry No. 790156-85-3, Nov. 28, 2004.
CAS Database Registry Accession No. 340968-07-2, Jun. 14, 2001.
CAS Database Registry Accession No. 359452-60-1, Sep. 28, 2001.
CAS Database Registry No. 1027177-28-1 Jun. 11, 2008.
CAS Database Registry No. 1935196-69-2 Jun. 20, 2016.

(56) References Cited

OTHER PUBLICATIONS

CAS Registry No. 724648-33-5; STN entry date Sep. 10, 2004; Chemical name: Quinazoline, 4-benzo[b]thien-2-yl-1,4-dihydro— (cited Aug. 1, 2017, obtained from https://scifinder.cas.org on Aug. 10, 2017).

CAS Registry No. 736880-30-1; STN entry date Sep. 1, 2004; Chemical name: Quinazoline, 4-benzo[b]thien-2-yl-1,4-dihydro-2-methyl—(cited Aug. 1, 2017, obtained from https://scifinder.cas.org on Aug. 10, 2017).

CAS Registry No. 775528-08-0; STN entry date Nov. 7, 2004; Chemical name: Quinazoline, 4-benzo[b]thien-2-yl-1,4-dihydro-2-methyl (cited Aug. 1, 2017, obtained from https://scifinder.cas.org on Aug. 10, 2017).

CAS Registry No. 790156-85-3; STN entry date Nov. 28, 2004; Chemical name: Quinazoline, 4-benzo[b]thien-2-yl-1,4-dihydro— (cited Aug. 1, 2017, obtained from https://scifinder.cas.org on Aug. 10, 2017).

CAS Registry No. 933704-221-3, Apr. 30, 2007.

CAS Registry No. 1541037-08-04 Feb. 10, 2014.

CDC.gov, "Treatment of ADHD," Jan. 30, 2016, [retrieved Mar. 16, 2019] retrieved from URL <https://www.cdc.gov/ncbddd/adhd/treatment.html>, 8 pages.

Chemical Abstracts STN Registry Database, record for RN 1784628-34-7, Entered into STN on Jun. 19, 2015. (Year: 2015).

Chihara, et al., "Preparation of Benzothiiophene Derivatives as Blood Platelt Aggregation Inhibitors", Retrieved from STN Database Ascession No. 1992:128652 and JP03223277a, Yoshitomi Pharmaceutical Industries Ltd., Oct. 2, 1991.

CN Office Action in Application No. 201410333332.1, dated Nov. 2, 2015 with translation.

Corbera, et al., "A Medicinal-Chemistry-Guided Approach to Selective and Druglike Sigma 1 Ligands", ChemMedChem, 1(1):140-154 (2006).

Dammacco, M., et al., "Lithiation of N-Alkyl-(o-totyl)aziridine: Stereoselective Synthesis of Isochromans", Journal of Organic Chemistry, 74:6319-6322 with supplemental material pp. S1-S34 (2009).

Debernadis, J.F., et. al., "Conformationally Defined Adrenergic Agents. 4. 1-(Aminomethyl)phthalans: Synthesis and Pharmacological Consequences of the Phtalan Ring Oxygen Atom", Journal of Medicinal Chemistry, 30:178-184 (1987).

Dehaven-Hudkins, et al., "Characterization of the Binding of [3H](+)pentazocine to σ Recognition Sites in Guinea Pig Brain", European Journal of Pharmacology—Molecular Pharmacology Section 227:371-378 (1992).

Deninno, M.P., et al., "Synthesis and Dopaminergic Activity of 3-Substituted 1-(Aminomethyl)-3,4-dihydro-5,6-dihydroxy-1H-2-benzopyrans: Characterization of an Auxiliary Binding Region in the D1 Receptor", Journal of Medicinal Chemistry, 34:2561-2569 (1991).

Disabled World Towards Tomorrow, "Neurological Disorders: Types, Research & Treatment" URL: https://www.disabled-world.com/health/neurology downloaded on Nov. 1, 2017; 5 pages.

Dobson, et al., "Pyrano Heterocycles I. The Synthesese of Isochromans and the Novel Thieno[3,2-c]pyran, Benzothieno[3,2-c]pyran, and Pyrano[4,3-b]benxofuran Systems", Journal of Hetercyclic Chemistry, 12(3):591-594, 1975, 4 pages.

Ellis, "Affective Disorders (Mood Disorders)", Healthline Part 1 of 7 Overview; URL: http://www.healthline.com/health/affective-disorders, 5 pages, downloaded Jul. 25, 2015.

Emedicine Health, "Brain Cancer: Get Facts on Treatment, Causes and Symptoms", URL: https://www.emedicinehealth.com/brain_cancer/article_em.htm?pf=2; 15 pages. downloaded 2015.

EP Application No. 123747266.8, Communication Pursuant to Article 94(63) EPC dated Dec. 21, 2017.

EP Application No. 13747266.8, Partial Supplementary Eruopean Search Report dated Aug. 14, 2015; 11 pages.

EP Application No. 10835185.9, Extended European Search Report dated Apr. 4, 2013, 15 pages.

EP Patent Application No. 13747266.8, Communication Pusuant to Article 94(3) dated Nov. 18, 2016.

Gaur,S., et al. "CoMFA and CoMSIA Studies on a set of Benzyl Piperazines, Piperadines, Pyrazinopyridoindoles, Pyrazinoisoquinolines and Semi Rigid analogs of Diphenydramine", Medicinal Chemistry Research, 13(8-9):746-757 (2004).

Ghaemi, et al., "Does Olanzapine have Antidepressant Properties? A Retrospective Preliminary Study", Bipolar Disorders, 2:196-199, 2000.

Ghasemi, et al., "The Role of NMDA Receptors in the Pathophysiology and Treatment of Mood Disorders", Neuroscience and Biobehavioral Reviews, 47:336-358, 2014.

Girke, W.P.K., "Elektrophile Aromatische Substitutionsreaktionen Mit Protonierten 1,3-Diazinen II. Darstellung and Eigenschaften 4-arylsubstituierter 3,4-Dichrochinazolin-Derivate", European Journal of Inorganic Chemistry, 112(4):1348-1358 (1979) [English Abstract and machine translation of entire referenc—24 pages].

Gleason, et al., "Blockade of Phencyclidine-Induced Hyperlocomotion by Olanzapine, Clozapine and Serotonin Receptor Subtype Selective Antagnoists in Mice", Psychopharmacology, 129:79-84, 1997.

Gould, P.L., "Sale Selection for Basic Drugs", International Journal of Pharmaceutics, 33:201-217 (1986).

Grilliot, A-L and Hart, D.J., "Guanidinium Carboxylates: Preparation of 3-Carboxyoctahydro-9aH-Pyrimidin-9a-Ylium Chloride", Hetercoycles, 39(2):435-438 (1994).

Gronowitz, et al, The Reaction of 5-Bromo- and 2-Bromopyrimidine with Organolithium Compounds, Acta Chemica Scandinavica 19(7):8 pages (1965).

Hanner, et al., "Purification Molecular Cloning, and Expression of the Mammalian Sigmai-Binding Site", Proc. Natl. Aca. Sci., 93:8072-8077 (1996).

Hayakawa, K., et al., "Addition Reactions of (Phenylsulfonyl)propadiene with 1-Pryrrolidinyl Enamines of Cyclic Ketones: Syntheses and Reactions of 1,3-Dienes Possessing an Allyl Sulfone Moiety", Journal of Organic Chemistry, 51:5100-5105 (1986).

Hejl, et al., "Prepulse Inhibition in Patients with Alzheimer's Disease", Neurobiology of Aging, 25:1045-1050 (2004).

Hörig, H. and Pullman, W., "From Bendch to Clinic and Back: Perspective on the 1st IQPC Translational Research Conference", Journal of Translational Medicine, 2:44, 8 pages (2004).

Huang, N-A, et al., "Thiation Reactions of Some Active Carbonyl Compoounds with Sulfur Transfer Reagents", The Journal of Organic Chemistry, 52(2):169-172 (1987).

Ingebrigsten, T., et al., "Palladium-Catalysed Synthesis of Pyrimidines", Heterocycles, 65(11):2593-2603 (2005).

International Application No. PCT/US2010/058884, International Search Report and Written Opinion dated Aug. 25, 2011, 10 pages.

International Application No. PCT/US2017/044511, International Preliminary Report on Patentability issued by the International Searching Authority, dated Jan. 29, 2019, 8 pages.

International Application No. PCT/US2017/044517, International Preliminary Report on Patentability issued by the International Searching Authority, dated Jan. 29, 2019, 6 pages.

International Application No. PCT/US2013/025260, International Preliminary Report on Patentability issued by the International Searching Authority, dated Aug. 12, 2014, 10 pages.

International Application No. PCT/US2013/025260, International Search Report and Written Opinion issued by the International Searching Authority, dated Apr. 17, 2013 10 pages.

International Application No. PCT/US2016/017527 International Search Report dated Apr. 13, 2016, 8 pages.

International Application No. PCT/US2016/017539, International Search Report dated May 2, 2016, 3 pages.

International Application No. PCT/US2016/017539, Written Opinion dated May 2, 2016, 5 pages.

International Application No. PCT/US2017/044511, International Search Report and Written Opinion dated Dec. 21, 2017, 10 pages.

International Application No. PCT/US2017/044517, International Search Report and Written Opinion dated Jan. 11, 2018, 9 pages.

International Application No. PCT/US2018/044854, International Search Report and Written Opinion dated Apr. 10, 2018, 13 pages.

(56) References Cited

OTHER PUBLICATIONS

Ito, N., et al., "A Medium-Term Rat Live Bioassy for Rapid in vivo Dection of Carcinogenic Potential of Chemicals", Cancer Science, 94(1):3-8 (2003).
Jacobs, et al., "1-Imidizolyl(alkyl)-Substituted Di- and Tetrahydroquinolines and Analogues: Syntheses and Evaluation fo Dual Inhibitors of Thromboxane A2 Synthase and Aromatase", Journal of Medicinal Chemistry, 43(9):1841-1851, 2000.
Jaskowska, J. and Kowalski, P., "N-Alkylation of Imides Using Phase Transfer Catalysts Under Solvent-Free Conditions", Journal Heterocyclic Chemistry, 45:1371-1375 (2008).
Jentsch, et al., "The Neuropsychopharmacology of Phencyclidine: From NMDA Receptor Hypfunction to the Dopamine Hypothesis of Schizophrenia", Neurpsychopharmacology, 20(3):201-225, 1999.
JP Application No. 2012-542219, Office Action dated Nov. 21, 2014, 9 pages including translation.
JP Application No. 2014-556702, Notice of Reasons for Rejection dated Jul. 19, 2016 (with translation).
JP Application No. 2014-556702, Notice of Reasons for Rejection dated Mar. 14, 2017 (with translation).
Kapur, et al., "NMDA Receptor Antagonists Ketamine and PCP Have Direct Effects on the Dopamine D2 and Serotonin 5-HT2 Receptors-Implications for Models of Schizophrenia", Molecular Psychiatry, 7:837-844, 2002.
Karran, et al., "The Amyloid Cascade Hypothesis for Alzheimer's Disease: An Appraisal for the Development of Therapeutics", Nature, 10:698-712 (2011).
Katsuki, et al., "Excitotoxic Degeneration of Hypthalamic Orexin Neurons in Slice Culture", Neurobiology of Disease, 15:61-69, 2004.
Kornev, et al. CAS STN Abstrack, publ 2009 RN 1202851-83-9.
Kostin, et al., "Lack of Hypocretin Attenuates Behavioral Changes Produced by Glutamatergic Activation of the Perifornical-Lateral Hypthalamic Area", Sleep, 37(5):1011-1020, 2014.
Krogsgaard-Larsen, et al., Texbook of Drug Design and Discovery Madsen, U. (Ed.). (2009). Textbook of Drug Design and Discovery, Fourth Edition. Boca Raton: CRC Press. (2002).
Kumar, A., et al., "Catecholamines in a Semi-Rigid Framework: Synthesis & Biological Activity of N-Substituted I-Aminomethyl-5,6- & 6,7-dihydroxyisochromans", Indian Journal of Chemistry 26B:47-51 (1987).
Kumar, A., et al., "Phenethylamine in a Semi-Rigid Framework: Synthesis & Biological Activity of N-Substituted I-Aminomethyl-5,6- & 6,7-dimethoxyisochromans", Indian Journal of Chemistry 16B:793-796 (1978).
Langa,et al., "Generation and Phenotypic Analysis of Sigma Receptor type 1 (σ1) Knockout Mice", European Journal of Neuroscience, 18:2188-2196 (2003).
Lima, et al., Bioisosterism: A Useful Strategy for Molecular Modification and Drug Design, Current Medicinal Chemistry, 12:23-49 (2005).
Lindvall, O. and Kokaia, Z., "Stem Cells for the Treatment of Neurological Disorders", Nature, 441:1094-1096 (2006).
Lowry, et al., "Protein Measurement with the Folin Phenol Reagent", Journal Biochemistry, 193:265 (1951).
Macchia, B., et al., "Conformationally Restrained Analogs of Sympathomimetic Catecholamines, Synthesis Conformational Analysis, and Adrenergic Activity of Isochroman Derivatives", Journal of Medicinal Chemistry, 36:3077-3086 (1993).
Maier, et al., "Novel Spiropiperdines as Highly Potent and Subtype Selective σ-Receptor Ligands. Part 1", Journal of Medicinal Chemistry, 45:438-448 (2002), Journal Medicinal Chemistry, 45:4923-4930 (2002).
Maier, et al., "Novel σ Receptor Ligands, Part 2. SAR of Spiro[[2]benxopyran-1,4-piperidines] and Spiro [[2]benzofuran-1,4'-piperidines] with Carbon Substituents in Position 3", Journal Medicinal Chemistry, 45:4923-4930 (2002).

Marcus, et al., "The Efficacy and Safety of Aripiprazole as Adjunctive Therapy in Major Depressive Disorder. A Second Multicenter, Randomized, Double-Blind, Placebo-Controlled Study", Journal of Clinical Psybhopharmacology, 28(2):156-165, 2008.
Mashkovskiy, Drugs, Moscow, New Wave, LLC, vol. 1, p. 11 (2002) with translation.
Mayo Clinic Symptoms and Causes, "Seasonal Affective Disorder (SAD)", URL: https://www.mayoclinic.org/diseases-conditions/seasonal-affective-disorder/syymptoms-causes; 2 pages, downloaded 2015.
Mokrosz, et al., "Structure-Activity Relationship Studies of CNS Agents. Part 14:3 Structural Requirements for the 5-HT1A and 5-HT2A Receptor of Simple 1-(2-pyrimidinyl)piperazine Derivatives", Pharmazie, 49(H11) 6 pages (1994).
Moreno, et al., "Preclinical Models of Antipsychotic Drug Action", International Journal of Neuropsychopharmacology, 16:2131-2144, 2013.
Movassaghi, M. and Hill, M.D., "Single-Step Synthesis of Pyrimidine Derivatives", Journal of American Chemical Society, 128:14254-14255 (2006).
MX Application No. MX/a/2012/006326, Examination Report dated Jul. 4, 2013, with English translation, 6 pages.
Nakashima, T., et al., "Regulation of Folding and Photochromic Reactivity of Teraylenes Through a Host-Guest Interaction", Chem. European Journal, 17:10951-10957 (2011).
Nemade et al., "Schizophrenia Medication Treatement Options," Feb. 15, 2006, [retreived Mar. 16, 2019] retreived from URL <https://www.mentalhelp.net/articles/schizophrenia-medication-treatement-options/>, 6 pages.
NIMH.nih.com [online] "Bipolar Disorder," Jan. 2016, [retreived on Mar. 16, 2019] retreived from URL <https://www.nimh.nih.gov/health/topics/bopolar-disorder/index/shtml>, 13 pages.
NIMH.nih.com [online] "Obsessive-Compulsive Disorder," Jan. 2016, [retreived on Mar. 16, 2019] retreived from URL <https://www.nimh.nih.gov/health/topics/obsessive-compulsive-disorder-ocd/index.shtml>, 10 pages.
Nishimura, Y., et al., "Syntheses and Activities of some Bactobolin Derivatives", Journal of Antibiotics, 45(5):735-741 (1992).
Nordquist, et al., "Effects of Aripiprazole/OPC-14597 on Motor Activity, Pharmacological Models of Psychosis, and Brain Activity in Rats", Neuropharmacology, 54:405-416, 2008.
NZ Application No. 600008, Firstt Examination Report dated Mar. 11, 2013 in NZ, 3 pages.
NZ Application No. 626068 Examination Report dated Oct. 8, 2015, 3 pages.
NZ Application No. 711802 Examination Report dated Oct. 8, 2015, 5 pages.
Papillion, J.P.N., et al., "Structure-Activity Relationships, Pharmacokinetics, and in Vivo Activity of CYP11B2 and CYP11B1 Inhibitors", Journal of Medicinal Chemistry, 58:4749-4770 (2015).
Pittenger, et al., "The NMDA Receptor as a Therapeutic Target in Major Depressive . Disorder", CNS & Neuroological Distorders—Drug Targets, 6(2): 101-115, 2007.
Pubchem CID 12175079, create date Feb. 7, 2007, p. 3 compound; accessed Nov. 13, 2017; 9 pages.
Quirion, et al., "A Proposal for the Classification of Sigma Binding Sites", Trends in Pharamcology Science, 13:85-86 (1992).
Quiroz, T., et al., "A Practical Method for the Synthesis of Pyrrolizidine, Indolizidine and Pyrroloazepinolizidine Nucleus", Tetrahedron Letters, 48:1571-1575 (2007).
Radesca, et al., "Synthesis and Receptor Binding of Enantiomeric N-Substituted cis-N[2-(3,4-Dichlorophenypethyl]-1-(1-pyrrolidinyl) cyclohexylamines as High-Affinity σ Receptor Ligands", Journal of Medicinal Chemistry, 34:3058-3065 (1991).
Ram, S., et al., "Synthesis & Structure-Activity Relationships of 1-Substituted-aminomethyl-3-phenyl/methyl-1,3-dihydroisobenzofurans & 4-Substituted-amino-1-phenyl/methylisochromans—A New Class of Antihistaminics", Indian Journal of Chemistry, Section B: Organic Chemistry Including Medicinal Chemistry, 23B(12):1261-1267 (1984).
Rekka, E., et al., Structural Features of some Diphenhydramine Analogs that Determine the Interaction with Rat Liver Cytochrome P-450, Agents and Actions, 27(1-2):184-187 (1989).

(56) References Cited

OTHER PUBLICATIONS

Ross, L.O., et al., "Potential Anticancer Agents. XVIII. Synthesis of Substituted 4,5-Trimethylenepyrimidines", Journal of American Chemical Society, 84(12):3108-3114 (1959).
Sakai, et al., "Facile and Efficient Synthesis of Polyfunctionalized Benzofurans: Three-Component Coupling Reactions from an Alkynylsilane, and o-Hydroxybenzaldehyde Derivative, and a Secondary Amine by a Cu(I)-Cu(II) Cooperative Calatytic System", RwreHWSEON 1WRRWEA, 49:3437-3440 (2008).
Salomone, A., et al., "Preparation o f Polysubstituted Isochromanes by Addition of ortho-Lithiated Aryloxiranes to Enaminones", Journal of Organic Chemistry, 78:11059-11065 (2013).
Saxena, M., et al., "Synthesis of some Substituted Pyrazinopyridoindoles and 3D QSAR Stuies along with Related Compounds: Piperazines, Piperidines, Pyrazinoisoquinolines. And Diphenhydramine, and its Semi-Rigid Analogs as Antihistamines (H1)", Bioorganic & Medicinal Chemistry 14:8249-8258 (2006).
Schäfer, S., "Failure is an Option: Learning from Unsuccessful Proof-of-Concept Trials", Drug Discovery Today, 13(21/22):913-916 (2008).
Schmitz, et al., "Hippocampal Neuron Loss Exceeds Amyloid Plaque Load in a Transgenic Mouse Model of Alzheimer's Disease", American Journal of Pathology, 164(4):1045-1050 (2004).
Schow, et al., "Novel Sigma Receptor Ligands 2.", Bioorganic & Medicinal Chemistry Letters, 3(2):221-224 (1993).
SG Application No. 201204089-5, Written Opinion dated Sep. 20, 2013, 12 pages.
Singapore Application No. 10201401661, Search Report and Written Opinion dated Jun. 15, 2015, 10 pages.
Snyder, et al., "Receptor Mechanisms in Antipsychotic Drug Action: Focus on Sigma Receptors", Journal of Neuropsychiatry, 1(1):7-15 (1989).
Steliou, K., et al., "Group 14 Metal Assisted Carbon-Sulfur Bond Formation", Journal of Organic Chemistry, 50(24):4969-4971 (1985).
Strekowski, et al., "Synthesis of 2-Chloro-4,6-di(heteraryl)pyrimidines", Journal of Heterocyclic Chemistry, 27:1393-1400 (1989).
Swerdlow et al., "Seroquel Restores Sensorimotor Gating in Phencyclidine-Treated Rats," Journal of Pharmacology and Experimental Therapeutics, vol. 279, No. 3, pp. 1290-1299, Dec. 1996.
The list of search results of CAPLUS, Apr. 21, 2016. {Total 20 pages.).
Toffano, M., et al., "Asymmetric Routes Towards Polyfunctionalized Pyrrolidines: Application to the Synthesis of Alkaloid Analogues", Tetrahedron: Asymmetry, 14:3365-3370 (2003).
Torrado, et al., "Novel Selective and Potent 5-HT Reuptake Inhibitors with 5-HT$_{1D}$ Antagonist Activity: Chemistry and Pharmacological Evaluation of a Series of Thienopyran Derivatives", Bioorganic & Medicinal Chemistry, 12(20):5277-5295, 2004, 19 pages.
Trehan, "A New Synthesis of 13-aza-18-nor-17oxo-A-nor-3-thiaestra-1,5(10), 9(11)-triene" Retrieved from STN Database Accession No. 1986:225089 & Indian Journal of Chemistry, Section 6: Organic Chemistry Including Medicinal Chemistry, 24B(6):659-661 (1985).
Trehan, "Synthesis of 2,3,13-Triaza-18-nor-17-oxo-3-phenyl-A-nor-estra-1,5(10), 9(11)-triene & 2,3,13-Triaza-7,7-dimethyl-18-nor-17-oxo-3-phenyl-A-nor-estra-1,5(10), 9(11)-triene", Indian Journal of Chemistry, 19B:243-245 (1980).
UMPC.com [online] , "Find the Best Epilepsy Treatment for You," May 23, 2015, [retreived on Mar. 16, 2019] retreived from URL <https://share.upmc.com/2015/05/epilepsy-treatement/>, 5 pages.
Van Der Stoel, et al., "Di-TT-methane Regarrangement of 4-Heteroaryl-1,4(or 3,4)-dihydropyrimidines", Journal of the Chemical Society, Perkin Transactions 1, 4 pages Nov. 2, 1978.
Vecchietti, et al. ,"(1S)-1-(Aminomethyl)-2-(arylacetyl)-1,2,3,4-tetrahydroisoquinoline and Heterocycle-Condensed Tetrahydropyridine Derivatives: Members of a Novel Class of Very Potent K Opioid Analgesics", Journal of Medicinal Chemistry, 34(8):2624-2633 1991.
Walker, et al., "Sigma Receptors: Biology and Function", Phamacological Reviews, 42(4):355-402 (1990).

Weis, et al., "The Crystal and Molecular Structure of 4,6,6-trimethyl-2-phenyl-1,6-dihydropyrimidine", Hetercycles, 19(3):6 pages (1982).
Werber et al., "The Beneficial effect of cholinesterase inhibitors on patients suffering from Parkinson's disease and dementia," J Neural Transm., Jun. 27, 2001, 108:1319-1325.
Wilkinson et al., "Cholinesterase Inhibitors Used in the Treatment of Alzheimers's Disease," Drugs Aging., 2004, 21(7):453-478.
Williams, M., et al., "Emerging Molecular Approaches to Pain Therapy", Journal of Medicinal Chemistry, 42(9):1481-1500 (1999).
Winhusen, T.M., et al., "A Placebo-Controlled Screening Trial of Tiagabine, Sertraline and Donepezil as Cocaine Dependence Treatments", Addiction, 100(Suppl.1):68-77 (2005).
Xi, Z., et al., Preparation of Partially Substituted 1-Halo- and 1,4-Dihalo-1,3-Dienes via Reagent-Controlled Desilyation of Halogenated 1,3-Dienes, Journal of Organic Chemistry, 71:3154-3158 (2006).
CAS Registry No. 1071058-54-2, Entered STN: Nov. 6, 2008, 4 pages.
CAS Registry No. 40196-93-8, Entered STN: Nov. 16, 1984, 2 pages.
CAS Registry No. 40196-92-7, Entered STN: Nov. 16, 1984, 2 pages.
CAS Registry No. 1027834-86-1, Entered STN: Jun. 13, 2008, 4 pages.
Datta et al., "Studies in Sulphur Heterocycles. Part 5. Further Use of 6,7Dihydribenzo[b]thiphen-4[5H]-one in the Synthesis of Substituted Benzo[b]thiophene Derivatives", J. Chem. Research (S), 1988, 72-73.
Davis et al., "Benzothiophene Containing Rho Kinase Inhibitors: Efficacy in an Animal Model of Glaucoma", Bioorganic & Medicinal Chemistry Letters, Jun. 1, 2010, 20(11):3361-3366.
Devani et al., "Synthesis of 2-Aminothiophenes & Thieno[2,3-d]pyrimidines", Indian Journal of Chemistry, May 1976, 14B:357-360.
Frohlich et al., "A Novel Synthesis of 3,3-(Spiro)Substituted Azetidines", Heterocycles, 1994, 37(3):1897-1891.
Google.com [online] "Parkinson's Disease—Symptoms, Diagnosis and Treatment." Jan. 22, 2006, [Retrieved on Dec. 28, 2018] Retrieved from URL <https://www.google.com/search?q=Parkinson+disease+treatment&source=Int&tbs=cdr%3 a 1%2Ccd_max%3A2%2F8%2F2012&tbm=>, 2 pages.
Hopkinsmedicine.org [online] "Treatment for Tourette Syndrome: Johns Hopkins Pediatric Neurology," Apr. 2006, [Retrieved on Dec. 28, 2018] Retrieved from URL <<https://www.hopkinsmedicine.org/neurology_neurosurgery/centers_clinics/pediatric-neurology/conditions/tourettes_syndrome/treatment.html>, 1 page.
Mayoclinic.org [online] "Fibromyalgia Treatment: Is Neurontin Effective?" Jul. 2009, [Retrieved Oct. 18, 2019], Retrieved from URL <https://www.mayoclinic.org/diseases-conditions/fibromyalgia/expert-answers/fibromyalgia-treatment/faq-20058273>, 3 pages.
Michaeljfox.org [online] "Parkinson's Disease," May 2007, [Retrieved Dec. 28, 2018] Retrieved from URL <https://www.michaeljfox.org/understanding-parkinsons/living-with-pd/topic.php?causes>, 5 pages.
Medicinenet.com [online] "Alzheimer's Disease Treatment, Symptoms, Stages & Life Expectancy." Jul. 2007, [Retrieved on Dec. 28, 2018], Retrieved from URL <https ://www .medicinenet.com/alzheimers disease causes stages and symptoms/article .htm#alzheimers_disease_medications>, 16 pages.
Medlineplus.gov [online] "Symptoms, Diagnosis and Treatment: Alzheimer's Disease." Fall 2010, [Retrieved on Dec. 28, 2018], Retrieved from URL <https://medlineplus.gov/magazine/issues/fall10/articles/fall10pg19.html>, 5 (3) : 19.
Pubchem CID 4878038, create date Sep. 17, 2005, accessed Feb. 22, 2019; 12 pages.
Pubchem CID 4878041, create date Sep. 17, 2005, accessed Feb. 22, 2019; 14 pages.
Ross et al., "a2 Adrenoceptor Agonists as Potential Analgesic Agents. 2. Discovery of 4(4-Imidazo)-1,3-dimethyl-6,7-dihydro-thianaphthene as a High-Affinity Ligand for the α2D Adrenergic Receptor", J. Med. Chem., 2000, 43:1423-1426.
Shklyaeva et al., "2-Amino-6-(3,4-ethylenedioxythiophen-2-yl)-4-(2-thienyl)-pyrimidine: Synthesis and Properties", Russian Journal of Organic Chemistry, 2010, 46(6):938-940.

(56) References Cited

OTHER PUBLICATIONS

Sridhar et al., "Synthesis and Anticancer Activity of Some Novel Pyrimidine Derivatives", International Journal of Pharmaceutical Sciences and Research, Sep. 29, 2011, 2(10):2562-2565.

Stanetty et al., "Heterocyclische Spiroverbindungen Spiroverbindungen: Spiro [benzo[b]thiophen-4(5H),3'-pyrrolidine]", Arch. Pharm., 1984, 317:168-176 With English Abstract.

U.S. Food and Drug Administration, "Highlights of Prescribing Information: Abilify," FDA label, last revised Dec. 2014, 84 pages.

Extended European Search Report in EP Application No. 17835385.0. dated Feb 26, 2020.

Bonner et al. "Mapping the Catechol Binding Site in Dopamine D1 Receptors: Synthesis and Evaluation of Two Parallel Series of Bicyclic Dopamine Analogues", CHEMMEDCHEM, vol. 6, No. 6, pp. 1024-1040. dated Jun. 6, 2011.

Nozawa et al. "Benzopyran Derivatives as Inhibitors for the Formation of Active Oxygen" Chemical Abstract Service, Database Accession No. 1989:553630. 1989.

Gaur et al. "CoMFA and CoMSIA Studies on a set of Benzyl Piperazines, Piperadines, Pyrazinopyridoindoles, Pyrazinoisoquinolines and Semi Rigid Analogs of Diphenydramine", Medicinal Chemistry Research, 13(8-9), pp. 746-757. 2004.

Bastin et al. "Salt Selection and Optimisation Procedures for Pharmaceutical New Chemical Entities", Organic 3rocess Research & Development, vol. 4, pp. 427-435. 2000.

International Search Report in International Application No. PCT/US2020/022642 dated Aug. 5, 2020.

Written Opinion in International Application No. PCT/US2020/022642 dated Aug. 5, 2020.

Morissette et al. "High-Throughput Crystallization: Polymorphs, Salts, Co-Crystals and Solvates of 3harmaceuticals Solids", Advanced Drug Delivery Reviews vol. 56, pp. 275-300, 2004.

\* cited by examiner

Compound of Example 2

Compound of Example 26

Compound of Example 2

Compound of Example 26

Compound of Example 2

Compound of Example 14

Compound of Example 17

Compound of Example 26

Compound of Example 14

Compound of Example 17

Compound of Example 26

* $p<0.05$
One-way ANOVA,
Dunnetts post
test

COMPOUNDS AND COMPOSITIONS AND USES THEREOF

FIELD OF THE INVENTION

The invention relates to 1-aminomethylisochroman compounds, and pharmaceutical compositions containing them, for the treatment of central nervous system diseases and disorders. Such diseases and disorders include depression, bipolar disorder, pain, schizophrenia, obsessive compulsive disorder, psychostimulation, addiction, social disorder, attention deficit hyperactivity disorder, an anxiety disorder, autism, a cognitive impairment, or a neuropsychiatric symptom such as apathy, depression, anxiety, cognitive impairment, psychosis, aggression, agitation, impulse control, and sleep disruption in neurological diseases such as Alzheimer's and Parkinson's diseases.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Central nervous system diseases and disorders affect a wide range of the population with differing severity. Neurological and psychiatric diseases and disorders include major depression, schizophrenia, bipolar disorder, obsessive compulsive disorder (OCD), panic disorder, and posttraumatic stress disorder (PTSD), among others. These diseases and disorders affect a person's thoughts, mood, behavior and social interactions and can significantly impair daily functioning. See, e.g., *Diagnostic and Statistical Manual of Mental Disorders*, 4th Ed., American Psychiatric Association (2000) ("DSM-IV-TR"); *Diagnostic and Statistical Manual of Mental Disorders*, 5th Ed., American Psychiatric Association (2013) ("DSM-5"). Furthermore, neuropsychiatric symptoms such as apathy, depression, anxiety, cognitive impairment, psychosis, aggression, agitation, impulse control and sleep disruption are now recognized as core impairments of neurological diseases and disorders such as Alzheimer's and Parkinson's diseases.

While medications exist for some aspects of these diseases, there remains a need for effective treatments for various neurological and psychiatric diseases and disorders. For example, while mood stabilizers such as lithium and valproate, antidepressants and antipsychotic drugs are used to treat mood disorders, more effective medications are necessary. And current antipsychotics may be successful in treating the positive symptoms of schizophrenia but fare less well for the negative and cognitive symptoms. Additionally, current antidepressants are typically effective only for a proportion of subjects suffering from depression. Furthermore, despite the fact that the behavioral and psychiatric symptoms of neurological disease such as Parkinson's disease and Alzheimer's disease are major reasons for the institutionalization of subjects, few drugs exist to treat them.

SUMMARY OF THE INVENTION

In one aspect, the invention relates to a compound of formula I:

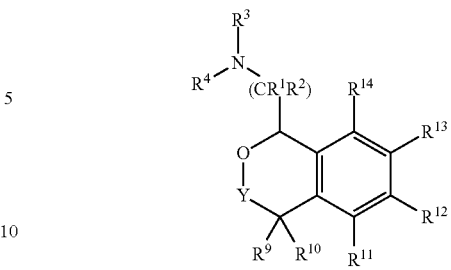

or a pharmaceutically acceptable salt thereof,
wherein:
Y is chosen from direct bond, —C($R^5R^6$)— and —C($R^5R^6$)C($R^7R^8$)—;
$R^1$, $R^2$, $R^3$ and $R^4$ are chosen independently from H, aliphatic ($C_1$-$C_8$)hydrocarbon and ($C_3$-$C_6$)cycloalkyl, wherein the aliphatic ($C_1$-$C_8$)hydrocarbon is optionally substituted with one or more of halogen, hydroxyl, ($C_1$-$C_6$)alkoxy, amino, ($C_1$-$C_6$)alkylamino and di($C_1$-$C_6$)alkylamino;
or, taken together, $R^1$ and $R^2$ may form ($C_3$-$C_6$)cycloalkyl;
$R^5$ and $R^6$ are chosen independently from H, fluorine, ($C_1$-$C_6$)alkyl and ($C_1$-$C_6$)haloalkyl;
$R^7$, $R^8$, $R^9$ and $R^{10}$ are chosen independently from H, halogen, hydroxyl, ($C_1$-$C_6$)alkyl, ($C_1$-$C_6$)haloalkyl and ($C_1$-$C_6$)alkoxy;
$R^{11}$, $R^{12}$, $R^{13}$, and $R^{14}$ are chosen independently from H, halogen, hydroxyl, cyano, aliphatic ($C_1$-$C_8$)hydrocarbon, ($C_3$-$C_6$)cycloalkyl, ($C_1$-$C_6$)haloalkyl, ($C_1$-$C_6$)alkoxy, aminocarbonyl, ($C_1$-$C_6$)alkylaminocarbonyl, di($C_1$-$C_6$)alkylaminocarbonyl, ($C_1$-$C_6$)acyl, ($C_1$-$C_6$)haloalkoxy, hydroxy ($C_1$-$C_6$)alkyl, carboxy, ($C_1$-$C_6$)alkoxycarbonyl, acetoxy, nitro, amino, ($C_1$-$C_6$)alkylamino, di($C_1$-$C_6$)alkylamino, and aminosulfonyl;
or, taken together, any adjacent pair of $R^{11}$, $R^{12}$, $R^{13}$, and $R^{14}$ may form a fused 1,3-dioxole, a dihydro-1,4-dioxine, difluoro-1,3-dioxole, 2,3-dihydrofuran optionally mono- or bisubstituted with fluorine, or 2,5-dihydrofuran optionally mono- or bi-substituted with fluorine.

In these compounds and compositions, at least one of $R^5$, $R^6$, $R^7$, $R^8$, $R^9$, $R^{10}$, $R^{11}$, $R^{12}$, $R^{13}$, and $R^{14}$ is other than hydrogen. Also, if only one of $R^{12}$ or $R^{13}$ is methoxy, then the remainder of $R^{11}$, $R^{12}$, $R^{13}$, and $R^{14}$ may not be H. Further, when one or two of $R^{11}$, $R^{12}$, $R^{13}$, and $R^{14}$ are methoxy, then $R^3$ and $R^4$ are each independently chosen from H and methyl.

In another aspect, the invention relates to a pharmaceutical composition comprising a compound disclosed herein, or a pharmaceutically acceptable salt thereof, and a pharmaceutically acceptable carrier, adjuvant, or vehicle.

In another aspect, the invention relates to a method for treating a neurological or psychiatric disease or disorder in a subject, comprising administering to said subject an effective amount of a compound, or a pharmaceutically acceptable salt thereof, or pharmaceutical composition disclosed herein.

DETAILED DESCRIPTION

Figure 1A:
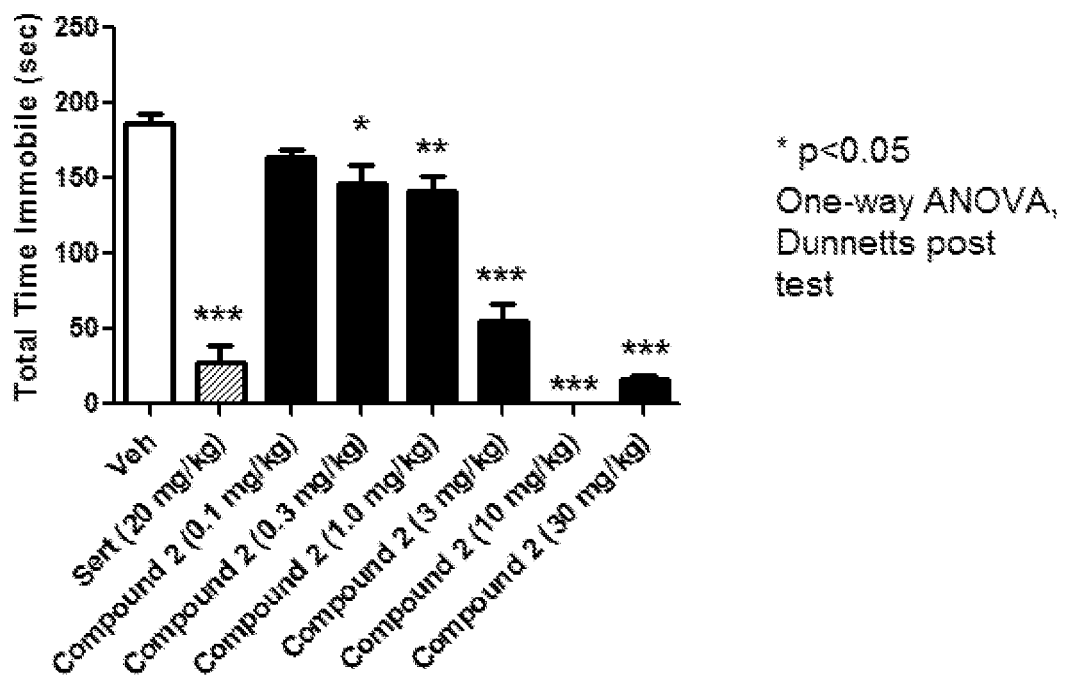
FIGS. 1a and 1b shows the effect of representative compounds of the invention on mice in a forced swim test.

The methods of the invention relate to the use of compounds and compositions disclosed herein to treat neurological or psychiatric diseases, disorders or impairments. In some embodiments, the neurological or psychiatric disease or disorder is depression, bipolar disorder, pain, schizophrenia, obsessive compulsive disorder, psychostimulation, addiction, social disorder, attention deficit hyperactivity disorder, an anxiety disorder, a movement disorder, epilepsy, autism, Alzheimer's disease, Parkinson's disease or cognitive impairments. In one embodiment, the disease or disorder is depression, particularly treatment-resistant depression (TRD), major depressive disorder (MDD), unipolar depression, bipolar depression or depression associated with another disease or disorder. In some embodiments, the impairments in neurological diseases or disorders such as Alzheimer's and Parkinson's diseases include neuropsychiatric symptoms such as apathy, depression, anxiety, cognitive impairment, psychosis, aggression, agitation, impulse control disorders, and/or sleep disorders.

In one embodiment, the invention relates to compounds of formula I:

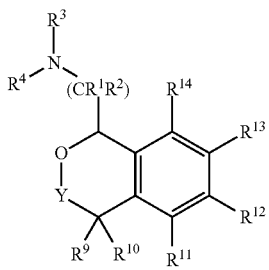

I or a pharmaceutically acceptable salt thereof,
wherein:
Y is chosen from direct bond, —$C(R^5R^6)$— and —$C(R^5R^6)C(R^7R^8)$—;
$R^1$, $R^2$, $R^3$ and $R^4$ are chosen independently from H and aliphatic ($C_1$-$C_8$)hydrocarbon, ($C_3$-$C_6$)cycloalkyl wherein the aliphatic ($C_1$-$C_8$)hydrocarbon is optionally substituted with one or more of halogen, hydroxyl, ($C_1$-$C_6$)alkoxy, amino, ($C_1$-$C_6$)alkylamino and di($C_1$-$C_6$)alkylamino;
or, taken together, $R^1$ and $R^2$ may form ($C_3$-$C_6$)cycloalkyl;
$R^5$ and $R^6$ are chosen independently from H, fluorine, ($C_1$-$C_6$)alkyl and ($C_1$-$C_6$)haloalkyl;
$R^7$, $R^8$, $R^9$ and $R^{10}$ are chosen independently from H, halogen, hydroxyl, ($C_1$-$C_6$)alkyl, ($C_1$-$C_6$)haloalkyl and ($C_1$-$C_6$)alkoxy;
$R^{11}$, $R^{12}$, $R^{13}$, and $R^{14}$ are chosen independently from H, halogen, hydroxyl, cyano, aliphatic ($C_1$-$C_8$)hydrocarbon, ($C_3$-$C_6$)cycloalkyl, ($C_1$-$C_6$)haloalkyl, ($C_1$-$C_6$)alkoxy, aminocarbonyl, ($C_1$-$C_6$)alkylaminocarbonyl, di($C_1$-$C_6$)alkylaminocarbonyl, ($C_1$-$C_6$)acyl, ($C_1$-$C_6$)haloalkoxy, hydroxy($C_1$-$C_6$)alkyl, carboxy, ($C_1$-$C_6$)alkoxycarbonyl, acetoxy, nitro, amino, ($C_1$-$C_6$)alkylamino, di($C_1$-$C_6$)alkylamino, and aminosulfonyl;

or, taken together, any adjacent pair of $R^{11}$, $R^{12}$, $R^{13}$, and $R^{14}$ may form a fused 1,3-dioxole, a dihydro-1,4-dioxine, difluoro-1,3-dioxole, 2,3-dihydrofuran optionally mono- or bisubstituted with fluorine, or 2,5-dihydrofuran optionally mono- or bi-substituted with fluorine.

In some embodiments, at least one of $R^5$, $R^6$, $R^7$, $R^8$, $R^9$, $R^{10}$, $R^{11}$, $R^{12}$, $R^{13}$, and $R^{14}$ is other than hydrogen. In some embodiments, if only one of $R^{12}$ or $R^{13}$ is methoxy, then the remainder of $R^{11}$, $R^{12}$, $R^{13}$, and $R^{14}$ may not be H. In some embodiments, when one or two of $R^{11}$, $R^{12}$, $R^{13}$, and $R^{14}$ are methoxy, then $R^3$ and $R^4$ are each independently chosen from H and methyl.

In one embodiment, the invention relates to compounds of formula I:

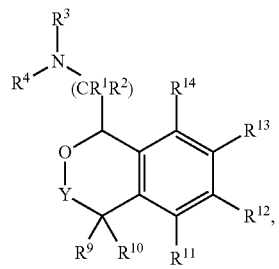

I or a pharmaceutically acceptable salt thereof,
wherein:
Y is chosen from direct bond, —$C(R^5R^6)$— and —$C(R^5R^6)C(R^7R^8)$—;
$R^1$, $R^2$, $R^3$ and $R^4$ are chosen independently from H, aliphatic ($C_1$-$C_8$)hydrocarbon and ($C_3$-$C_6$)cycloalkyl, wherein the aliphatic ($C_1$-$C_8$)hydrocarbon is optionally substituted with one or more of halogen, hydroxyl, ($C_1$-$C_6$) alkoxy, amino, ($C_1$-$C_6$)alkylamino and di($C_1$-$C_6$)alkylamino;
or, taken together, $R^1$ and $R^2$ may form ($C_3$-$C_6$)cycloalkyl;
$R^5$ and $R^6$ are chosen independently from H, fluorine, ($C_1$-$C_6$)alkyl and ($C_1$-$C_6$)haloalkyl;
$R^7$, $R^8$, $R^9$ and $R^{10}$ are chosen independently from H, halogen, hydroxyl, ($C_1$-$C_6$)alkyl, ($C_1$-$C_6$)haloalkyl and ($C_1$-$C_6$)alkoxy;
$R^{11}$, $R^{12}$, $R^{13}$, $R^{14}$ are chosen independently from H, halogen, hydroxyl, cyano, aliphatic ($C_1$-$C_8$)hydrocarbon, ($C_3$-$C_6$)cycloalkyl, ($C_1$-$C_6$)haloalkyl, aminocarbonyl, ($C_1$-$C_6$)alkylaminocarbonyl, di($C_1$-$C_6$)alkylaminocarbonyl, ($C_1$-$C_6$)acyl, ($C_1$-$C_6$)haloalkoxy, hydroxy($C_1$-$C_6$)alkyl, carboxy, ($C_1$-$C_6$)alkoxycarbonyl, acetoxy, nitro, amino, ($C_1$-$C_6$)alkylamino, di($C_1$-$C_6$)alkylamino or aminosulfonyl.

In one embodiment, the configuration is of formula Ia:

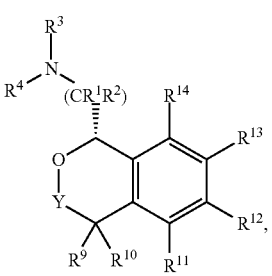

Ia, or a pharmaceutically acceptable salt thereof.

In one embodiment, the configuration is of formula Ib:

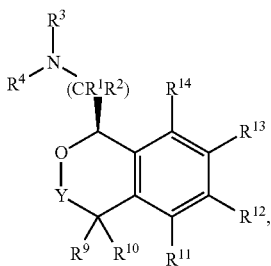

or a pharmaceutically acceptable salt thereof.

In one embodiment, Y is —C(R$^5$R$^6$)—, and the compounds are of formula II:

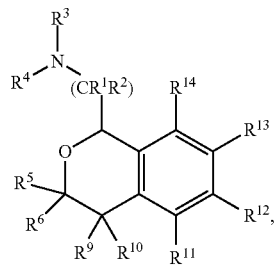

or a pharmaceutically acceptable salt thereof

In one embodiment, the configuration is of formula IIa:

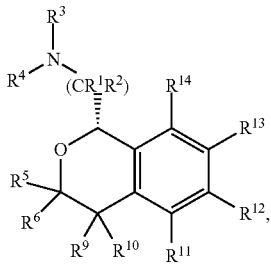

or a pharmaceutically acceptable salt thereof.

In one embodiment, the configuration is of formula IIb:

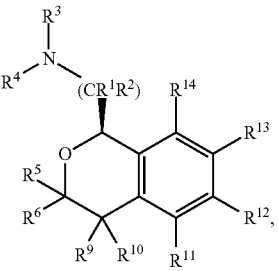

or a pharmaceutically acceptable salt thereof.

In some embodiments, R$^1$ is hydrogen. In some embodiments, R$^2$ is hydrogen or methyl.

In some embodiments, R$^3$ is hydrogen. In some embodiments, R$^4$ is hydrogen or methyl.

In some embodiments, R$^5$, R$^6$, R$^7$, and R$^8$ are each hydrogen.

In some embodiments, R$^9$ and R$^{10}$ are chosen independently from H, fluoro, and methyl.

In some embodiments, R$^1$ is hydrogen; R$^2$ is hydrogen or methyl; R$^3$ is hydrogen; R$^4$ is hydrogen or methyl; R$^5$ is hydrogen; and R$^6$ is hydrogen.

In some embodiments, R$^5$ and R$^6$ are each hydrogen, and R$^9$ and R$^{10}$ are chosen independently from H, fluoro, and methyl.

In some embodiments, R$^{11}$, R$^{12}$, R$^{13}$, and R$^{14}$ are H. In other embodiments, one of R$^{11}$, R$^{12}$, R$^{13}$, and R$^{14}$ is fluoro, chloro, methyl or cyano and the remaining three are H. In some of these embodiments, R$^{12}$ and R$^{13}$ are H, one of R$^{11}$ and R$^{14}$ is chosen from fluoro, chloro, methyl and cyano, and the other of R$^{11}$ and R$^{14}$ is H. In still other embodiments, two of R$^{11}$, R$^{12}$, R$^{13}$, and R$^{14}$ are fluoro, chloro, methyl or cyano and the remaining two are H. In some of these embodiments, R$^{12}$ and R$^{13}$ are H, and R$^{11}$ and R$^{14}$ are chosen from fluoro, chloro, methyl and cyano. In yet other embodiments, two of R$^{11}$, R$^{12}$, R$^{13}$, and R$^{14}$ form a fused 1,3-dioxole and the remaining two are H. In further embodiments, two of R$^{11}$, R$^{12}$, R$^{13}$, and R$^{14}$ form a fused dihydro-1,4-dioxine and the remaining two are H. For example, the structures below show instances where R$^{13}$ and R$^{14}$ form a fused 1,3-dioxole and a fused dihydro-1,4-dioxine, respectively:

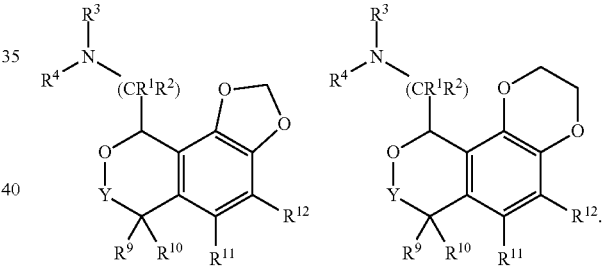

In some embodiments, R$^1$ is hydrogen; R$^2$ is hydrogen or methyl; R$^3$ is hydrogen; R$^4$ is hydrogen or methyl; R$^5$, R$^6$, R$^9$ and R$^{10}$ are hydrogen. In some of these embodiments, two of R$^{11}$, R$^{12}$, R$^{13}$, and R$^{14}$ form a fused 1,3-dioxole and the remaining two are H. In other of these embodiments, R$^{12}$ and R$^{13}$ are H, one of R$^{11}$ and R$^{14}$ is chosen from fluoro, chloro, methyl and cyano, and the other of R$^{11}$ and R$^{14}$ is H. In still other of these embodiments, R$^{12}$ and R$^{13}$ are H, and R$^{11}$ and R$^{14}$ are chosen from fluoro, chloro, methyl and cyano. In some of these embodiments, R$^{14}$ is chosen from fluoro, chloro, methyl and cyano.

In some embodiments, R$^1$ is hydrogen; R$^2$ is hydrogen or methyl; R$^3$ is hydrogen; R$^4$ is hydrogen or methyl; R$^5$, R$^6$, R$^9$ and R$^{10}$ are hydrogen; and R$^{13}$ and R$^{14}$ form a fused 1,3-dioxole and R$^{11}$ and R$^{12}$ are H.

In some embodiments, R$^1$ is hydrogen; R$^2$ is hydrogen or methyl; R$^3$ is hydrogen; R$^4$ is hydrogen or methyl; R$^5$, R$^6$, R$^9$ and R$^{10}$ are hydrogen; and R$^{14}$ is chosen from fluoro, chloro, methyl and cyano, and R$^{11}$, R$^{12}$ and R$^{13}$ are H.

In some embodiments, R$^3$ is hydrogen or methyl; R$^1$, R$^2$, R$^4$, R$^5$, R$^6$, R$^{11}$, and R$^{14}$ are hydrogen; R$^9$ and R$^{10}$ are hydrogen; one of R$^{12}$ and R$^{13}$ is chosen from fluoro, chloro, methyl and cyano, and the other of R$^{12}$ and R$^{13}$ is hydrogen.

In some embodiments, $R^3$ is hydrogen or methyl; $R^1$, $R^2$, $R^4$, $R^5$, $R^6$, $R^{11}$, and $R^{14}$ are hydrogen; one or both of $R^9$ and $R^{10}$ is chosen from methyl and fluoro; and $R^{12}$ and $R^{13}$ are hydrogen. In some of these embodiments, $R^3$ is methyl.

In some embodiments, $R^3$ is methyl; $R^1$, $R^2$, $R^4$, $R^5$, and $R^6$, are hydrogen; $R^9$, $R^{10}$ and $R^{11}$ are hydrogen, and one of $R^{12}$, $R^{13}$ or $R^{14}$ is chosen from fluoro, chloro, methyl and cyano, and the remaining three are H.

In some embodiments, $R^3$ is methyl; $R^1$, $R^2$, $R^4$, $R^5$, $R^6$, $R^9$, and $R^{10}$ are hydrogen; $R^{11}$ and $R^{14}$ are fluoro; and $R^{12}$ and $R^{13}$ are H.

In some embodiments, $R^1$ and $R^3$ are hydrogen or methyl; $R^2$, $R^4$, $R^5$, $R^6$, $R^9$, $R^{10}$, $R^{13}$ and $R^{14}$ are hydrogen and one of $R^{11}$ and $R^{12}$ is fluoro and the other is hydrogen.

In some embodiments, $R^1$ and $R^3$ are hydrogen or methyl; $R^2$, $R^4$, $R^5$, $R^6$, $R^{10}$, $R^{12}$ are hydrogen; $R^9$ is hydrogen or fluoro; $R^{11}$ is hydrogen or fluoro; and $R^{13}$ and $R^{14}$ are hydrogen, or, taken together, $R^{13}$ and $R^{14}$ form a fused 1,3-dioxole or dihydro-1,4-dioxine.

In some embodiments, $R^1$ and $R^3$ are hydrogen or methyl; $R^2$, $R^4$, $R^5$, $R^6$, $R^9$, are hydrogen; $R^{10}$ is hydrogen or methyl; $R^{11}$ and $R^{14}$ are hydrogen; and $R^{12}$ and $R^{13}$ form a fused 1,3-dioxole.

In some embodiments, $R^1$ and $R^3$ are hydrogen or methyl; $R^2$, $R^4$, $R^5$, $R^6$, $R^9$, are hydrogen; $R^{10}$ is hydrogen or methyl; $R^{11}$ and $R^{12}$ are hydrogen; and $R^{13}$ and $R^{14}$ form a fused 1,3-dioxole.

In some embodiments, $R^1$ and $R^3$ are hydrogen or methyl; $R^2$, $R^4$, $R^5$, $R^6$, $R^9$, are hydrogen; $R^{10}$ is hydrogen or methyl; $R^{13}$ and $R^{14}$ are hydrogen; and $R^{11}$ and $R^{12}$ form a fused 1,3-dioxole.

In some embodiments, $R^1$ and $R^3$ are hydrogen or methyl; $R^2$, $R^4$, $R^5$, $R^6$, $R^9$, are hydrogen; $R^{10}$ is hydrogen or methyl; $R^{11}$ is hydrogen or fluorine; $R^{12}$ and $R^{13}$ are hydrogen; and $R^{14}$ is chosen from hydrogen, fluoro, chloro, methyl and cyano. In some of these embodiments, $R^{10}$ is hydrogen. In some of these embodiments, C(1) of the isochroman is of absolute configuration:

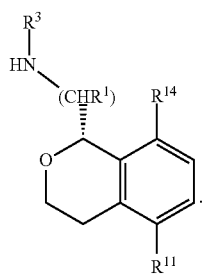

In other embodiments, C(1) of the isochroman is of absolute configuration:

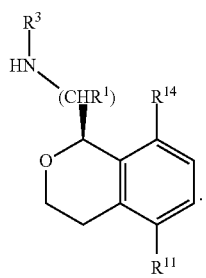

In some embodiments, $R^1$ is hydrogen; $R^2$ is hydrogen or methyl; $R^3$ is hydrogen; $R^4$ is hydrogen or methyl; $R^5$ is hydrogen; and $R^6$ is hydrogen. In some of these embodiments, $R^4$ is hydrogen; and $R^9$ and $R^{10}$ are each independently hydrogen, methyl or fluoro.

In some embodiments, $R^1$ is hydrogen; $R^2$ is hydrogen or methyl; $R^3$ and $R^4$ are both hydrogen; $R^5$ and $R^6$ are both hydrogen; $R^9$ and $R^{th}$ are each selected from hydrogen, methyl, and fluoro; $R^{11}$ is hydrogen, fluoro, chloro, or methyl; and $R^{12}$ is hydrogen or fluoro. In some of these embodiments, $R^{13}$ is hydrogen or fluoro, and $R^{14}$ is selected from hydrogen, methyl, and fluoro. In other of these embodiments, $R^{13}$ and $R^{14}$ form a fused 1,3-dioxole. In some of these embodiments, $R^2$ is methyl. In some of these embodiments, $R^9$ and $R^{10}$ are both hydrogen. In some of these embodiments, only one of $R^{11}$, $R^{12}$, $R^{13}$ and $R^{14}$ is other than hydrogen. In some of these embodiments, $R^{13}$ and $R^{14}$ form a fused 1,3-dioxole and and $R^{12}$ are both hydrogen. In some embodiments, C(1) of the isochroman is of absolute configuration:

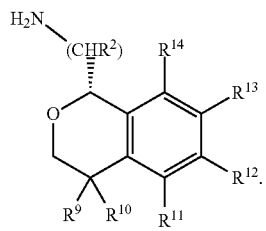

In other embodiments, C(1) of the isochroman is of absolute configuration:

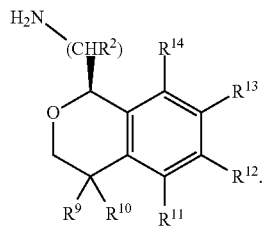

In one embodiment, provided are compounds of formula (I) which are greater than 90% enantiomerically pure. In another embodiment, provided are compounds of formula I which are greater than 95% enantiomerically pure.

In one embodiment, provided is a compound according to formula (I), wherein said compound is:

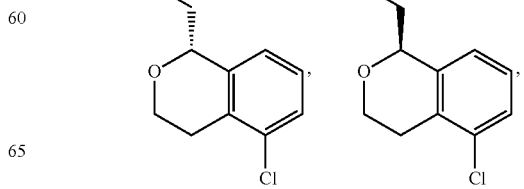

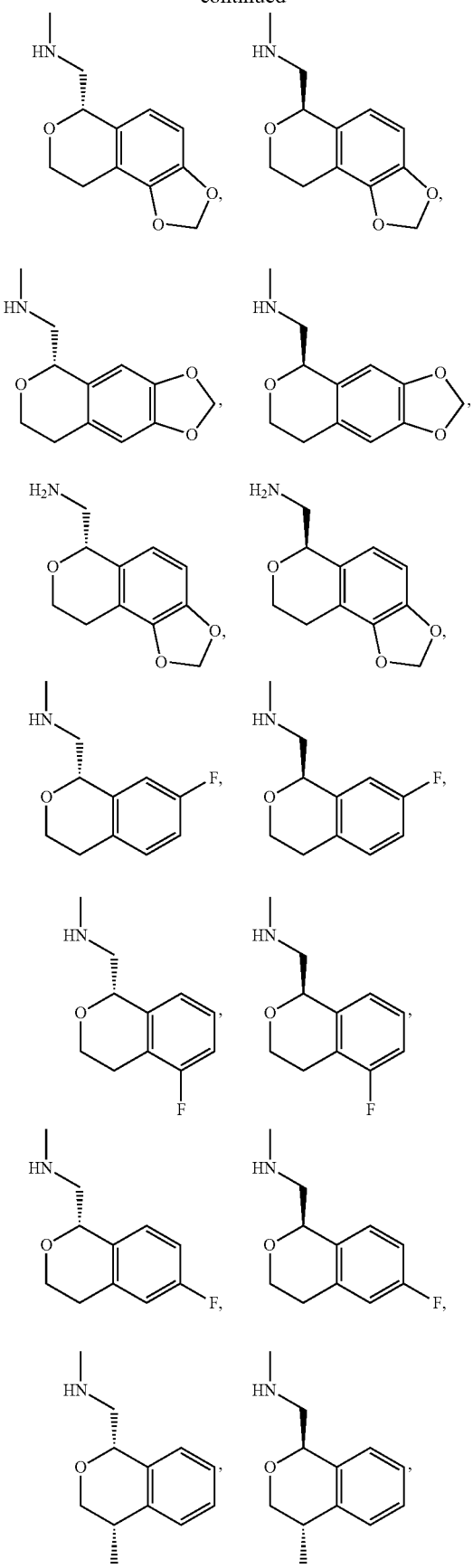

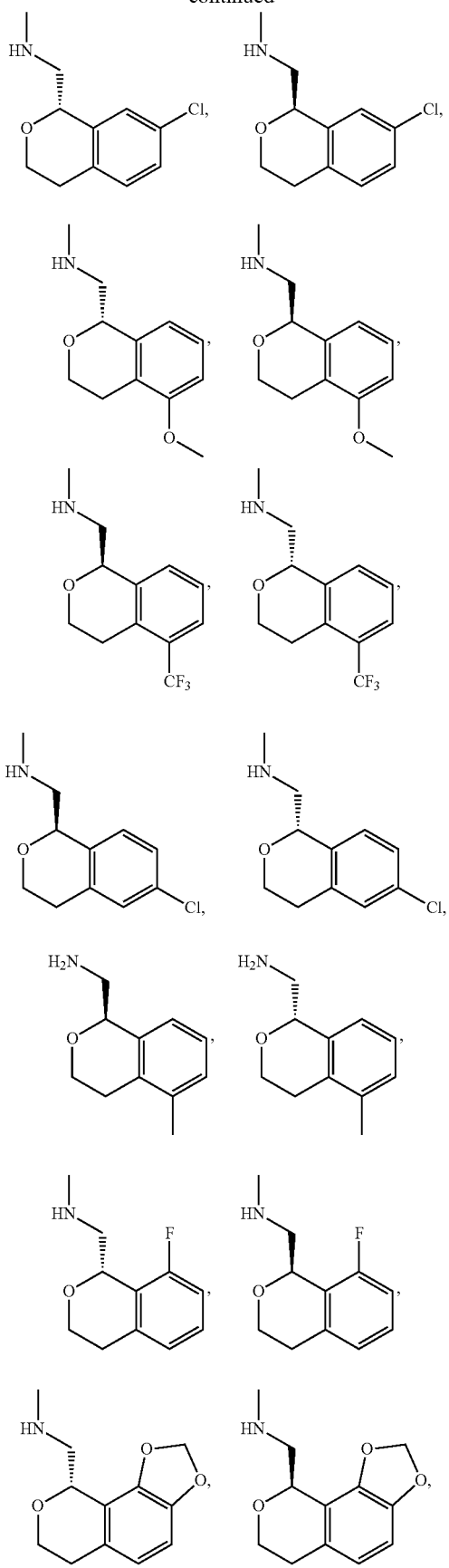
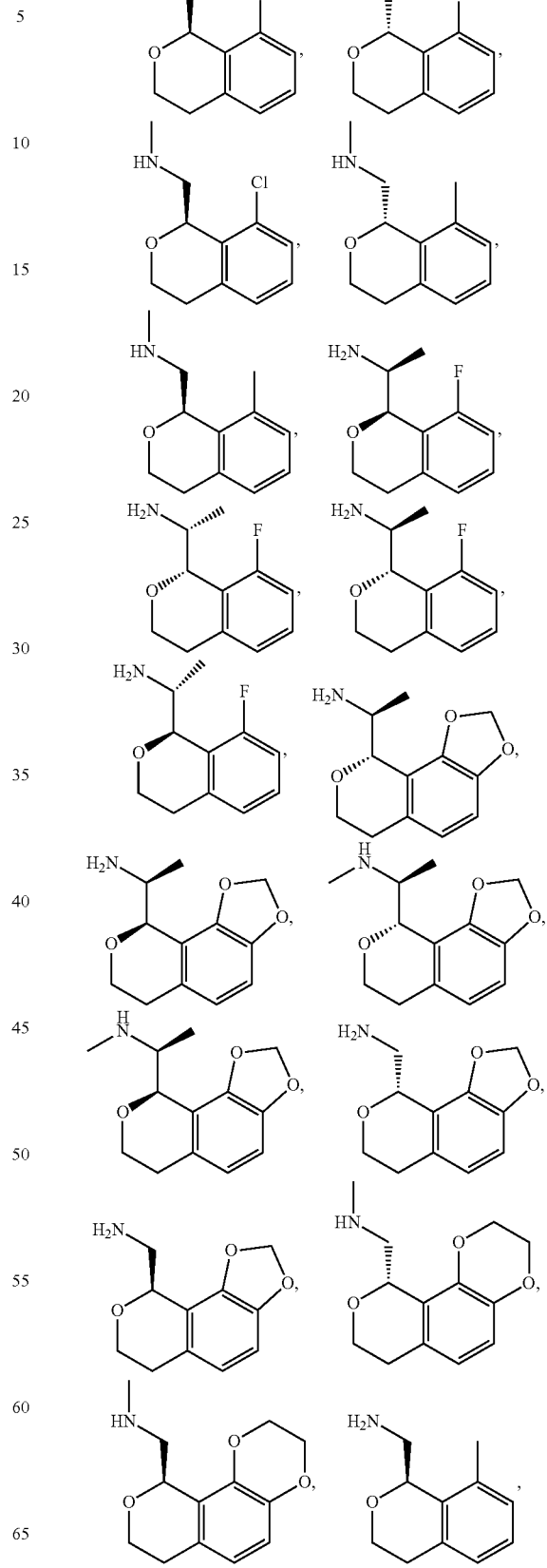

-continued
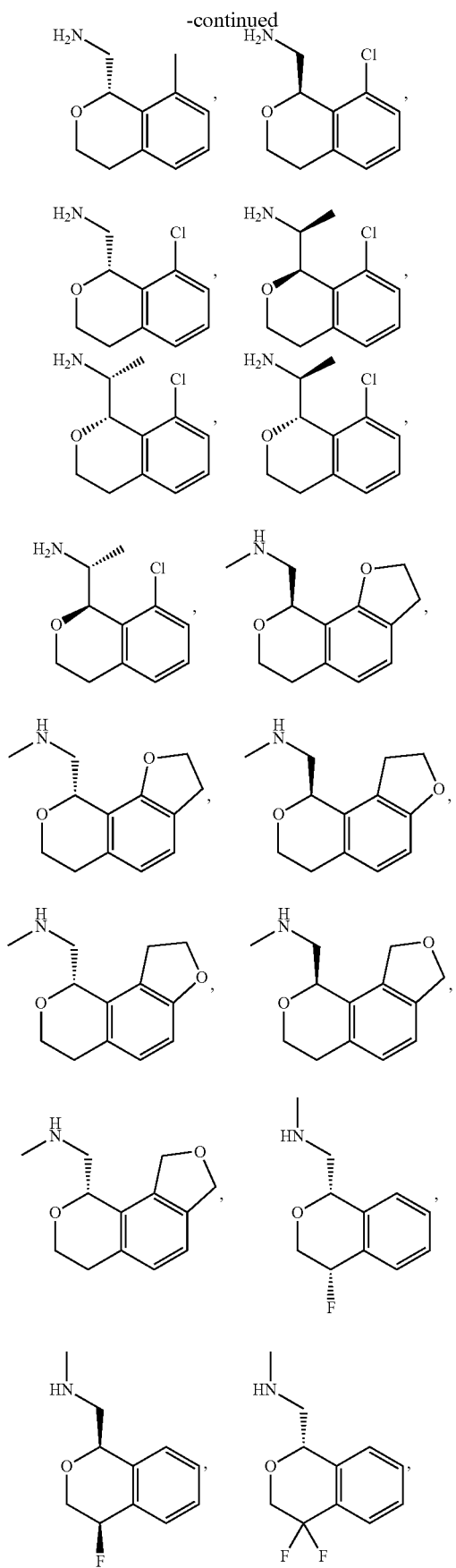
-continued
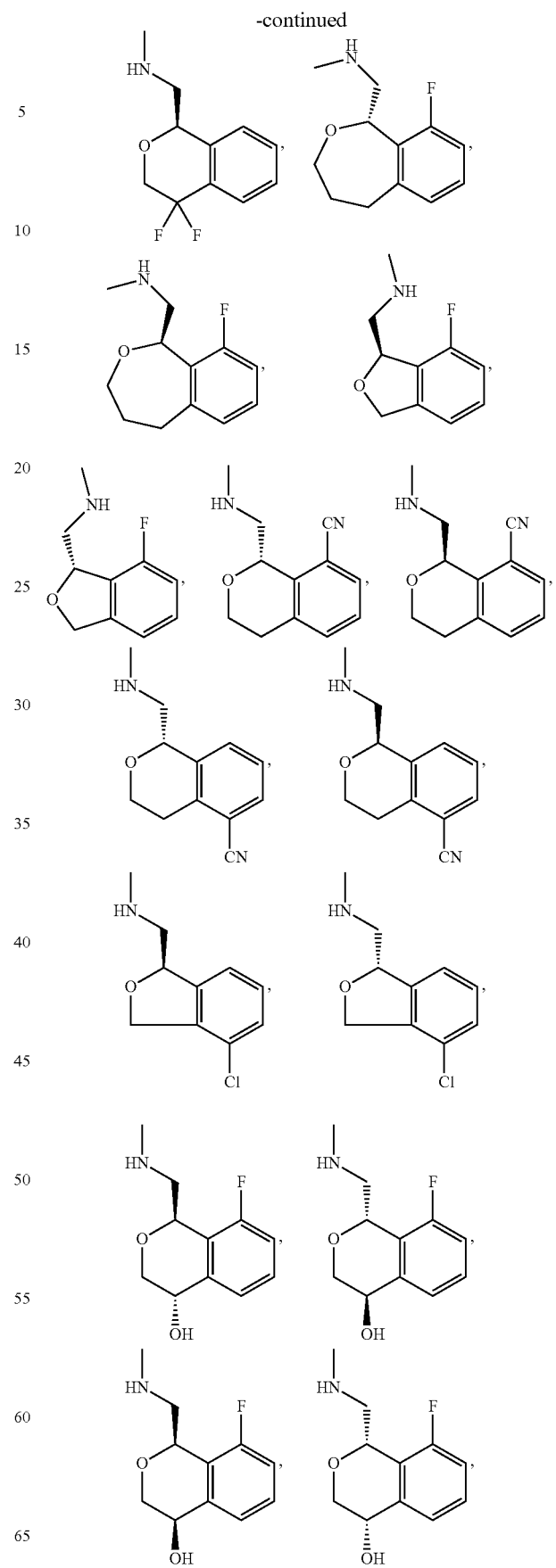

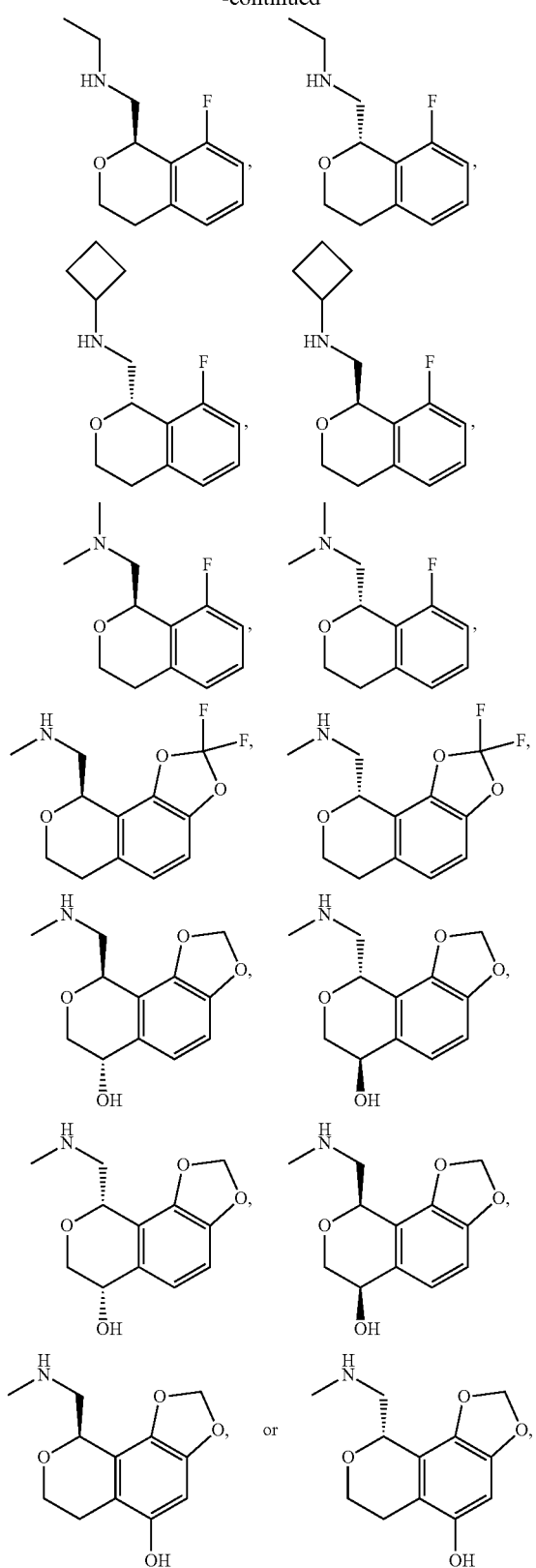

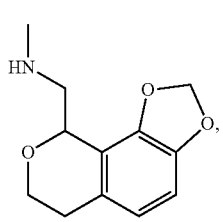

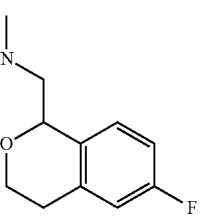

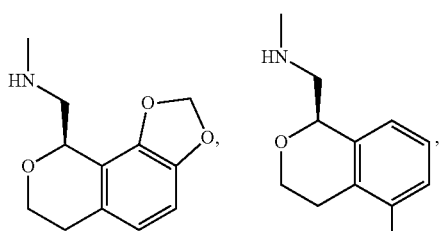

or a pharmaceutically acceptable salt thereof

In another embodiment, provided is a compound according to formula (I), wherein said compound is:

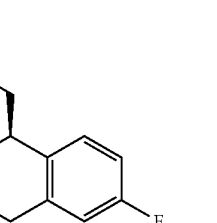

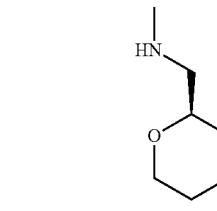

or a pharmaceutically acceptable salt thereof

In another embodiment, provided is a compound according to formula (I), wherein said compound is:

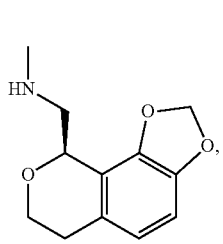

or a pharmaceutically acceptable salt thereof

In one embodiment, provided is a compound according to formula I, wherein said compound is:

-continued

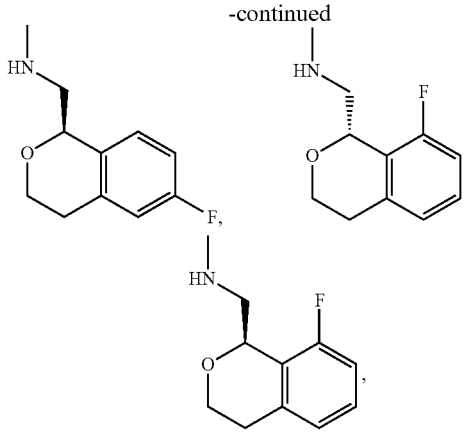

and has greater than 90% enantiomeric purity. In another embodiment, said compound has greater than 95% enantiomeric purity.

Compounds and Compositions and Definitions:

Compounds and compositions of this invention include those described generally above, and are further illustrated by the classes, subclasses, and species disclosed herein. As used herein, the following definitions shall apply unless otherwise indicated. A comprehensive list of abbreviations utilized by organic chemists (i.e. persons of ordinary skill in the art) appears in the first issue of each volume of the Journal of Organic Chemistry. The definitions therein, which are typically presented in a table entitled "Standard List of Abbreviations" are the definitions used herein.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of the indicated relative stereochemistry of indeterminate absolute configuration. For example, the graphic representation:

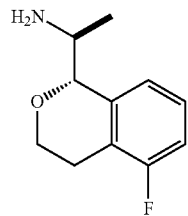

indicates a trans relationship between the two chiral centers, that is, either or both of the two representations below:

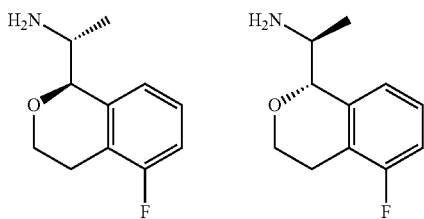

in any ratio, from pure enantiomers to racemates, while the representation:

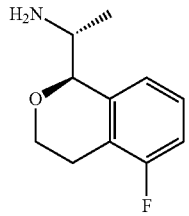

indicates a single enantiomer with the absolute configuration depicted, e.g., ((R)-1-((R)-5-fluoroisochroman-1-yl) ethan-1-amine in the illustration above. In the text describing the stereochemistry of the examples, the convention of Chemical Abstracts is used. Thus "(R)-1-((R)-5-rel- . . . " indicates that the two chiral centers are in that relative relationship, which would be depicted in a structural diagram by solid bold and dashed lines, whereas "(R)-1-((R)-5- . . . " without the "rel" indicates a single enantiomer of that absolute configuration, which would be depicted in a structural diagram by solid and broken wedges.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer. ee=(90-10)/100=80%.

Thus, a composition containing 90% of one enantiomer and 10% of the other enantiomer is said to have an enantiomeric excess of 80%. Some compositions described herein contain an enantiomeric excess of at least about 50%, 75%, 90%, 95%, or 99% of the S enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In certain embodiments, the compound provided herein is made up of at least about 90% by weight of one enantiomer. In other embodiments, the compound is made up of at least about 95%, 98%, or 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Hydrocarbyl refers to any substituent comprised of hydrogen and carbon as the only elemental constituents. $C_1$ to $C_{20}$ hydrocarbon includes, for example, alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Aromatic hydrocarbons include benzene (phenyl), naphthalene (naphthyl), anthracene, etc. Aliphatic hydrocarbons are hydrocarbons that are not aromatic; they may be saturated or unsaturated, cyclic, linear or branched, or combinations thereof. Aliphatic hydrocarbons include, for example, alkyl, alkenyl, alkynyl, cycloalkyl, cycloalkenyl, cycloalkynyl, and combinations thereof. Non-limiting examples of aliphatic hydrocarbons include isopropyl, 2-butenyl, 2-butynyl, cyclopentyl, cyclopropylmethyl, norbornyl, and the like.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cyclopropyl, cyclobutyl, cyclopentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene; ($C_8$-$C_{12}$) carbopolycycle refers to such systems as norbornane, decalin, indane and naphthalene. Carbocycle, if not otherwise limited, refers to monocycles, bicycles and polycycles, including bridged structures.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non- aromatic (heteroaliphatic) or aromatic (heteroaryl). Heterocycle, if not otherwise limited, refers to monocycles, bicycles and polycycles, including bridged structures. Examples of heterocycles include, but are not limited to, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, atrophine, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl, dihydrofuryl, dioxole, dihydrodioxine and tetrahydroquinolinyl.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons. The term "halogen" means fluorine, chlorine, bromine or iodine atoms.

The term "halogen" means fluorine, chlorine, bromine or iodine. In one embodiment, halogen may be fluorine or chlorine. In a further embodiment, the halogen is fluorine.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower -acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, hydrocarbyl, acyl, alkoxyalkyl, hydroxy lower alkyl, carbonyl, phenyl, heteroaryl, benzenesulfonyl, hydroxy, hydrocarbyloxy, haloalkoxy, oxaalkyl, carboxy, alkoxycarbonyl [—C(=O)O-alkyl], alkoxycarbonylamino [HNC(=O)O-alkyl], aminocarbonyl (also known as carboxamido) [—C(=O)NH$_2$], alkylaminocarbonyl [—C(=O)NH-alkyl], dialkylaminocarbonyl [—C(=O)N(alkyl)$_2$], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In particular embodiments, substituents are halogen, halo($C_1$-$C_4$)hydrocarbyl, halo($C_1$-$C_4$)hydrocarbyloxy, cyano, thiocyanato, ($C_1$-$C_4$)hydrocarbylsulfinyl, ($C_1$-$C_4$)hydrocarbyl-sulfonyl, aminosulfonyl, nitro, acetyl, and acetamido. Preferred substituents are halogen, ($C_1$-$C_4$)alkyl, ($C_1$-$C_4$)alkoxy, ($C_1$-$C_4$) fluoroalkyl, ($C_1$-$C_4$)fluoroalkoxy, hydroxy, amino, ($C_1$-$C_4$) alkylamino, di($C_1$-$C_4$)alkylamino, ($C_1$-C4)acylamino, ($C_1$-$C_4$)fluoroalkyl and ($C_1$-$C_4$)fluoroalkoxy.

Substituents Rn are generally defined when introduced and retain that definition throughout the specification and claims.

As used herein, and as would be understood by the person of skill in the art, the recitation of "a compound"—unless expressly further limited—is intended to include salts of that compound. Thus, for example, the recitation "a compound of formula I" as depicted above, which contains a basic amine residue —NR$^3$R$^4$, would include salts —NHR$^3$R$^4$ $_+$X$^-$ wherein X$^-$ is any counterion. In a particular embodiment, the term "compound of formula I" refers to the compound or a pharmaceutically acceptable salt thereof; this term refers to a pharmaceutically acceptable salt of the compound, even if not explicitly stated. Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cistrans isomeric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. In addition to therapeutic uses, such compounds are useful, for example, as analytical tools or probes in biological assays.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

According to another embodiment, the invention provides a composition comprising a compound of this invention (or its pharmaceutically acceptable salt) and a pharmaceutically acceptable carrier, adjuvant, or vehicle. In some embodiments, the amount of compound in compositions of this invention is such that is effective to treat, prevent, and/or manage various neurological and/or psychiatric diseases, disorders and/or symptoms in a subject. In some embodiments, a composition of this invention is formulated for administration to a subject in need of such composition. In some embodiments, a composition of this invention is formulated for oral administration to a subject.

As used herein, the term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

In certain embodiments, provided herein is a composition (e.g., a pharmaceutical composition) comprising a compound described herein and a pharmaceutically acceptable excipient or carrier. In some embodiments, provided herein is a method of treating neurological or psychiatric diseases and disorders in a subject in need thereof in a subject, comprising administering an effective amount of a compound or a pharmaceutical composition described herein. Examples of carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Compositions of the present invention may be administered orally, parenterally, by inhalation, topically, rectally, nasally, buccally, sublingually, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. Pharmaceutically acceptable compositions of this invention may be orally administered in any orally acceptable dosage form including capsules, tablets, aqueous suspensions or solutions.

The amount of compounds of the present invention that may be combined with the carrier materials to produce a composition in a single dosage form will vary depending upon a variety of factors, including the host treated and the particular mode of administration. It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the invention provides a method for treating a neurological or psychiatric disease or disorder in a subject, comprising administering to the subject an effective amount of a compound of this invention (or its pharmaceutically acceptable salt), or composition comprising a compound of this invention (or its pharmaceutically acceptable salt). Neurological and/or psychiatric diseases and disorders can exhibit a variety of psychiatric and behavioral symptoms, including apathy, depression, anxiety, cognitive impairment, psychosis, aggression, agitation, poor impulse control and sleep disruptions.

In one embodiment, the neurological or psychiatric disease or disorder is bipolar disorder, anxiety, depression, Alzheimer's Disease with agitation, Alzheimer's Disease with aggression or Alzheimer's Disease with agitation aggression.

In one embodiment, the neurological or psychiatric disease or disorder is bipolar disorder, anxiety, depression, dementia, Alzheimer's Disease, Alzheimer's Disease with agitation, Alzheimer's Disease with aggression or Alzheimer's Disease with agitation aggression, a neurocognitive disorder, a neurocognitive disorder with behavioral and psychological symptoms.

In one embodiment, the neurological or psychiatric disease or disorder are behavioral and psychological symptoms of a neurocognitive disorder including dementia and Alzheimer's disease. The behavioral and psychological symptoms include disturbances in perception, thought content, mood, or behaviors including delusions (distressing beliefs), hallucinations, agitation (easily upset, repeating questions, arguing or complaining, hoarding, pacing, inappropriate screaming, crying out, disruptive sounds, rejection of care leaving home), aggression (physical or verbal), depression or dysphoria, anxiety (worrying, shadowing), apathy or indifference, disinhibition (socially inappropriate behavior, sexually inappropriate behavior, irritability or lability, motor disturbance (repetitive activities without purpose, wandering, rummaging, night-time behaviors (waking and getting up at night) impulsivity, attentional deficits, executive dysfunction.

Assays were used herein to identify representative candidate treatments. Examples of candidate treatments include, without limitation, treatment of Alzheimer's Disease with agitation, Alzheimer's Disease with aggression and Alzheimer's Disease with agitation aggression. Aggression and agitation are common symptoms in neurological and psychiatric diseases and disorders. Aggression and agitation have been associated with hyperactivity in subcortical brain regions, which can be modelled in animals using psychostimulants (eg PCP, Amphetamine). For example, psychostimulants induce hyperlocomotor activity (HLA) in animals. Antipsychotics (eg. haloperidol, clozapine and risperidone) have been shown to reduce psychostimulant-induced HLA and are efficacious against agitation in Alzheimer's disease. Other drugs used off-label, or are currently under study in clinical trials, for agitation in Alzheimer's disease are mood stabilizers, such as lithium (which also decreases Amphetamine-induced HLA), and antidepressants (eg. citalopram). Antidepressants demonstrate activity in assays such as the forced swim and tail suspension tests. Therefore, the aforementioned assays were helpful in identifying candidate treatments for agitation in Alzheimer's disease and agitation/aggression in other neurological and psychiatric diseases and disorders.

In one embodiment, provided is a method of treating a bipolar disorder in a subject in need thereof, comprising the step of administering to said subject an effective amount of the compound according to formula I or a pharmaceutically acceptable salt thereof In one embodiment, provided is a method of treating anxiety in a subject in need thereof, comprising the step of administering to said subject an effective amount of the compound according to formula I or a pharmaceutically acceptable salt thereof In one embodiment, provided is a method of treating a neurological or psychiatric disease or disorder selected from bipolar disorder, anxiety, depression, Alzheimer's Disease with agitation, Alzheimer's Disease with aggression or Alzheimer's Disease with agitation aggression in a subject in need thereof, comprising the step of administering to said subject an effective amount of a compound selected from:

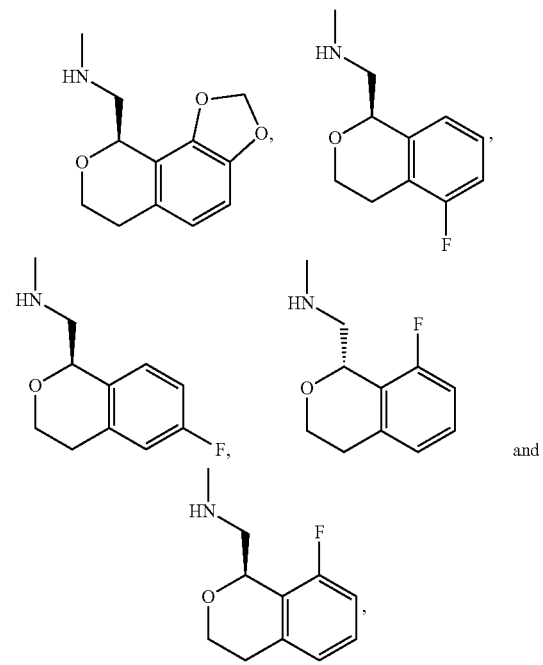

or a pharmaceutically acceptable salt thereof

In one embodiment, provided is a method of treating bipolar disorder in a subject in need thereof, comprising the step of administering to said subject an effective amount of a compound selected from:

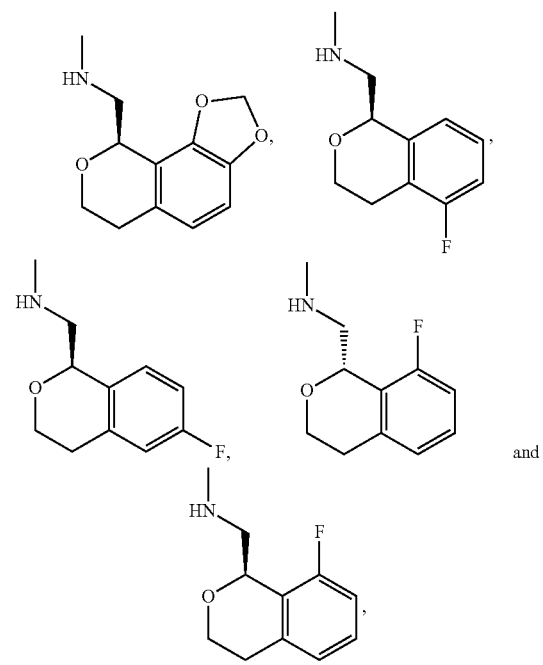

or a pharmaceutically acceptable salt thereof

In one embodiment of the invention, provided is a method of treating anxiety in a subject in need thereof, comprising the step of administering to said subject an effective amount of a compound selected from:

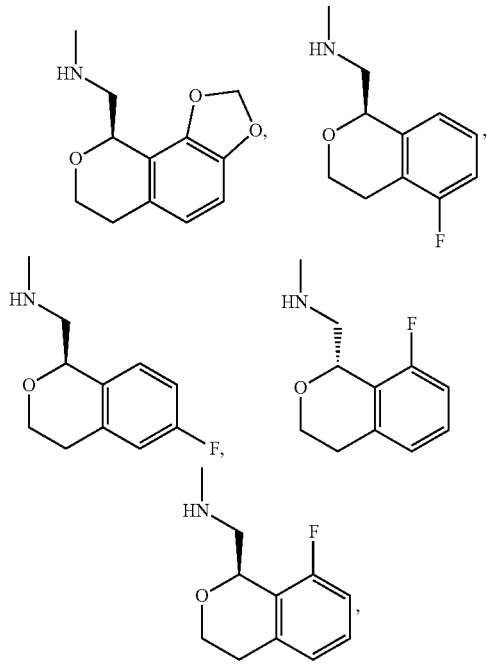

or a pharmaceutically acceptable salt thereof

In one embodiment of the invention, provided is a method of treating depression in a subject in need thereof, comprising the step of administering to said subject an effective amount of a compound selected from:

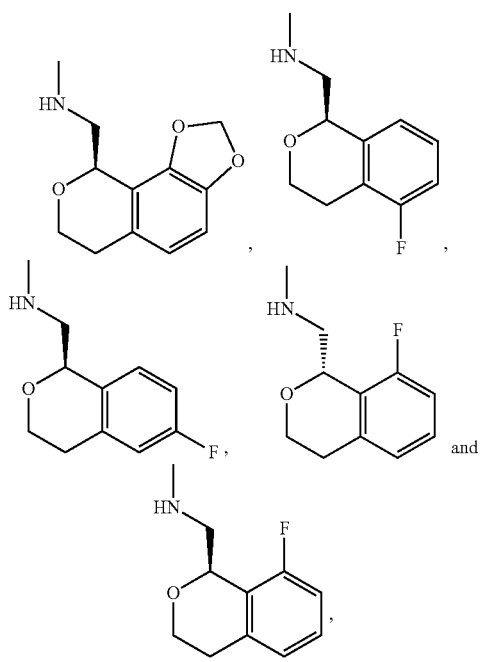

or a pharmaceutically acceptable salt thereof

In one embodiment of the invention, provided is a method of treating Alzheimer's Disease with agitation in a subject in need thereof, comprising the step of administering to said subject an effective amount of a compound selected from:

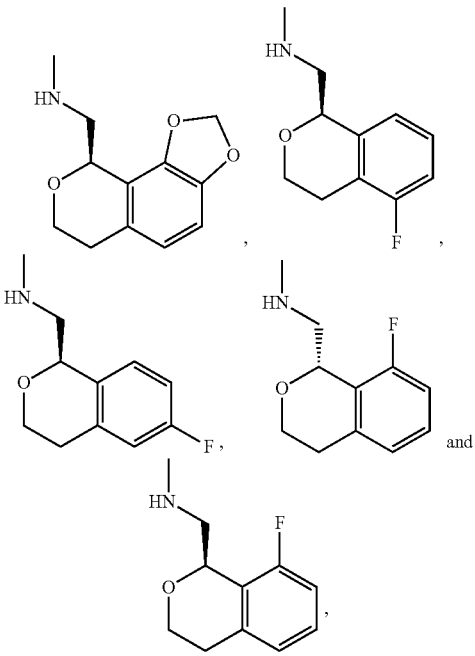

or a pharmaceutically acceptable salt thereof

In one embodiment of the invention, provided is a method of treating Alzheimer's Disease with aggression in a subject in need thereof, comprising the step of administering to said subject an effective amount of a compound selected from:

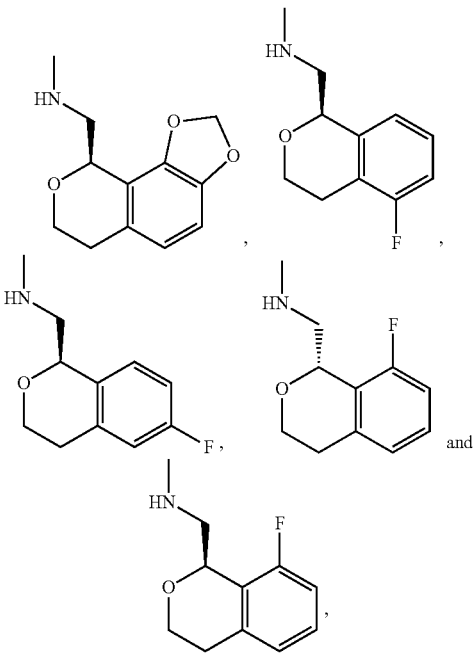

or a pharmaceutically acceptable salt thereof

In one embodiment of the invention, provided is a method of treating Alzheimer's Disease with agitation aggression in a subject in need thereof, comprising the step of administering to said subject an effective amount of a compound selected from:

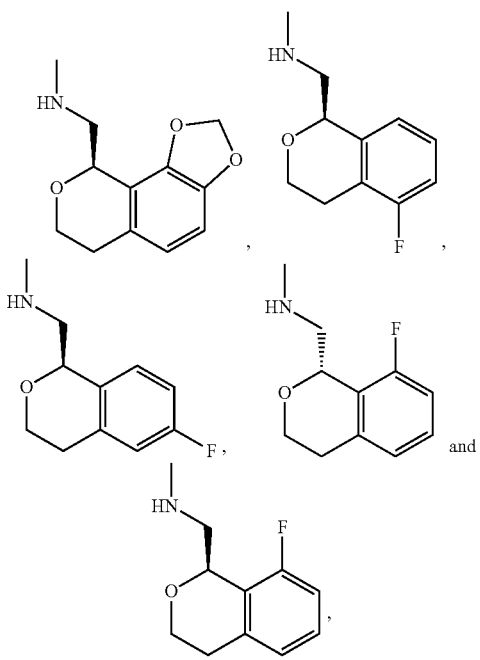

or a pharmaceutically acceptable salt thereof

In some embodiments, the neurological or psychiatric disease or disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (e.g., phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; cognitive disorders including dementia (semantic dementia, frontotemporal dementia, dementia with depressive features, persisting, subcortical dementia, dementia with Lewy Bodies, Parkinsonism-ALS Dementia Complex, and dementia associated with Alzheimer's disease, ischemia, multi-infarct dementia, trauma, vascular problems, stroke, HIV disease, Parkinson's disease, Huntington's disease, Down syndrome, Pick's disease, Creutzfeldt-Jacob disease, perinatal hypoxia, or substance abuse), delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); eating disorders such as obesity, bulimia nervosa, pica and compulsive eating disorders; ; bipolar disorders, including bipolar I disorder, bipolar II disorder, cyclothymic disorder, substance/medication-induced bipolar and related disorders, bipolar and related disorder due to another medical condition, other specified bipolar and related disorder, and unspecified bipolar and related disorders, depressive disorders including unipolar depression, seasonal depression and post-partum depression, atypical depression, catatonic depression, elderly depression, endogenous depression, melancholic depression, perinatal depression, situational depression, chronic depression, premenstrual syndrome (PMS) and premenstrual dysphoric disorder (PDD), mood disorders due to a general medical condition, and substance-induced mood disorders; attention, learning and development disorders such as pervasive developmental disorder including autistic disorder, attention disorders including attention-deficit hyperactivity disorder (ADHD) and conduct disorder, disorders such as autism and autism spectrum disorders (including Asperger's syndrome, pervasive developmental disorder, Rett Syndrome and Fragile X Syndrome), depression, benign forgetfulness, childhood learning disorders, specific learning disorders, intellectual development disorders, and closed head injury; movement disorders and symptoms, including tremorts, dyskinesia, dystonia, tics, dysphonia, ataxia, myoclonus, Essential Tremor, Tardive Dyskinesia, Restless Leg Syndrome, Tourette Syndrome, Multiple System Atrophy, Multiple Sclerosis, Huntington's Disease, Parkinson's Disease and Atypical Parkinsonisms; epilepsy; urinary incontinence; neuronal damage including ocular damage, retinopathy or macular degeneration of the eye, tinnitus, hearing impairment and loss, and brain edema; emesis; and sleep disorders including insomnia, disturbed sleep, jet lag, hypersomnia, cataplexy, sleep apnea, obstructive sleep apnia, REM sleep behavior disorder, Restless Leg Syndrome, periodic limb movement disorder, circadian rhythm sleep disorders, delayed sleep phase disorder, sleepwalking, night terrors, bed wetting, rapid eye movement sleep behavior disorder, shift work sleep disorder, excessive daytime sleepiness, non-24-hour sleep-wake disorder, sleep paralysis and narcolepsy.

In some embodiments, the neurological or psychiatric disease or disorder is Alzheimer's disease, Parkinson's disease, depression, cognitive impairment, stroke, schizophrenia, Down syndrome, or Fetal Alcohol Syndrome. In some embodiments, the neurological or psychiatric disorder is Alzheimer's disease. In some embodiments, the neurological or psychiatric disorder is Parkinson's disease. In some embodiments, the neurological or psychiatric disorder is depression. In some embodiments, the neurological or psychiatric disorder is cognitive impairment. In some embodiments, the cognitive impairment is cognitive dysfunction associated with depression, for example, major depressive disorder. In some embodiments, the neurological or psychiatric disorder is stroke. In some embodiments, the neurological or psychiatric disorder is schizophrenia. In some embodiments, the neurological or psychiatric disorder is Down syndrome. In some embodiments, the neurological or psychiatric disorder is Fetal Alcohol Syndrome.

In some embodiments, the neurological or psychiatric disease or disorder is bipolar disorder. Bipolar disorders (including both bipolar I and bipolar II) are serious psychiatric disorders that have a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although subjects spend considerable more time in the depressive state. Other related conditions include cyclothymic disorder.

In some embodiments, the neurological or psychiatric disease or disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the catatonic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the subject suffers from a lack of normal experiences, such as anhedonia and lack of social interaction. The cognitive symptoms relate to cognitive impairment in schizophrenics, such as lack of sustained attention and deficits in decision making.

In some embodiments, the neurological or psychiatric disease or disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

In some embodiments, the neurological or psychiatric disease or disorder involves a deficit in cognition (cognitive domains as defined by the DSM-5 are: complex attention, executive function, learning and memory, language, perceptual-motor, social cognition). In some embodiments, the neurological or psychiatric disorder is associated with a deficit in dopamine signaling. In some embodiments, the neurological or psychiatric disorder is associated with basal ganglia dysfunction. In some embodiments, the neurological or psychiatric disorder is associated with dysregulated locomotor activity. In some embodiments, the neurological or psychiatric disorder is associated with impairment of prefrontal cortex functioning.

In some embodiments, the present invention provides a method of treating one or more symptoms of a neurological and/or psychiatric disease or disorder provided herein. Such diseases or disorders include mood disorders, including bipolar I disorder, bipolar II disorder, mania, cyclothymic disorder, substance/medication-induced bipolar and related disorders, bipolar and related disorder due to another medical condition, other specified bipolar and related disorder, and unspecified bipolar and related disorders; psychotic disorders, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), schizoaffective disorder, agitation, aggression, delirium, catalepsy, catatonia, dissociative identity disorder, paranoid personality disorder, psychotic depression, Schizotypical Personality Disorder, Childhood Disintegrative Disorder (Heller's Syndrome), Disintegrative Psychosis, Dissociative Amnesia, Somatic Symptom Disorder, Parkinson's psychosis, excitative psychosis, Tourette's syndrome, and organic or NOS psychosis; depressive disorders, including disruptive mood dysregulation disorder, major depressive disorder (MDD) (including major depressive episode), dysthymia, persistent depressive disorder (dysthymia), treatment resistant depression, premenstrual dysphoric disorder, substance/medication-induced depressive disorder, depressive disorder due to another medical condition, other specified depressive disorder, and unspecified depressive disorder; anxiety disorders; and other disorders including substance abuse or dependency (e.g., nicotine, alcohol, cocaine), addiction, internet gaming disorder, eating disorders, behavior disorder, seizure, vertigo, epilepsy, agitation, aggression, neurodegenerative disease, Alzheimer's disease, Parkinson's disease, dyskinesias, Huntington's disease, dementia, premenstrual dysphoria, attention deficit disorder (ADD) and attention deficit hyperactivity disorder (ADHD)), hyperkinetic syndrome, autism, autism spectrum disorder, obsessive-compulsive disorder, pain, fibromyalgia, migraine, cognitive impairment, movement disorder, restless leg syndrome (RLS), multiple sclerosis, Primary Progressive Multiple Sclerosis, Parkinson's disease, Huntington's disease, dyskinesias multiple sclerosis, sleep disorder, sleep apnea, narcolepsy, excessive daytime sleepiness, jet lag, drowsy side effect of medications, insomnia, sexual dysfunction, hypertension, emesis, Lesche-Nyhane disease, Wilson's disease, Rett syndrome, and Huntington's chorea. In some embodiments, the neurological and/or psychiatric disorders include agitation and aggression.

In some embodiments, the agitation and aggression are associated with Alzheimer's disease, Parkinson's disease, and/or autism.

In some embodiments, the neurological and/or psychiatric disease or disorders are obsessive-compulsive disorder and related disorders (e.g., body dysmorphic disorder, hoarding disorder, trichotillomania, excoriation disorder).

In some embodiments, the neurological and/or psychiatric diseases or disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

Depressive disorders include major depressive disorder and dysthymia, and are associated with depressed mood (sadness), poor concentration, insomnia, fatigue, appetite disturbances, excessive guilt and thoughts of suicide.

In some embodiments, the present invention provides a method of treating one or more symptoms including depression (e.g., major depressive disorder or dysthymia); bipolar disorder, seasonal affective disorder; cognitive deficit; sleep related disorder (e.g., sleep apnea, insomnia, narcolepsy, cataplexy) including those sleep disorders which are produced by psychiatric conditions; chronic fatigue syndrome; anxieties (e.g., general anxiety disorder, social anxiety disorder, panic disorder); obsessive compulsive disorder; post-menopausal vasomotor symptoms (e.g., hot flashes, night sweats); neurodegenerative disease (e.g., Parkinson's disease, Alzheimer's disease, amyotrophic lateral sclerosis, primary lateral sclerosis, progressive muscular atrophy, progressive bulbar (atrophy) palsy, pseudobulbar palsy spinal muscular atrophy diseases (e.g., SMA type I, also called Werdnig-Hoffmann disease, SMA type II, SMA type III, also called Kugelberg-Welander disease, and Kennedy Disease, also called progressive spinobulbar muscular atrophy), Hallervorden-Spatz disease, Seitelberger disease (Infantile Neuroaxonal Dystrophy), adrenoleukodystrophy, Alexander Disease, autosomal dominant cerebellar ataxia (ADCA), pure autonomic failure (Bradbury -Eggleston Syndrome), CADASIL Syndrome, and neuronal ceroids lipofuscinose disorders such as Batten Disease (Spielmeyer-Vogt-Sjogren)); manic disorder; dysthymic disorder; and obesity.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, a provided compound does not increase the risk of suicidal thinking and/or behavior in children, adolescents and/or young adults with a depressive disorder, e.g., with MDD. In some embodiments, the present invention provides a method of treating one or more symptoms of a depressive disorder (e.g., MDD) in children, adolescents and/or young adults without increasing the risk of suicidal thinking and/or behavior.

In some embodiments, the present invention provides a method of treating one or more symptoms including senile dementia, Early Onset Alzheimer's Disease, Alzheimer's type dementia, cognition, memory loss, amnesia/amnestic syndrome, disturbances of consciousness, coma, lowering of attention, speech disorder, agnosia, aphasia, apraxia , Mild Cognitive Impairment (MCI), benign forgetfulness, mild neurocognitive disorder, major neurocognitive disorder, neurocognitive disorder due to disease (e.g., Huntington's Disease, Parkinson's disease, Prion Disease, Traumatic Brain Injury, HIV or AIDS), Binswanger's Disease (subcortical leukoencephalopathy), and Capgras Syndrome.

In some embodiments, the present invention provides a method of treating one or more symptoms of pain, e.g., neuropathic pain, sensitization accompanying neuropathic pain, or inflammatory pain. In some embodiments, the pain is neuropathic pain, including post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use). In some embodiments, the pain is acute pain, nociceptive pain, arthritis pain, rheumatoid arthritis, osteoarthritis, joint pain, muscoskeletal pain, back pain, dorsalgia, bulging disc, hip pain, visceral pain, headache, tension headache, acute tension headache, chronic tension headache, chronic cluster headache, common migraine, classic migraine, cluster headache, mixed headache, post -traumatic headache, eye strain headache, Short-lasting Unilateral Neuralgiform (SUNCT) headache, SUNCT Syndrome, herpes zoster, acute herpes zoster, shingles, postherpetic neuralgia (shingles), causalgia, central pain, central pain syndrome, chronic back pain, neuralgia, neuropathic pain syndrome, neuropathy, diabetic neuropathy, diabetes-related neuropathy, diabetes-related nerve pain, fibrositis, peripheral neuropathy caused by chemotherapy, peripheral nerve disease, peripheral neuropathy, nerve pain, nerve trauma, sensitization accompanying neuropathic pain, complex regional pain syndrome, compression neuropathy, craniofacial pain, chronic joint pain, chronic knee pain, chronic pain syndrome, cancer pain, trigeminal neuralgia, tic doloreaux, reflex sympathetic causalgia, painful peripheral neuropathy, spinal nerve injury, arachnoiditis, spinal pain, Bernhardt-Roth Syndrome (meralgia parasthetica), carpal tunnel syndrome, cerebrospinal fluid syndrome, Charcot-Marie-tooth disease, hereditary motor and sensory neuropathy, peroneal muscular atrophy, cluster-tic syndrome, coccygeal pain syndromes, compartment syndrome, degenerative disc disease, failed back surgery syndrome, genito-pelvic pain/penetration disorder, gout, inflammatory pain, lumbar radiculopathy, neuroma (painful scar), pain associated with multiple sclerosis, pelvic floor disorders, phantom limb pain, piriformis syndrome, psychogenic pain, radicular pain syndrome, Raeder's syndrome, referred pain, reflex sympathetic dystrophy syndrome, sciatica, sciatica pain, scoliosis, slipped disc, somatic pain, spinal stenosis, stiff-person syndrome/stiff-man syndrome, stump pain, sympathetically maintained pain, tolosa-hunt syndrome, whiplash, or pain associated with Lyme disease.

In some embodiments, the present invention provides a method of treating one or more symptoms including obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In some embodiments, the present invention provides a method of suppressing rapid eye movement (REM) during both sleep and daytime equivalent.

In some embodiments, the present invention provides a method of suppressing or eliminating pathological or excessive REM during the night or daytime equivalent.

In some embodiments, the present invention provides a method of treating one or more symptoms including cataplexy (sudden involuntary transient bouts of muscle weakness or paralysis while awake); nighttime sleep disturbance/sleep fragmentation associated with narcolepsy or other conditions; sleep paralysis associated with narcolepsy or other conditions; hypnagogic and hypnapompic hallucinations associated with narcolepsy or other conditions; and excessive daytime sleepiness associated with narcolepsy, sleep apnea or shift work disorder and other medical conditions such as cancer, chronic fatigue syndrome and fibromyalgia.

In some embodiments, the present invention provides a method of treating one or more symptoms of movement diseases or disorders, including akinesias, akinetic-rigid syndromes, dyskinesias and dystonias. Examples of akinesias and akinetic-rigid syndromes include Parkinson's disease, drug-induced Parkinsonism, postencephalitic Parkinsonism, secondary Parkinsonism, Parkinson plus syndromes, atypical Parkinsonism, idiopathic Parkinsonism, progressive supranuclear palsy, multiple system atrophy, corticobasal degeneration, Parkinsonism-ALS dementia complex and basal ganglia calcification, medication-induced Parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors. Examples of dyskinesias include drug (e.g. L-DOPA) induced dyskinesia tremor (such as rest tremor, postural tremor, intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics). Examples of dystonias include generalized dystonia, iodiopathic dystonia, drug-induced dystonia, symptomatic dystonia, paroxymal dystonia, focal dystonia, blepharospasm, oromandibular dystonia, spasmodic dysphonia, spasmodic torticollis, axial dystonia, dystonic writer's cramp and hemiplegic dystonia. Other examples of movement diseases or disorders include stereotypic movement disorder, persistent (chronic) motor disorder, medication-Induced movement disorder, psychogenic movement disorders, substance/medication-Induced movement disorder, extrapyramidal movement disorders, hyperkinetic movement disorders, hypokinetic movement disorders, alternating hemiplegia, Angelman syndrome, Hallervorden-Spatz Disease, ataxia, dentate cerebellar ataxia, ataxia telangiectasia (Louis-Bar syndrome), Friedreich's Ataxia, hereditary spinal ataxia, hereditary spinal sclerosis, Machado-Joseph Disease, spinocerebellar ataxia, progressive myoclonic ataxia, athetosis, ballismus, blepharospasm (eye twitching), cerebral palsy, tardive dystonia, tardive dyskinesia, idiopathic torsion dystonia, torsion dystonia, focal dystonia, idiopathic familial dystonia, Idiopathic nonfamilial dystonia, cervical dystonia (spasmodic torticollis), primary dystonia, orofacial dystonia, developmental coordination disorder, bulbospinal muscular atrophy (Kennedy's Disease), Shy-Drager Syndrome, and Stiff-Person (Stiff-Man) Syndrome.

In some embodiments, the present invention provides a method of treating one or more symptoms of epilepsy and/or seizures, including abdominal epilepsy, absence seizure, acquired epilepsy, acquired epileptiform aphasia, Aicardi syndrome, Alpers' disease, Alpers -Huttenlocher syndrome, Angelman syndrome, benign focal epilepsy, benign focal epilepsy of childhood, benign intracranial hypertension, benign rolandic epilepsy (BRE), CDKLS disorder, childhood absence epilepsy, dentate cerebellar ataxia, Doose syndrome, Dravet syndrome, dyscognitive focal seizure, epilepsy with grand mal seizures, epilepsy with myoclonic-absences, epileptic hemiplegia, febrile seizures, focal seizure, frontal lobe epilepsy, generalized tonic-clonic seizures, genetic epilepsy, Glutl deficiency syndrome, hypothalmic hamartoma, idiopathic epilepsy, idiopathic generalized epilepsy, idopathic localization-related epilepsies, idopathic partial epilepsy, idopathic seizure, juvenile absence epilepsy, juvenile myoclonic epilepsy, Lafora disease, Lafora progressive myoclonus epilepsy, Landau-Kleffner syndrome, Lassueur-Graham-Little syndrome, Lennox syndrome, Lennox-Gastaut syndrome, medically refractory epilepsy, mesial-temporal lobe sclerosis, myoclonic seizure, neonatal epilepsy, occipital lobe epilepsy, Ohtahara syndrome, Panayiotopoulos syndrome, parietal lobe epilepsy, PCDH19 epilepsy, photosensitive epilepsy, progressive myoclonic epilepsies, Rasmussen's encephalitis, Rasmussen's syndrome, refractory epilepsy, seizure disorder, status epilepticus, Sturge-Weber syndrome, symptomatic generalized epilepsy, symptomatic parital epilepsy, TBCK-related ID syndrome, temporal lobe epilepsy, temporal lobe seizures, tonic-clonic seizure, West syndrome, tremor, cerebellar tremor, cerebellar outflow tremor, intention tremor, essential tremor, benign essential tremor, Parkinsonian tremor, and medication-induced postural tremor.

In some embodiments, the present invention provides a method of treating a neurological and/or psychiatric disease or disorder described herein, comprising administering a compound of the invention in conjunction with one or more pharmaceutical agents. Suitable pharmaceutical agents that may be used in combination with the compounds of the present invention include anti-Parkinson's drugs, anti-Alzheimer's drugs, anti -depressants, anti-psychotics, anti-ischemics, CNS depressants, anti-cholinergics, nootropics, epilepsy medication, attention (e.g., ADD/ADHD) medications, sleep-promoting medications, wakefulness-promoting medications, and pain medications. In some embodiments, suitable pharmaceutical agents are anxiolytics.

Suitable anti-Parkinson's drugs include dopamine replacement therapy (e.g. L-DOPA, carbidopa, COMT inhibitors such as entacapone or tolcapone), dopamine agonists (e.g. D1 agonists, D2 agonists, mixed D1/D2 agonists, bromocriptine, pergolide, cabergoline, ropinirole, pramipexole, piribedil, or apomorphine in combination with domperidone), histamine H2 antagonists, monoamine oxidase inhibitors (such as selegiline, rasagiline, safinamide and tranylcypromine), certain atypical antipsychotics such as pimavanserin (a non-dopaminergic atypical antipsychotic and inverse agonist of the serotonin 5-HT$_{2A}$ receptor), and amantadine.

In some embodiments, compounds of the invention can be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone or tolcapone, MAO A/B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, cholinesterase inhibitors such as donepezil, galantamine or rivastigmine, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, a-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine, duloxetine; aprepitant; bupropion, vilazodone, mirtazapine, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, reboxetine, vortioxetine, clorazepate, and ketamine and pharmaceutically acceptable salts thereof. In some embodiments, suitable anti-depressant and anti-anxiety agents are tianeptine, or pharmaceutically acceptable salts thereof Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, perphenazine, thioridazine, trifluoperazine, aripiprazole, asenapine, clozapine, olanzapine, paliperidone, brexpiprazole, paliperidone, cariprazine, pimavanserin, iloperidone, lumateperone, MIN-101, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid, iloperidone, thiothixene, gabapentin, tiagabine and pharmaceutically acceptable salts thereof Suitable epilepsy medications include levetiracetam, oxcarbazepine, clobazam, retigabine, zonisamide, felbamate, esclicarbazepine acetate, lacosamide, carbamazepine, tiagabine, methsuximide, progabide, valproic acid, lamotrigine, brivaracetam, rufinamide, topiramate and perampanel.

Suitable attention medications include methyl phenidate, atomoxetine, guanfacine, D-amphetamine, lisdexamphetamine, methylamphetamine, and clonidine.

Suitable sleep-promoting medications include ramelteon, triazolam, zopiclone, eszopiclone, zolpidem, temazepam, and trazodone.

Suitable wakefulness-promoting medications include Modafinil, D-Amphetamine, caffeine, and armodafinil.

Suitable pain medications include dextromethorphan, tapentadol, buprenorphine, codeine, fentanyl, hydrocodone, hydromorphone, morphine, naloxegol, oxycodone, tramadol, gabapentil, difluprednate, pregabalin, acetyl salicyclic acid, bromfenac, diclofenac, diflunisal, indomethacin, ketorolac, meoxican, and naproxen.

In some embodiments, compounds and compositions of the invention may be used in combination with other therapies. Suitable therapies include psychotherapy, cognitive behavioral therapy, electroconvulsive therapy, transcranial magnetic stimulation, vagus nerve stimulation, and deep-brain stimulation.

The exact amount required will vary from subject to subject, depending on the species, age, and general condition of the subject, the severity of the condition, the particular agent, its mode of administration, and the like. The compounds and compositions of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the present invention will be decided by the attending physician within the scope of sound medical judgment.

The pharmaceutically acceptable compositions of this invention can be administered to humans and other animals orally, rectally, parenterally, intracisternally, intravaginally, intraperitoneally, topically (as by powders, ointments, or drops), bucally, sublingually, as an oral or nasal spray, or the like, depending on the severity of the infection being treated. In some embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In some embodiments, a combination of two or more therapeutic agents may be administered together with the compounds of the invention. In some embodiments, a combination of three or more therapeutic agents may be administered with the compounds of the invention.

Other examples of agents the compounds and compositions of this invention may also be combined with include: vitamins and nutritional supplements, antiemetics (e.g. 5-HT3 receptor antagonists, dopamine antagonists, NK1 receptor antagonists, histamine receptor antagonists, cannabinoids, benzodiazepines, or anticholinergics), agents for treating Multiple Sclerosis (MS) such as beta interferon (e.g., Avonex® and Rebif®, dalfampridine, alemtuzumab), Copaxone®, and mitoxantrone; treatments for Huntington's disease such as tetrabenazine; treatments for asthma such as albuterol and Singulair®; anti-inflammatory agents such as corticosteroids, TNF blockers, IL-1 RA, azathioprine, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In some embodiments, a compound of the present invention, or a pharmaceutically acceptable salt thereof, is administered in combination with an antisense agent, a monoclonal or polyclonal antibody, or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, or a pharmaceutically acceptable salt thereof, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one compound of formula I, or a pharmaceutically acceptable salt thereof, and a pharmaceutically acceptable carrier, adjuvant, or vehicle.

In some embodiments, the present invention provides the use of a compound of formula I, or a pharmaceutically acceptable salt thereof, in the manufacture of a medicament for the treatment of a neurological and/or psychiatric disease or disorder.

EXAMPLES

As depicted in the Examples below, in some embodiments, compounds are prepared according to the following procedures. It will be appreciated that, although the general methods depict the synthesis of certain compounds of the present invention, the following methods, and other methods known to persons skilled in the art, can be applied to all compounds and subclasses and species of each of these, as described herein.

General Schemes

Schemes below provide exemplary synthetic methods for the preparation of the compounds provided herein. One of ordinary skills in the art will understand that similar methods may be employed to prepare the compounds provided herein. In other words, one of ordinary skills in the art will recognize that suitable adjustments to reagents, protecting groups, reaction conditions, reaction sequences, purification methods, and chiral separation conditions may be employed to prepare a desired embodiment. The reactions may be scaled upwards or downwards to suit the amount of material to be prepared.

In one embodiment, the compound of formula (I) may be prepared following Schemes 1-10 using suitable starting materials known in the art and/or available from a commercial source. In one embodiment, the starting materials of Schemes 1-10 may be prepared from commercially available compounds using procedures and conditions known in the art.

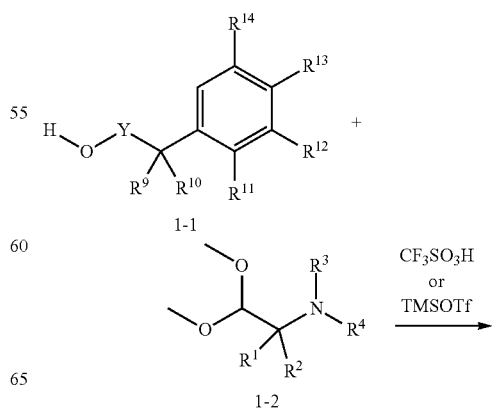

Scheme 1

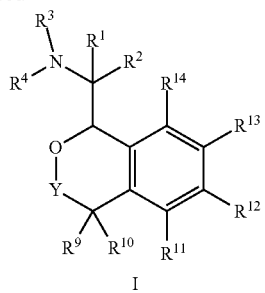

I

In one embodiment, a suitable hydroxyalkyl substituted benzene (1-1) is reacted with a suitable 2,2-dialkoxy-ethanamine or N-protected 2,2-dialkoxy-ethanamine (1-2) in the presence of an acid or a Lewis acid such as trifluoromethanesulfonic acid or trimethylsilyl trifluoromethanesulfonate to render the cyclized product (I) (Scheme 1), which may be separated using chiral HPLC to provide single enantiomers of formula (I). In some cases, to facilitate the purification of I, crude I was N-protected with a BOC-protecting group by reacting I with di-tert-butyl dicarbonate. After purification, the BOC-group was removed under acidic conditions to afford compound of formula (I). The stereoisomers of I are separated using HPLC/chiral HPLC to provide single enantiomers Scheme 2

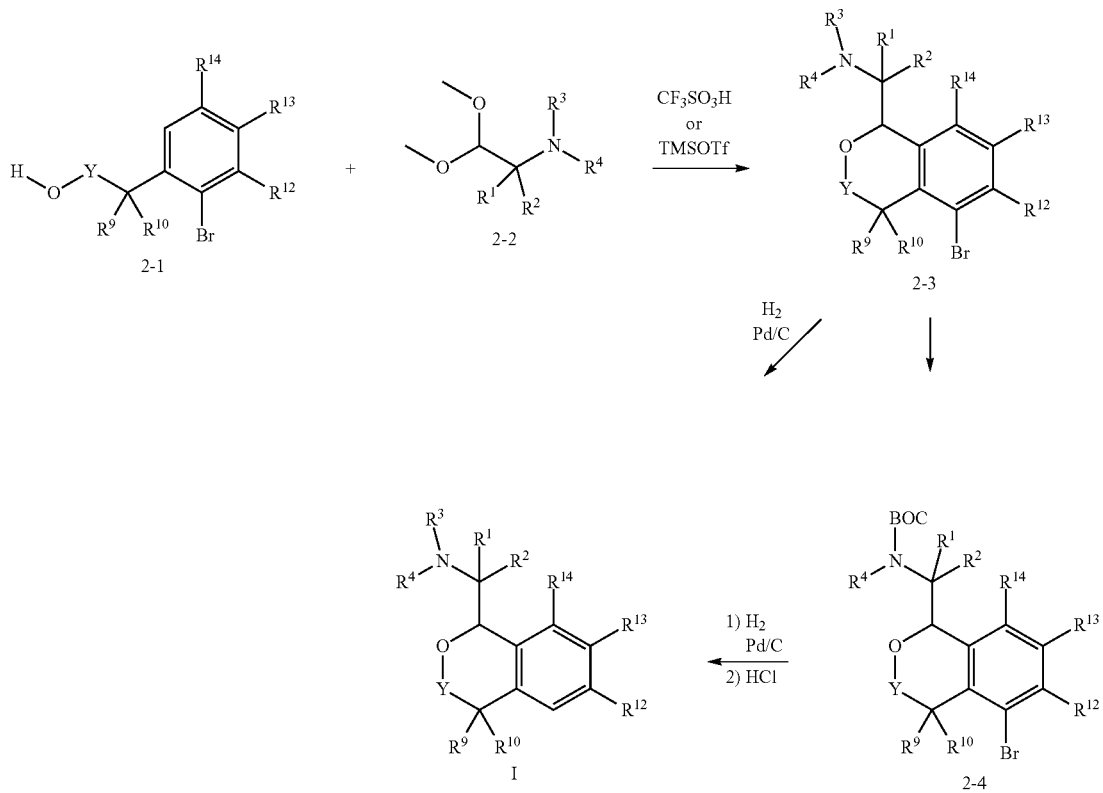

In another embodiment, a suitable 1-hydroxyalkyl 2-bromo-substituted benzene (2-1) is reacted with a suitable 2,2-dialkoxy-ethanamine or N-protected 2,2-dialkoxy-ethanamine (2-2) in the presence of an acid or a Lewis acid such as trifluoromethanesulfonic acid or trimethylsilyl trifluoromethanesulfonate to render the cyclized product (2-3) (Scheme 2). Pd -C catalyzed hydrodehalogenation of 2-3 affords compound I, which may be separated using chiral HPLC to provide single enantiomers of formula (I). In some cases, 2-3 is first N -protected with a BOC group followed by hydrodehalogenation and deprotection to provide compound I, which may be separated using chiral HPLC to provide single enantiomers of formula (I).

Scheme 3

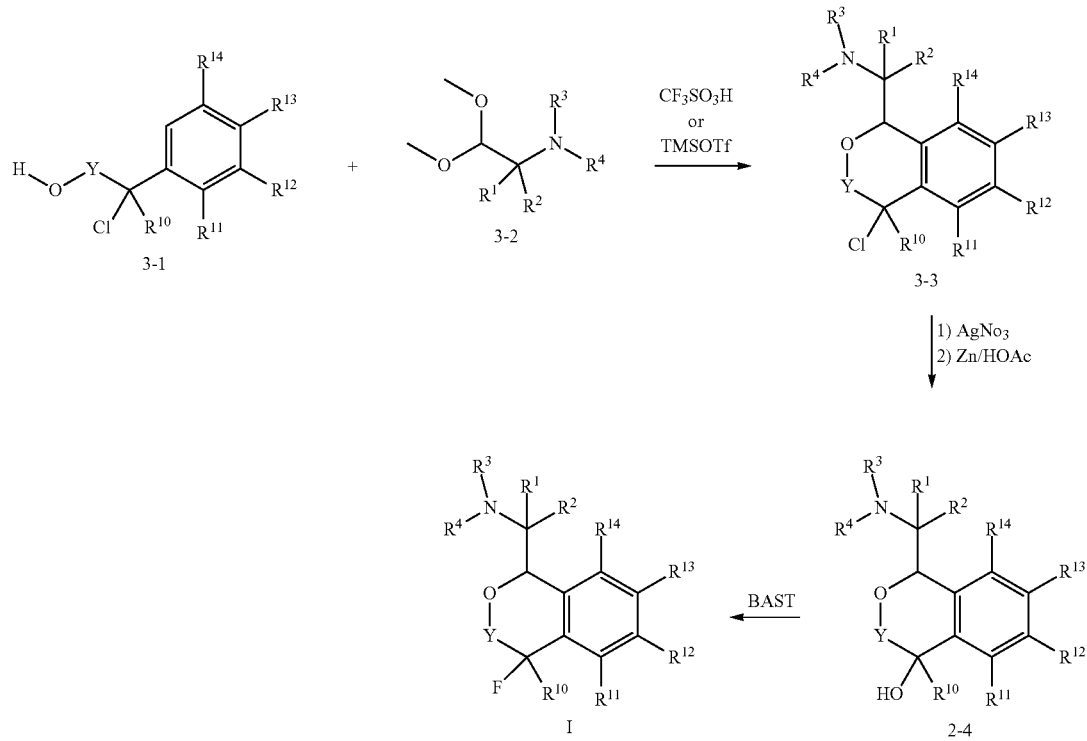

In another embodiment, a suitable hydroxyl-1-chloroalkyl substituted benzene (3-1) is reacted with a suitable 2,2-dialkoxy-ethanamine or N-protected 2,2-dialkoxy-ethanamine (3-2) in the presence of an acid or a Lewis acid such as trifluoromethanesulfonic acid or trimethylsilyl trifluoromethanesulfonate to render the cyclized product (3-3, or I where $R^9$=Cl)) (Scheme 3). Treatment of 3-3 with silver nitrate followed by zinc powder in acetic acid affords the hydroxyl compound 3-4, or I where $R^9$=OH), which is converted to compound I ($R^9$=F) with a fluorinating reagent such as BAST. The stereoisomers of I are separated using HPLC/chiral HPLC to provide single enantiomers of formula (I).

Scheme 4

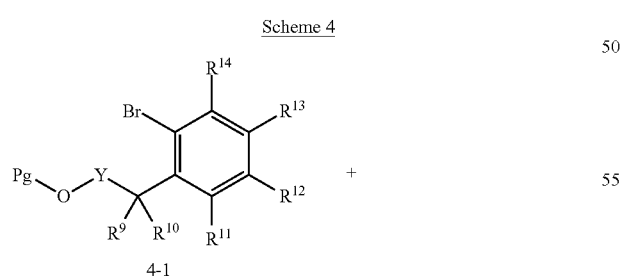

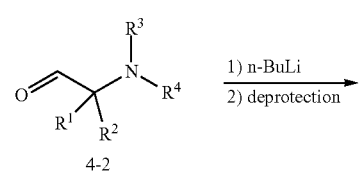

-continued

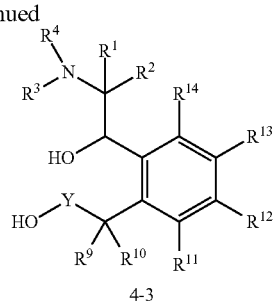

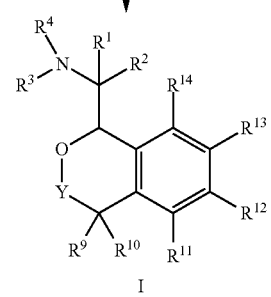

In another embodiment, a suitable O-protected hydroxylalkyl substituted bromobenzene (4-1) is treated with a lithium reagent such as n-BuLi, followed by reaction with an aminoacetaldehyde or an N-protected aminoacetaldehyde (4-2) and then removal of the O-protecting group to give compound 4-3 (Scheme 4). Treatment of 4-3 with methanesulfonyl chloride and TEA, followed by reaction with t-BuOK provides compound I, which is separated using chiral HPLC to provide single enantiomers of formula (I).

Scheme 5

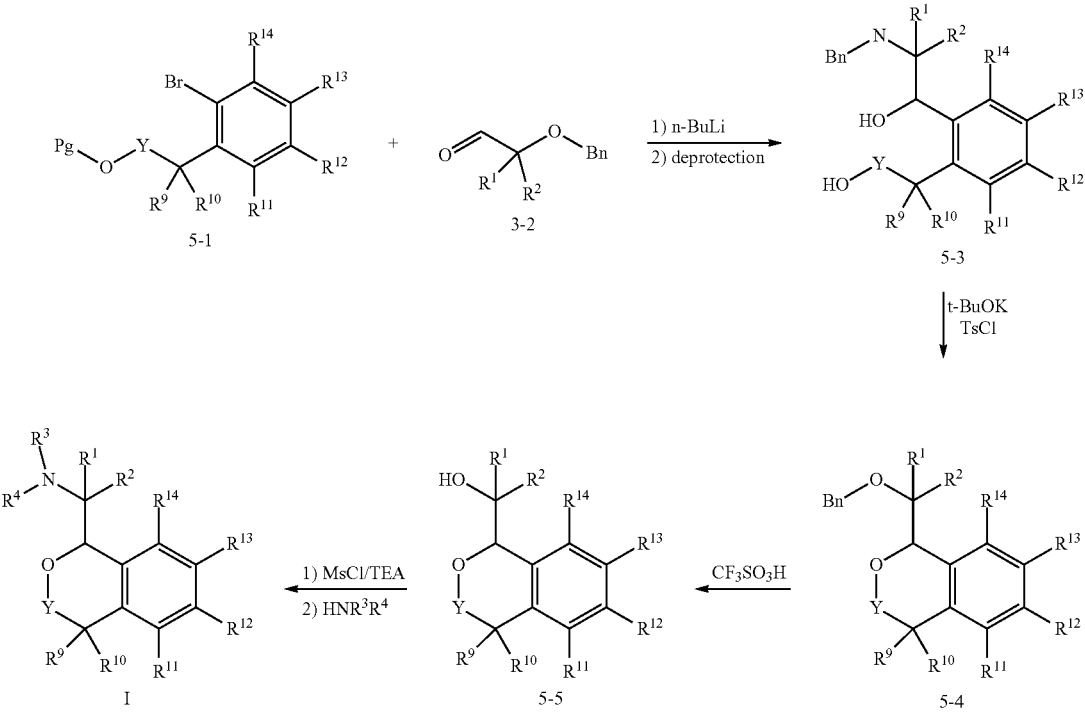

In another embodiment, a suitable O-protected hydroxylalkyl substituted bromobenzene (5-1) is treated with a lithium reagent such as n-BuLi, followed by reaction with a suitable O-protected hydroxyacetaldehyde (5-2) and then selective removal of the O-protecting group (Pg) to give compound 5-3 (Scheme 5). Treatment of 5-3 with 4-toluenesulfonyl chloride and t-BuOK provides cyclized compound 5-4, which is reacted with trifluoromethanesulfonic acid to remove the benzyl protecting group to afford compound 5-5. Compound I is produced by treating 5-5 with MsCl/TEA, followed by reaction with a suitable amine. I is separated using chiral HPLC to provide single enantiomers of formula (I).

Scheme 6

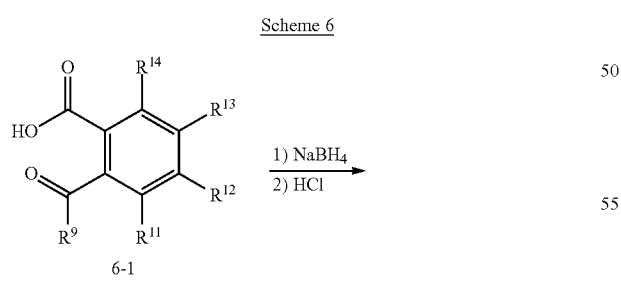

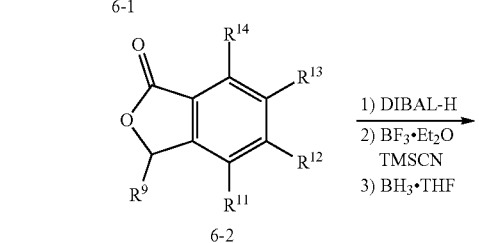

-continued

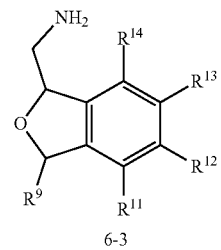

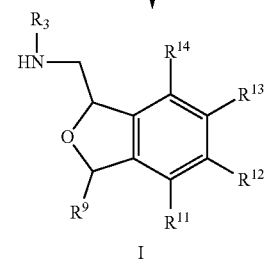

In another embodiment, a suitable 2-acyl-substituted benzoic acid (6-1) is reacted with sodium borohydride, followed by ring closure in the presence of an acid to give isobenzofuran-1(3H)-one (6-2). Isobenzofuran-1(3H)-yl-methanamine (6-3) was prepared using standard methodologies via isobenzofuran-1(3H)-carbonitrile intermediate. Reaction of 6-3 with di-tert-butyldicarbonate, followed by alkylation and deprotection, gave compound I. The stereoisomers of I are separated using HPLC/chiral HPLC to provide single enantiomers (I).

Scheme 7

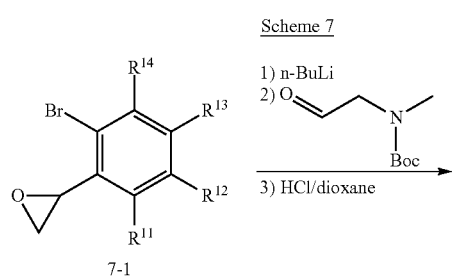

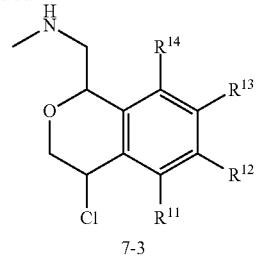

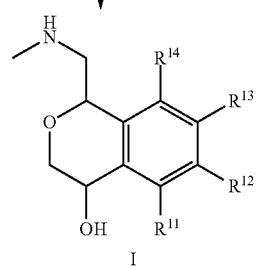

In another embodiment, a suitable 2-(2-bromophenyl) oxirane (7-1) is reacted with n-BuLi and tert-butyl methyl (2-oxoethyl)carbamate, followed by treatment with HCl to form intermediate 7-2. Treatment of 7-2 with TMS trifluoromethanesulphonate yields 1-(4-chloroisochroman-1-yl)-N-methylmethanamine (7-3, or I where $R^9$=Cl). Treatment of Boc-protected 7-3 with silver nitrate followed by zinc powder in acetic acid converts the chloride to the corresponding hydroxide. Removal of the protecting Boc-group affords compound I. The stereoisomers of I are separated using HPLC/chiral HPLC to provide single enantiomers (I).

Scheme 8

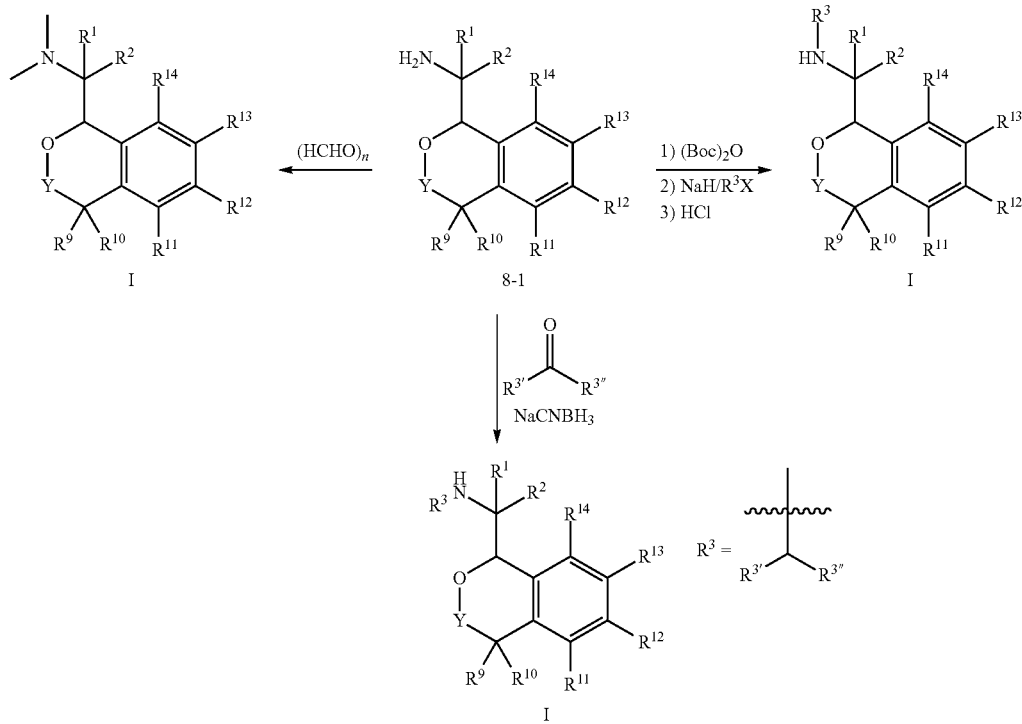

In another embodiment, a suitable N-unsubstituted compound I (8-1) can be alkylated to give compounds of formula I by direct alkylation with an alkyl halide via its Boc-protected intermediate or by reductive amination using a ketone or an aldehyde. The stereoisomers of I are separated using HPLC/chiral HPLC to provide single enantiomers (I).

Scheme 9

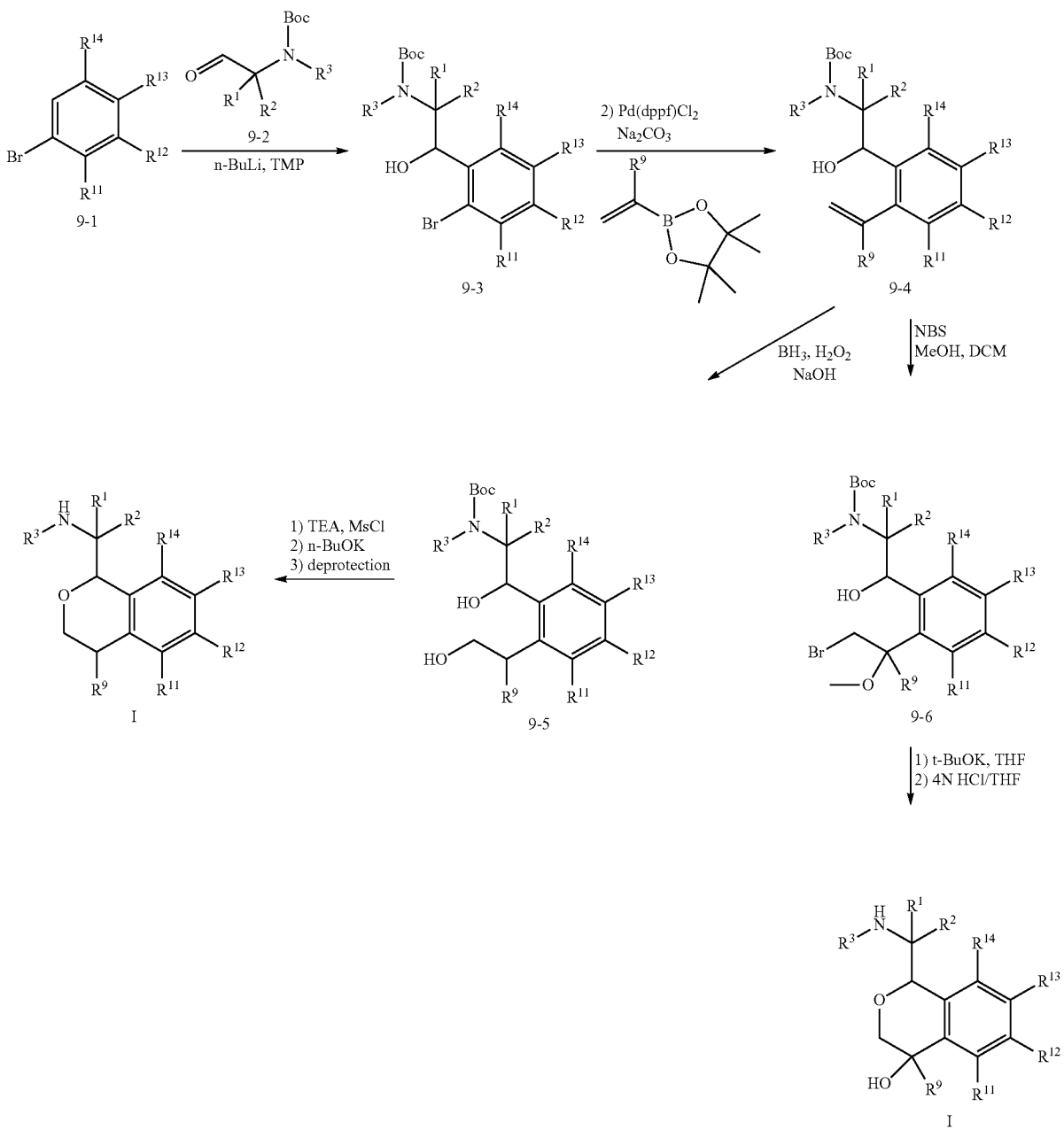

In another embodiment, a suitable aryl bromide (9-1) is reacted with n-BuLi and a suitable N-protected aminoacetaldehyde 9-2 to form intermediate 9-3. Coupling of 9-3 with a suitable vinyl-1,3,2-dioxaborolane such as 3,3,4,4-tetramethyl-1-vinylborolane provides 9-4. Hydroboration-oxidation of 9-4 yields 9-5. Mesylation, cyclization, then BOC-deprotection affords compound I. Alternatively, bromination of 9-4 yields 9-6, which is cyclized and depretected to yield I. The stereoisomers of I are separated using HPLC/chiral HPLC to provide single enantiomers (I).

Scheme 10

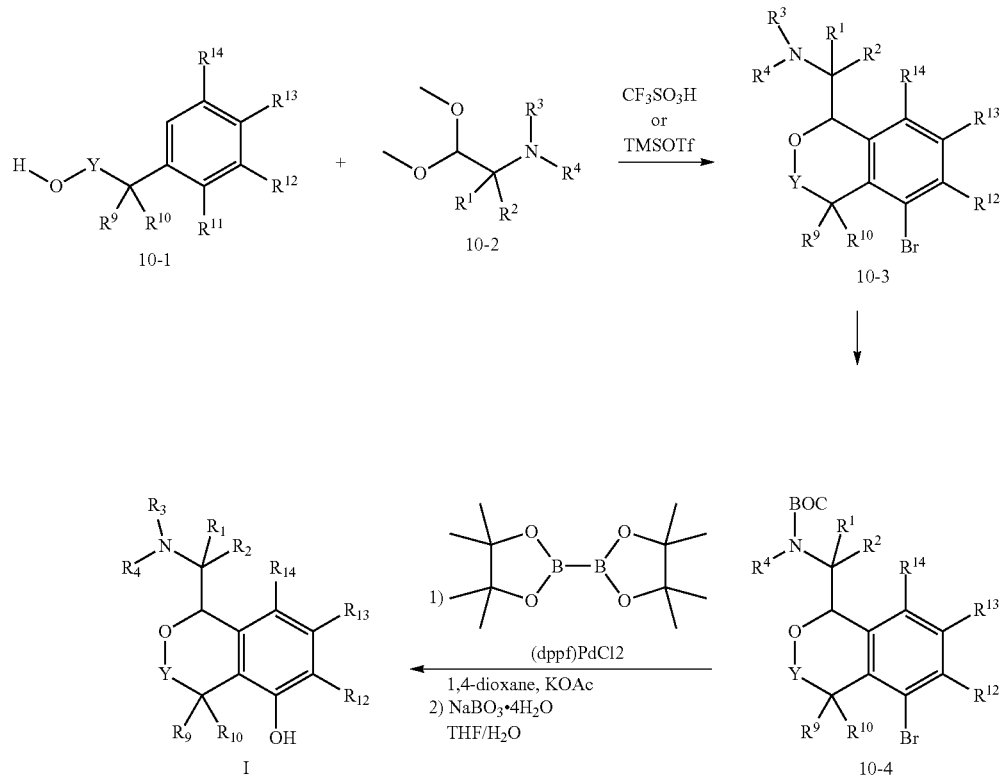

In another embodiment, a suitable 1-hydroxyalkyl 2-bromo-substituted benzene (10-1) is reacted with a suitable 2,2-dialkoxy-ethanamine or N-protected 2,2-dialkoxy-ethanamine (10-2) in the presence of an acid or a Lewis acid such as trifluoromethanesulfonic acid or trimethylsilyl trifluoromethanesulfonate to render the cyclized product (10-3) (Scheme 10). Protection of 10-3 followed by Pd-catalyzed borylation then treatment with sodium perborate affords compound I, which may be separated using chiral HPLC to provide single enantiomers of formula (I). In some cases, 2-3 is first N-protected with a BOC group followed by hydrodehalogenation and deprotection to provide compound I, which may be separated using chiral HPLC to provide single enantiomers of formula (I).

Examples 1-114

Representative compounds of the invention were prepared in the following Examples utilizing the general schemes above and procedures below.

General Procedure A:

1.1 Preparation of (S)-1-(5-chloroisochroman-1-yl)-N-methylmethanamine (32) and (R)-1-(5-chloroisochroman-1-yl)-N-methylmethanamine (33)

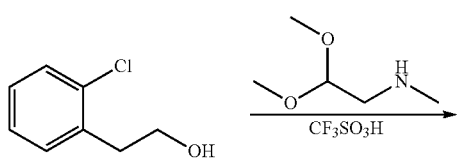

-continued

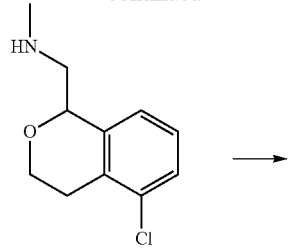

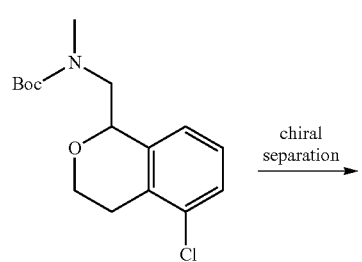

chiral separation

-continued

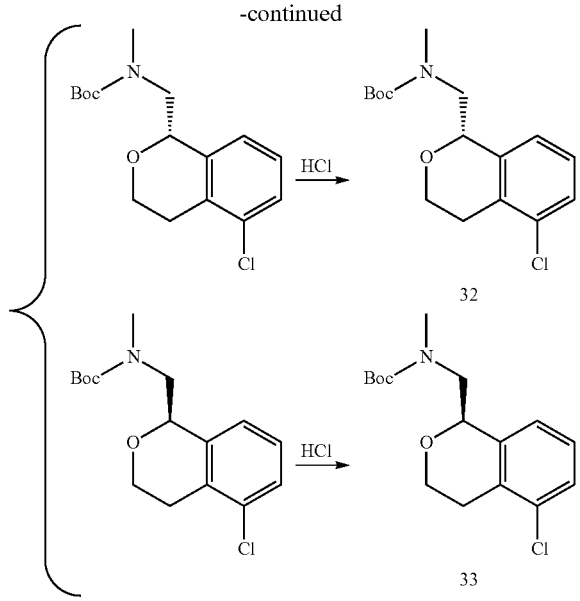

(a). 1-(5-chloroisochroman-1-yl)-N-methylmethanamine

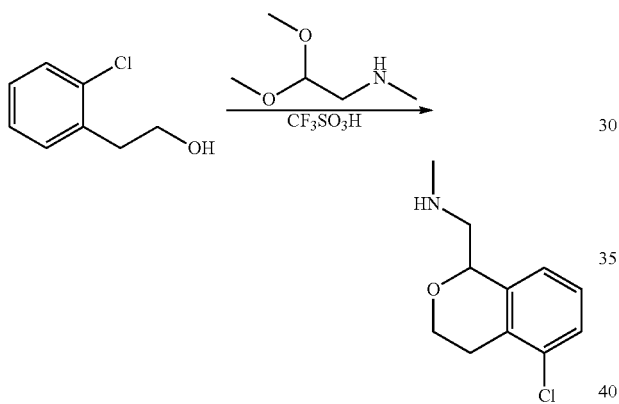

To a solution of 2-(2-chlorophenyl)ethanol (3 g, 19.1 mmol) in dichloromethane (15 mL) was added 2,2-dimethoxy-N-methylethanamine (4.55 g, 25.4 mmol) and trifluoromethanesulfonic acid (8.4 mL) at 0° C. The mixture was stirred at ambient temperature for 1 h. Trifluoromethanesulfonic acid (8.4 mL) was added at 0° C. again. The reaction was stirred at ambient temperature for an additional 2 h. The mixture was neutralized with 2N sodium hydroxide (aq.) to pH=8, extracted with dichloromethane (3×150 mL). The organic layer was dried over sodium sulfate, filtered and then concentrated to give the crude product which was used for next step without further purification.

(b). tert-butyl (5-chloroisochroman-1-yl)methyl(methyl)carbamate

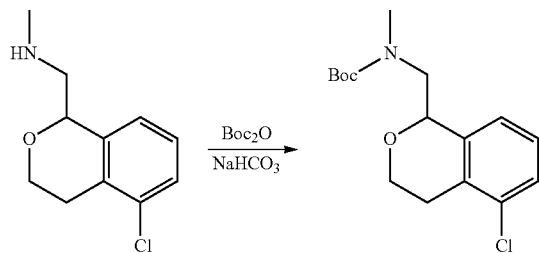

To a solution of 1-(5-chloroisochroman-1-yl)-N-methylmethanamine (9.31 g, 44 mmol) in tetrahydrofuran (100 mL) was added di-tert-butyl dicarbonate (19.2 g, 88.0 mmol) and sodium bicarbonate (11.0 g, 132 mmol). The reaction was stirred at ambient temperature for 2 h. Upon the completion, the mixture was extracted with dichloromethane (80 mL×3). The organic layer was dried over sodium sulfate, filtered and concentrated to give the crude product which was purified by column chromatography (petroleum either: ethyl acetate=10:1) to give tert-butyl ((5-chloroisochroman-1-yl)methyl) (methyl)carbamate (13 g) as yellow oil.

(c). (S)-1-(5-chloroisochroman-1-yl)-N-methylmethanamine (32) and (R)-1-(5-chloroisochroman-1-yl)-N-methylmethanamine (33)

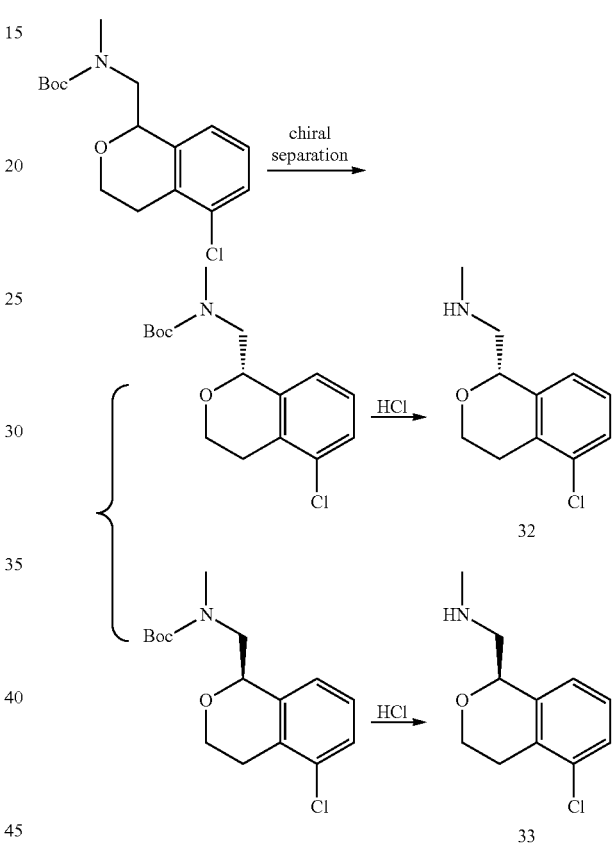

Tert-butyl ((5-chloroisochroman-1-yl)methyl)(methyl) carbamate (1 g) was separated by chiral HPLC: IC 20×250 mm, Sum (Dacel), mobile phase: CO$_2$/IPA{0.2% Ammonia (7M methanal)}=85/15, flow rate: 80 g/min, back pressure: 100 bar, cycle time: 4.7 min to give (S)-tert-butyl ((5-chloroisochroman-1-yl)methyl)(methyl)carbamate (350 mg) and (R)-tert-butyl ((5-chloroisochroman-1-yl)methyl) (methyl)carbamate (350 mg) as colorless oil.

To a solution of (S)-tert-butyl ((5-chloroisochroman-1-yl) methyl) (methyl)carbamate (320 mg, 1.02 mmol) in ethyl acetate (1 mL) was added HCl/MeOH (733 mg, 20.4 mmol) at 0° C. The reaction was stirred at ambient temperature for 16 h. Upon the completion, the mixture was concentrated to give the HCl salt of 32 (0.22 g) as a white solid. ESI: m/z=212 [M+H]$^+$. $^1$H NMR (500 MHz, CD$_3$OD) δ 7.39 (d, J=7.9 Hz, 1H), 7.29 (t, J=7.5 Hz, 1H), 7.21 (d, J=7.5 Hz, 1H), 5.11-5.09 (m, 1H), 4.31-4.27 (m, 1H), 3.91-3.86 (m, 1H), 3.64 (dd, J=12.5, 3.0 Hz, 1H), 3.36-3.34 (m, 1H), 2.98-2.85 (m, 2H), 2.79 (s, 3H).

To a solution of (R)-tert-butyl ((5-chloroisochroman-1-yl)methyl) (methyl)carbamate (320 mg, 1.02 mmol) in ethyl acetate (10 mL) was added HCl/MeOH (733 mg, 20.4 mmol) at 0° C. The reaction was stirred at ambient temperature for 16 h. Upon the completion, the mixture was concentrated to give the HCl salt of 33 (0.22 g) as a white solid. ESI: m/z=212 [M+H]⁺. ¹H NMR (500 MHz, CD₃OD) δ 7.39 (d, J=8 Hz, 1H), 7.29 (t, J=7.5 Hz, 1H), 7.21 (d, J=7.5 Hz, 1H), 5.11-5.09 (m, 1H), 4.31-4.27 (m, 1H), 3.91-3.86 (m, 1H), 3.64 (dd, J=12.9, 3.0 Hz, 1H), 3.36-3.34 (m, 1H), 2.96-2.85 (m, 2H), 2.79 (s, 3H).

1.2 Preparation of (S)-1-(8,9-dihydro-6H-[1,3]dioxolo[4,5-f]isochromen-6-yl)-N-methylmethanamine (3) and (R)-1-(8,9-dihydro-6H-[1,3]dioxolo[4,5-f]isochromen-6-yl)-N-methylmethanamine (4)

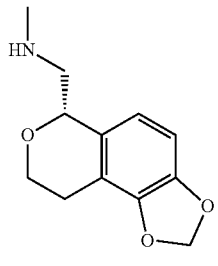

3

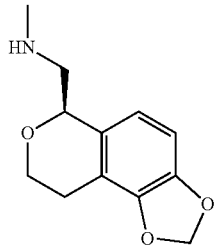

4

(S)-1-(8,9-dihydro-6H-[1,3]dioxolo[4,5-f]isochromen-6-yl)-N-methylmethanamine (3) and (R)-1-(8,9-dihydro-6H-[1,3]dioxolo[4,5-f]isochromen-6-yl)-N-methyl-methanamine (4) were prepared using General Procedure A and Scheme 1 starting with 2-(benzo[d][1,3]dioxol-4-yl)ethan-1-ol and 2,2-dimethoxy-N-methylethanamine.

(S)-1-(8,9-dihydro-6H-[1,3]dioxolo[4-f]isochromen-6-yl)-N-methylmethanamine (3): MS (ESI): m/z 222.1 (M+1)+. ¹HNMR (400 MHz, DMSO-d6, HCl salt) d 8.87 (bs, 1H), 6.82 (d, J=8.0 Hz, 1H), 6.70 (d, J=8.0 Hz, 1H), 6.02 (d, J=3.2 Hz, 2 H), 5.00 (d, J=8.0 Hz, 1 H), 4.05-4.10 (m, 1H), 3.72-3.78 (m, 1H), 3.48-3.45 (m, 1H), 3.21-3.15 (m, 1H), 2.61-2.71 (m, 2H), 2.57 (s, 3H).

(R)-1-(8,9-dihydro-6H-[1,3]dioxolo[4,5-f]isochromen-6-yl)-N-methyl-methanamine (4): MS (ESI): m/z 222.1 (M+1)⁺. 1H NMR (400 MHz, DMSO-d6, HCl salt) d 8.66 (bs, 1 H), 6.82 (d, J=8.0 Hz, 1H), 6.70 (d, J=8.0 Hz, 1H), 6.02 (d, J=3.2 Hz, 2 H), 5.01 (d, J=8.6 Hz, 1H), 3.72-3.78 (m, 1H), 4.05-4.10 (m, 1H), 3.48-3.45 (m, 1H), 3.21-3.15 (m, 1H), 2.61-2.75 (m, 2 H), 2.57 (s, 3H).

1.3 Preparation of (S)-1-(7,8-dihydro-5H-[1,3]dioxolo[4,5-g]isochromen-5-yl)-N-methylmethanamine (5) and (R)-1-(7,8-dihydro-5H-[1,3]dioxolo[4,5-g]isochromen-5-yl)-N-methylmethanamine (6)

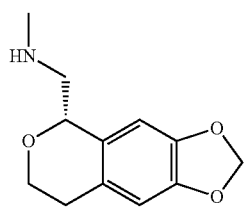

5

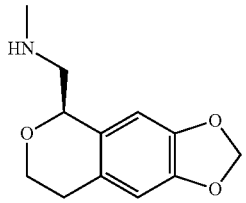

6

(S)-1-(7,8-dihydro-5H-[1,3]dioxolo[4,5-g]isochromen-5-yl)-N-methylmethanamine (5) and (R)-1-(7,8-dihydro-5H-[1,3]dioxolo[4,5-g]isochromen-5-yl)-N-methylmethanamine (6) were prepared using General Procedure A and Scheme 1 starting with 2-(benzo[d][1,3]dioxo1-5-yl)ethanol and 2,2-dimethoxy-N-methylethanamine.

(S)-1-(7,8-dihydro-5H-[1,3]dioxolo[4,5-g]isochromen-5-yl)-N-methylmethanamine (5): MS ESI: m/z=222 [M+H]⁺. ¹H NMR (400 MHz, CD₃OD, HCl salt) δ 6.70 (s, 1H), 6.68 (s, 1H), 5.93 (d, J=1.2 Hz, 2H), 4.97 (d, J=7.3 Hz, 1H), 4.18~4.13 (m, 1H), 3.81~3.75 (m, 1H), 3.54~3.50 (dd, J₁=12.9, J₂=2.8 Hz, 1H), 3.28~3.25 (m, 1H), 2.91~2.87 (m, 1H), 2.75 (s, 3H), 2.8~2.62 (m, 1H).

(R)-1-(7,8-dihydro-5H-[1,3]dioxolo[4,5-g]isochromen-5-yl)-N-methylmethanamine (6): MS (ESI): m/z=222 [M+H]⁺. ¹H NMR (400 MHz, CDCl₃) δ 6.58 (s, 1H), 6.57 (s, 1H), 5.90~5.89 (m, 2H), 4.79~4.77 (d, J=6.4 Hz, 1H), 4.11~4.07 (m, 1H), 3.76~3.70(m, 1H), 2.96~2.81 (m, 3H), 2.61-2.57 (m, 1H), 2.48 (s, 3H).

1.4 Preparation of (S)-(8,9-dihydro-6H-[1,3]dioxolo[4,5-f]isochromen-6-yl)methanamine (11) and (R)-(8,9-dihydro-6H-[1,3]dioxolo[4,5-f]isochromen-6-yl)methanamine (12)

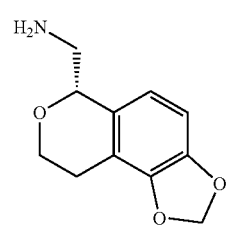

11

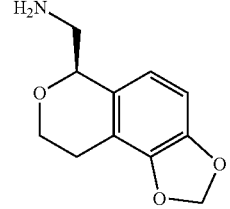

12

(S)-(8,9-dihydro-6H-[1,3]dioxolo[4,5-f]isochromen-6-yl)methanamine 11 and (R)-(8,9-dihydro-6H-[1,3]dioxolo[4,5-f]isochromen-6-yl)methanamine 12 were prepared using General Procedure A and Scheme 1 starting with 2-(benzo[d][1,3]dioxol-4-yl)ethanol and 2,2-dimethoxyethanamine in the presence of trimethylsilyl trifluoromethanesulfonate instead of trifluoromethanesulfonic acid.

(S)-(8,9-dihydro-6H-[1,3]dioxolo[4,5-f]isochromen-6-yl) methanamine (11): MS (ESI): m/z=208 [M+H]⁺. ¹H NMR (400 MHz, CD₃OD, HCl salt) δ 6.76~6.74 (d, J=8.1 Hz, 1H), 6.69~6.67 (d, J=8.1 Hz, 1H), 5.979 (s, 2H), 4.95~4.93 (dd, J₁=8.6, J₂=2.2 Hz, 1H), 4.23~4.18 (m, 1H), 3.83~3.76

(m, 1H), 3.49~3.45 (dd, J₁=13.1, J₂=3.1 Hz, 1H), 3.20~3.15 (m, 1H), 2.84~2.80 (m, 1H), 2.73~2.68 (dt, J₁=16.6, J₂=3.5 Hz, 1H).

(R)-(8,9-dihydro-6H[1,3]dioxolo[4,5-f]isochromen-6-yl)methanamine (12): MS (ESI): m/z=208[M+H]⁺. ¹H NMR (400 MHz, CD₃OD, HCl salt) δ 6.76~6.74 (d, J=8.1 Hz, 1H), 6.70~6.68 (d, J=8.2 Hz, 1H), 5.977 (s, 2H), 4.96~4.93 (dd, J₁=8.6, J₂=2.2 Hz, 1H), 4.23~4.18 (m, 1H), 3.83~3.76 (m, 1H), 3.50~3.46 (dd, J₁=13.1, J₂=3.1 Hz, 1H), 3.20~3.15 (m, 1H), 2.84~2.80 (m, 1H), 2.73~2.68 (dt, J₁=16.6, J₂=3.5 Hz, 1H).

1.5 Preparation of (S)-1-(7-fluoroisochroman-1-yl)-N-methylmethanamine (13) and (R)-1-(7-fluoroisochroman-1-yl)-N-methylmethanamine (15)

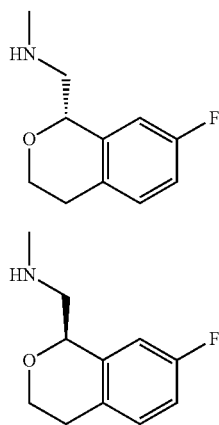

13

15

(S)-1-(7-fluoroisochroman-1-yl)-N-methylmethanamine (13) and (R)-1-(7-fluoroisochroman-1-yl)-N-methylmethanamine (15) were prepared using General Procedure A and Scheme 1 starting with 2-(4-fluorophenyl)ethanol and 2,2-dimethoxy-N-methylethanamine.

(S)-1-(7-fluoroisochroman-1-yl)-N-methylmethanamine (13): MS (ESI) m/z=196 [M+H]⁺. ¹H NMR (400 MHz, CD₃OD, HCl salt) δ 7.25~7.23 (m, 1H), 7.03~6.98 (m, 2H), 5.09-5.07 (m, 1H), 4.245~4.21 (m, 1H), 3.86~3.82 (m, 1H), 3.63~3.60 (dd, J₁=12.9, J₂=3.2 Hz, 1H), 3.35~3.32 (m, 1H), 3.03~2.95 (m, 1H), 2.78 (s, 3H), 2.74-2.72 (m 1H).

(R)-1-(7-fluoroisochroman-1-yl)-N-methylmethanamine (15): MS (ESI): m/z=196 [M+H]⁺. ¹H NMR (400 MHz, CD₃OD, HCl salt) δ 7.26~7.23 (m, 1H), 7.04~7.01 (m, 2H), 5.09~5.07 (m, 1H), 4.245~4.21 (m, 1H), 3.87~3.82 (m, 1H), 3.63~3.60 (dd, J₁=12.9, J₂=3.2 Hz, 1H), 3.356~3.34 (m, 1H), 3.03~2.95 (m, 1H), 2.78 (s, 3H), 2.74-2.72 (m 1H).

1.6 Preparation of (S)-1-(5-fluoroisochroman-1-yl)-N-methylmethanamine (18) and (R)-1-(5-fluoroisochroman-1-yl)-N-methylmethanamine (14)

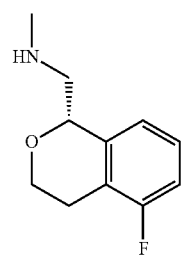

18

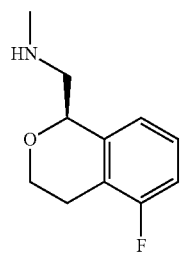

14

(S)-1-(5-fluoroisochroman-1-yl)-N-methylmethanamine (18) and (R)-1-(5-fluoroisochroman-1-yl)-N-methylmethanamine (14) were prepared using General Procedure A and Scheme 1 starting with 2-(2-fluorophenyl)ethanol and 2,2-dimethoxy-N-methylethanamine.

(S)-1-(5-fluoroisochroman-1-yl)-N-methyl-methanamine (18): MS (ESI) : m/z 196 [M+H]⁺. ¹H NMR (400 MHz, CD₃OD, HCl salt) δ 7.31-7.26 (m, 1H), 7.07-7.01 (m, 2H), 5.11-5.09 (m, 1H), 4.28-4.23 (m, 1H), 3.88-3.82 (m, 1H), 3.66-3.62 (m, 1H), 3.37-3.30 (m, 1H), 2.89-2.83 (m, 2H), 2.77 (s, 3H).

(R)-1-(5-fluoroisochroman-1-yl)-N-methylmethanamine (14): MS (ESI): m/z=196 [M+H]⁺. ¹H NMR (400 MHz, CD₃OD, HCl salt) δ 7.31-7.26 (m, 1H), 7.06-7.02 (m, 2H), 5.10 (d, J=8.5 Hz, 1H), 4.28-4.23 (m, 1H), 3.88-3.82 (m, 1H), 3.63 (dd, J=12.9, 3.2 Hz, 1H), 3.37-3.33 (m, 1H), 2.96-2.79 (m, 2H), 2.77 (s, 3H).

1.7 Preparation of (S)-1-(6-fluoroisochroman-1-yl)-N-methylmethanamine (16) and (R)-1-(6-fluoroisochroman-1-yl)-N-methylmethanamine (17)

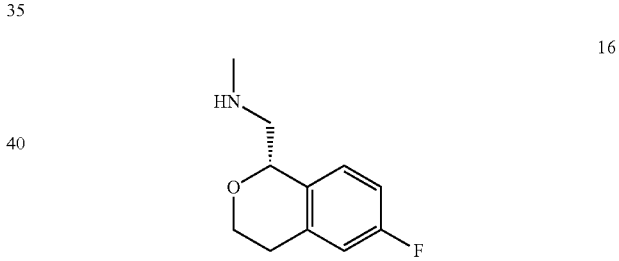

(S)-1-(6-fluoroisochroman-1-yl)-N-methylmethanamine (16) and (R)-1-(6-fluoroisochroman-1-yl)-N-methylmethanamine (17) were prepared using General Procedure A and Scheme 1 starting with 2-(3-fluorophenyl)ethanol and 2,2-dimethoxy-N-methylethanamine.

(S)-1-(6-fluoroisochroman-1-yl)-N-methylmethanamine (16): MS (ESI): m/z=196 [M+H]⁺. ¹H-NMR (400 MHz, CD₃OD, HCl salt) δ 7.25-7.21 (m, 1H), 7.03~6.97 (m, 2H), 5.08 (d, J=8.8 Hz, 1H), 4.23~4.18 (m, 1H), 3.87~3.81 (m, 1H), 3.61~3.57 (m, 1H), 3.31~3.27 (m, 1H), 3.06~2.98 (m, 1H), 2.81~2.76 (m, 4H).

(R)-1-(6-fluoroisochroman-1-yl)-N-methylmethanamine (17): MS (ESI): m/z=196 [M+H]⁺. ¹H NMR (400 MHz, CD$_3$OD, HCl salt) δ 7.27-7.21(m, 1H), 7.02~6.97(m, 2H), 5.09 (d, J=8.0 Hz, 1H), 4.23~4.18 (m, 1H), 3.87~3.81 (m, 1H), 3.62~3.58 (m, 1H), 3.31~3.27 (m, 1H), 3.06~2.98 (m, 1H), 2.81~2.75 (m, 4H).

1.8 Preparation of N-methyl-1-((1S,4S)-4-methylisochroman-1-yl)methanamine (19) and N-methyl-1-((1R,4S)-4-methylisochroman-1-yl)methanamine (20)

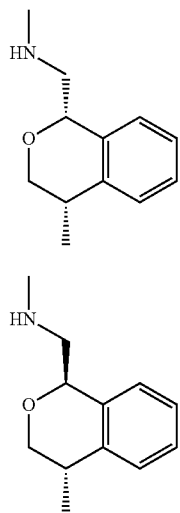

19

20

N-methyl-1-((1S,4S)—4-methylisochroman-1-yl)methanamine (19) and N-methyl-1-((1R,4S)-4-methylisochroman-1-yl)methanamine (20) were prepared using General Procedure A and Scheme 1 starting with (S)-2-phenylpropan-1-ol and 2,2-dimethoxy-N-methylethanamine.

N-methyl-1-((1S,4S)-4-methylisochroman-1-yl)methanamine (19): MS (ESI) m/z: 192 (M+H)$^+$. $^1$H NMR (500 MHz, CD$_3$OD, HCl salt) δ 7.30-7.25 (m, 3H), 7.18 (d, J=7.6 Hz, 1H), 5.05 (dd, J=9.4, 3.1 Hz, 1H), 3.99-3.92 (m, 2H), 3.68-3.65 (m, 1H), 3.31-3.27 (m, 1H), 2.92-2.86 (m, 1H), 2.79 (s, 3H), 1.39 (d, J=7.1 Hz, 3H).

N-methyl-1-((1R,4S)-4-methylisochroman-1-yl)methanamine (20): MS (ESI) m/z: 192 [M+H]$^+$. $^1$H NMR (500 MHz, CD$_3$OD, HCl salt) δ 7.38 (d, J=7.5 Hz, 1H), 7.33-7.25 (m, 2H), 7.18 (d, J=7.6 Hz, 1H), 5.12 (dd, J=9.5, 2.9 Hz, 1H), 4.16 (dd, J=11.3, 4.8 Hz, 1H), 3.60-3.51 (m, 2H), 3.35-3.32 (m, 1H), 3.07-3.04 (m, 1H), 2.78 (s, 3H), 1.29 (d, J=7.0 Hz, 3H).

1.9 Preparation of (S)-1-(4,4-dimethylisochroman-1-yl)-N-methylmethanamine (23) and (R)-1-(4,4-dimethylisochroman-1-yl)-N-methylmethanamine (24)

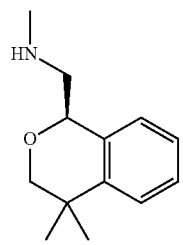

23

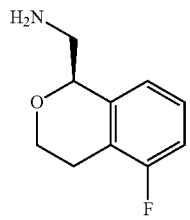

24

(S)-1-(4,4-dimethylisochroman-1-yl)-N-methylmethanamine (23) and (R)-1-(4,4-dimethylisochroman-1-yl)-N-methylmethanamine (24) were prepared using General Procedure A and Scheme 1 starting with 2-methyl-2-phenylpropan-1-ol and tert-butyl (2,2-dimethoxyethyl)(methyl)carbamate.

(S)-1-(4,4-dimethylisochroman-1-yl)-N-methylmethanamine (23): MS (ESI) m/z: 206 [M+H]$^+$, $^1$H NMR (400 MHz, CD$_3$OD, HCl salt): δ 7.46 (d, J=7.8 Hz, 1H), 7.34-7.12 (m, 3H), 5.11 (d, J=9.8 Hz, 1H), 3.81 (d, J=11.3 Hz, 1H), 3.68-3.55 (m, 2H), 3.31-3.27 (m, 1H), 2.79 (s, 3H), 1.35 (s, 3H), 1.26 (s, 3H).

(R)-1-(4,4-dimethylisochroman-1-yl)-N-methylmethanamine (24): MS (ESI) m/z: 206 [M+H]$^+$, $^1$H NMR (400 MHz, CD$_3$OD, HCl salt): δ 7.46 (d, J=7.8 Hz, 1H), 7.34-7.12 (m, 3H), 5.11 (d, J=9.8 Hz, 1H), 3.81 (d, J=11.3 Hz, 1H), 3.68-3.55 (m, 2H), 3.31-3.27 (m, 1H), 2.79 (s, 3H), 1.35 (s, 3H), 1.26 (s, 3H).

1.10 Preparation of (R)-(5-fluoroisochroman-1-yl)methanamine (29)

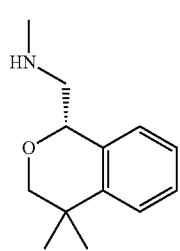

29

(R)-(5-fluoroisochroman-1-yl)methanamine (29) was prepared using General Procedure A and Scheme 1 starting with 2-(2-fluorophenyl) ethanol and 2,2-dimethoxyethanamine.

(R)-(5-fluoroisochroman-1-yl)methanamine (29): MS (ESI) m/z: 182 [M+H]$^+$, $^1$H NMR (500 MHz, CD$_3$OD, HCl salt) δ 7.32~7.27 (m, 1H), 7.06~7.03(m, 2H), 5.04~5.02 (m, 1H), 4.28~4.24 (m, 1H), 3.87~3.82 (m, 1H), 3.57~3.54 (dd, J$_1$=13.1, J$_2$=3.2 Hz, 1H), 3.26~3.21 (m, 1H), 2.90~2.87 (m, 1H), 2.83~2.80 (m, 1H).

1.11 Preparation of (S)-1-(5,8-difluoroisochroman-1-yl)-N-methylmethanamine (30) and (R)-1-(5,8-difluoroisochroman-1-yl)-N-methylmethanamine (31)

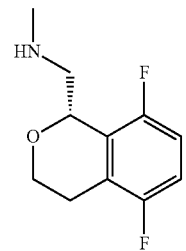

30

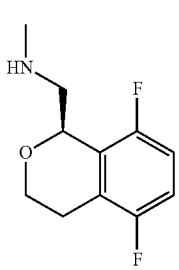

31

(S)-1-(5,8-difluoroisochroman-1-yl)-N-methylmethanamine (30) and (R)-1-(5,8-difluoroisochroman-1-yl)-N-methylmethanamine (31) were prepared using General Procedure A and Scheme 1 starting with 2-(2,5-difluorophenyl)ethanol and 2,2-dimethoxy-N-methylethanamine.

(S)-1-(5,8-difluoroisochroman-1-yl)-N-methylmethanamine (30): MS (ESI) m/z: 214 [M+H]⁺. ¹H NMR (500 MHz, CD₃OD, HCl salt) δ 7.15-7.05 (m, 2H), 5.27-5.25 (m, 1H), 4.22-4.17 (m, 1H), 3.92-3.87 (m, 1H), 3.59-3.56 (m, 1H), 3.50-3.42 (m, 1H), 2.85 (t, J=5.5 Hz, 2H), 2.80 (s, 3H).

(R)-1-(5,8-difluoroisochroman-1-yl)-N-methylmethanamine (31): MS (ESI) m/z: 214 [M+H]⁺, ¹H NMR (500 MHz, CD₃OD, HCl salt), δ 7.15-7.05 (m, 2H), 5.26-5.25 (m, 1H), 4.22-4.17 (m, 1H), 3.92-3.87 (m, 1H), 3.59-3.56 (m, 1H), 3.47-3.43 (m, 1H), 2.87-2.84 (m, 2H), 2.80 (s, 3H).

1.12 Preparation of (S)-N-methyl-1-(5-methylisochroman-1-yl)methanamine (38) and (R)-N-methyl-1-(5-methylisochroman-1-yl)methanamine (39)

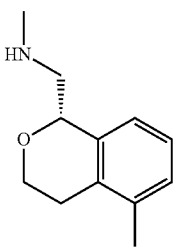

38

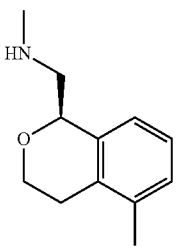

39

(S)-N-methyl-1-(5-methylisochroman-1-yl)methanamine (38) and (R)-N-methyl-1-(5-methylisochroman-1-yl)methanamine (39) were prepared using General Procedure A and Scheme 1 starting with 2-(o-tolyl)ethan-1-ol and 2,2-dimethoxy-N-methylethanamine.

(S)-N-methyl-1-(5-methylisochroman-1-yl)methanamine (38): MS (ESI) m/z: 192 [M+H]⁺, ¹H NMR (400 MHz, CD₃OD, HCl salt) δ 7.18-7.12 (m, 2H), 7.04-7.02 (m, 1H), 5.09-5.06 (m, 1H), 4.28-4.23 (m, 1H), 3.89-3.83 (m, 1H), 3.61-3.57 (m, 1H), 3.31-3.26 (m, 1H), 2.85-2.81 (m, 1H), 2.76 (s, 3H), 2.72-2.67 (m, 1H), 2.27 (s, 3H).

(R)-N-methyl-1-(5-methylisochroman-1-yl)methanamine (39): MS (ESI) m/z: 192 [M+H]⁺, ¹H NMR (400 MHz, CD₃OD, HCl salt) δ 7.18-7.12 (m, 2H), 7.05-7.03 (m, 1H), 5.09-5.07 (m, 1H), 4.28-4.23 (m, 1H), 3.89-3.83 (m, 1H), 3.61-3.57 (m, 1H), 3.31-3.26 (m, 1H), 2.88-2.81 (m, 1H), 2.76 (s, 3H), 2.72-2.66 (m, 1H), 2.27 (s, 3H).

1.13 Preparation of compounds (42), (43), (52), and (53): ((R)-1-((R)-5-fluoroisochroman-1-yl)ethan-1-amine, ((S)-14(S)-5-fluoroisochroman-1-yl)ethan-1-amine, (R)-14(S)-5-fluoroisochroman-1-yl)ethan-1-amine and (S)-14(R)-5-fluoroisochroman-1-yl)ethan-1-amine, order unknown

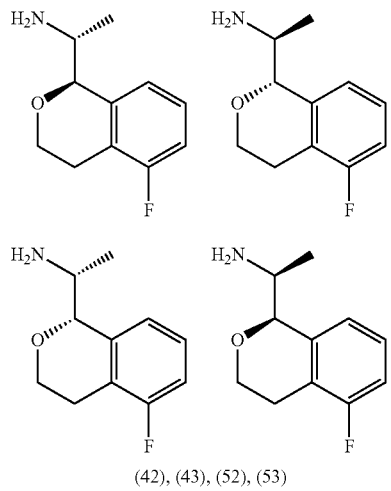

(42), (43), (52), (53)

((R)-1-((R)-5-fluoroisochroman-1-yl)ethan-1-amine, ((S)-1-((S)-5-fluoroisochroman-1-yl)ethan-1-amine, (R)-1-((S)-5-fluoroisochroman-1-yl)ethan-1-amine and (S)-1-((R)-5-fluoroisochroman-1-yl)ethan-1-amine were prepared using General Procedure A and Scheme 1 starting with 2-(2-fluorophenyl)ethan-1-ol and tert-butyl (1-oxopropan-2-yl)carbamate. All four stereoisomers were synthesized and characterized.

(42): MS (ESI) m/z: 196 (M+H)⁺, ¹H NMR (500 MHz, CD₃OD, HCl salt) δ 7.36-7.32 (m, 1H), 7.16 (d, J=8 Hz, 1H), 7.09-7.06 (m, 1H), 4.89 (s,1H), 4.36-4.33 (m, 1H), 3.98-3.94 (m, 1H), 3.80-3.75 (m, 1H), 2.94-2.80 (m, 2H), 1.55-1.54 (d, J=6.5 Hz, 3H).

(43): MS (ESI) m/z: 196 (M+H)⁺, ¹H NMR (500 MHz, CD₃OD, HCl salt) δ 7.36-7.32 (m, 1H), 7.15-7.14 (d, J=7.5 Hz, 1H), 7.09-7.06 (m, 1H), 4.89 (s,1H), 4.36-4.33 (m, 1H), 3.98-3.94 (m, 1H), 3.80-3.75 (m, 1H), 2.94-2.80 (m, 2H), 1.55-1.54 (d, J=7 Hz, 3H).

(53): MS (ESI) m/z: 196 (M+1)⁺, ¹H NMR (400 MHz, CD₃OD, HCl salt) δ 7.33-7.28 (m, 1H), 7.07-7.02 (m, 2H), 5.07 (s, 1H), 4.38-4.33 (m, 1H), 4.01-3.96 (m, 1H), 3.79-3.72 (m, 1H), 2.88-2.79 (m, 2H), 1.05-1.04 (d, J=6.4 Hz, 3H).

(52): MS (ESI) m/z: 196 (M+1)⁺, ¹H NMR (400 MHz, CD₃OD, HCl salt) δ 7.33-7.28 (m, 1H), 7.07-7.02 (m, 2H), 5.07 (s,1H), 4.37-4.33 (m, 1H), 4.00-3.96 (m, 1H), 3.79-3.72 (m, 1H), 2.87-2.79 (m, 2H), 1.05-0.98 (m, 3H).

1.14 (R)-(6-fluoroisochroman-1-yl)methanamine (34)

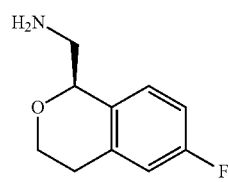

34

(R)-(6-fluoroisochroman-1-yl)methanamine (34) was prepared using General Procedure A and Scheme 1 starting with 2-(3-fluorophenyl)ethanol.

(R)-(6-fluoroisochroman-1-yl)methanamine (34): (ESI) m/z=182 [M+H]+, 1H NMR (500 MHz, CD3OD, HCl salt): 7.25~7.23 (m, 1H), 7.03~7.00 (m, 2 H), 5.01 (d, J=9 Hz, 1H), 4.23~4.19 (m, 1H), 3.87~3.82 (m, 1H), 3.51-3.55 (m, 1H), 3.23~3.19 (m, 1H), 3.07~3.00 (m, 1H), 2.81~2.76 (m, 1H).

1.15 Preparation of (S)-(5-chloroisochroman-1-yl)methanamine (66) and (R)-(5-chloroisochroman-1-yl)methanamine (67)

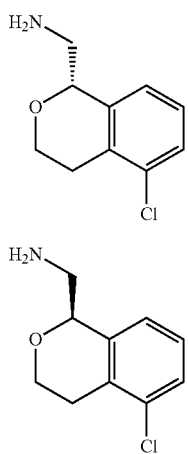

(S)-(5-chloroisochroman-1-Amethanamine (66) and (R)-(5-chloroisochroman-1-Amethanamine (67) were prepared using General Procedure A and Scheme 1 starting with 2-(2-chlorophenyl)ethan-1-ol and 2,2-dimethoxyethanamine.

(S)-(5-chloroisochroman-1-Amethanamine (66): MS (ESI) m/z: 198 [M+H]+, 1H NMR (400 MHz, CD3OD, HCl salt) δ 7.39 (d, J=8 Hz, 1H), 7.28 (t, J=8 Hz, 1H), 7.19 (d, J=7.6 Hz, 1H), 5.04-5.02 (m, 1H), 4.30-4.25 (m, 1H), 3.90-3.84 (m, 1H), 3.58-3.54 (m, 1H), 3.26-3.21 (m, 1H), 2.99-2.84(m, 2H).

(R)-(5-chloroisochroman-1-Amethanamine (67): MS (ESI) m/z: 198 [M+H]+, 1H NMR (400 MHz, CD3OD, HCl salt) δ 7.39 (d, J=8 Hz, 1H), 7.28 (t, J=8 Hz, 1H), 7.19 (d, J=7.6 Hz, 1H), 5.03-5.01 (m, 1H), 4.30-4.25 (m, 1H), 3.90-3.84 (m, 1H), 3.57-3.53 (m, 1H), 3.26-3.21 (m, 1H), 2.97-2.84 (m, 2H).

1.16 Preparation of (S)-1-(7-chloroisochroman-1-yl)-N-methylmethanamine (64) and (R)-1-(7-chloroisochroman-1-yl)-N-methylmethanamine (65)

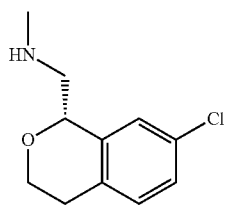

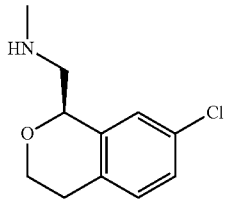

(S)-1-(7-chloroisochroman-1-yl)-N-methylmethanamine (64) and (R)-1-(7-chloroisochroman-1-yl)-N-methylmethanamine (65) were prepared using General Procedure A and Scheme 1 starting with 2-(4-chlorophenyl)ethan-1-ol and 2,2-dimethoxy-N-methylethanamine.

(S)-1-(7-chloroisochroman-1-yl)-N-methylmethanamine (64): MS (ESI) m/z: 212 [M+H]+, 1H NMR (400 MHz, CD3OD, HCl salt) δ 7.30-7.22 (m, 3H), 5.08-5.06 (m, 1H), 4.26-4.21 (m, 1H), 3.88-3.82 (m, 1H), 3.64-3.60 (m, 1H), 3.37-3.32 (m, 1H), 3.04-2.96 (m, 1H), 2.80-2.72 (m, 4H).

(R)-1-(7-chloroisochroman-1-yl)-N-methylmethanamine (65): MS (ESI) m/z: 212 [M+H]+, 1H NMR (400 MHz, CD3OD, HCl salt) δ 7.30-7.22 (m, 3H), 5.08-5.06 (m, 1H), 4.26-4.20 (m, 1H), 3.88-3.82 (m, 1H), 3.64-3.60 (m, 1H), 3.37-3.32 (m, 1H), 3.04-2.96 (m, 1H), 2.80-2.74 (m, 4H).

1.17 Preparation of (S)-1-(5-methoxyisochroman-1-yl)-N-methylmethanamine (62) and
(R)-1-(5-methoxyisochroman-1-yl)-N-methylmethanamine (63)

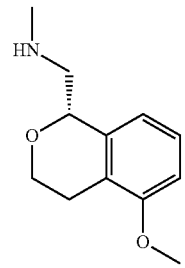

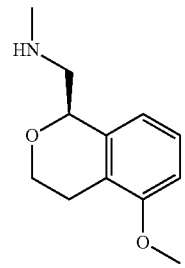

(S)-1-(5-methoxyisochroman-1-yl)-N-methylmethanamine (62) and (R)-1-(5-methoxyisochroman-1-yl)-N-methylmethanamine (63) were prepared using General Procedure A and Scheme 1 starting with 2-(2-methoxyphenyl)ethan-1-ol and 2,2-dimethoxy-N-methylethanamine.

(S)-1-(5-methoxyisochroman-1-yl)-N-methylmethanamine (62): MS (ESI) m/z: 208 [M+H]+, 1H NMR (500 MHz, CD3OD, HCl salt) δ 7.25 (t, J=8 Hz, 1H), 6.90 (d, J=8.5 Hz, 1H), 6.80 (d, J=7.5 Hz, 1H), 5.07-5.04 (m, 1H), 4.26-4.21 (m, 1H), 3.86 (s, 3H), 3.84-3.79 (m, 1H), 3.62-3.58 (m, 1H), 3.32-3.29 (m, 1H), 2.79-2.77 (m, 5H).

R)-1-(5-methoxyisochroman-1-yl)-N-methylmethanamine (63): MS (ESI) m/z: 208 [M+H]⁺, ¹H NMR (400 MHz, CD₃OD, HCl salt) δ 7.25 (t, J=8 Hz, 1H), 6.90 (d, J=8.5 Hz, 1H), 6.80 (d, J=7.5 Hz, 1H), 5.06-5.04 (m, 1H), 4.26-4.21 (m, 1H), 3.86 (s, 3H), 3.84-3.79 (m, 1H), 3.62-3.58 (m, 1H), 3.32-3.28 (m, 1H), 2.79-2.77 (m, 5H).

1.18 Preparation of (R)-N-methyl-1-(5-(trifluoromethyl)isochroman-1-yl-methanamine (79) and (S)-N-methyl-1-(5-(trifluoromethyl)isochroman-1-yl)-methanamine (78)

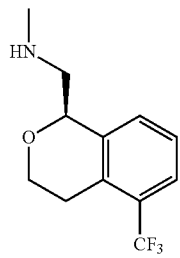

79

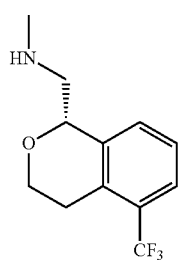

78

(R)-N-methyl-1-(5-(trifluoromethyl)isochroman-1-yl-methanamine (79) and (S)-N-methyl-1-(5-(trifluoromethyl)isochroman-1-yl)-methanamine (78) were prepared using General Procedure A and Scheme 1 starting with 2-(2-(trifluoromethyl)phenyl)ethanol and 2,2-dimethoxy-N-methylethanamine.

(R)-N-methyl-1-(5-(trifluoromethyl)isochroman-1-yl-methanamine (79): MS(ESI) m/z=246 [M+H]⁺. ¹H NMR (400 MHz, methanol-d₄): δ 7.67 (d, J=7.2 Hz, 1H), 7.53 (d, J=8.0 Hz, 1H), 7.46 (t, J=8.0 Hz, 1H), 5.22- 5.20 (m, 1H), 4.28- 4.23 (m, 1H), 3.91-3.85 (m, 1 H), 3.68-3.64 (m, 1H), 3.40-3.35 (m, 1H), 3.16-3.08 (m, 1H), 3.01-2.97 (m, 1H), 2.80 (s, 3 H).

(S)-N-methyl-1-(5-(trifluoromethyl)isochroman-1-yl)-methanamine (78): MS(ESI) m/z=246 [M+H]⁺. ¹H NMR (400 MHz, methanol-d₄) δ 7.67 (d, J=7.2 Hz, 1H), 7.53 (d, J=8.0 Hz, 1H), 7.46 (t, J=8.0 Hz, 1H), 5.22-5.20 (m, 1H), 4.28-4.23 (m, 1H), 3.91-3.85 (m, 1 H), 3.68-3.64 (m, 1H), 3.40-3.35 (m, 1H), 3.16-3.08 (m, 1H), 3.01-2.97 (m, 1H), 2.80 (s, 3 H).

1.19 Preparation of (R)-1-(6-chloroisochroman-1-yl)-N-methylmethanamine (81) and (S)-1-(6-chloroisochroman-1-yl)-N-methylmethanamine (80)

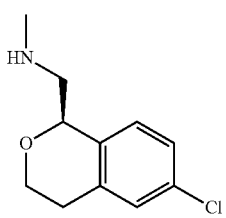

81

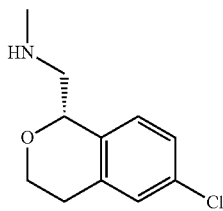

80

(R)-1-(6-chloroisochroman-1-yl)-N-methylmethanamine (81) and (S)-1-(6-chloroisochroman-1-yl)-N-methylmethanamine (80) were prepared using General Procedure A and Scheme 1 starting with 2-(3-chlorophenyl)ethanol and 2,2-dimethoxy-N-methylethanamine.

(R)-1-(6-chloroisochroman-1-yl)-N-methylmethanamine (81): MS (ESI): m/z=212 [M+H]⁺.

¹H NMR (400 MHz, D20-d2): δ 7.21-7.18 (m, 2 H), 7.07-7.05 (m, 1H), 5.07-5.04 (m, 1H), 4.07-4.02 (m, 1H), 3.79-3.73 (m, 1H), 3.45-3.35 (m, 2 H), 2.89-2.81 (m, 1H), 2.72-2.70 (m, 1H), 2.65 (s, 3 H).

(S)-1-(6-chloroisochroman-1-yl)-N-methylmethanamine (80): MS (ESI): m/z=212 [M+H]⁺.

¹H NMR (400 MHz, D20-d2): δ 7.20-7.18 (m, 2 H), 7.07-7.05 (m, 1H), 5.06-5.04 (m, 1H), 4.07-4.02 (m, 1H), 3.79-3.73 (m, 1H), 3.45-3.35 (m, 2 H), 2.89-2.81 (m, 1H), 2.72-2.70 (m, 1H), 2.65 (s, 3 H).

1.20 Preparation of (R)-(5-methylisochroman-1-yl)methanamine (73) and (S)-(5-methylisochroman-1-yl)methanamine (72)

73

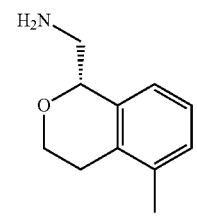

72

(R)-(5-methylisochroman-1-yl)methanamine (73) and (S)-(5-methyliso-chroman-1-yl)methanamine (72) were prepared using General Procedure A and Scheme 1 starting with 2-(o-tolyl)ethanol and 2,2-dimethoxy-ethanamine.

(R)-(5-methylisochroman-1-yl)methanamine (73): (ESI) m/z: 178 [M+H]⁺. ¹H NMR (400 MHz, MeOD-d₄) δ 7.19-7.13 (m, 2 H), 7.04-7.02 (m, 1H), 4.28-4.23 (m, 1H), 3.90-3.84 (m, 1H), 3.54-3.50 (dd, J=3.2, 13.2 Hz, 1H), 3.22-3.16 (dd, J=9.2, 13.2 Hz, 1H), 2.90-2.82 (m, 1H), 2.73-2.67 (m, 1H).

(S)-(5-methylisochroman-1-yl)methanamine (72): (ESI) m/z: 178 [M+H]⁺. ¹H NMR (400 MHz, MeOD-d₄) δ 7.19-7.13 (m, 2 H), 7.04-7.02 (m, 1H), 4.28-4.23 (m, 1H), 3.90-3.84 (m, 1H), 3.54-3.50 (dd, J=3.2, 13.2 Hz, 1H), 3.22-3.16 (dd, J=9.2, 13.2 Hz, 1H), 2.90-2.82 (m, 1H), 2.73-2.67 (m, 1H).

2. General procedure B 2.1 Preparation of (S)-1-(8-fluoroisochroman-1-yl)-N-methylmethanamine (25) and (R)-1-(8-fluoroisochroman-1-yl)-N-methylmethanamine (26)

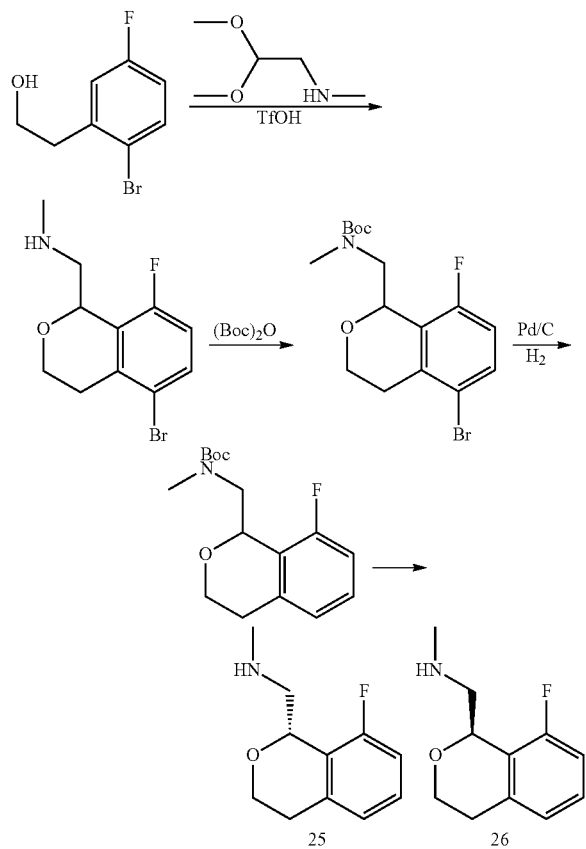

(a). 1-(5-bromo-8-fluoroisochroman-1-yl)-N-methylmethanamine

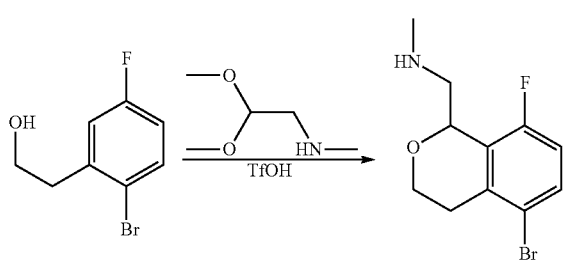

To a solution of 2-(2-bromo-5-fluorophenyl) ethanol (8 g, 36.5 mmol) in DCM (10 mL) was added 2, 2-dimethoxy-N-methylethanamine (6.51 g, 54.7 mmol) and trifluoromethanesulfonic acid (32.7 g, 218 mmol) at 0° C. The reaction was stirred at ambient temperature for 16 h. Upon completion, water was added to quench the reaction and sodium hydroxide (1N, aq.) was added until pH 10~11. The resulting solution was used for the next step without further purification.

(b). tert-butyl (5-bromo-8-fluormsochroman-1-yl) methyl (methyl) carbamate

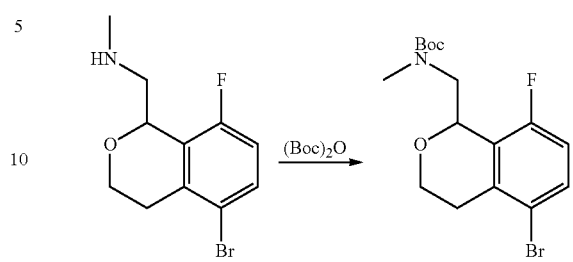

To a solution of 1-(5-bromo-8-fluoroisochroman-1-yl)-N-methylmethanamine (8 g, 29.1 mmol) in water (150 mL) was added di-tert-butyl dicarbonate (9.50 g, 43.6 mmol). The reaction was stirred at ambient temperature for 3 h. Upon completion, the mixture was extracted with DCM (100mL ×2). The organic layers were dried and concentrated to give the crude which was purified by silica gel chromatography (eluted from PE to PE: EA=20:1) to give the desired compound (9.26 g) as a colorless oil.

(c). tert-butyl (8-fluormsochroman-1-yl) methyl (methyl) carbamate

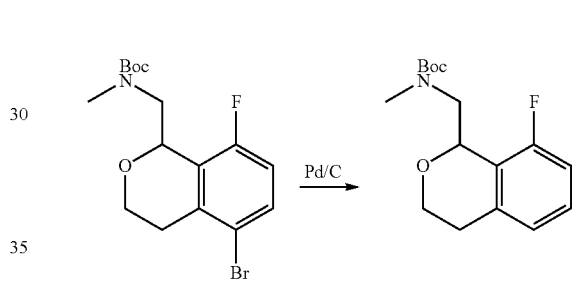

To a solution of tert-butyl ((5-bromo-8-fluoroisochroman-1-yl) methyl) (methyl) carbamate (9.26 g, 24.7 mmol) in methanol (100 mL) was added Pd/C (2.59 g, 24.7 mmol). The reaction was stirred at ambient temperature for 4 h under H2 atmosphere. Upon completion, the mixture was filtered and concentrated. The crude was dissolved in EA (100 mL), washed with water (100 mL ×2), dried and concentrated to give the crude product (6.7 g), which was used for next step without further purification.

(d). (S)-1-(8-fluoroisochroman-1-yl)-N-methylmethanamine (25) and (R)-1-(8-fluoroisochroman-1-yl)-N-methylmethanamine (26)

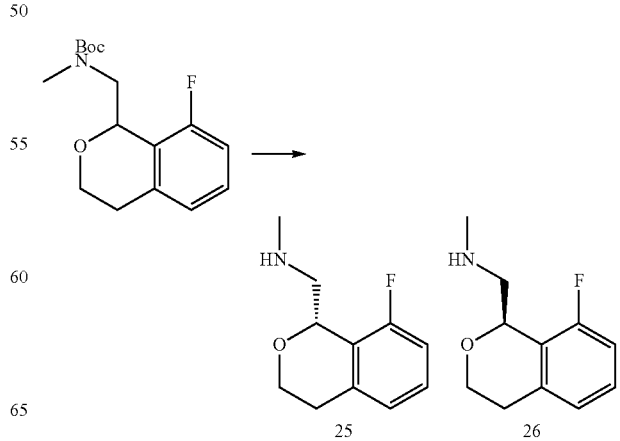

To a solution of tert-butyl ((8-fluoroisochroman-1-yl)methyl)(methyl) carbamate (6.7 g, 22.6 mmol) in EA (20 mL) was added HCl/EA (3M, 30 mL). The mixture was stirred at ambient temperature for 16 h. Upon completion, the solvent was removed and the residue was dissolved in DCM (50 mL). The solution was neutralized with sodium hydroxide (15%, aq.), washed with water (50 mL ×2) and brine (50 mL), dried and concentrated to get the racemic mixture of the desired product (3.6 g) as an oil. The mixture was separated by chiral HPLC {Column: AY-H (250×4.6 mm Sum) and Mobile Phase: n-Hexane (0.1% DEA): ethanol (0.1% DEA)=90:10} to give (R)-1-(8-fluoroisochroman-1-yl)-N-methylmethanamine (1.25 g, 26) as an oil and (S)-1-(8-fluoroisochroman-1-yl)-N-methylmethanamine (1.01 g, 25) as an oil.

To a solution of (S)-1-(8-fluoroisochroman-1-yl)-N-methylmethanamine (1.01 g, 25) in ethyl acetate (20 mL) was added HCl in ethyl acetate (3M, 2 mL) at 0° C. The mixture was stirred at ambient temperature for 30 mins and solvent was removed. The residue was washed with ethyl acetate (30 mL), filtered and dried to give the HCl salt of (S)-1-(8-fluoroisochroman-1-yl)-N-methylmethanamine (25).

To a solution of (R)-1-(8-fluoroisochroman-1-yl)-N-methylmethanamine (1.25 g, 26) in ethyl acetate (20 mL) was added HCl in ethyl acetate (3M, 2 mL) at 0° C. The mixture was stirred at ambient temperature for 30 mins and solvent was removed. The residue was washed with ethyl acetate (30 mL), filtered and dried to give the HCl salt of (R)-1-(8-fluoroisochroman-1-yl)-N-methylmethanamine (26).

(S)-1-(8-fluoroisochroman-1-yl)-N-methylmethanamine (1.01 g, 25): MS (ESI): m/z=196 [M+H]$^+$. $^1$H NMR (400 MHz, CD$_3$OD, HCl salt) δ 7.34~7.28 (m, 1H), 7.08 (d, J=7.6 Hz, 1H), 7.04~6.99 (m, 1H), 5.26~5.24 (m, 1H), 4.19-4.14 (m, 1H), 3.89~3.83 (m, 1H), 3.59~3.54 (m, 1H), 3.43~3.37 (m, 1H), 2.96~2.93 (m, 1H), 2.89~2.84 (m, 1H), 2.77 (s, 3H).

(R)-1-(8-fluoroisochroman-1-yl)-N-methylmethanamine (1.25 g, 26): MS (ESI): m/z=196 [M+H]$^+$. $^1$H NMR (400 MHz, CD$_3$OD, HCl salt) δ 7.34~7.29 (m, 1H), 7.08 (d, J=7.6 Hz, 1H), 7.04~6.99 (m, 1H), 5.26~5.24 (m, 1H), 4.19-4.14 (m, 1H), 3.89~3.83 (m, 1H), 3.59~3.54 (m, 1H), 3.43~3.37 (m, 1H), 2.96~2.93 (m, 1H), 2.89~2.84 (m, 1H), 2.78 (s, 3H).

2.2 Preparation of (S)-1-(6,9-dihydro-7H-[1,3]dioxolo[4,5-h]isochromen-9-yl)-N-methylmethanamine (1) and (R)-1-(6,9-dihydro-7H-[1,3]dioxolo[4,5-h]isochromen-9-yl)-N-methylmethanamine (2)

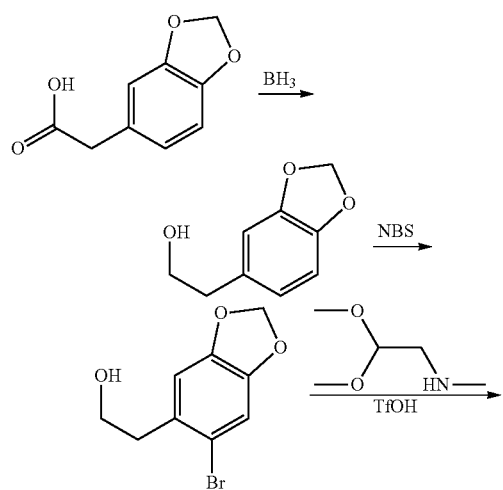

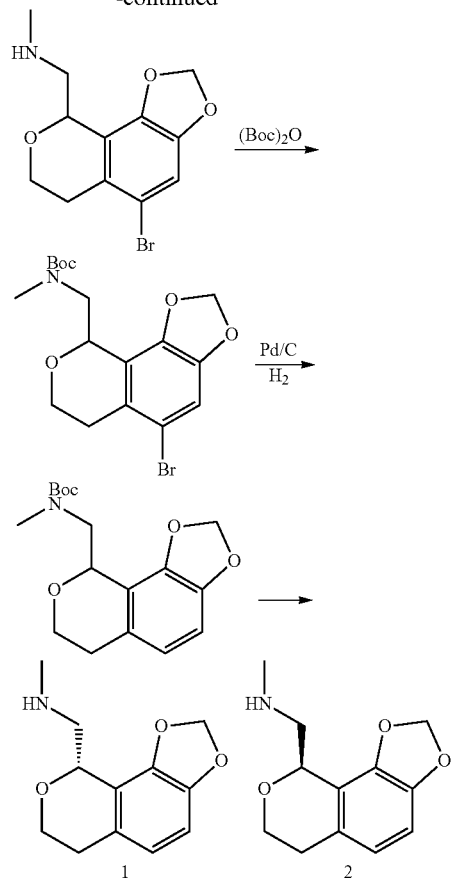

(a). 2-(benzo[d][1,3]thoxol-5-yl)ethan-1-ol

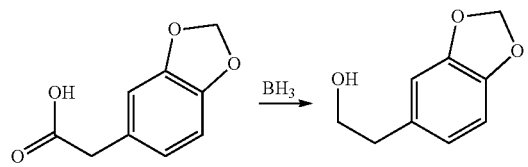

To a solution of 2-(benzo[d][1,3]dioxol-5-yl)acetic acid (25 g, 138 mmol) in THF (100 mL) was added BH3/THF (1 M, 160 mL) at 0° C. The reaction was stirred at ambient temperature until complete (~16 h). Upon completion, ice water was added to quench the reaction and the mixture was extracted with EA, dried, and concentrated. The crude material (21.3 g, purity ~93%) was used for next step without further purification. MS(ESI): m/z 149 [M-18+H]$^+$ (b). 2-(6-bromobenzo[d][1,3]choxol-5-yl)ethan-1-ol

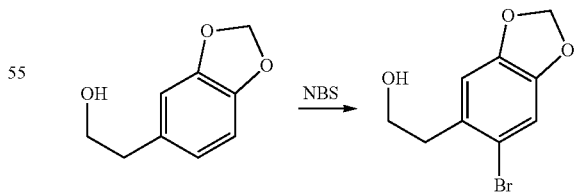

To a solution of 2-(benzo[d][1,3]dioxo1-5-yl)ethan-1-ol (22 g, 132 mmol) in DCM (500 mL) was added N-bromosuccinimide (25.8 g, 145 mmol). The reaction was stirred at ambient temperature until complete (~3 h). Upon completion, the mixture was washed with NaHSO3, brine, dried and concentrated. The crude material (24 g, purity ~90%) was used for next step without further purification. MS(ESI): m/z 227,229 [M-18+H]$^+$.

(c). 1-(5-bromo-6,9-dihydro-7H-[1,3]dioxolo[4,5-h]isochromen-9-yl)-N-methylmethanamine

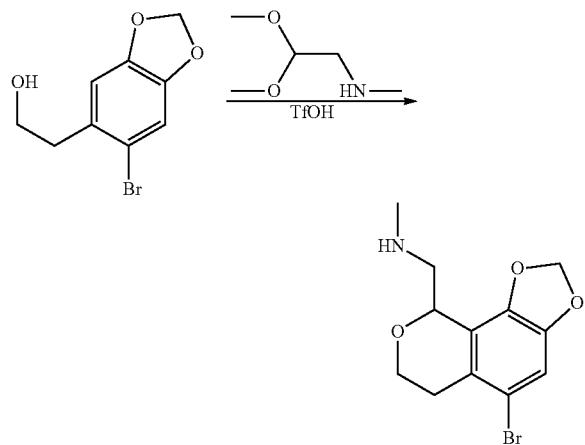

To a solution of 2-(6-bromobenzo[d][1,3]dioxol-5-yl)ethan-1-ol (8.76 g, 35.7.5 mmol) in DCM (50 mL) was added 2, 2-dimethoxy-N-methylethanamine (5.10 g, 42.8 mmol) and trifluoromethanesulfonic acid (26.7 g, 178 mmol) at 0° C. The reaction was stirred at ambient temperature until complete (~16 h). Upon completion, ice water was added to quench the reaction and sodium hydroxide (1N, aq.) was added until pH 9~10. The resulting solution was extracted with DCM, dried and concentrated. The crude material (purity ~95%) was used for next step without further purification. MS(ESI): m/z 300,302 [M, M+2]$^+$ (d). tert-butyl ((5-bromo-6,9-dihydro-7H-[1,3]dioxolo[4,5-h]isochromen-9-yl)methyl)(methyl) carbamate

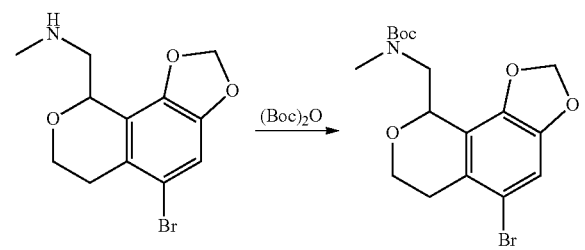 [SMILES: "(Boc)2O" ; CNCC1OCCc2c(Br)cc3c(c21)OCO3 ; CN(CC1OCCc2c(Br)cc3c(c21)OCO3)C(=O)OC(C)(C)C]

To a solution of 1-(5-bromo-6,9-dihydro-7H-[1,3]dioxolo[4,5-h]isochromen-9-yl)-N-methylmethanamine (9.2 g, 30.6 mmol) in DCM (100 mL) was added Et$_3$N (3.09 g, 30.6 mmol) and di-tert-butyl dicarbonate (9.34 g, 42.8 mmol). The reaction was stirred at ambient temperature for 16 h. The mixture was then washed with water, dried and concentrated). The resulting oil was purified by silica gel chromatography (eluted from PE: EA=100:0 to 85:15) to give the desired compound (12.0 g, 29.9 mmol, Yield: 98%) as a colorless oil. MS(ESI): m/z 300,302 [M-100, M-100+2]$^+$ (e). tert-butyl ((6,9-dihydro-7H-[1,3]clioxolo[4,5-h]isochromen-9-yl)methyl)(methyl)carbamate

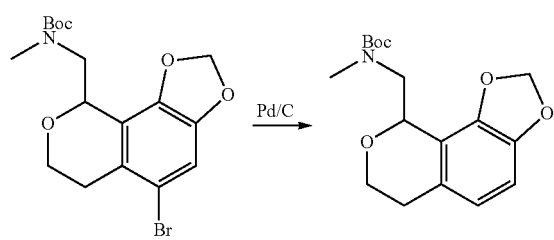 [SMILES: CN(CC1OCCc2c(Br)cc3c(c21)OCO3)C(=O)OC(C)(C)C ; CN(CC1OCCc2ccc3c(c21)OCO3)C(=O)OC(C)(C)C]

To a solution of tert-butyl ((5-bromo-6,9-dihydro-7H-[1,3]dioxolo[4,5-h]isochromen-9-yl)methyl)(methyl) carbamate (12.0 g, 29.9 mmol) in methanol (100 mL) was added Pd/C (3.19 g, 29.9 mmol). The reaction was stirred at ambient temperature for 3 h under H$_2$ atmosphere. Upon completion, the mixture was filtered and concentrated. The crude was dissolved in EA, washed with water, dried and concentrated to give the crude product, which was used for next step without further purification. MS(ESI): m/z 266,222 [M-56+1,M-100+1]$^+$ (f). (S)-1-(6,9-dihydro-7H-[1,3]dioxolo[4,5-h]isochromen-9-yl)-N-methylmethanamine (1) and (R)-1-(6,9-dihydro-7H-[1,3]dioxolo[4,5-h]isochromen-9-yl)-N-methylmethanamine (2)

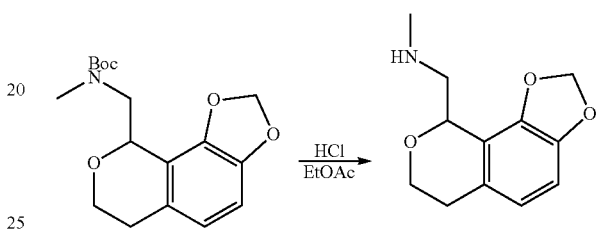

To a solution of tert-butyl ((6,9-dihydro-7H-[1,3]dioxolo[4,5-h]isochromen-9-yl)methyl)(methyl)carbamate (14 g, 43.5 mmol) in EtOAc (50 mL) was added HCl/dioxane (50 mL) at 0° C. The mixture was stirred at ambient temperature for 3 h. Upon completion, the mixture was filtered and the residue was dissolved in water, neutralized with NH$_4$OH (50 mL) and extracted with EtOAc (50 mL×2), the combined organic phase was washed with brine (100 mL), dried over Na$_2$SO$_4$ and concentrated to dry to get the racemic mixture of the desired product (7.31 g, 76%) as a white solid.

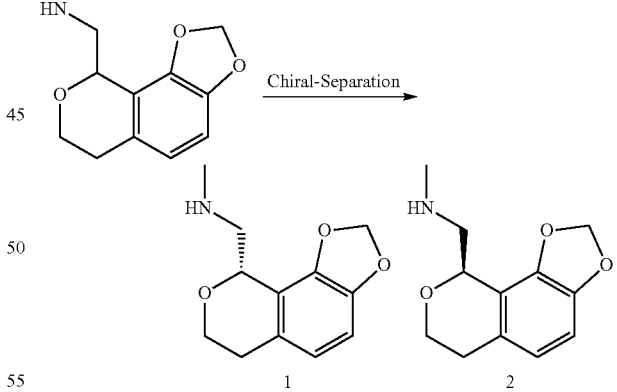

The racemic mixture (7.31 g) was separated by chiral HPLC {Column: Chiralpak IC (250×4.6 mm, 5 um) and Mobile Phase: n-Hexane (0.1% DEA): ethanol (0.1% DEA)=80:20}.

(S)-1-(6,9-dihydro-7H-[1,3]dioxolo[4,5-h]isochromen-9-yl)-N-methylmethanamine (1) (3.0 g, Yield: 41%) as an oil.
$^1$H NMR (400 MHz, CDCl$_3$): δ 6.68~6.70 (d, J=8 Hz, 1H), 6.62~6.60 (d, J=8 Hz, 1H), 5.97 (d, J=1.2 Hz, 1H), 5.89 (d, J=1.6 Hz, 1H), 4.94~4.97 (dd, J$_1$=8.4, J$_2$=2.2 Hz, 1H), 4.06~4.11 (m, 1H), 3.72~3.78 (m, 1H), 3.15~3.19 (dd, $J_1$=12.6, $J_2$=2.8 Hz, 1H), 2.94~2.99 (m, 1H), 2.82~2.86 (m, 1H), 2.65~2.70 (m, 1H), 2.50 (s, 3H).

(R)-1-(6,9-dihydro-7H-[1,3]dioxolo[4,5-h]isochromen-9-yl)-N-methylmethanamine (2) (3.0 g, Yield: 41%) as an oil. $^1$H NMR (400 MHz, CDCl$_3$): δ 6.69~6.71 (d, J=7.9 Hz, 1H), 6.62~6.60 (d, J=7.9 Hz, 1H), 5.98~6.97 (d, J=1.4 Hz, 1H), 5.90 (d, J=1.4 Hz, 1H), 4.95~4.98 (dd, $J_1$=8.4, $J_2$=2.3 Hz, 1H), 4.07~4.12 (m, 1H), 3.73~3.79 (m, 1H), 3.16~3.19 (dd, $J_1$=12.6, $J_2$=2.8 Hz, 1H), 2.94~3.0 (m, 1H), 2.83~2.87 (m, 1H), 2.66~2.71 (m, 1H), 2.51 (s, 3H).

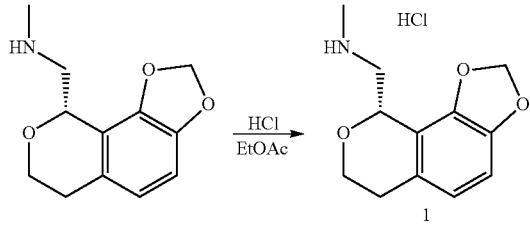 [SMILES: "EtOAc" ; CNC[C@H]1OCCc2ccc3c(c21)OCO3 ; Cl ; CNC[C@H]1OCCc2ccc3c(c21)OCO3 ; Cl]

1

To a solution of (S)-1-(7,9-dihydro-6H-[1,3]dioxolo[4,5-h]isochromen-9-yl)-N-methylmethanamine (1) (3.0 g) in EtOAc (50 mL) was added HCl/EA (4M, 5.5 mL) at 0° C. The reaction was stirred at ambient temperature for 30 min. Upon the completion, the solvent was removed and the residue was the desired compound (1, 3.26 g, Yield: 93%) hydrochloride salt as a white solid. Chiral HPLC: Column Chiralpak IC (250×4.6 mm, 5 um; Mobile Phase: n-Hexane (0.1% DEA):EtOH (0.1% DEA)=80:20; Temp=40° C.; Flow rate=1.0 mL/min; Ret Time=7.17 min; Enantiopurity: 100% ee. MS(ESI): m/z 222 [M+H]$^+$. $^1$H NMR (500 MHz, CD$_3$OD): δ 6.78 (d, J=8 Hz, 1H), 6.71 (d, J=8 Hz, 1H), 6.01 (s, 1H), 5.96 (s, 1H), 5.10 (m, 1H), 4.18 (m, 1H), 3.82 (m, 1H), 3.67 (m, 1H), 3.41 (m, 1H), 2.88 (m, 1H), 2.76 (s, 3H), 2.74~2.68 (m, 1H).

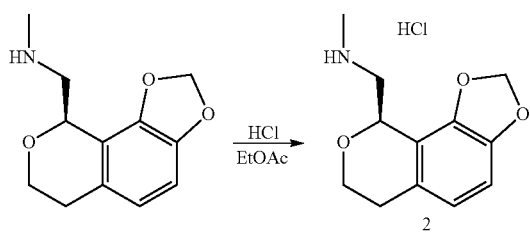 [SMILES: "EtOAc" ; CNC[C@@H]1OCCc2ccc3c(c21)OCO3 ; Cl ; CNC[C@@H]1OCCc2ccc3c(c21)OCO3 ; Cl]

2

To a solution of (R)-1-(7,9-dihydro-6H-[1,3]dioxolo[4,5-h]isochromen-9-yl)-N-methylmethanamine (2) (3.0 g) in EtOAc (50 mL) was added HO/EA (4M, 5.5 mL) at 0° C. The reaction was stirred at ambient temperature for 30 min. Upon the completion, the solvent was removed and the residue was the desired compound (2, 3.26 g, Yield: 93%) hydrochloride salt as a white solid. Chiral HPLC: Column Chiralpak IC (250×4.6 mm, 5 um; Mobile Phase: n-Hexane (0.1% DEA):EtOH (0.1% DEA)=80:20; Temp=40° C.; Flow rate=1.0 mL/min; Ret Time=6.18 min; Enantiopurity: 100% ee. MS(ESI): m/z 222 [M+H]$^+$. $^1$H NMR (500 MHz, CD$_3$OD): δ 6.78 (d, J=8 Hz, 1H), 6.71 (d, J=8 Hz, 1H), 6.01 (s, 1H), 5.96 (s, 1H), 5.10 (m, 1H), 4.18 (m, 1H), 3.82 (m, 1H), 3.67 (m, 1H), 3.41 (m, 1H), 2.88 (m, 1H), 2.76 (s, 3H), 2.74-2.68 (m, 1H).

2.3 Preparation of (R)-(8-fluoroisochroman-1-yl)methanamine (35)

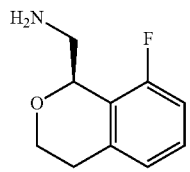

35

(R)-(8-fluoroisochroman-1-yl)methanamine (35) was prepared using General Procedure B and Scheme 2 starting with 2-(5-bromo-2-fluorophenyl)ethanol and 2,2-dimethoxyethanamine.

(R)-(8-fluoroisochroman-1-yl)methanamine (35): MS (ESI) m/z 182 [M+H]$^+$, $^1$H NMR (500 MHz, CD$_3$OD, HCl salt): 7.34~7.30 (m, 1H), 7.09 (d, J=8.0 Hz, 1H), 7.04~7.00 (m, 1H), 5.19-5.18 (m, 1H), 4.18~4.14 (m, 1H), 3.89~3.85 (m, 1H), 3.51 (d, J=13 Hz, 1H), 3.33-3.27 (m, 1H), 2.99-2.94 (m, 1H), 2.89~2.84 (m, 1H).

2.4 Preparation of (S)-1-(8-chloroisochroman-1-yl)-N-methylmethanamine (36) and (R)-1-(8-chloroisochroman-1-yl)-N-methylmethanamine (37)

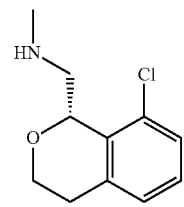

36

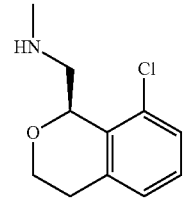

37

(S)-1-(8-chloroisochroman-1-yl)-N-methylmethanamine (36) and (R)-1-(8-chloroisochroman-1-yl)-N-methylmethanamine (37) were prepared using General Procedure B and Scheme 2 starting with 2-(2-bromo-5-chlorophenyl)ethanol and 2,2-dimethoxy-N-methylethanamine.

(S)-1-(8-chloroisochroman-1-yl)-N-methylmethanamine (36): MS (ESI): m/z=212 [M+H]$^+$. $^1$H NMR (400 MHz, CD$_3$OD, HCl salt): 7.33~7.28 (m, 2 H), 7.23 (d, J=6.4 Hz, 1H), 5.27 (dd, J=2.4, 9.6 Hz, 1H), 4.17~4.11 (m, 1H), 3.9~3.86 (m, 1H), 3.64 (dd, J=3.2, 13.6 Hz, 1H), 3.44 (dd, J=10.0, 13.2 Hz, 1H), 2.94~2.90 (m, 2 H), 2.80 (s, 3 H).

(R)-1-(8-chloroisochroman-1-yl)-N-methylmethanamine (37): MS (ESI): m/z=212 [M+H]$^+$. $^1$H-NMR (400 MHz, CD$_3$OD, HCl salt): 7.34~7.28 (m, 2 H), 7.23 (d, J=6.8 Hz, 1H), 5.28 (dd, J=2.8, 10.4 Hz, 1H), 4.17~4.11 (m, 1H), 3.91~3.86 (m, 1H), 3.64 (dd, J=2.8, 13.2 Hz, 1H), 3.44 (dd, J=10.0, 12.8 Hz, 1H), 2.94~2.90 (m, 2 H), 2.80 (s, 3 H).

2.5 Preparation of (S)-N-methyl-1-(8-methylisochroman-1-yl)methanamine (40) and (R)-N-methyl-1-(8-methylisochroman-1-yl)methanamine (41)

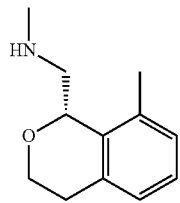

40

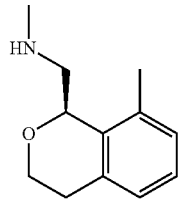

41

(S)-N-methyl-1-(8-methylisochroman-1-yl)methanamine (40) and (R)-N-methyl-1-(8-methylisochroman-1-yl)methanamine (41) were prepared using General Procedure B and Scheme 2 starting with 2-(2-bromo-5-methylphenyl)ethanol and 2,2-dimethoxy-N-methylethanamine.

(S)-N-methyl-1-(8-methylisochroman-1-yl)methanamine (40): MS (ESI): m/z=192 [M+H]$^+$. $^1$H NMR (500 MHz, CD$_3$OD, HCl salt): 7.19~7.16 (m, 1H), 7.10~7.04 (m, 2 H), 5.26-5.24 (m, 1H), 4.17~4.14 (m, 1H), 3.84~3.80 (m, 1H), 3.38~3.35 (m, 1H), 3.33~3.27 (m, 1H), 2.89~2.88 (m, 2 H), 2.80 (s, 3 H)), 2.33 (s, 3 H).

(R)-N-methyl-1-(8-methylisochroman-1-yl)methanamine (41): MS (ESI): m/z=192 [M+H]$^+$. $^1$H NMR (400 MHz, CD$_3$OD, HCl salt): 7.19~7.16 (m, 1H), 7.10~7.04 (m, 2H), 5.26~5.25 (m, 1H), 4.17~4.14 (m, 1H), 3.84~3.80 (m, 1H), 3.38~3.35 (m, 1H), 3.33~3.27 (m, 1H), 2.89~2.88 (m, 2 H), 2.80 (s, 3 H)), 2.33 (s, 3 H).

2.6 Preparation of compounds (48), (49), (50), and (51): (S)-1-((R)-8-fluoroisochroman-1-yl)ethan-1-amine, (R)-1-((S)-8-fluoroisochroman-1-yl)ethan-1-amine, (S)-1-((S)-8-fluoroisochroman-1-yl)ethan-1-amineand (R)-1-((R)-8-fluoroisochroman-1-yl)ethan-1-amine, order unknown

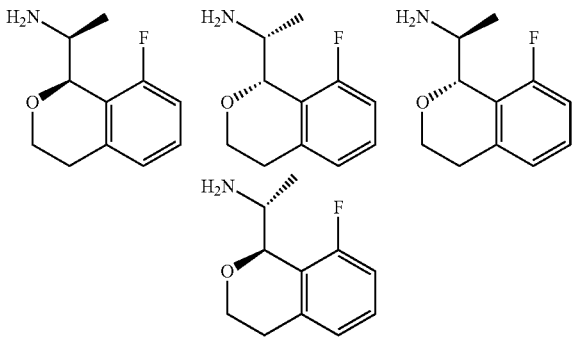

((S)-1-((R)-8-fluoroisochroman-1-yl)ethan-1-amine, (R)-1-((S)-8-fluoroisochroman-1-yl)ethan-1-amine, (S)-1-((S)-8-fluoroisochroman-1-yl)ethan-1-amine and (R)-1-((R)-8-fluoroisochroman-1-yl)ethan-1-amine were prepared using General Procedure B and Scheme 2 starting with 2-(2-bromo-5-fluorophenyl) ethanol and tert-butyl (1-oxopropan-2-yl)carbamate. All four stereoisomers were synthesized and characterized.

(48): MS (ESI): m/z=196 [M+H]$^+$. $^1$H NMR (400 MHz, CD$_3$OD, HCl salt) δ 7.35~7.29 (dd, J$_1$=13.7, J$_2$=7.9 Hz, 1H), 7.10~7.08 (d, J=7.6 Hz, 1H), 7.04~6.99 (dd, J$_1$=10.9, J$_2$=8.5 Hz, 1H), 5.25 (s, 1H), 4.31~4.27 (m, 1H), 4.09~4.00 (m, 1H), 3.74~3.68 (td, J$_1$=11.6, J$_2$=2.4 Hz, 1H), 3.11~2.98 (m, 1H), 2.75~2.71 (d, J=16.3 Hz, 1H), 1.06~1.05 (d, J=6.7 Hz, 3H).

(49): MS (ESI): m/z=196 [M+H]$^+$. $^1$H NMR (400 MHz, CD$_3$OD, HCl salt) δ 7.35~7.29 (dd, J$_1$=13.7, J$_2$=7.9 Hz, 1H), 7.10~7.08 (d, J=7.6 Hz, 1H), 7.04~6.99 (dd, J$_1$=10.9, J$_2$=8.5 Hz, 1H), 5.25 (s, 1H), 4.31~4.27 (m, 1H), 4.09~4.00 (m, 1H), 3.74~3.68 (td, J$_1$=11.6, J$_2$=2.4 Hz, 1H), 3.11~2.98 (m, 1H), 2.75~2.71 (d, J=16.3 Hz, 1H), 1.06~1.05 (d, J=6.7 Hz, 3H).

(50): MS (ESI): m/z=196 [M+H]$^+$. $^1$H NMR (400 MHz, CD$_3$OD) δ 7.35~7.31 (dd, J$_1$=13.8, J$_2$=7.8 Hz, 1H), 7.13~7.01 (m, 2H), 5.07 (s, 1H), 4.34~4.28 (dd, J$_1$=11.0, J$_2$=5.0 Hz, 1H), 3.95~3.93 (m, 1H), 3.74~3.67 (td, J$_1$=11.3, J$_2$=2.3 Hz, 1H), 3.13~3.05 (m, 1H), 2.75~2.71 (d, J=16.3 Hz, 1H), 1.51~1.50(d, J=6.8 Hz, 3H).

(51): MS (ESI): m/z=196 [M+H]$^+$. $^1$H NMR (400 MHz, CD$_3$OD) δ 7.35~7.31 (dd, J$_1$=13.8, J$_2$=7.8 Hz, 1H), 7.13~7.01 (m, 2H), 5.07 (s, 1H), 4.34~4.28 (dd, J$_1$=11.0, J$_2$=5.0 Hz, 1H), 3.95~3.93 (m, 1H), 3.74~3.67 (td, J$_1$=11.3, J$_2$=2.3 Hz, 1H), 3.13~3.05 (m, 1H), 2.75~2.71 (d, J=16.3 Hz, 1H), 1.51~1.50 (d, J=6.8 Hz, 3H).

2.7 Preparation of compounds (55) and (54): (S)-14(S)-6,9-dihydro-7H-[1,3]dioxolo[4,5-h]isochromen-9-yl)ethan-1-amine and (S)-14(R)-6,9-dihydro-7H-[1,3]dioxolo[4,5-h]isochromen-9-yl)ethan-1-amine, order unknown

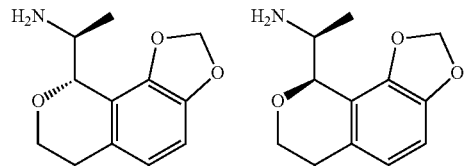 [SMILES: C[C@H](N)[C@H]1OCCc2ccc3c(c21)OCO3 ; C[C@H](N)[C@@H]1OCCc2ccc3c(c21)OCO3]

((S)-1-((S)-6,9-dihydro-7H-[1,3]dioxolo[4,5-h]isochromen-9-yl)ethan-1-amine and (S)-1-((R)-6,9-dihydro-7H-[1,3]dioxolo[4,5-h]isochromen-9-yl)ethan-1-amine were prepared using General Procedure B and Scheme 2 starting with 2-(6-bromobenzo[d][1,3]dioxol-5-yl)ethanol and (S)-tert-butyl (1-oxopropan-2-yl)carbamate. These two stereoisomers were synthesized and characterized.

(55): MS (ESI): m/z=222 [M +H]$^+$. $^1$H NMR (400 MHz, CD$_3$OD, HCl salt): δ 6.82 (d, J=8.0 Hz, 1H), 6.74 (d, J=7.6 Hz, 1H), 6.05-5.97 (m, 2 H), 4.91 (s, 1H), 4.29-4.25 (m, 1H), 4.17-4.13 (m, 1H), 3.77-3.71 (m, 1H), 3.06-2.98 (m, 1H), 2.66 (d, J=16.0 Hz, 1H), 1.52 (d, J=7.2 Hz, 3 H).

(54): MS (ESI): m/z=222 [M +H]$^+$. $^1$H NMR (400 MHz, CD$_3$OD, HCl salt): δ 6.80-6.71 (m, 2H), 6.01-5.94 (m, 2 H), 5.09 (s, 1H), 4.30-4.25 (m, 1H), 4.16 (s, 1H), 3.77-3.71 (m, 1H), 3.00-2.92 (m, 1H), 2.66 (d, J=15.6 Hz, 1H), 1.12 (d, J=6.8 Hz, 3H).

2.8 Preparation of compounds (57) and (56): (S)-1-((S)-6,9-dihydro-7H-[1,3]dioxolo[4,5-h]isochromen-9-yl)-N-methylethan-1-amine and (S)-1-((R)-6,9-dihydro-7H-[1,3]dioxolo[4,5-h]isochromen-9-yl)-N-methylethan-1-amine, order unknown

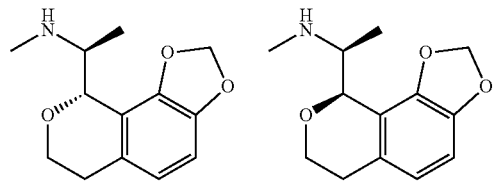

(S)-1-((S)-6,9-dihydro-7H-[1,3]dioxolo[4,5-h]iso-chromen-9-yl)-N-methylethan-1-amine and (S)-1-((R)-6,9-dihydro-7H-[1,3]dioxolo[4,5-h]isochromen-9-yl)-N-methylethan-1-amine were prepared using General Procedure B and Scheme 2 starting with 2-(6-bromobenzo[d][1,3]dioxol-5-yl)ethanol and tert-butyl (S)-methyl(1-oxopropan-2-yl)carbamate. These two stereoisomers were synthesized and characterized.

(57): MS (ESI): m/z=236 [M +H]$^+$. $^1$H NMR (400 MHz, CD$_3$OD, HCl salt): δ 6.84 (d, J=8.0 Hz, 1H), 6.76 (d, J=8.0 Hz, 1H), 6.06-5.97 (m, 2 H), 4.96 (s, 1H), 4.31-4.27 (m, 1H), 4.10-4.05 (m, 1H), 3.79-3.73 (m, 1H), 3.07-2.99 (m, 1H), 2.69 (d, J=16.0 Hz, 1H), 2.59 (s, 3H), 1.55 (d, J=6.8 Hz, 3H).

(56): MS (ESI): m/z=236 [M +H]+. $^1$H NMR (400 MHz, CD$_3$OD, HCl salt): δ 6.80 (d, J=8.0 Hz, 1H), 6.74 (d, J=8.0 Hz, 1H), 6.01-5.95 (m, 2H), 5.23 (s, 1H), 4.29-4.25 (m, 1H), 4.03-3.97 (m, 1H), 3.79-3.73 (m, 1H), 3.01-2.93 (m, 1H), 2.81 (s, 3 H), 2.67 (d, J=16.4 Hz, 1H), 1.14 (d, J=6.8 Hz, 3 H).

2.9 Preparation of (S)-(6,9-dihydro-7H-[1,3]dioxolo[4,5-h]isochromen-9-yl)methanamine (7) and (R)-(6,9-dihydro-7H-[1,3]dioxolo[4,5-h]isochromen-9-yl)methanamine (8)

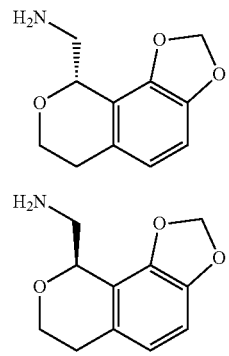

(S)-(6,9-dihydro-7H-[1,3]dioxolo[4,5-h]isochromen-9-yl)methanamine (7) and (R)-(6,9-dihydro-7H-[1,3]dioxolo[4,5-h]isochromen-9-yl)methanamine (8) were prepared using General Procedure B and Scheme 2 starting with 2-(6-bromobenzo[d][1,3]dioxol-5-yl)ethanol and 2,2-dimethoxyethanamine.

(S)-(6,9-dihydro-7H-[1,3]dioxolo[4,5-h]isochromen-9-yl)methanamine (7): MS (ESI): m/z=208 [M+H]$^+$. $^1$H NMR (400 MHz, CD$_3$OD, HCl salt) δ 6.78 (d, J=7.8 Hz, 1H), 6.71 (d, J=8 Hz, 1H), 6.00 (d, J=1.2 Hz, 1H), 5.95 (d, J=1.2 Hz, 1H), 5.05~5.02(m, 1H), 4.19~4.14 (m, 1H), 3.84~3.78 (m, 1H), 361~3.56 (m, 1H), 3.31~3.26 (m, 1H), 2.95~2.87 (m, 1H), 2.73~2.67(m, 1H).

(R)-(6,9-dihydro-7H-[1,3]dioxolo[4,5-h]isochromen-9-yl)methanamine (8): MS (ESI): m/z=208 [M +H]+. $^1$HNMR (400 MHz, CD$_3$OD, HCl salt) δ 6.78 (d, J=7.8 Hz, 1H), 6.71 (d, J=8 Hz, 1H), 6.00 (d, J=1.2 Hz, 1H), 5.95 (d, J=1.2 Hz, 1H), 5.05~5.02(m, 1H), 4.19~4.14 (m, 1H), 3.84~3.78 (m, 1H), 361~3.56 (m, 1H), 3.31~3.26 (m, 1H), 2.95~2.87 (m, 1H), 2.73~2.67(m, 1H).

2.10 Preparation of (S)-N-methyl-1-(2,3,7,10-tetrahydro-8H-[1,4]dioxino[2,3-h]sochromen-10-yl)methanamine (9) and (R)-N-methyl-1-(2,3,7,10-tetrahydro-8H-[1,4]dioxino[2,3-h]sochromen-10-yl)methanamine (10)

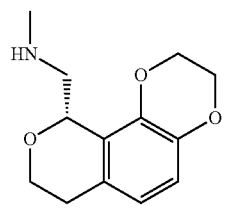

(S)-N-methyl-1-(2,3,7,10-tetrahydro-8H-[1,4]dioxino[2,3-h]isochromen-10-yl)methanamine (9) and (R)-N-methyl-1-(2,3,7,10-tetrahydro-8H-[1,4]dioxino[2,3-h]isochromen-10-yl)methanamine (10) were prepared using General Procedure B and Scheme 2 starting with 2-(7-bromo-2,3-dihydrobenzo[b][1,4]dioxin-6-yl)ethanol and 1,3-dimethoxy-N-methylpropan-2-amine.

(S)-N-methyl-1-(2,3,7,10-tetrahydro-8H-[1,4]dioxino[2,3-h]isochromen-10-yl)methanamine (9): MS (ESI): m/z=236 (M+H)$^+$. $^1$H NMR (500 MHz, CD$_3$OD, HCl salt): δ 6.78-6.80 (d, J=9.0 Hz, 1H), 6.69-6.71 (d, J=8.5 Hz, 1H), 4.93-5.11 (m, 1H), 4.34-4.39 (m, 1H), 4.22-4.29 (m, 3H), 4.06-4.11 (m, 1H), 3.78-3.82 (m, 1H), 3.61-3.64 (m, 1H), 3.32-3.38 (m, 1H), 2.71-2.83 (m, 5H).

(R)-N-methyl-1-(2,3,7,10-tetrahydro-8H-[1,4]dioxino[2,3-h]isochromen-10-yl)methanamine (10): MS (ESI): m/z=236 [M +H]$^+$. $^1$H NMR (500 MHz, CD$_3$OD, HCl salt): δ 6.79-6.80 (d,J=8.9 Hz, 1H), 6.69-6.71 (d, J=8.5 Hz, 1H), 4.93-5.13 (m, 1H), 4.34-4.39 (m, 1H), 4.21-4.29 (m, 3H), 4.06-4.11 (m, 1H), 3.78-3.82 (m, 1H), 3.61-3.64 (m, 1H), 3.32-3.38 (m, 1H), 2.71-2.84 (m, 5H).

2.11 Preparation of (R)-(8-methylisochroman-1-yl)methanamine (75) and (S)-(8-methylisochroman-1-yl)methanamine (74)

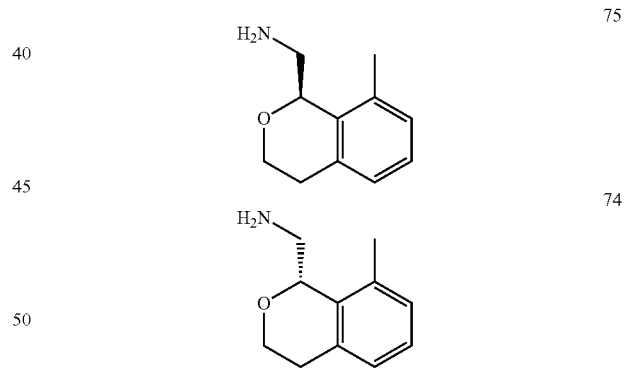

(R)-(8-methylisochroman-1-yl)methanamine (75) and (S)-(8-methylisochroman-1-yl)-methanamine (74) were prepared using General Procedure B and Scheme 2 starting with 2-(2-bromo-5-methylphenyl)ethanol and 1,3-dimethoxy-N-methyl- propan-2-amine.

(R)-(8-methylisochroman-1-yl)methanamine (75): MS (ESI): m/z=178 (M+H)$^+$. $^1$H NMR (400 MHz, methanol-d$_4$): δ 7.18 (t, J=14.8 Hz, 1H), 7.07 (dd, J$_1$=7.2 Hz, J$_2$=7.2 Hz, 2H), 5.18-5.15 (m,1H), 4.16-4.10 (m,1H), 3.86-3.80 (m, 1H), 3.28-3.21 (m, 1H), 3.18-3.15 (m, 1H), 2.90-2.87 (m, 2H), 2.31 (s, 3H).

(S)-(8-methylisochroman-1-yl)-methanamine (74): MS (ESI): m/z=178 [M +H]$^+$. $^1$HNMR (400 MHz, methanol-d$_4$): δ 7.18 (t, J=14.8 Hz, 1H), 7.07 (dd , J$_1$=7.2 Hz, J$_2$=7.2

Hz, 2H), 5.18-5.15 (m, 1H), 4.16-4.10 (m, 1H), 3.86-3.80 (m, 1H), 3.28-3.21 (m, 1H), 3.18-3.15 (m, 1H), 2.90-2.87 (m, 2H), 2.31 (s, 3H).

2.12 Preparation of (R)-(8-chloroisochroman-1-yl)methanamine (71) and (S)-(8-chloroisochroman-1-yl)methanamine (70)

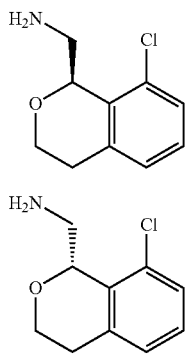

(R)-(8-chloroisochroman-1-yl)methanamine (71) and (S)-(8-chloroisochroman-1-yl)-methanamine (70) were prepared using General Procedure B and Scheme 2 starting with 2-(2-bromo-5-chlorophenyl)ethanol and 1,3-dimethoxy-N-methyl-propan-2-amine.

(R)-(8-chloroisochroman-1-yl)methanamine (71): MS (ESI): m/z=198 (M+H)+. 1H NMR (400 MHz, methanol-d4): δ 7.33-7.27 (m, 2 H), 7.23-7.21 (m, 1H), 5.22-5.18 (m, 1H), 4.16-4.10 (m, 1H), 3.93-3.87 (m, 1H), 3.61-3.56 (m, 1H), 3.31-3.28 (m, 1H),), 2.95-2.87 (m, 2H).

(S)-(8-chloroisochroman-1-yl)-methanamine (70): MS (ESI): m/z=198 [M +H]+. 1H NMR (400 MHz, methanol-d4): δ 7.33-7.27 (m, 2 H), 7.23-7.21 (m, 1H), 5.22-5.18 (m, 1H), 4.16-4.10 (m, 1H), 3.93-3.87 (m, 1H), 3.60-3.57 (m, 1H), 3.32-3.28 (m, 1H),), 2.98-2.87 (m, 2H).

2.13 Preparation of compounds (88) (89), (90), and (91): (S)-14(R)-8-chloroisochroman-1-yl)ethan-1-amine, (R)-14 (S)-8-chloroisochroman-1-yl)ethan-1-amine), (S)-1-((S)-8-chloroiso-chroman-1-yl)ethan-1-amine) and (R)-14(R)-8-chloroisochroman-1-yl)-ethan-1-amine, order unknown

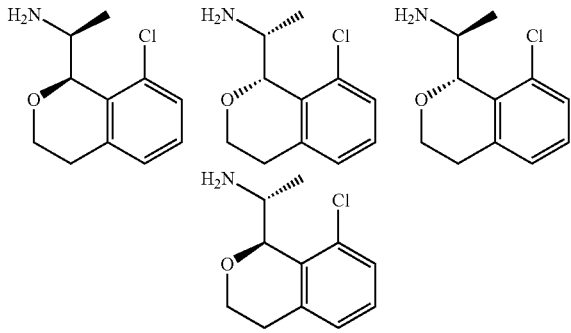

((S)-1-((R)-8-chloroisochroman-1-yl)ethan-1-amine, (R)-1-((S)-8-chloroiso-chroman-1-yl)ethan-1-amine, (S)-1-((S)-8-chloroisochroman-1-yl)ethan-1-amine and (R)-1-((R)-8-chloroisochroman-1-yl)ethan-1-amine were prepared using General Procedure B and Scheme 2 starting with 2-(2-bromo-5-chlorophenyl)ethanol and t-butyl (1-oxopropan-2-yl)carbamate.

(88): MS(ESI) m/z=212 [M+1]+. 1H NMR (400 MHz, methanol-d4): δ 7.37-7.23 (m, 3H), 5.33 (s, 1H), 4.30-4.25 (m, 2 H), 3.63 (t, J=26.2 Hz, 1H), J=26.4 Hz, 1H), 2.73 (d, J=16 Hz, 1H), 1.00 (d, J=6.4 Hz, 3H).

(89): MS (ESI) m/z=212 [M+H]+. 1H NMR (400 MHz, methanol-d4) δ 7.37-7.23 (m, 3H), 5.33 (s, 1H), 4.30-4.25 (m, 2 H), 3.63 (t, J=26.2 Hz, 1H), 3.05 (t, J=26.4 Hz, 1H), 2.73 (d, J=16 Hz, 1H), 1.00 (d, J=6.4 Hz, 3H).

(90): MS(ESI) m/z=212 [M+H]+. 1H NMR (400 MHz, methanol-d4): δ 7.38 (d, J=8 Hz , 1H), 7.32 (t, J=15.2 Hz, 1H), 7.24 (d, J=7.6 Hz, 1H), 5.12 (s, 1H), 4.30-4.26 (m, 1H), 4.09-4.07 (m, 1H), 3.63 (t, J=24.8 Hz, 1H), 3.34-3.08 (m, 1H), 2.72 (d, J=16.4 Hz, 1H), 1.51 (d, J=6.8 Hz, 3H).

(91): MS(ESI) m/z=212 [M+H]+. 1H NMR (400 MHz, methanol-d4): δ 7.38 (d, J=8 Hz , 1H), 7.32 (t, J=15.2 Hz, 1H), 7.24 (d, J=7.6 Hz, 1H), 5.12 (s, 1H), 4.30-4.26 (m, 1H), 4.09-4.07 (m, 1H), 3.63 (t, J=24.8 Hz, 1H), 3.34-3.08 (m, 1H), 2.72 (d, J=16.4 Hz,1H), 1.51 (d, J=6.8 Hz, 3H).

2.14 Preparation of compounds (105) and (106): (R)-N-methyl-1-(2,3,6,9-tetrahydro-7H-furo[3,2-h]sochromen-9-yl)methanamine and (S)-N-methyl-1-(2,3,6,9-tetrahydro-7H-furo[3,2-h]sochromen-9-yl)methanamine

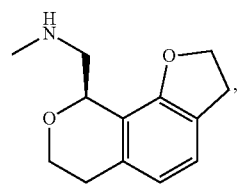

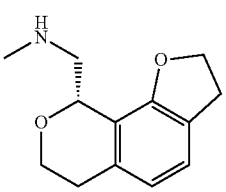

(R)-N-methyl-1-(2,3,6,9-tetrahydro-7H-furo[3,2-h]isochromen-9-yl)methanamine and (S)-N-methyl-1-(2,3,6,9-tetrahydro-7H-furo[3,2-h]isochromen-9-yl)methanamine were prepared using General Procedure B and Scheme 2 starting with 2-(5-bromo-2,3-dihydrobenzofuran-6-yl)ethan-1-ol and 2,2-dimethoxy-N-methylethan-1-amine.

(a). 2-(5-bromo-2,3-dihydrobenzofuran-6-yl)ethan-1-ol

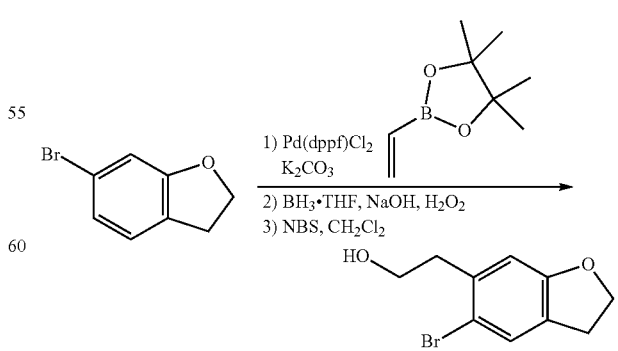

To a solution of 6-bromo-2,3-dihydrobenzofuran (3.8 g, 19.0 mmol) in 1.4-dioxane/H2O (100 mL/25 mL) was added 4,4,5,5-tetramethyl-2-vinyl-1,3,2-dioxaborolane (5.85 g, 38.0 mmol), $K_2CO_3$ (5.24 g, 38.0 mmol) and Pd(dppf)$Cl_2$ (2.77 g, 3.80 mmol). The reaction mixture was heated to 105° C. and stirred at that temperature until the reaction was complete (~16 h). The reaction was concentrated, diluted with water and EtOAc. The combined organics were dried over anhydrous $Na_2SO_4$, filtered and concentrated in vacuo. The residue was purified via silica chromatography, eluting with petroleum ether:EtOAc=20:1 to afford 6-vinyl-2,3-dihydrobenzofuran as brown oil, 2.6 g, yield=79.4%.

To a solution of 6-vinyl-2,3-dihydrobenzofuran (2.5 g, 17.1 mmol) in THF (20 mL) was added $BH_3$·THF (17.1 mL, 1.0 M, 17.1 mmol) at ambient temperature. The reaction was stirred at ambient temperature for 3 h, then quenched with the addition of water. A solution of sodium hydroxide in water was added followed by the addition of $H_2O_2$. The mixture was exothermic and then stirred at room temperature for 2 hours. The mixture was extracted with EtOAc, and the separated organic layer was washed with 1N $FeSO_4$ solution and brine, dried over sodium sulfate, filtered and concentrated, then purified by chromatography to give 2-(2,3-dihydrobenzofuran-6-yl)ethan-1-ol as a white solid. MS (ESI): m/z 165 [M+H]+.

To a solution of 2-(2,3-dihydrobenzofuran-6-yl)ethanol (2.2 g, 13.3 mmol) in DCM (30 mL) was added NBS (2.58 g, 14.6 mmol). The reaction was stirred at ambient temperature until complete (~2 h). Upon the completion, the mixture was washed with $Na_2SO_3$ solution, brine and then dried. The residue was purified via silica chromatography, eluting with petroleum ether: EtOAc=5:1 to afford 2-(5-bromo-2,3-dihydrobenzofuran-6-yl)ethan-1-ol as white solid, 2.8 g, yield=87%. MS (ESI): m/z 225,227 [M-18]+.

(b). Chiral separation, deprotection and salt formation (106)

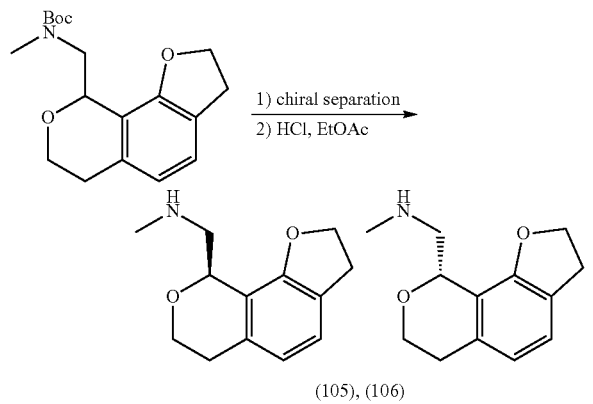

(105), (106)

Tert-butylmethyl((3,6,7,9-tetrahydro-2H-furo[3,2-h]isochromen-9-yl)methyl) carbamate (1.4 g, 4.38 mmol) was separated into its enantiomers (R)-tert-butyl methyl((3,6,7,9-tetrahydro-2H-furo[3,2-h]isochromen-9-yl)methyl)carbamate and (R)-tert-butylmethyl((3,6,7,9-tetrahydro-2H-furo[3,2-h]isochromen-9-yl)methyl)carbamate by SFC -200 (Thar, Waters) using AD 20×250 mm, 5 um (Dacel) and mobile phase $CO_2$/MeOH (0.2% methanol in ammonia)=90/10, Flow rate=140 g/min; Back pressure=100 Bar; Cycle time of stack injections=2.5 min.

Chiral HPLC for ee determination: Column AY-H (250*4.6 mm, 5 um; Mobile Phase: n-Hexane (0.1% DEA): EtOH (0.1% DEA)=80:20; Temp=40° C.; Flow rate=1.0 mL/min.

Compound 105: Ret Time=7.471 min; Enantiopurity: 99.7% ee. MS (ESI): m/z 220 [M+H]+. $^1$H-NMR (400 MHz, methanol-$d_4$): δ 7.13 (d, 1H), 6.71 (d, 1H), 5.07-5.05 (m, 1H), 4.68- 4.54 (m, 2H), 4.18-4.13 (m, 1H), 3.85-3.79 (m, 1H), 3.70-3.67 (m, 1H), 3.39-3.32 (m, 1H), 3.21 (t, 2H), 2.96-2.89 (m, 1H), 2.75 (s, 3H), 2.76-2.72 (m, 1H).

Compound 106: Ret Time=6.274 min; Enantiopurity: 100% ee. MS (ESI): m/z 220 [M+H]+. $^1$H-NMR (400 MHz, methanol-$d_4$): δ 7.13 (d, 1H), 6.71 (d, 1H), 5.07-5.05 (m, 1H), 4.68-4.54 (m, 2H), 4.18-4.13 (m, 1H), 3.85-3.79 (m, 1H), 3.70-3.67 (m, 1H), 3.39-3.32 (m, 1H), 3.21 (t, 2H), 2.96-2.89 (m, 1H), 2.75 (s, 3H), 2.76-2.72 (m, 1H).

2.15 Preparation of compounds (107) and (108): (R)-N-methyl-1-(3,4,8,9-tetrahydro-1H-furo[2,3-h]isochromen-1-yl)methanamine and (S)-N-methyl-1-(3,4,8,9-tetrahydro-1H-furo[2,3-h]isochromen-1-yl)methanamine

(107)

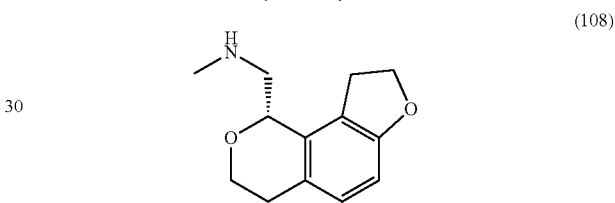

(108)

(R)-N-methyl-1-(3,4,8,9-tetrahydro-1H-furo[2,3-h]isochromen-1-yl)methanamine and (S)-N-methyl-1-(3,4,8,9-tetrahydro-1H-furo[2,3-h]isochromen-1-yl)methanamine were prepared using General Procedure B and Scheme 2 starting with 2-(7-bromo-2,3-dihydrobenzofuran-5-yl)ethan-1-ol and 2,2-dimethoxy-N-methylethan-1-amine.

(a). 2-(7-bromo-2,3-dihydrobenzofuran-5-yl)ethan-1-ol

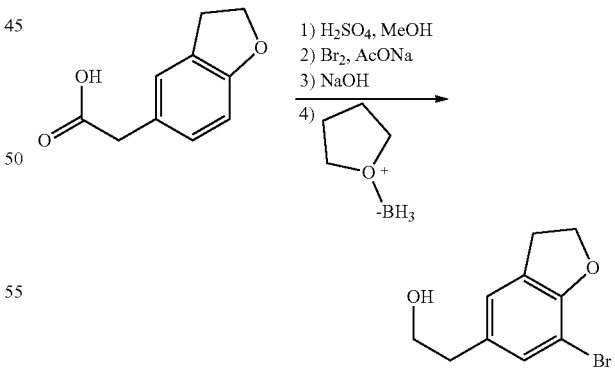

To a solution of 2-(2,3-dihydrobenzofuran-5-yl)acetic acid (4 g, 22.4 mmol) in methanol (40 mL) was added sulfuric acid (219 mg, 2.24 mmol). The reaction mixture was heated to 70° C. and stirred at that temperature for 2 h. The mixture was concentrated and the residue was added ethyl acetate (50 mL). The solution was washed with brine, then the organic phase was dried over anhydrous sodium sulfate, filtered and concentrated in vacuo to provide methyl 2-(2, 3-dihydrobenzofuran-5-yl)acetate (4.0 g, yield: 93%) as a yellow oil. MS(ESI): m/z 193 [M+H]+.

To a solution of methyl 2-(2,3-dihydrobenzofuran-5-yl) acetate (4 g, 20.8 mmol) in AcOH (40 mL) was added sodium acetate (1.70 g, 20.8 mmol) and bromine (4.31 g, 27.0 mmol) at 0° C. The reaction was stirred at ambient temperature for 2 h. Water was added, and the mixture was extracted with EtOAc. The combined organic phase was washed with brine, then dried over anhydrous $Na_2SO_4$, filtered and concentrated in vacuo. The residue was purified by flash column chromatography (petroleum ether/EtOAc=5/1) to provide methyl 2-(7-bromo-2,3-dihydrobenzofuran-5-yl) acetate (4.60 g, 16.9 mmol) as a yellow oil. MS(ESI): m/z 271 [M+H]+. $^1$H-NMR (CDCl$_3$) δ 7.17 (s, 1H), 7.05 (s, 1H), 4.65 (t, J=8.8 Hz, 2 H), 3.70 (s, 3 H), 3.52 (s, 2 H), 3.30 (t, J=8.8 Hz, 2 H).

To a solution of methyl 2-(7-bromo-2,3-dihydrobenzofuran-5-yl)acetate (9.0 g, 33.1 mmol) in THF/H2O (2/1) (100 mL) was added sodium hydroxide (3.97 g, 99.3 mmol). The reaction was stirred at ambient temperature for 16 h. Then the mixture was concentrated to remove THF. The residue was acidified by 2 M HCl(aq) to pH=2. The mixture was extracted with EtOAc, and the combined organics were dried over anhydrous $Na_2SO_4$, filtered and concentrated in vacuo to provide 2-(7-bromo-2,3-dihydrobenzofuran-5-yl) acetic acid (8.10 g, yield: 95%) as a yellow solid. MS(ESI): m/z 257 [M+H]+. $^1$H-NMR (CDCl$_3$) δ 7.18 (s, 1H), 7.05 (s, 1H), 4.66 (t, J=8.6 Hz, 2H), 3.53 (s, 2 H), 3.30 (t, J=8.8 Hz, 2 H).

To a solution of 2-(7-bromo-2,3-dihydrobenzofuran-5-yl) acetic acid (4.0 g, 15.5 mmol) in THF (10 mL) was added BH$_3$-THF (31.0 mL, 31.0 mmol). The reaction was stirred at ambient temperature for 2 h. Water (10 mL) was added slowly to quench the reaction. The mixture was extracted with EtOAc, and the combined organics were dried over anhydrous $Na_2SO_4$, filtered and concentrated in vacuo. The resulting oil was purified by flash column chromatography (petroleum ether/EtOAc=5/1) to provide 2-(7-bromo-2,3-dihydrobenzofuran-5-yl)ethanol (3.55 g, yield: 47%) as a yellow oil. MS(ESI): m/z 225 [M-OH—]+.

(b). Chiral separation, deprotection and salt formation.

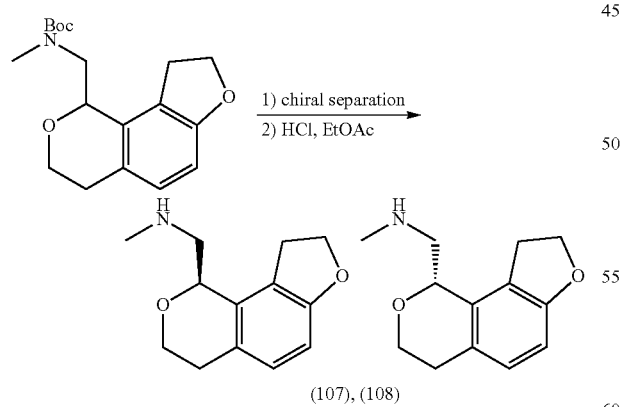

Tert-butylmethyl((3,4,8,9-tetrahydro-1H-furo[2,3-h]isochromen-1-yl)methyl) carbamate (1 g, 3.13 mmol) was separated into its enantiomers by SFC-80 (Thar, Waters) using column: IC 20×250 mm, 10 um (Daicel) and mobile phase: CO$_2$/IPA(0.2% methanol in ammonia)=80/20; Flow rate=80 g/min; Back pressure=100 bar.

Chiral HPLC for ee determination: Column AY-H (250*4.6 mm, 5 um; Mobile Phase: n-Hexane (0.1% DEA): EtOH (0.1% DEA)=90:10; Temp=40° C.; Flow rate=1.0 mL/min.

Compound 107 hydrochloride salt: Ret Time=12.37 min; Enantiopurity: 100% ee. MS(ESI): m/z 220 [M+H]+. $^1$H-NMR (methanol-d$_4$) δ 6.97 (d, J=8.5 Hz, 1H), 6.69 (d, J=8.0 Hz, 1H), 5.11 (dd, J=2.5/9.5 Hz, 1H), 4.67-4.64 (m, 1H), 4.52-4.47 (m, 1H), 4.17-4.13 (m, 1H), 3.84-3.80 (m, 1H), 3.45-3.42 (m, 1H), 3.36-3.32 (m, 1H), 3.25-3.20 (m, 1H), 3.18-3.13 (m, 1H), 2.90-2.86 (m, 1H), 2.85 (s, 3 H), 2.85-2.73 (m, 1H).

Compound 108 hydrochloride salt: Ret Time=11.53 min; Enantiopurity: 99.7% ee. MS(ESI): m/z 220 [M+H]+. $^1$H-NMR (methanol-d$_4$) δ 6.97 (d, J=8.5 Hz, 1H), 6.69 (d, J=8.0 Hz, 1H), 5.11 (dd, J=2.5/9.5 Hz, 1H), 4.67-4.64 (m, 1H), 4.52-4.47 (m, 1H), 4.17-4.13 (m, 1H), 3.84-3.80 (m, 1H), 3.45-3.42 (m, 1H), 3.36-3.32 (m, 1H), 3.25-3.20 (m, 1H), 3.18-3.13 (m, 1H), 2.90-2.86 (m, 1H), 2.85 (s, 3 H), 2.85-2.73 (m, 1H).

2.16 Preparation of compounds (109) and (110): (R)-N-methyl-1-(1,6,7,9-tetrahydro-3H-furo[3,4-h]isochromen-9-yl) methanamine and (S)-N-methyl-1-(1,6,7,9-tetrahydro-3H-furo[3,4-h]isochromen-9-yl)methanamine, order unknown

(R)-N-methyl-1-(1,6,7,9-tetrahydro-3H-furo[3,4-h]isochromen-9-yl)methanamine and (S)-N-methyl-1-(1,6,7,9-tetrahydro-3H-furo[3,4-h]isochromen-9-yl)methanamine were prepared using General Procedure B and Scheme 2 starting with 2-(6-bromo-1,3-dihydroisobenzofuran-5-yl) ethanol and 2,2-dimethoxy-N-methylethan-1-amine(a). 2-(6-bromo-1,3-dihydroisobenzofuran-5-yl)ethan-1-ol

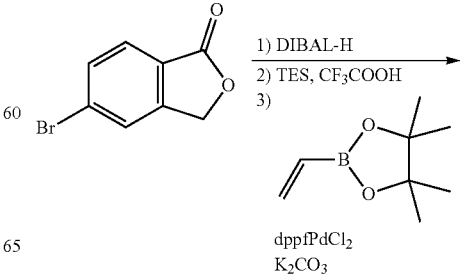

-continued

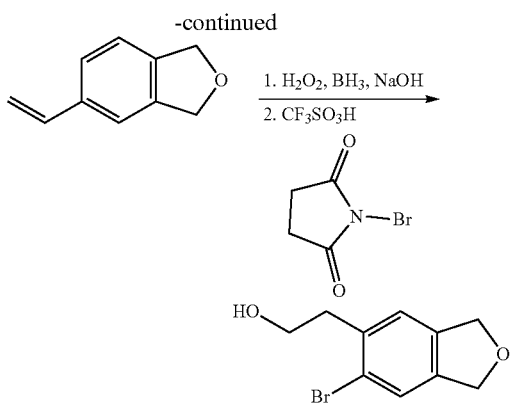

To a solution of 5-bromoisobenzofuran-1(3H)-one (21.3 g, 100 mmol) in DCM (200 mL) was added diisobutylaluminium hydride (184 g, 130 mmol) at −78° C. The reaction was stirred at −78° C. until the reaction was complete (~2 h). 10 mL water was added, and 10 mL 4M NaOH (aq.) was added, then 40 mL was water was added, the mixture was stirred at room temperature for 30 mins. The mixture was filtered, the filtrate was concentrated. The resulting solid was purified by flash column chromatography (petroleum ether: EtOAc 100:0 to 80:20) to provide 5-bromo-1,3-dihydroisobenzofuran-1-ol (13 g, 60.4 mol) as a white solid. MS (ESI): m/z 196.9 [M-16+1]+.

To a solution of 5-bromo-1,3-dihydroisobenzofuran-1-ol (12 g, 105 mmol) in DCM (10 mL) was added triethylsilane (32 g, 278 mmol) and 2,2,2-trifluoroacetic acid (12.6 g, 111 mmol) at 0° C. The reaction was stirred at ambient temperature for 12 h. The mixture was concentrated. 3M aqueous NaOH (40 mL) was added to the reaction vessel and the resulting biphasic mixture was transferred to a separatory funnel. The layers were separated and the aqueous phase was washed with EtOAc (2×25 mL). The combined organics were washed with saturated aqueous NaCl (2×50 mL), dried over anhydrous $Na_2SO_4$, filtered and concentrated in vacuo. The resulting solid was purified by flash column chromatography with a gradient elution of EtOAc (0%) and petroleum ether (100%) to EtOAc (20%) and petroleum ether (80%) to provide 5-bromo-1,3-dihydroisobenzofuran (10.2 g, 51.2 mmol) as a white solid. MS (ESI): m/z 200 [M+H]+.

To a solution of 5-bromo-1,3-dihydroisobenzofuran (7.9 g, 39.6 mmol) in 1,4-dioxane/$H_2O$ (60 mL) was added $K_2CO_3$ (10.9 g, 79.2 mmol), 4,4,5,5-tetramethyl-2-vinyl-1,3,2-dioxaborolane (9.14 g, 59.4 mmol) and 1,1′-Bis(diphenylphosphino)ferrocene]dichloropalladium(II) (2.89 g, 3.96 mmol). The reaction mixture was heated to 100° C. and stirred at that temperature for 12 h. EtOAc and $H_2O$ were added. The layers were separated and the aqueous phase was washed with EtOAc. The combined organics were saturated aqueous NaCl and dried over anhydrous $Na_2SO_4$, filtered and concentrated in vacuo. The resulting oil was purified by flash column chromatography (petroleum ether: EtOAc 100:0 to 90:10) to provide 5-vinyl-1,3-dihydroisobenzofuran (4.50 g, 30.7 mmol) as a colorless oil. MS(ESI): m/z 147 [M+H]+

To a solution of 5-vinyl-1,3-dihydroisobenzofuran (1.46 g, 10 mmol) in THF (10 mL) was added $BH_3$·THF (83 mg, 600 mmol). The reaction was stirred at room temperature for 3 h quenched with the addition of water, then sodium hydroxide (4 g, 100 mmol) was added followed by the addition of $H_2O_2$ (3.4 g, 1000 mmol). The mixture was exothermic and then stirred at room temperature for 2 hours. The mixture was washed with $FeSO_4$ solution, EtOAc (50 mL) was added, the layers were separated and the organic phase was washed with EtOAc. The combined organics were washed with saturated aqueous NaCl and dried over anhydrous $Na_2SO_4$, filtered and concentrated in vacuo. The resulting oil was purified by flash column chromatography (petroleum ether: EtOAc 100:0 to 80:20) to provide 2-(1,3-dihydroisobenzofuran-5-yl)ethanol (2.80 g, 17.0 mmol) as a colorless oil. MS(ESI): m/z 165 [M+H]+.

To a solution of 2-(1,3-dihydroisobenzofuran-5-yl)ethanol (656 mg, 4 mmol) in DCM (10 mL) was added 1-bromopyrrolidine-2,5-dione (711 mg, 4.00 mmol) and trifluoromethanesulfonic acid (3.00 g, 20.0 mmol) at 0° C. The reaction was stirred at 0° C. for 30 min. Ice-water (10 mL) was added. NaOH solid was added to adjust to pH=14, then the layers were separated and the aqueous phase was washed with DCM. The combined organics were washed with saturated aqueous NaCl and dried over anhydrous $Na_2SO_4$, filtered and concentrated in vacuo. The resulting oil was purified by flash column chromatography (petroleum ether to EtOAc 100:0 to 80:20) to provide 2-(6-bromo-1,3-dihydroisobenzofuran-5-yl)ethanol (1.10 g, 4.52 mmol) as a colorless oil. MS(ESI): m/z 227 [M-17+H]+.

(b). Chiral separation, deprotection and salt formation.

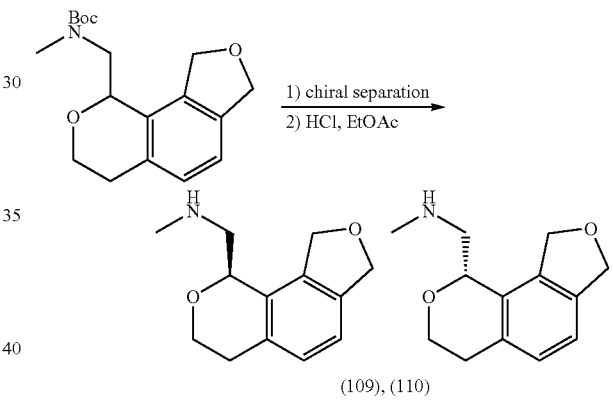

(109), (110)

Tert-butylmethyl((3,6,7,9-tetrahydro-1H-furo[3,4-h]isochromen-9-yl)methyl) carbamate (1 g, 3.13 mmol) was separated into its enantiomers (S)-tert-butylmethyl((3,6,7,9-tetrahydro-1H-furo[3,4-h]isochromen-9-yl)methyl)carbamate (400 mg, 1.25 mmol) and (R)-tert-butylmethyl((3,6,7,9-tetrahydro-1H-furo[3,4-h]isochromen-9-yl)methyl) carbamate (400 mg, 1.25 mmol) by SFC-80 (Thar, Waters) using Column: IC 20×250 mm, 10 um (Daicel) and mobile phase: $CO_2$/MeOH (0.2% Methanol Ammonia)=87/13. Flow rate=80 g/min; Back pressure=100 bar; Cycle time of stack injections: 6.5 min.

Chiral HPLC for ee determination: Column AY-H (100*4.6 mm, 5 um; Cosolvent: EtOH (0.1% methanol in amonia); Temp=44° C.; Flow rate=1.0 mL/min.

Compound 109 hydrochloride salt; Ret Time=1.02 min; Enantiopurity: 100% ee. MS (ESI): m/z 220[M +H]+. 1H-NMR (400 MHz, DMSO-$d_6$): δ 9.41 (s, 1H), 8.68 (s, 1H), 7.20 (d, J=7.6 Hz, 1H), 7.12 (d, J=8.0 Hz, 1H), 5.15-4.96 (m, 5H), 4.08-4.02 (m, 1H), 3.83-3.78 (m, 1H), 3.33-3.26 (m, 1H), 3.10-3.04 (m, 1H), 2.84-2.82 (m, 2H), 2.59 (t, J=4.8 Hz, 3H).

Compound 110 hydrochloride salt: Ret Time=1.81 min; Enantiopurity: 99.2% ee. MS (ESI): m/z 220 [M+H]+. $^1$H-NMR (400 MHz, DMSO-$d_6$): δ 9.52 (s, 1H), 8.72 (s, 1H), 7.20 (d, J=7.6 Hz, 1H), 7.12 (d, J=8.8 Hz, 1H), 5.16-4.96 (m, 5H), 4.08-0.02 (m, 1H), 3.83-3.78 (m, 1H), 3.33-3.26 (m, 1H), 3.08-3.05 (m, 1H), 2.84-2.76 (m, 2H), 2.59 (s, 3H).

General Procedure C 3.1 Preparation of 1-((1S,4S)-4-fluoroisochroman-1-yl)-N-methylmethanamine (21) and 1-((1R,4R)-4-fluoroisochroman-1-yl)-N-methylmethanamine (22)

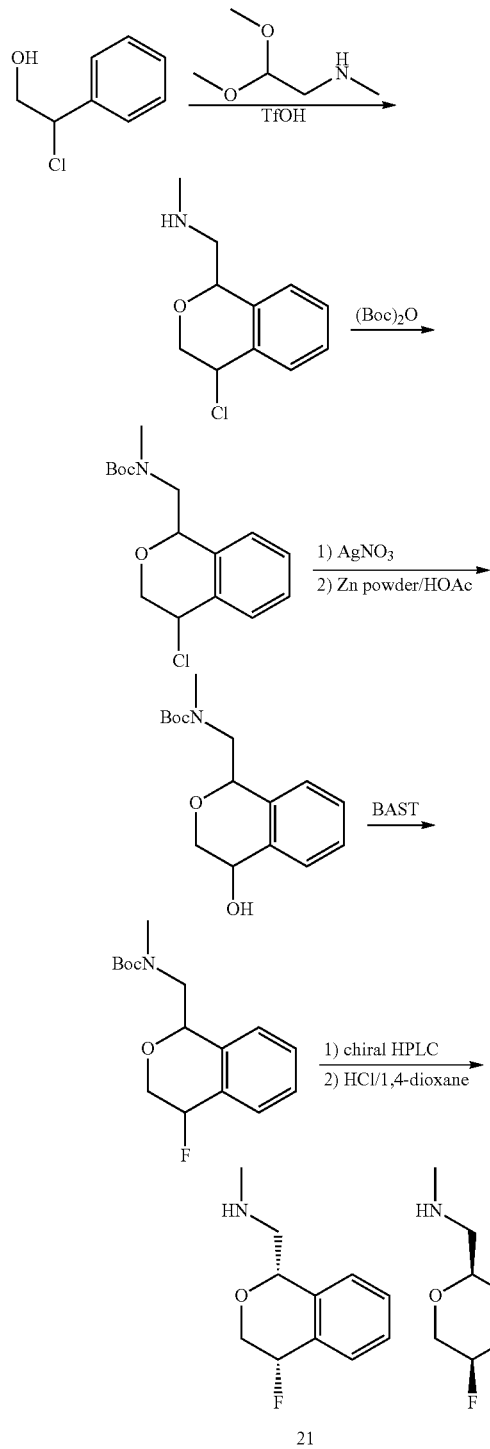

(a). 1-(4-chloroisochroman-1-yl)-N-methylmethanamine

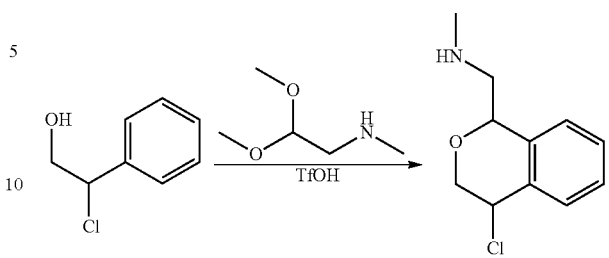

To a solution of 2-chloro-2-phenylethanol (8 g, 33.7 mmol) and 2,2-dimethoxy-N-methylethanamine (9.72 g 81.6 mmol) in DCM (100 mL) was added trifluoromethanesulfonic acid (36.6 g, 244 mmol). The mixture was stirred at 15° C. for 1 day. The reaction was quenched with iced-water, and neutralized with sodium hydroxide (3N aq.) to pH=8. Then it was extracted with DCM (3×150 mL). The organic layer was separated, dried over sodium sulfate, filtered and then concentrated to give the residue. The residue was used for next step without further purification. MS (ESI): m/z=212 [M+H]$^+$.

(b). tert-butyl (4-chloroisochroman-1-yl)methyl(methyl)carbamate

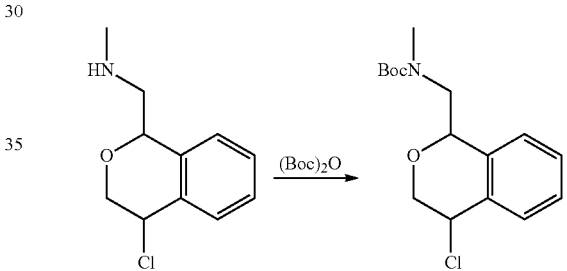

To a solution of 1-(4-chloroisochroman-1-yl)-N-methylmethanamine (12 g, 31.7 mmol) in DCM (100 mL) was added sodium hydroxide (1.89 g, 47.5 mmol) and di-tert-butyl dicarbonate (8.29 g, 38.0 mmol). The reaction was stirred at ambient temperature for 3 h. Upon completion, the mixture was washed with water (100 mL×3). The organic layer was dried over sodium sulfate, filtered and then concentrated to give the crude product, which was purified by column chromatography (PE:EA=80:1 to 10:1) to give tert-butyl ((4-chloroisochroman-1-yl)methyl)(methyl)carbamate(6.3 g).

(c). tert-butyl (4-hydroxylsochroman-1-yl)methyl(methyl)carbamate

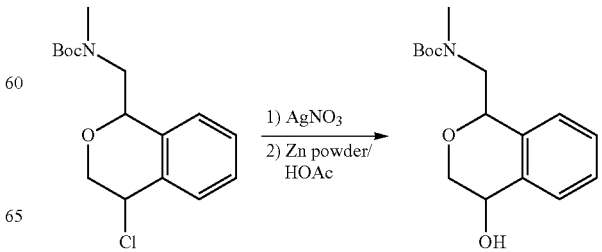

To a solution of tert-butyl ((4-chloroisochroman-1-yl)methyl)(methyl)carbamate (5 g, 14.1 mmol) in THF/water (80 mL, 1:1) was added silver nitrate (11.9 g, 70.4 mmol). The mixture was stirred at 50° C. for 4 h. The mixture was filtered, and the filtrate extracted by ethyl acetate (100 mL×3). The organic layer was dried over sodium sulfate and concentrated. The residue was dissolved in acetic acid (30 mL) and to it was added zinc (4.31 g, 66.0 mmol). The mixture was stirred at ambient temperature for 16 h. The mixture was diluted with ethyl acetate (200 mL), washed with water (150 mL×4). The organic layer was dried over sodium sulfate, filtered and concentrated to give the crude product, which was purified by column chromatography (PE:EA=4:1 to 1:1) to give tert-butyl ((4-hydroxyisochroman-1-yl)methyl)(methyl)carbamate (2.9 g).

(d). tert-butyl (4-fluoroisochroman-1-yl)methyl(methyl)carbamate

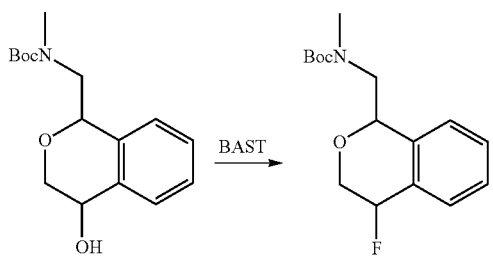 [SMILES: CN(CC1OCC(O)c2ccccc21)C(=O)OC(C)(C)C ; CN(CC1OCC(F)c2ccccc21)C(=O)OC(C)(C)C]

A solution of tert-butyl ((4-hydroxyisochroman-1-yl)methyl)(methyl)carbamate (3 g, 10.2 mmol) in BAST (9 mL) was stirred at 70° C. for 3 h. Upon completion, it was poured into iced water, extracted with ethyl acetate, The organic layer was dried over sodium sulfate, filtered and concentrated to give a residue, which was purified/separated by HPLC to give tert-butyl ((4-fluoroisochroman-1-yl)methyl)(methyl)carbamate (4 g) as yellow oil.

(e). 1-((1S,4S)-4-fluoroisochroman-1-yl)-N-methylmethanamine (21) and 1-((1R,4R)-4-fluoroisochroman-1-yl)-N-methylmethanamine (22)

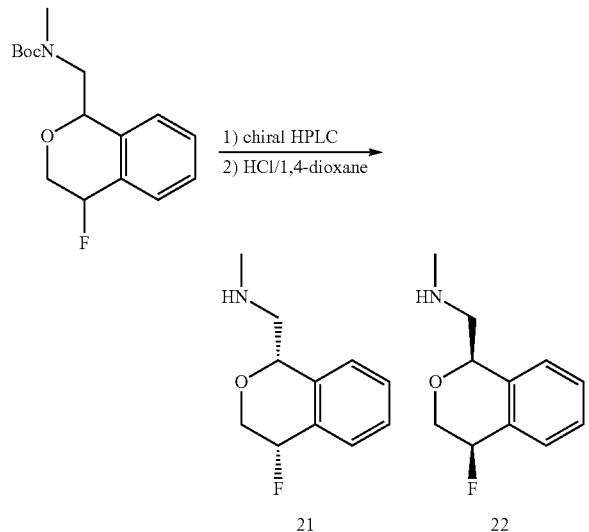

Tert-butyl ((4-fluoroisochroman-1-yl)methyl)(methyl)carbamate (900 mg, 3.04 mmol) was separated by chiral HPLC: {Gilson-281, column: AY-H 20×250mm, 5um (Dacel), mobile phase: Hexane(0.1% DEA)/Ethanol(0.1% DEA)=95/5, flow rate: 50 mL/min and Cycle time: 15 min} to give tert-butyl (((1S,4S)-4-fluoroisochroman-1-yl)methyl)(methyl)carbamate as yellow oil (300 mg) and tert-butyl (((1R,4R)-4-fluoroisochroman-1-yl)methyl)(methyl) carbamate as yellow oil (300 mg).

1-((1S,4S)-4-fluoroisochroman-1-yl)-N-methylmethanamine (21): To a solution of tert-butyl (((1S,4S)-4-fluoroisochroman-1-yl)methyl) (methyl)carbamate (300 mg, 1.01 mmol) in ethyl acetate (20 mL) was added HCl/1,4-dioxane (36.3 mg, 1.01 mmol). The reaction was stirred at ambient temperature for 16 h. Upon completion, the mixture was concentrated to give (21) as yellow solid (0.15 g). MS (ESI): m/z=196 [M+H]+. 1H NMR (500 MHz, CD3OD, HCl salt) δ 7.56 (d, J=7.3 Hz, 1H), 7.50-7.41 (m, 2H), 7.31 (d, J=7.2 Hz, 1H), 5.57-5.45 (m, 1H), 5.22-5.21 (m,1H), 4.35-4.27(m, 1H), 4.09-4.03 (m,1H), 3.50-3.43 (m, 2H), 2.82 (s, 3H).

1-((1R,4R)-4-fluoroisochroman-1-yl)-N-methylmethanamine (22): To a solution of tert-butyl(((1R,4R)-4-fluoroisochroman-1-yl) methyl) (methyl)carbamate (300 mg, 1.01 mmol) in ethyl acetate (20 mL) was added HCl/1,4-dioxane (181 mg, 5.05 mmol). The reaction was stirred at ambient temperature for 6 h. Upon completion, the mixture was concentrated to give (22) as yellow solid (0.16 g). MS (ESI): m/z=196 (M+H)+. 1H NMR (500 MHz, CD3OD, HCl salt) δ 7.56-7.54 (d, J=7.5 Hz, 1H), 7.48-7.42 (m, 2H), 7.31 (d, J=7 Hz, 1H), 5.51 (m, 1H), 5.22 (s, 1H), 4.35-4.27 (m 1H), 4.09-4.03 (m, 1H), 3.50-3.43(m, 2H), 2.82 (s, 3H).

General Procedure D 4.1 Preparation of (S)-1-(4,4-difluoroisochroman-1-yl)-N-methylmethanamine (27) and (R)-1-(4,4-difluoroisochroman-1-yl)-N-methylmethanamine (28)

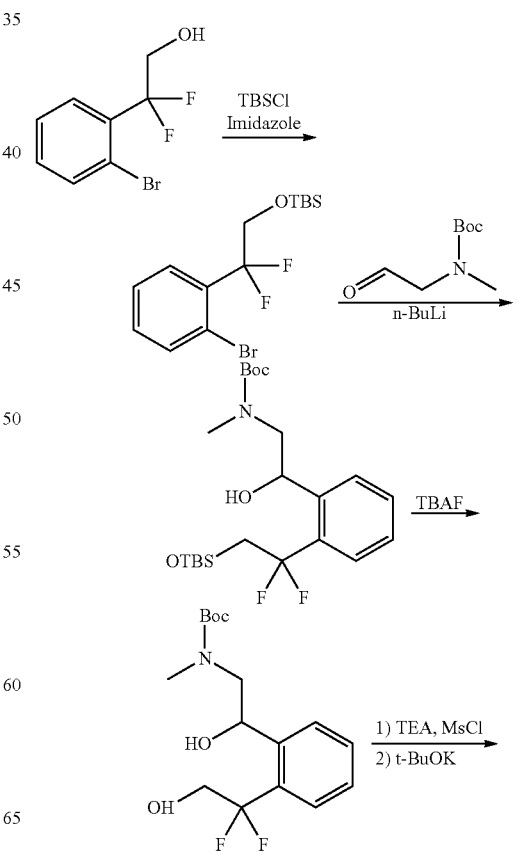

-continued

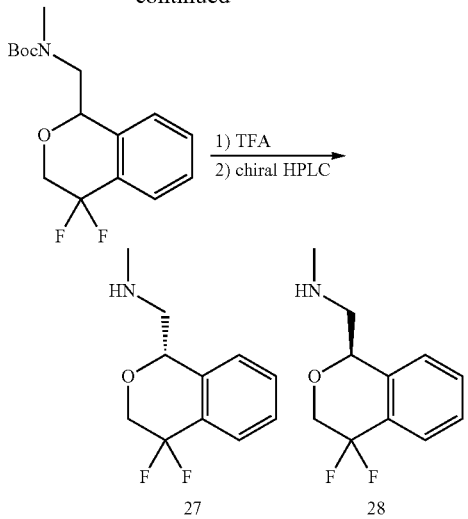

(a). (2-(2-bromophenyl)-2,2-difluoroethoxy)(tert-butyl)dimethyl silane

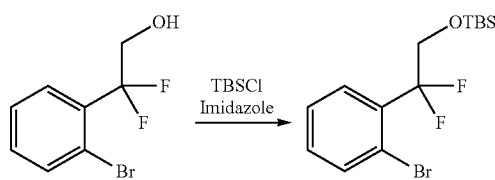 [SMILES: OCC(F)(F)c1ccccc1Br ; CC(C)(C)[Si](C)(C)OCC(F)(F)c1ccccc1Br]

To a solution of 2-(2-bromophenyl)-2,2-difluoroethanol (30 g, 126.3 mmol) in dichloromethane (200 mL) was added 1H-imidazole (17.2 g, 252.6 mmol) and tert -butylchlorodimethylsilane (28.5 g, 189.3 mmol). The reaction was stirred at ambient temperature for 12 h. water (200 mL) was added to the reaction vessel and the resulting biphasic mixture was transferred to a separatory funnel and extracted with dichloromethane (500 mL×2). The combined organics were dried over anhydrous sodium sulfate, filtered and concentrated in vacuo. The resulting oil was purified by flash column chromatography with an isocratic elution of ethyl acetate (10%) and petroleum ether (90%) to provide (2-(2-bromophenyl)-2,2-difluoroethoxy) (tert-butyl)dimethyl silane (35 g) as a colorless oil.

(b) tert-butyl 2-((2-(3-(tert-butyldimethylsilyloxy)propyl)-5-fluorophenyl) (hydroxy)-methyl)pyrrolidine-1-carboxylate

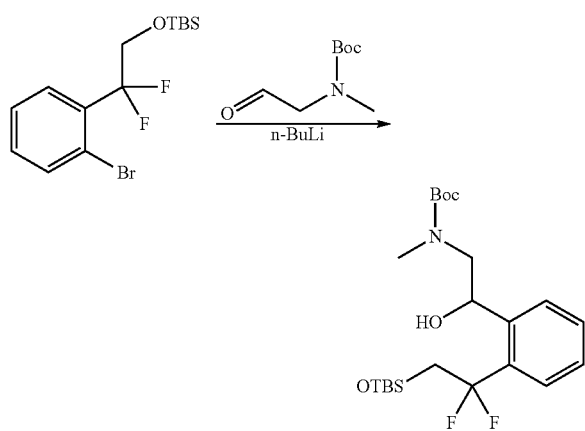

To a solution of (2-(2-bromophenyl)-2,2-difluoroethoxy) (tert-butyl)dimethylsilane (3.5 g, 9.96 mmol) in THF(40 mL) was added n-butyllithium (14.9 mmol, 2.5 N, 6 mL) at −78° C. under nitrogen. The mixture was stirred at this temperature for 2 h, then a solution of tert-butyl methyl(2-oxoethyl)carbamate(2.58 g, 14.9 mmol) in THF (5 mL) was added. After addition, the mixture was stirred at this temperature for 1 h, then allowed to warm to r.t. The mixture was quenched with water(100 mL), extracted with EtOAc (60 mL×2), dried and concentrated in vacuo to give a residue, which was purified by silica gel chromatography eluted with PE/EtOAc=10: 1 to provide tert-butyl 2-(2-(2-(tert-butyldimethylsilyloxy)-1,1-difluoroethyl)phenyl)-2-hydroxyethyl(methyl)-carbamate(900 mg) as a yellow oil.

(c). 2-(2-(1,1-ddluoro-2-hydroxyethyl)phenyl)-2-hydroxyethyl(methyl)carbamate

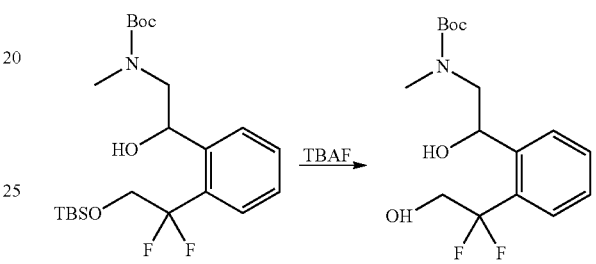

To a solution of tert-butyl (2-(2-(2-((tert-butyldimethylsilyl)oxy)-1,1-difluoroethyl) phenyl)-2-hydroxyethyl)(methyl)carbamate (891 mg, 2.0 mmol) in THF (20 mL) was added
TBAF (1.04 g, 4.00 mmol). The mixture was stirred at r.t. for 2 h. Upon completion, the mixture was quenched with water(100 mL), extracted with EtOAc(60 mL×2), dried and concentrated in vacuo to give tert-butyl 2-(2-(1,1-difluoro-2-hydroxyethyl)phenyl)-2-hydroxyethyl(methyl)carbamate (700 mg) as a yellow oil.

(d). tert-butyl (4,4-difluoroisochroman-1-yl)methyl(methyl) carbamate

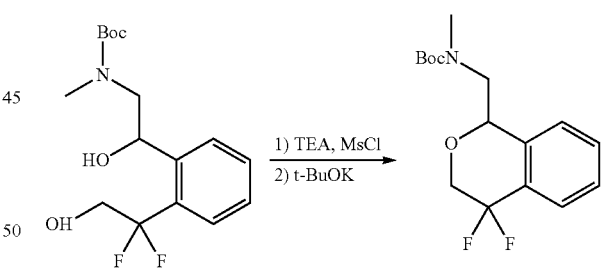

To a solution of tert-butyl (2-(2-(1,1-difluoro-2-hydroxyethyl)phenyl)-2-hydroxyethyl)(methyl)carbamate (650 mg, 1.96 mmol) and TEA (808 mg, 8.0 mmol) in ethyl acetate (30 mL) was added a solution of MsCl (269 mg, 2.35 mmol) in ethyl acetate (10 mL) at 0° C. After addition, the mixture was stirred at this temperature for 2 h. The mixture was quenched with water (30 mL), extracted with ethyl acetate (20 mL×2), dried and concentrated in vacuo. The residue was dissolved in THF (20 mL) and to the solution was added t-BuOK (436 mg, 3.90 mmol) at 0° C. The mixture was stirred at this temperature for 4 h. The mixture was quenched with water (100 mL), extracted with EtOAc (50 mL×2), dried and concentrated in vacuo to give the crude, which was purified by prep. TLC eluted with PE: EtOAc=5:1 to yield tert-butyl (4,4-difluoroisochroman-1-yl)methyl(methyl) carbamate(400 mg) as an oil.

(e). (S)-1-(4,4-difluoroisochroman-1-yl)-N-methylmethanamine (27) and (R)-1-(4,4-difluoroisochroman-1-yl)-N-methylmethanamine (28)

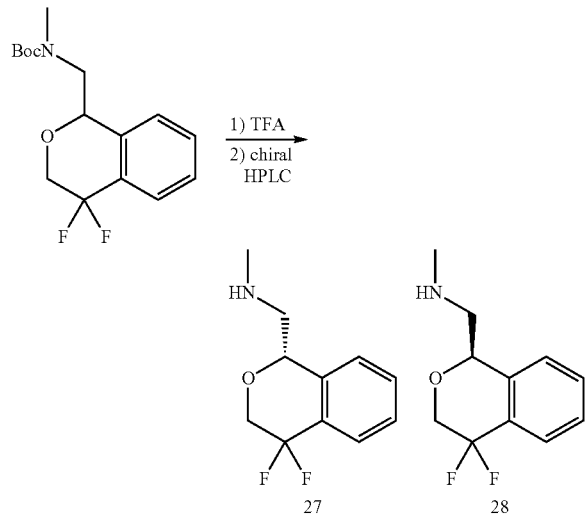

To a solution of tert-butyl ((4,4-difluoroisochroman-1-yl)methyl)(methyl) carbamate (800 mg, 2.55 mmol) in DCM (15 mL) was added TFA (6 mL). The mixture was stirred at r.t. for 4 h. The mixture was evaporated in vacuo to remove the solvent, neutralized with 25% aq. ammonia, extracted with DCM (30 mL×2), dried and concentrated in vacuo to give 1-(4,4-difluoroisochroman-1-yl)-N-methylmethanamine (560 mg) as a yellow oil and a racemic mixture. The mixture was separated into its enantiomers (S)-1-(4,4-difluoroisochroman-1-yl)-N-methylmethanamine (27, 250 mg oil) and (R)-1-(4,4-difluoroisochroman-1-yl)-N-methylmethanamine (28, 250 mg oil) by Preparative-SFC using Instrument: SFC-80 (Thar, Waters), Column: OJ 20×250mm, 5um (Dacel), Column temperature: 35 °C. and Mobile phase: CO2/ MeOH{0.5% Ammonia (7M methanal)}=85/15. The Flow rate was 80 g/min, Back pressure was 100 bar, Detection wavelength was 240 nm and Cycle time was 3.6 min.

(S)-1-(4,4-difluoroisochroman-1-yl)-N-methylmethanamine (27): MS (ESI): m/z=214 [M+H]$^+$. $^1$H NMR (500 MHz, CDCl$_3$): 7.75 (d, J=8.0 Hz, 1H), 7.49~7.41 (m, 2 H), 7.22 (d, J=7.5 Hz, 1H), 4.94-4.93 (m, 1H), 4.36~4.31 (m, 1H), 3.99~3.91 (m, 1H), 3.14~3.11 (dd, J=3.0, 12.5 Hz, 1H), 3.03~2.99 (m,1H), 2.53 (s, 3H), 1.75 (brs, 1H).

(R)-1-(4,4-difluoroisochroman-1-yl)-N-methylmethanamine (28): MS (ESI): m/z=214 [M+H]$^+$. $^1$H-NMR of freebase (500 MHz, CDCl$_3$): 7.75 (d, J=8.0 Hz, 1H), 7.49~7.41 (m, 2 H), 7.21 (d, J=8.0 Hz, 1H), 4.94-4.92 (m, 1H), 4.36~4.30 (m, 1H), 3.99~3.91 (m, 1 H), 3.14~3.11 (dd, J=3.0, 12.5 Hz, 1H), 3.03~2.99 (m,1H), 2.53 (s, 3H), 1.71 (brs, 1H).

4.2 Preparation of (S)-1-(9-fluoro-1,3,4,5-tetrahydrobenzokloxepin-1-yl)-N-methylmethanamine (60) and (R)-1-(9-fluoro-1,3,4,5-tetrahydrobenzokloxepin-1-yl)-N-methylmethanamine (61)

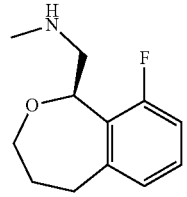

60

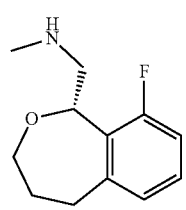

61

(S)-1-(9-fluoro-1,3,4,5-tetrahydrobenzo[c]oxepin-1-yl)-N-methylmethanamine (60) and (R)-1-(9-fluoro-1,3,4,5-tetrahydrobenzo[c]oxepin-1-yl)-N-methylmethanamine (61) were prepared using General Procedure D and Scheme 4 starting with 3-(2-bromo-3-fluorophenyl)propan-1-ol.

((S)-1-(9-fluoro-1,3,4,5-tetrahydrobenzo[c]oxepin-1-yl)-N-methylmethanamine (60): MS (ESI): m/z=210 [M+H]$^+$. $^1$H NMR (400 MHz, CD$_3$OD, HCl salt): 7.33-7.28 (m, 1H), 7.07-7.00 (m, 2H), 5.35-5.33 (m, 1H), 4.19-4.13 (m, 1H), 3.74-3.67 (m, 1H), 3.52-3.46 (m, 1H), 3.40-3.33 (m, 2H), 2.79-2.72 (m, 4H), 2.17-2.11 (m, 1H), 1.83-1.76 (m, 1H).
(R)-1-(9-fluoro-1,3,4,5-tetrahydrobenzo[c]oxepin-1-yl)-N-methylmethanamine (61): MS (ESI): m/z=210 [M+H]$^+$. $^1$H NMR (400 MHz, CD$_3$OD, HCl salt): 7.33-7.28 (m, 1H), 7.07-7.00 (m, 2H), 5.35-5.33 (m, 1H), 4.19-4.13 (m, 1H), 3.74-3.67 (m, 1H), 3.52-3.46 (m, 1H), 3.40-3.32 (m, 2H), 2.79-2.74 (m, 4H), 2.17-2.11 (m, 1H), 1.83-1.77 (m, 1H).

4.3 Preparation of (R)-1-(7-fluoro-1,3-dihydroisobenzofuran-1-yl)-N-methyl-methanamine (69) and (S)-1-(7-fluoro-1,3-dihydroisobenzofuran-1-yl)-N-methyl-methanamine (68)

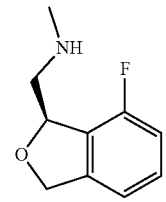

69

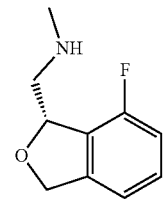

68

(R)-1-(7-fluoro-1,3-dihydroisobenzofuran-1-yl)-N-methylmethanamine (69) and (S)-1-(7-fluoro-1,3-dihydroisobenzofuran-1-yl)-N-methylmethanamine (68) were prepared using General Procedure D and Scheme 5 starting with ((2-bromo-3-fluorobenzyl)oxy)-(tert-butyl)dimethylsilane and 2-(benzyloxy)acetaldehyde.

(R)-1-(7-fluoro-1,3-dihydroisobenzofuran-1-yl)-N-methylmethanamine (69): ESI: m/z=182 [M+H]$^+$. $^1$H-NMR (500 MHz, MeOH-d$_4$): δ 7.48-7.44 (m, 1H), 7.19 (d, J=7.5 Hz, 1H), 7.13-7.09 (m, 1H), δ 5.69-5.67 (m, 1H), 5.32-5.29 (dd, J=3 Hz, 13 Hz, 1H), 5.18 (d, J=12 Hz, 1H), 3.59-3.56 (dd, J=2.5 Hz, 12.5 Hz, 1H), 3.34-3.3 (m, 1H), 2.80 (s, 3H).

(S)-1-(7-fluoro-1,3-dihydroisobenzofuran-1-yl)-N-methylmethanamine (68): ESI: m/z=182 [M+H]$^+$. $^1$H NMR (500 MHz, MeOH-d$_4$): δ 7.48-7.44 (m, 1H), 7.19 (d, J=7.5 Hz, 1H), 7.11 (t, J=18.0 Hz, 1H), δ 5.69-5.67 (m, 1H), 5.32-5.29

(dd, J=2.5 Hz, 12.5 Hz, 1H), 5.18 (d, J=13 Hz, 1H), 3.59-3.56 (dd, J=3 Hz, 13 Hz, 1H), 3.34-3.3 (m, 1H), 2.80 (s, 3H).

General Procedure E 5.1 Preparation of (S)-1-((methylamino)methyl)isochromane-8-carbonitrile (44) and (R)-1-((methylamino)methyl)isochromane-8-carbonitrile (45)

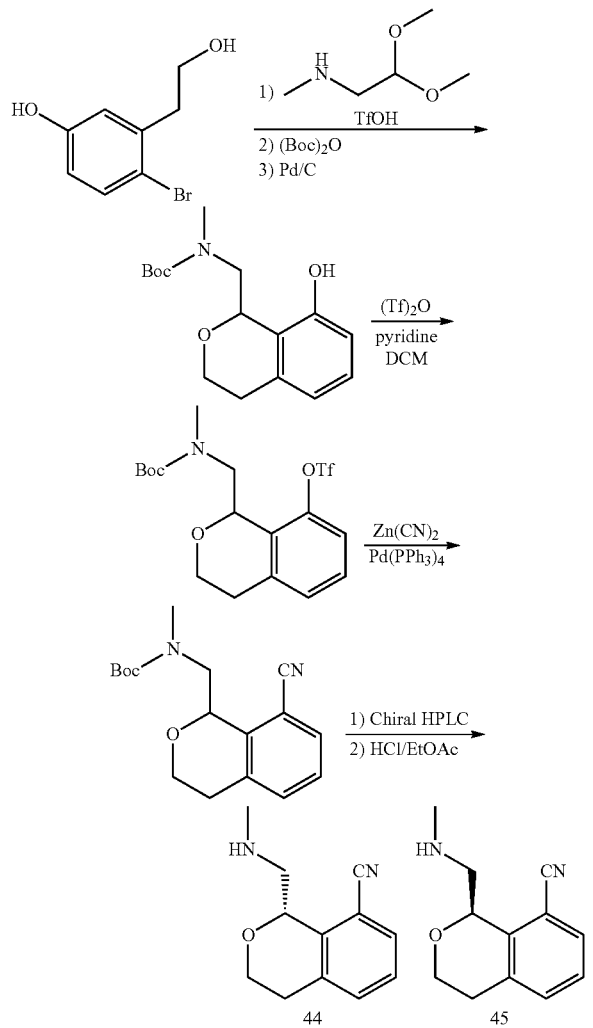

(a). tert-butyl ((8-hydroxylsochroman-1-yl)methyl)(methyl) carbamate

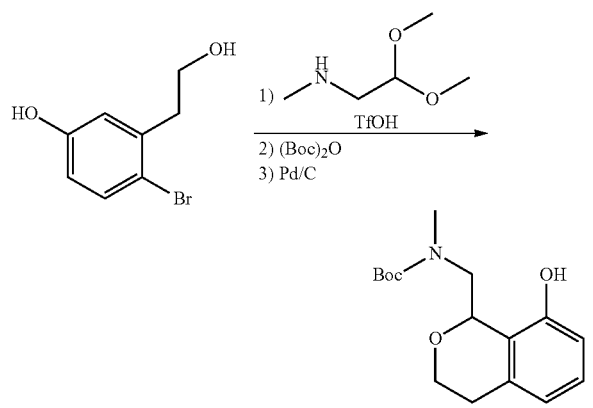

tert-Butyl ((8-hydroxyisochroman-1-yl)methyl)(methyl) carbamate was prepared using General Procedure B (steps a,b,c in experimental 2.1) starting from 4-bromo-3-(2-hydroxyethyl)phenol and 2,2-dimethoxy-N-methylethan-1-amine.

(b). 1-(((tert-butoxycarbonyl)(methyl)amino)methyl)isochroman-8-yl trifluoromethanesulfonate

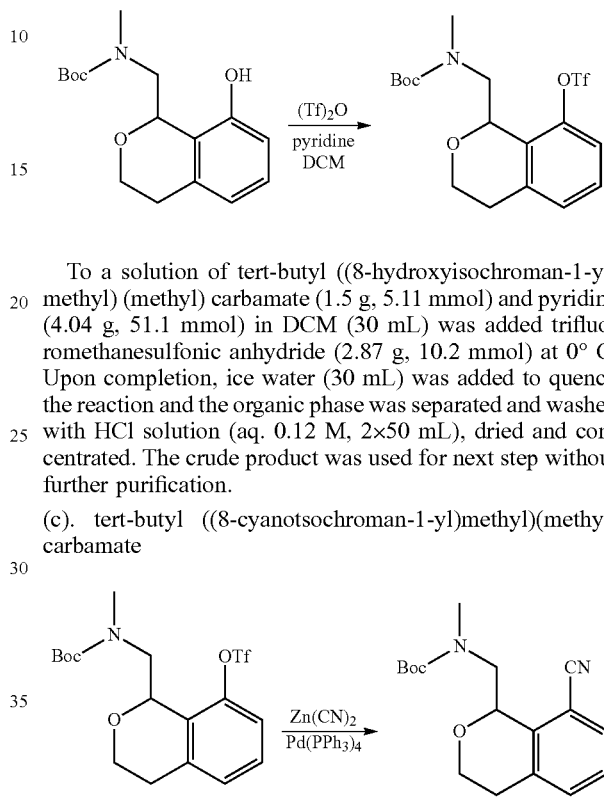

To a solution of tert-butyl ((8-hydroxyisochroman-1-yl) methyl) (methyl) carbamate (1.5 g, 5.11 mmol) and pyridine (4.04 g, 51.1 mmol) in DCM (30 mL) was added trifluoromethanesulfonic anhydride (2.87 g, 10.2 mmol) at 0° C. Upon completion, ice water (30 mL) was added to quench the reaction and the organic phase was separated and washed with HCl solution (aq. 0.12 M, 2×50 mL), dried and concentrated. The crude product was used for next step without further purification.

(c). tert-butyl ((8-cyanotsochroman-1-yl)methyl)(methyl) carbamate

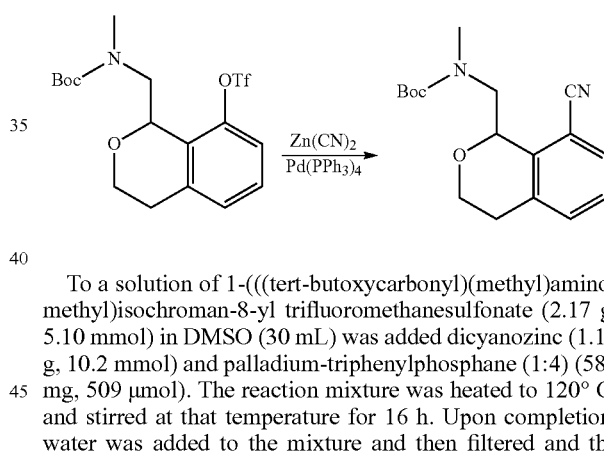

To a solution of 1-(((tert-butoxycarbonyl)(methyl)amino) methyl)isochroman-8-yl trifluoromethanesulfonate (2.17 g, 5.10 mmol) in DMSO (30 mL) was added dicyanozinc (1.19 g, 10.2 mmol) and palladium-triphenylphosphane (1:4) (588 mg, 509 µmol). The reaction mixture was heated to 120° C. and stirred at that temperature for 16 h. Upon completion, water was added to the mixture and then filtered and the solid was washed with EtOAc (50 mL). The combined filtrate was concentrated. The resulting oil was purified by flash column chromatography with an isocratic elution of petroleum ether (100%) and EtOAc (0%) to petroleum ether (80%) and EtOAc (20%) to provide tert-butyl ((8-cyanoisochroman-1-yl)methyl)(methyl)carbamate as a white solid (racemic mixture) (1.35 g).

(d). (S)-1-((methylamino)methyl)isochromane-8-carbonitrile (44) and (R)-1-((methylamino)methyl)isochromane-8-carbonitrile (45)

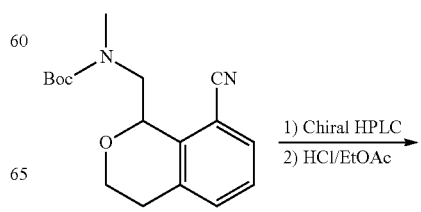

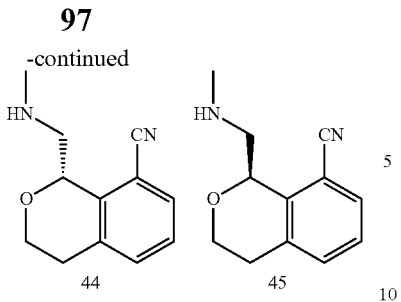
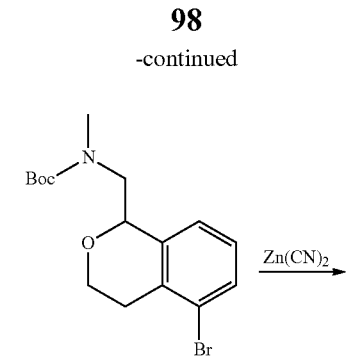

The racemic mixture (1.35 g) of tert-butyl ((8-cyanoisochroman-1-yl)methyl)(methyl)carbamate obtained above was separated by chiral HPLC: {Column: Cellulose-2 (4.6*250 mm 5 um); Mobile Phase: n-Hexane (0.1% DEA)/ethanol (0.1% DEA)=90:10} to give (S)-tert-butyl ((8-cyanoisochroman-1-yl) methyl) (methyl) carbamate and (R)-tert-butyl ((8-cyanoisochroman-1-yl) methyl) (methyl) carbamate.

To a solution of (S)-tert-butyl ((8-cyanoisochroman-1-yl) methyl) (methyl) carbamate (0.45 g, 1.48 mmol) in EtOAc (20 mL) was added 3 M HCl/EtOAc (3 M, 6 mL). The reaction was stirred at ambient temperature for 16 h. Upon the completion, the solvent was removed and the residue was washed with EtOAc, filtered and dried. (S)-1-((methylamino)methyl)isochromane-8-carbonitrile (44) was obtained as a white solid (HCl salt, 281.04 mg). MS (ESI): m/z=203 [M+H]$^+$. $^1$H NMR (400 MHz, CD$_3$OD) δ 7.70 (d, J=7.6 Hz, 1H), 7.59(d, J=7.7 Hz, 1H), 7.48 (t, J=7.7 Hz, 1H), 5.41~5.38 (dd, J$_1$=9.6, J$_2$=3.2 Hz, 1H), 4.21~4.19(m, 1H), 3.94~3.91 (m, 1H), 3.60~3.55 (m, 2H), 2.98~2.95 (m, 2H), 2.84 (s, 3H).

To a solution of (R)-tert-butyl ((8-cyanoisochroman-1-yl) methyl) (methyl) carbamate (0.45 g, 1.48 mmol) in EtOAc (20 mL) was added 3M HCl/EtOAc (3M, 6 mL). The reaction was stirred at ambient temperature for 16 h. Upon completion, the solvent was removed and the residue was washed with EtOAc, filtered and dried. (R)-1-((methylamino)methyl)isochromane-8-carbonitrile (45) was obtained as a white solid (HCl salt, 270.33 mg). MS (ESI): m/z=203 [M+H]$^+$. $^1$H NMR (400 MHz, CD$_3$OD) δ 7.70~7.69 (d, J =7.6 Hz, 1H), 7.60~7.58(d, J=7.8 Hz, 1H), 7.51~7.47 (t, J=7.7 Hz, 1H), 5.41~5.38 (dd, J$_1$=9.8, J$_2$=2.9 Hz, 1H), 4.22~4.17(m, 1H), 3.94~3.89 (m, 1H), 3.63~3.50 (m, 2H), 2.99~2.95 (m, 2H), 2.84 (s, 3H).

General Procedure F 6.1 Preparation of (S)-1-((methylamino)methyl)isochromane-5-carbonitrile (46) and (R)-1-((methylamino)methyl) isochromane-5-carbonitrile (47)

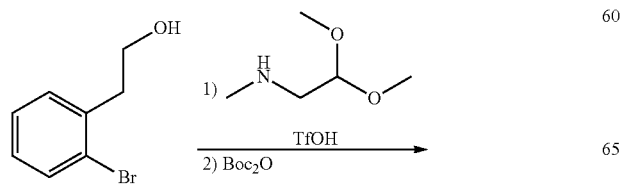

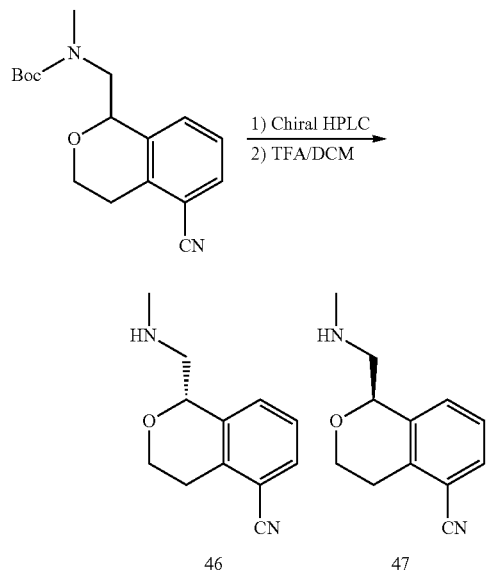

(a). tert-butyl ((5-bromoisochroman-1-yl)methyl)(methyl) carbamate

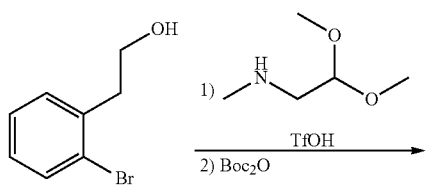

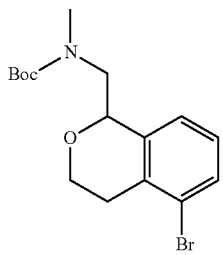

tert-Butyl ((5-bromoisochroman-1-yl)methyl)(methyl) carbamate was prepared using General Procedure B (steps a,b in experimental 2.1) starting from 2-(2-bromophenyl) ethan-1-ol and 2,2-dimethoxy-N-methylethan-1-amine.

(b). tert-butyl ((5-cyanotsochroman-1-yl)methyl)(methyl) carbamate

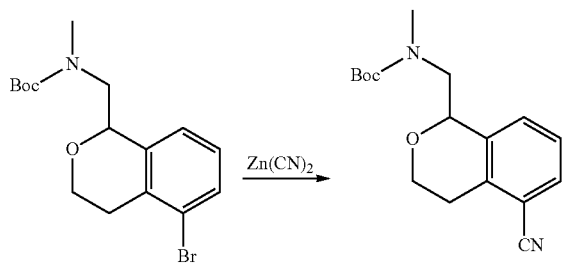

To a solution of tert-butyl ((5-bromoisochroman-1-yl) methyl)(methyl)carbamate (2.0 g, 5.61 mmol) in DMSO (20 mL) was added dicyanozinc (1.31 g, 11.2 mmol) and palladium-triphenylphosphane (1:4) (648 mg, 561 µmol). The reaction mixture was heated to 120° C. and stirred at that temperature for 16 h. Upon completion, water was added to the mixture and then filtered and the solid was washed with EtOAc (50 mL). The combined filtrate was concentrated. The resulting oil was purified by flash column chromatography with an isocratic elution of petroleum ether (100%)/ EtOAc (0%) to petroleum ether (80%)/EtOAc (20%) to provide tert-butyl ((5-cyanoisochroman-1-yl)methyl) (methyl)carbamate as a colorless oil (racemic mixture, 1.5 g).

(c). (S)-tert-butyl ((5-cyanoisochroman-1-yl)methyl) (methyl)carbamate (46) and (R)-tert-butyl ((5-cyanoisochroman-1-yl)methyl)(methyl)carbamate (47)

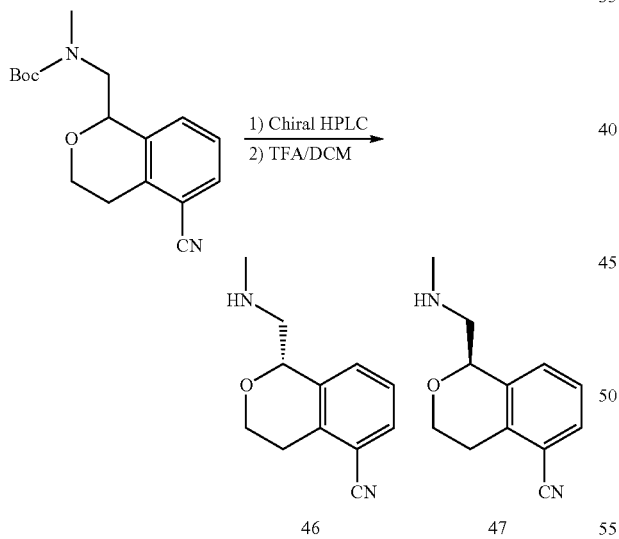

tert-Butyl ((5-cyanoisochroman-1-yl)methyl)(methyl)carbamate (a racemic mixture, 1.5 g) obtained above was separated into its enantiomers (S)-tert-butyl ((5-cyanoisochroman-1-yl)methyl)(methyl)carbamate and (R)-tert-butyl ((5-cyanoisochroman-1-yl)methyl)(methyl)carbamate by chiral HPLC: {preparative-SFC; co-solvent: n-Hexane (0.1% DEA)/EtOH(0.1% DEA)=90:10; column: AY-H (250*4.6 mm 5 um); column temperature: 40° C.; flow rate: 10 mL/min; detection wavelength: 240 nm; cycle time: 6.7 min}.

(S)-tert-butyl (5-cyanoisochroman-1-yl)methyl(methyl) carbamate (550 mg) in DCM (2 mL) was added TFA (1 mL). The mixture was stirred at r.t. overnight and concentrated in vacuo. To the residue was added EtOAc (3 mL) and HCl in EtOAc (3M, 0.99 mL, 2.96 mmol). The mixture was stirred at r.t. for 15 mins. The mixture was concentrated in vacuo and the residue was washed with EtOAc (10 mL) to give (S)-1-((methylamino)methyl)isochromane-5-carbonitrile (46) (305 mg HCl salt) as a white solid. MS (ESI): m/z=203 [M+H]$^+$. $^1$H NMR (400 MHz, CD$_3$OD, HCl salt): 7.71 (d, J=7.6 Hz, 1H), 7.59~7.56 (m, 1H), 7.49~7.44 (m, 1H), 5.16-5.15 (m, 1H), 4.34~4.28 (m, 1H), 3.96~3.90 (m, 1H), 3.67-3.65 (m, 1H), 3.40-3.37 (m, 1H), 3.18-3.10 (m, 1H), 3.02~2.98 (m, 1H), 2.80 (s, 3H).

(R)-tert-butyl (5-cyanoisochroman-1-yl)methyl(methyl) carbamate (650 mg) in DCM (2.75 mL) DCM was added TFA (1.25 mL). The mixture was stirred at r.t. overnight and concentrated in vacuo. To the residue was added EtOAc (3 mL) and HCl in EtOAc (3M, 1.31 mL). The mixture was stirred at r.t. for 15 mins and concentrated in vacuo. The residue was washed with EtOAc (10 mL) to give (R)-1-((methylamino)methyl)isochromane-5-carbonitrile (47) (401 mg HCl salt) as a white solid. MS (ESI): m/z=203 [M+H]$^+$. $^1$H NMR (400 MHz, CD$_3$OD): 7.71 (d, J=7.6 Hz, 1H), 7.59~7.56 (m, 1H), 7.48~7.44 (m, 1H), 5.16-5.14 (m, 1H), 4.34~4.28 (m, 1H), 3.96~3.90 (m, 1H), 3.69-3,66 (m, 1H), 3.40-3.37 (m, 1H), 3.18-3.10 (m, 1H), 3.02~2.98 (m, 1H), 2.80(s, 3 H).

Other compounds that can be made by the methods described above include the following non-limiting examples:

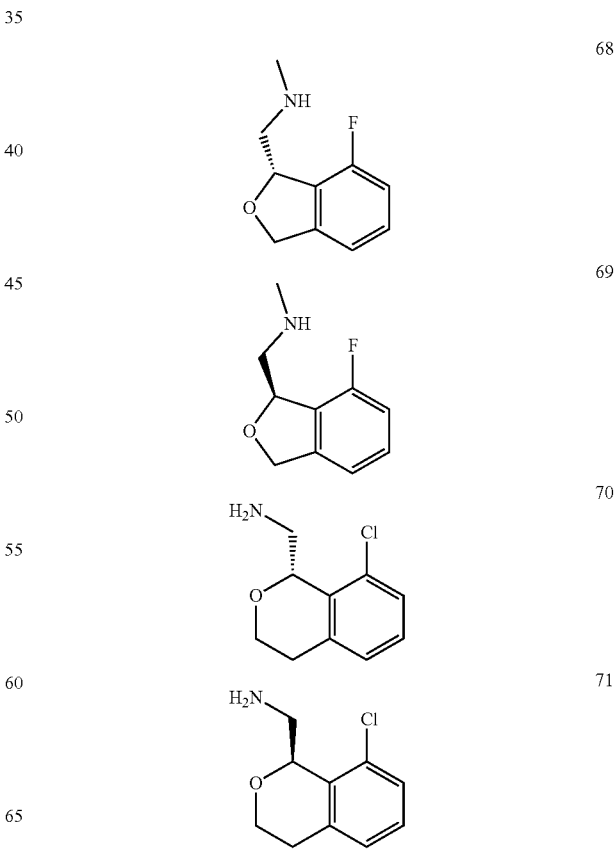

72 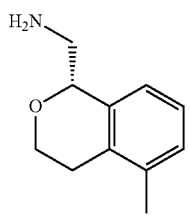
73 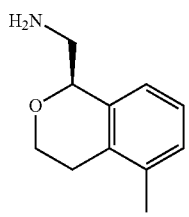
74 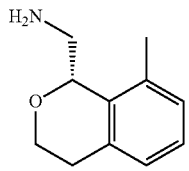
75 
76 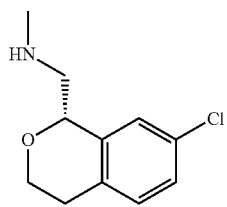
77 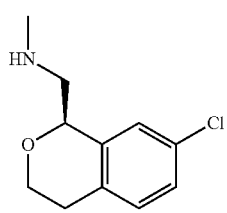
78 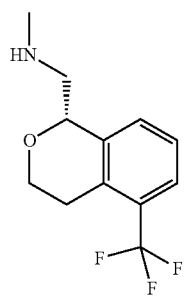
79 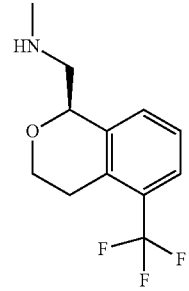
80 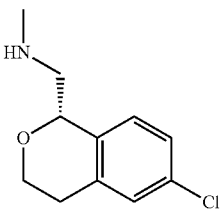
81 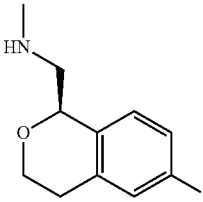
82 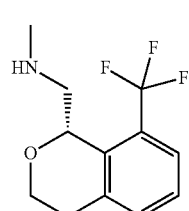
83 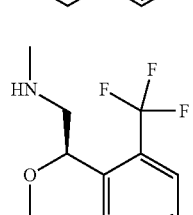
84 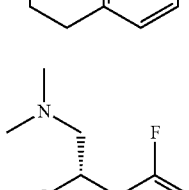
85 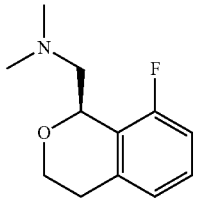

| | |
|---|---|
| 86 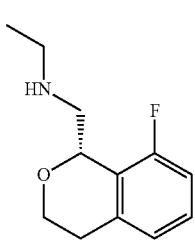 | 93 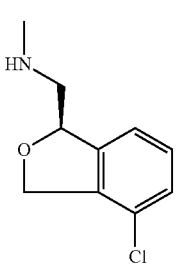 |
| 87 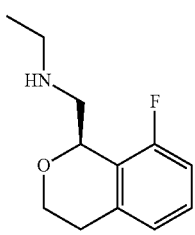 | 94 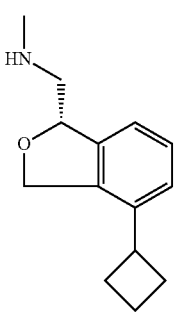 |
| 88 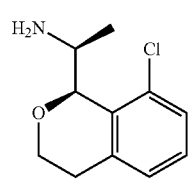 | 95 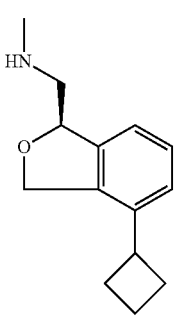 |
| 89 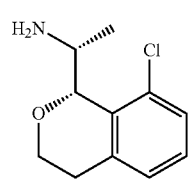 | 96 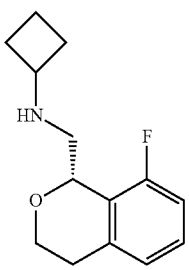 |
| 90 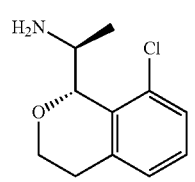 | 97 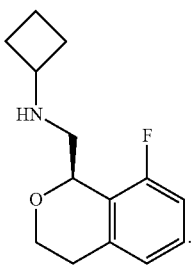 |
| 91 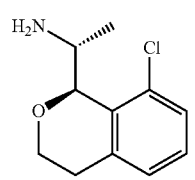 | |
| 92 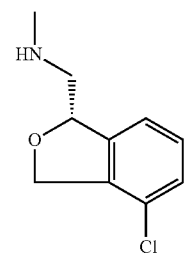 | |

General Procedure G 7.1 Preparation of (R)-1-(4-chloro-1,3-dihydroisobenzofuran-1-yl)-N-methyl-methanamine (93) and (S)-1-(4-chloro-1,3-dihydroisobenzofuran-1-yl)-N-methylmethanamine (92)

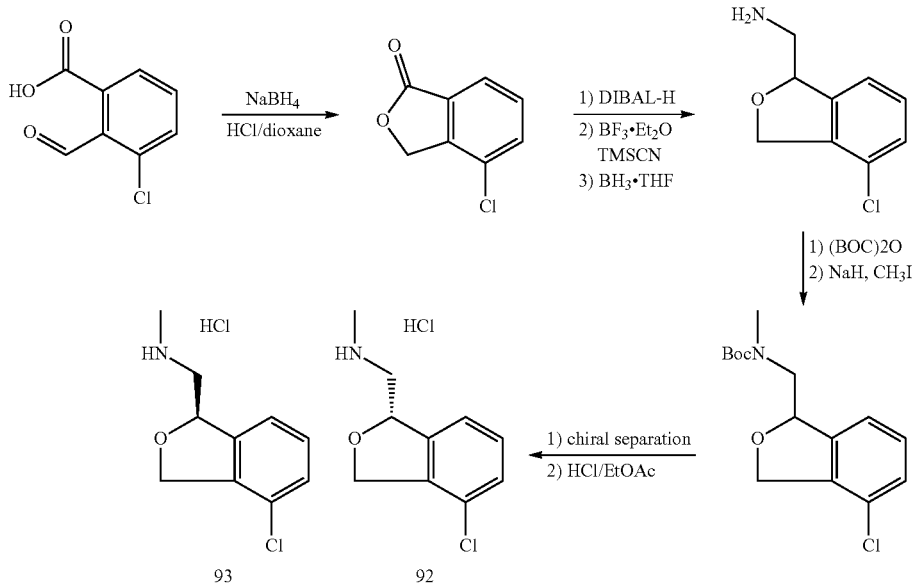

(a). 4-chloroisobenzofuran-1 (3H)-one

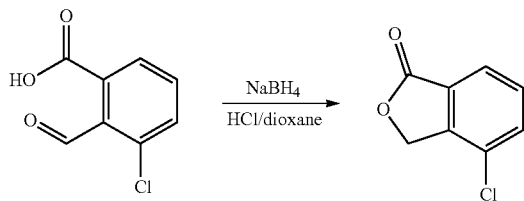 [SMILES: O=Cc1c(Cl)cccc1C(=O)O ; "NaBH4" ; O=C1OCc2c(Cl)cccc21]

To a solution of 3-chloro-2-formylbenzoic acid (24 g, 91.0 mmol) in methanol (250 mL) was added NaBH₄ (5.14 g, 136 mmol). The reaction was stirred at ambient temperature for 2 h. The mixture was concentrated to dryness to provide 3-chloro -2-(hydroxymethyl)benzoic acid as a yellow oil. To the oil in THF (80 mL) was added hydrogen chloride in dioxane (6N, 20 mL). The mixture was stirred at ambient temperature for 2 h and then extracted with EtOAc (3×50 mL). The combined organic phase was dried over sodium sulfate, filtered and the filtrate was concentrated in vacuo. The residue was purified by flash chromatography (PE/EtOAc=5/1) to provide 4-chloroisobenzofuran-1(3H)-one (12 g) as a yellow solid. MS (ESI) m/z=169 [M+H]+.

(b). (4-chloro-1,3-dihydroisobenzofuran-1-yl)methanamine

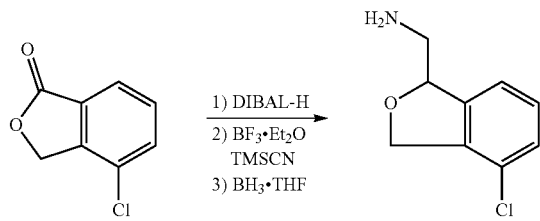 [SMILES: O=C1OCc2c(Cl)cccc21 ; NCC1OCc2c(Cl)cccc21]

To a solution of 4-chloroisobenzofuran-1(3H)-one (7 g, 41.5 mmol) in DCM (120 mL) was cooled to −78° C., was added diisobutylaluminum hydride (7.66 g, 53.9 mmol). The mixture was stirred at −78° C. for 3 h and water (2.2 mL) was added. The mixture was warmed to 0° C. and 15% NaOH (2.2 mL) and then H₂O (5.4 mL) was added. The mixture was stirred at RT for 1 h and was filtered. The filtrate was dried over sodium sulfate and concentrated to provide 4-chloro-1,3-dihydroisobenzofuran-1-ol (5.00 g) as a yellow oil.

To a solution of 4-chloro-1,3-dihydroisobenzofuran-1-ol (5 g, 29.3 mmol) in DCM (80 mL) was added BF₃·Et₂O (12.4 g, 87.9 mmol) and trimethylsilanecarbonitrile (14.4 g, 146 mmol) at −20° C. The reaction was stirred at this temperature for 1 h and NaOH (60 mL, aq. 1M) was added. The resulting biphasic mixture was transferred to a separatory funnel. The aqueous layer was extracted with DCM (2×30 mL). The combined organics were dried over anhydrous Na₂SO₄, filtered and concentrated in vacuo to provide 4-chloro-1,3-dihydroisobenzofuran-1-carbonitrile (5.00 g) as a yellow oil.

To a solution of 4-chloro-1,3-dihydroisobenzofuran-1-carbonitrile (5 g, 27.8 mmol) in THF (40 mL) was added BH₃-THF (7.08 g, 83.4 mmol). The reaction was stirred at ambient temperature for 3 h. Water (50 mL) was added slowly to quench the reaction. The resulting mixture was extracted with EA (3×30 mL). The combined organic phase was dried over sodium sulfate, filtered and the filtrate was concentrated to provide (4-chloro-1,3-dihydroisobenzofuran-1-yl)methanamine (4.00 g) as a yellow oil. MS(ESI) m/z=184 [M+H]⁺

(c). tert-butyl ((4-chloro-1,3-dihydroisobenzofuran-1-yl)methyl)(methyl)carbamate

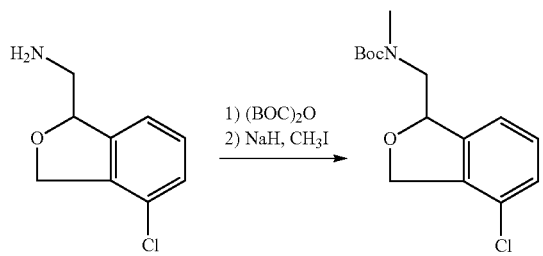 [SMILES: NCC1OCc2c(Cl)cccc21 ; CN(CC1OCc2c(Cl)cccc21)C(=O)OC(C)(C)C]

To a solution of (4-chloro-1,3-dihydroisobenzofuran-1-yl)methanamine (8 g, 43.5 mmol) in DCM (100 mL) was added triethylamine (13.1 g, 130 mmol) and di-tert-butyl dicarbonate (14.2 g, 65.2 mmol). The reaction was stirred at ambient temperature for 3 h. The mixture was then concentrated and residue purified by flash chromatography (PE/EtOAc=10/1) to provide tert-butyl (4-chloro-1,3-dihydroisobenzofuran-1-yl) methyl) carbamate (10.0 g) as a white solid. MS(ESI) m/z=184 [M-100+H]$^+$ To a solution of tert-butyl ((4-chloro-1,3-dihydroisobenzofuran-1-yl)methyl) carbamate (900 mg, 3.17 mmol) in DMF (30 mL) was added sodium hydride (152 mg, 6.34 mmol) and iodomethane (899 mg, 6.34 mmol). The reaction was stirred at ambient temperature for 1 h. water (100 mL) was added to the reaction vessel and the resulting biphasic mixture was transferred to a separatory funnel. The layers were separated and the organic phase was washed with EtOAc (2×50 mL) and water (2×60 mL). The combined organics were dried over anhydrous Na$_2$SO$_4$, filtered and concentrated in vacuo. The resulting oil was purified by flash column chromatography with an isocratic elution of EtOAc (10%) and petroleum ether (90%) to provide tert-butyl((4-chloro-1,3-dihydroisobenzofuran-1-yl)methyl)(methyl)carbamate (900 mg) as a colorless oil.

(d). (R)-1-(4-chloro-1,3-dihydroisobenzofuran-1-yl)-N-methyl-methanamine (93) and (S)-1-(4-chloro-1,3-dihydroisobenzofuran-1-yl)-N-methyl-methanamine (92)

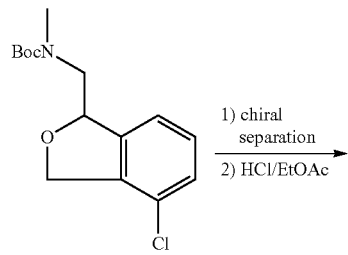

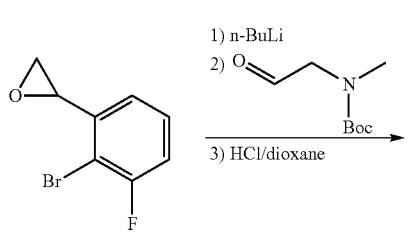

ter t-Butyl ((4-chloro-1,3-dihydroisobenzofuran-1-yl)methyl)(methyl) carbamate (a racemic mixture, 900 mg) obtained above was separated into its enantiomers by chiral HPLC {solvent: MeOH (0.2% ammonia); EnantioPak AD 4.6*100 mm 5 um} to provide (R)-tert -butyl ((4-chloro-1,3-dihydroisobenzofuran-1-yl)methyl)(methyl) carbamate (500 mg, 100% ee) as a colorless oil and (S)-tert-butyl ((4-chloro-1,3-dihydroisobenzofuran-1-yl) methyl)(methyl) carbamate (480 mg, 98% ee) as a colorless oil.

A solution of (R)-tert-butyl ((4-chloro-1,3-dihydroisobenzofuran-1-yl)methyl) (methyl) carbamate (500 mg, 1.67 mmol) in HCl/EtOAc (10 mL) was added HCl/EtOAc (10 mL, 3N). The mixture was stirred at ambient temperature for 24 h. The mixture was evaporated in vacuo to give the crude product as a white solid, which was washed with EtOAc to afford compound 93 hydrochloride salt as a white solid (250 mg, 100% ee). MS (ESI): m/z=198 (M+1). $^1$H-NMR (400 MHz, methanol-d$_4$) δ 7.41-7.39 (m, 2H), 7.35-7.33 (m, 1H), 5.62-5.60 (m, 1H), 5.30-5.26 (m, 1H) 5.19-5.15 (m, 1H), 3.57- 3.53 (m, 1H), 3.31-3.26 (m, 1H), 2.79 (s, 3H).

A solution of (S)-tert-butyl ((4-chloro-1,3-dihydroisobenzofuran-1-yl)methyl) (methyl)carbamate (480 mg, 1.61 mmol) in HCl/EtOAc (10 ml) was stirred at room temperature overnight. Upon completion, the mixture was evaporated in vacuo to give the crude product, which was washed with EtOAc to give compound 92 as a white powder hydrochloride salt (240 mg, 99% ee). MS (ESI): m/z=198 (M+1). $^1$H-NMR (400 MHz, methanol-d$_4$) δ 7.41-7.40 (m, 2H), 7.34-7.33 (m, 1H), 5.62-5.60 (m, 1H), 5.29-5.25 (m, 1H) 5.18-5.15 (m, 1H), 3.57- 3.53 (m, 1H), 3.31-3.26 (m, 1H), 2.79 (s, 3H).

General Procedure H 8.1 Preparation of (1R,4R)-8-fluoro-1-((methylamino)methyl)isochroman-4-ol (99) and (1S,4S)-8-fluoro-1-((methylamino)methyl)isochroman-4-ol (98)

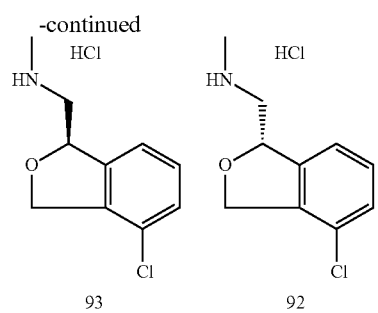

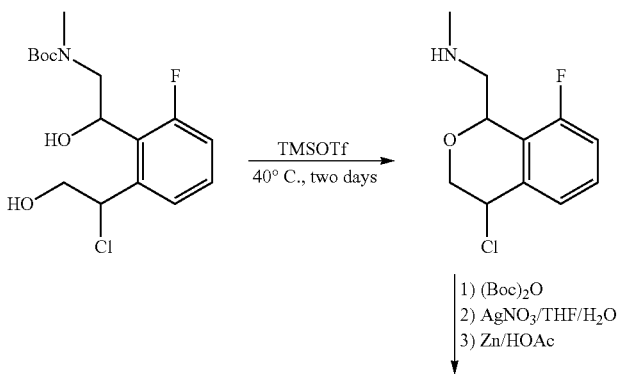

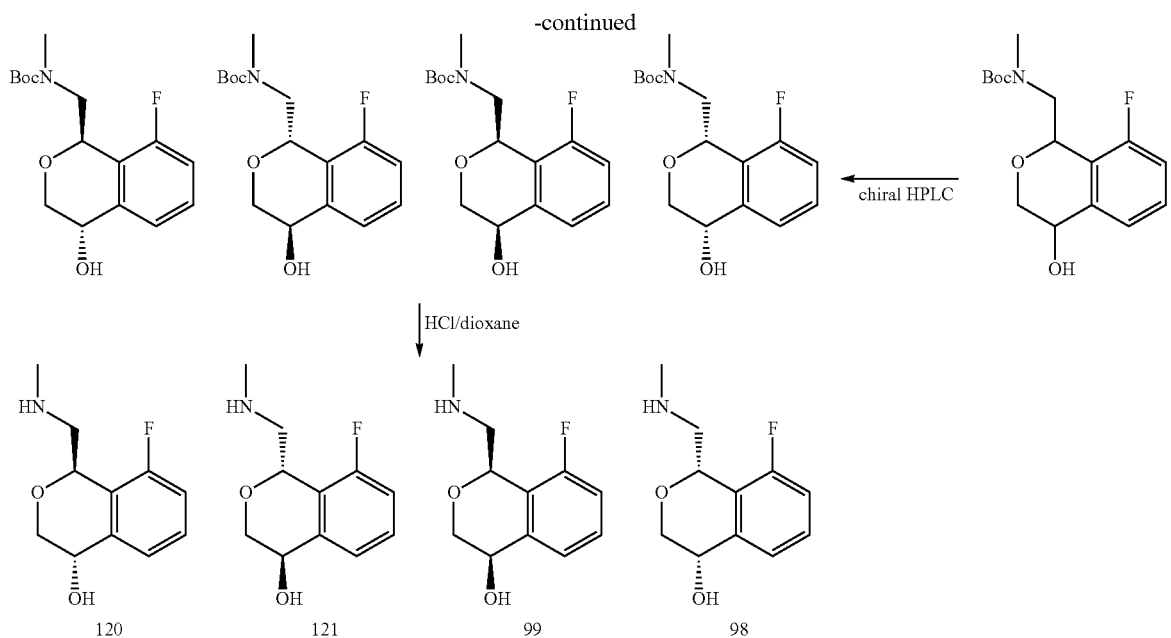

(a). tert-Butyl 2-(2-fluoro-6-(waran-2-yl)phenyl)-2-hydroxyethyl (methyl) carbamate

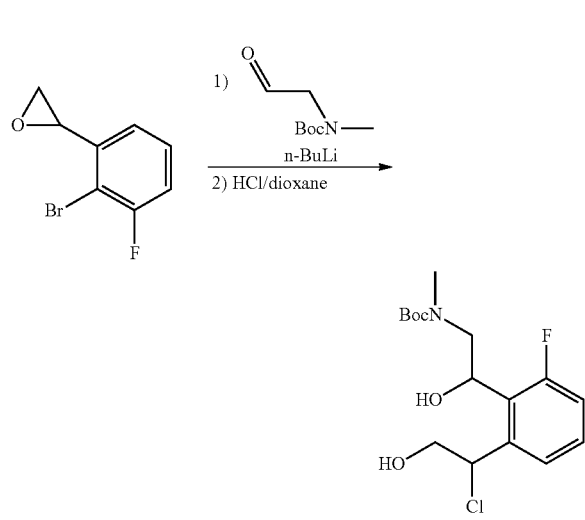

To a solution of 2-(2-bromo-3-fluorophenyl)oxirane (11.7 g, 53.9 mmol) in tetrahydrofuran(100 mL) was added n-butyllithium(2.5 M) (24 mL, 59.2 mmol) at −78° C. After stirring at −78° C. for 1 h, tert-butyl methyl(2-oxoethyl) carbamate (13.9 g, 80.8 mmol) in THF (5 mL) was added. After the mixture was stirred at this temperature for 2 h, HCl in dioxane (4M, 40 mL) was added, and the resulting mixture was warmed to RT overnight. The mixture was filtered and the filtrate was washed with water (2×50 mL), dried and concentrated. The resulting oil was purified by flash column chromatography with an isocratic elution of petroleum ether (100%) and EtOAc (0%) to petroleum ether (100%) and EtOAc (45%) to provide tert-butyl (2-(2-(1-chloro-2-hydroxyethyl)-6-fluorophenyl)-2-hydroxyethyl) (methyl) carbamate(8.60 g) as a yellow oil. MS (ESI): m/z=248 [M+H]$^+$.

(b). tert-Butyl 1-(4-chloro-8-fluoroisochroman-1-yl)-N-methylmethanamine

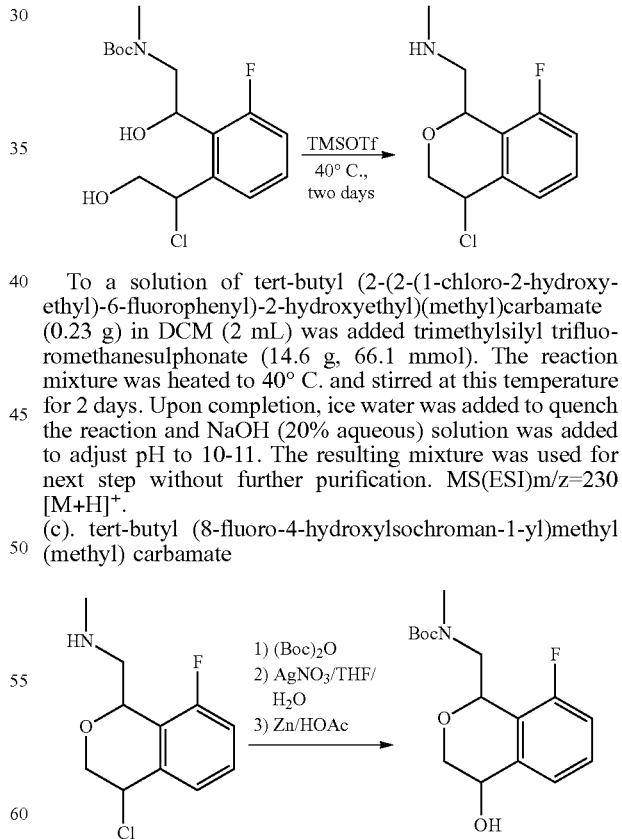

To a solution of tert-butyl (2-(2-(1-chloro-2-hydroxyethyl)-6-fluorophenyl)-2-hydroxyethyl)(methyl)carbamate (0.23 g) in DCM (2 mL) was added trimethylsilyl trifluoromethanesulphonate (14.6 g, 66.1 mmol). The reaction mixture was heated to 40° C. and stirred at this temperature for 2 days. Upon completion, ice water was added to quench the reaction and NaOH (20% aqueous) solution was added to adjust pH to 10-11. The resulting mixture was used for next step without further purification. MS(ESI)m/z=230 [M+H]$^+$.

(c). tert-butyl (8-fluoro-4-hydroxylsochroman-1-yl)methyl (methyl) carbamate

To a solution of 1-(4-chloro-8-fluoroisochroman-1-yl)-N-methylmethanamine (0.143 g) in water (10 mL) was added di-tert-butyl dicarbonate (202 mg). The reaction was stirred at ambient temperature for 3 h. Upon completion, the mixture was extracted with DCM (2×50 mL), dried and concentrated. The crude was purified by pre-TLC (PE:

EtOAc=20:1) to give tert-butyl ((4-chloro-8-fluoroisochroman-1-yl)methyl)(methyl) carbamate (130 mg). ESI: m/z=230 [M-100+H]⁺.

To a solution of tert-butyl ((4-chloro-8-fluoroisochroman-1-yl)methyl)(methyl) carbamate (130 mg) in THF/water (1:1) (30 mL) was added (nitrooxy)silver (334 mg, 1.97 mmol). The reaction mixture was stirred at ambient temperature for 30 min and then at 60° C. for 6 h. Upon completion, water (100 mL) was added to the reaction vessel and the resulting biphasic mixture was transferred to a separatory funnel. The layers were separated and the organic phase was washed with EtOAc (2×50 mL) and water (2×50 mL). The combined organics were dried over anhydrous Na$_2$SO$_4$, filtered and concentrated in vacuo. The crude oil was dissolved in HOAc (5 mL) and Zn powder was added. The mixture was stirred at RT for 6 h and water (100 mL) was added to the reaction vessel. The resulting biphasic mixture was transferred to a separatory funnel. The layers were separated and the organic phase was washed with EtOAc (2×100 mL) and water (2×50 mL). The combined organics were dried over anhydrous Na$_2$SO$_4$, filtered and concentrated in vacuo to give an oil, which was purified by preparative HPLC to give tert-butyl (8-fluoro-4-hydroxyisochroman-1-yl)-methyl(methyl) carbamate (3.6 g).

(d). (1R, 4R)-tert-butyl (8-fluoro-4-hydraryisochroman-1-yl)methyl(methyl) carbamate and (1S,4S)-tert-butyl (8-fluoro-4-hydroxyisochroman-1-yl)methyl(methyl) carbamate

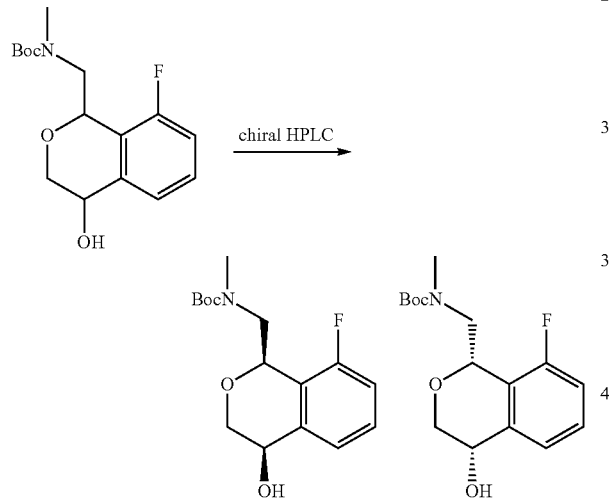

The resulting tert-butyl (8-fluoro-4-hydroxyisochroman-1-yl)-methyl(methyl) carbamate (3.6 g) was purified by chiral HPLC {MeOH (0.2% ammonia); AD-H (4.6*100*5 um)} to provide the two enantiomers: (1R,4R)-tert-butyl (8-fluoro-4-hydroxyisochroman-1-yl)methyl(methyl) carbamate (1.53 g, 100% ee) and (1S,4S)-tert-butyl (8-fluoro-4-hydroxyisochroman-1-yl)methyl(methyl) carbamate (1.69 g, 97% ee) as a colorless oil.

(e). (1R,4R)-8-fluoro-1-((methylamino)methyl)isochroman-4-ol (99) and (1S,4S)-8-fluoro-1-((methylamino)methyl)isochroman-4-ol (98)

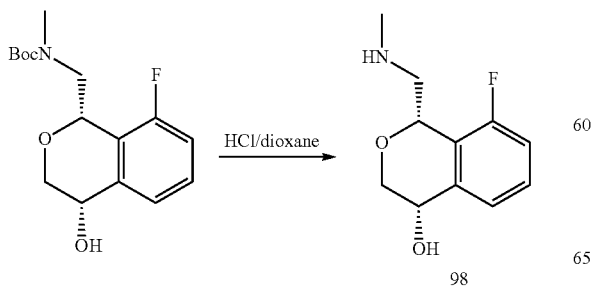

98

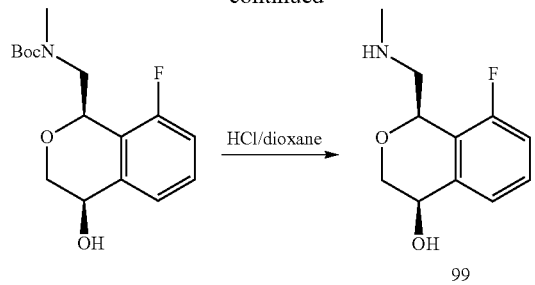

To a solution of (1S,4S)-tert-butyl (8-fluoro-4-hydroxyisochroman-1-yl)methyl-(methyl) carbamate (1.69 g, 5.42 mmol) in DCM (25 mL) was added HCl in dioxane (4M, 15 mL). The mixture was stirred at ambient temperature for 3 h. Solvent was removed and the residue was dissolved in water (50 mL), the mixture was extracted with EtOAc (2×50 mL). The aqueous phase was lyophilized to give (1S,4S)-8-fluoro-1-((methylamino)methyl)isochroman-4-ol (98) as a white solid (1.12 g, purity: 100%, yield: 92.5%, 98% ee). ESI: m/z=212 [M+H]⁺. ¹H-NMR (400 MHz, DMSO-d$_6$) δ 9.52 (brs, 1H), 8.83 (brs, 1H), 7.43-7.35 (m, 2 H), 7.18-7.13 (m, 1H), 5.34-5.31 (m, 1H), 4.54(t, J=4.4 Hz, 1H), 4.10-4.06 (m, 1H), 3.61-3.57 (m, 1H), 3.32- 3.24 (m, 2 H), 2.59 (t, J=4.8 Hz, 3H).

To a solution of (1R,4R)-tert-butyl (8-fluoro-4-hydroxyisochroman-1-yl)methyl-(methyl) carbamate (1.53 g, 4.91 mmol) in DCM (25 mL) was added HCl/dioxane (4M, 15 mL). The reaction was stirred at ambient temperature for 3 h. Solvent was removed and the residue was dissolved in water (50 mL) and the mixture was extracted with EtOAc (2×50 mL). The aqueous phase was lyophilized to give (1R,4R)-8-fluoro-1-((methylamino)methyl)isochroman-4-ol (99) as a white solid (1.16 g, purity: 100%, yield: 95.8%, 99% ee). ESI: m/z=212 [M+H]⁺. ¹H-NMR (400 MHz, DMSO-d$_6$) δ 9.52 (brs, 1H), 8.83 (brs, 1H), 7.43-7.35 (m, 2 H), 7.18-7.13 (m, 1H), 5.34-5.31 (m, 1H), 4.54 (t, J=4.4 Hz, 1H), 4.10-4.06 (m, 1H), 3.61-3.57 (m, 1H), 3.32-3.24 (m, 2 H), 2.59 (t, J=4.8 Hz, 3H).

General Procedure I 9.1 Preparation of (R)-N-((8-fluoroisochroman-1-yl)methyl)ethanamine (87) and (S)-N-((8-fluoroisochroman-1-yl)methyl)ethanamine (86)

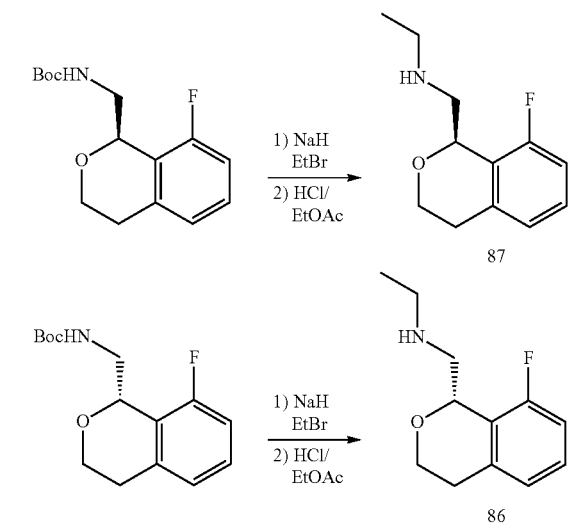

(a). (R)-N-((8-fluoroisochroman-1-yl)methyl)ethanamine (87)

To a solution of (R)-tert-butyl ((8-fluoroisochroman-1-yl)methyl)carbamate (0.5 g, 1.77 mmol) in DMF (10 mL) was added NaH (60%) (212 mg, 5.31 mmol). After stirring for 1h, bromoethane (385 mg, 3.54 mmol) was added. The reaction was stirred at ambient temperature for 2 h. Upon the completion, EtOAc (50 mL) was added and then the mixture washed with brine (5×100 mL), dried and concentrated. The resulting oil was purified by flash column chromatography with a gradient elution of petroleum ether (100%) to petroleum ether (92%)/EtOAc (8%) to provide a colorless oil, which was dissolved in EtOAc (20 mL). To the solution was added HCl in EtOAc (3M, 6 mL). The mixture was stirred at ambient temperature for 16 h and the solvent was removed. The residue was dissolved with EtOAc (50 mL), and then filtered and dried. (R)-N-((8-fluoroisochroman-1-yl)methyl)ethanamine (326 mg, yield: 82.9%) as a white solid was collected. (ESI) m/z: 210 [M+H]$^+$. $^1$H-NMR (400 MHz, methanol-d$_4$) δ 7.35-7.29 (dd, J=8.0, 14.0 Hz, 1H), 7.10 (d, J=7.6 Hz, 1H), 7.04 (t, J=9.4 Hz, 1H), 5.29 (d, J=8.8 Hz, 1H), 4.21-4.15 (m, 1H), 3.91-3.85 (m, 1H), 3.58-3.54 (dd, J=2.0, 13.2 Hz, 1H), 3.41-3.36 (dd, J=10.0, 12.8 Hz, 1H), 3.21-3.16 (m, 2 H), 3.01-2.93 (m, 1H), 2.90-2.83 (m, 1H), 1.39 (m, 3 H).

(b). (S)-N-((8-fluoroisochroman-1-yl)methyl)ethanamine (86)

(S)-N-((8-fluoroisochroman-1-yl)methyl)ethanamine (86) was prepared similarly to (R)-N-((8-fluoroisochroman-1-yl)methyl)ethanamine (87) starting from (S)-tert- butyl ((8-fluoroisochroman-1-yl)methyl)carbamate. (ESI)m/z: 210 [M+H]$^+$. $^1$H-NMR (400 MHz, methanol-d$_4$) δ 7.35-7.29 (dd, J=8.0, 14.0 Hz, 1H), 7.10 (d, J=7.6 Hz, 1H), 7.04 (t, J=9.4 Hz, 1H), 5.29 (d, J=8.8 Hz, 1H), 4.21-4.15 (m, 1H), 3.91-3.85 (m, 1H), 3.58-3.54 (dd, J=2.0, 13.2 Hz, 1H), 3.41-3.36 (dd, J=10.0, 12.8 Hz, 1H), 3.21-3.16 (m, 2 H), 3.01-2.93 (m, 1H), 2.90-2.83 (m, 1H), 1.39 (m, 3 H).

General Procedure J 10.1 Preparation of (S)-N-((8-fluoroisochroman-1-yl)methy)eyelobutanamine (96) and (S)-N-((8-fluoroisochroman-1-yl)methyl)ethanamine (97)

(a). (S)-N-((8-fluoroisochroman-1-yl)methyl)cyclobutanamine (96)

To a solution of (S)-(8-fluoroisochroman-1-yl)methanamine (0.8 g, 4.41 mmol) and cyclobutanone (401 mg, 5.73 mmol) in MeOH (30 mL) was added sodium cyanoborohydride (554 mg, 8.82 mmol). The reaction was stirred at ambient temperature for 16 h. Upon the completion, the solvent was removed and the residue was purified by pre-HPLC (0.01% aqueous TFA) to give (S)-N-((8-fluoroisochroman-1-yl)methyl)cyclobutanamine as a yellow oil (202 mg). (ESI) m/z: 236 [M+H]$^+$.

To a solution of (S)-N-((8-fluoroisochroman-1-yl)methyl)cyclobutanamine (0.202 g) in EtOAc (10 mL) was added HCl in EtOAc (3 M, 0.4 mL) at 0° C. The reaction was stirred at ambient temperature for 10 mins. The solvent was removed and the residue was washed with EtOAc and PE, filtered and dried to give (S)-N-((8-fluoroisochroman-1-yl)methyl)cyclobutanamine hydrochloride salt (154 mg) as a white solid. (ESI) m/z: 236 [M+H]$^+$. $^1$H-NMR (400 MHz, methanol-d$_4$) δ 7.35-7.29 (m, 1H), 7.10 (d, J=7.6 Hz, 1H), 7.04-6.99 (dd, J=8.8, 10.4 Hz, 1H), 5.25-5.22 (m, 1H), 4.20-4.14 (m, 1H), 3.91-3.82 (m, 2 H), 3.44-3.40 (m, 1H), 3.31-3.25 (dd, J=10.0, 13.2 Hz, 1H), 3.00-2.93 (m, 1H), 2.90-2.83 (m, 1H), 2.42-2.21 (m, 4 H), 1.99-1.90 (m, 2 H).

(b). (R)-N-((8-fluoroisochroman-1-yl)methyl)cyclobutanamine (97)

(R)-N-((8-fluoroisochroman-1-yl)methyl)cyclobutanamine was prepared similarly to (S)-N-((8-fluoroisochroman-1-yl)methyl)cyclobutanamine starting from (R)-N-((8-fluoroisochroman-1-yl)methyl)cyclobutanamine. (ESI) m/z: 236 [M+H]$^+$.

$^1$HNMR (400 MHz, methanol-d$_4$) δ 7.35-7.29 (m, 1H), 7.10 (d, J=7.6 Hz, 1H), 7.04-6.99 (dd, J=8.8, 10.4 Hz, 1H), 5.25-5.22 (m, 1H), 4.20-4.14 (m, 1H), 3.91-3.82 (m, 2H), 3.44-3.40 (m, 1H), 3.31-3.25 (dd, J=10.0, 13.2 Hz, 1H), 3.00-2.93 (m, 1H), 2.90-2.83 (m, 1H), 2.42-2.21 (m, 4 H), 1.99-1.90 (m, 2H).

General Procedure K 11.1 Preparation of (R)-1-(8-fluoroisochroman-1-yl)-N,N-dimethylmethanamine (85) and (S)-1-(8-fluoroisochroman-1-yl)-N,N-dimethylmethanamine (84)

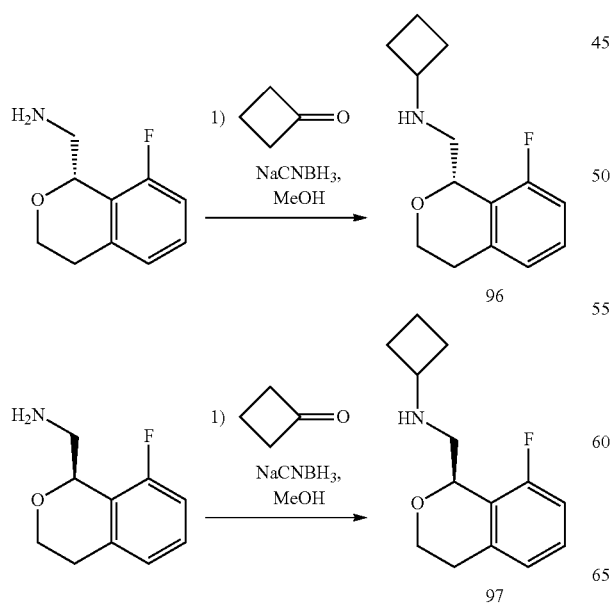

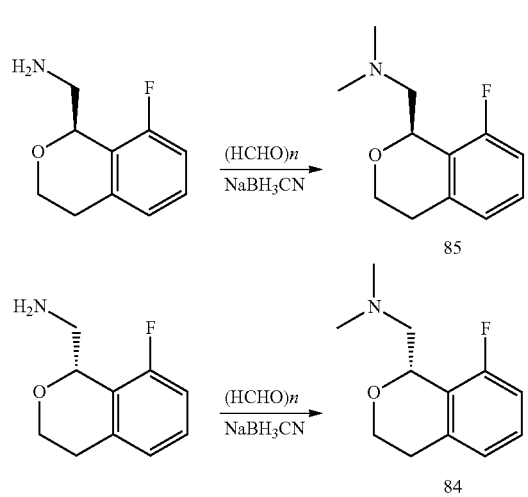

(a). (R)-1-(8-fluoroisochroman-1-yl)-N,N-dimethylmethanamine (85)

To a solution of (R)-(8-fluoroisochroman-1-yl)methanamine (0.8 g, 4.41 mmol) in MeOH (30 mL) was added paraformaldehyde (396 mg, 13.2 mmol) and sodium cyanoborohydride (554 mg, 8.82 mmol). The reaction was stirred at ambient temperature for 3 h. Upon the completion, the solvent was removed and the residue was purified by pre-HPLC (0.01% aq. TFA) to give (R)-1-(8-fluoroisochroman-1-yl)-N,N-dimethylmethanamine as a yellow oil (402 mg), which was dissolved in EtOAc (15 mL). To the solution was added HCl in EtOAc (3M, 1 mL) and the mixture was stirred at ambient temperature for 30 mins. Solvent was removed and the residue was washed with EtOAc, filtered and dried to give (R)-1-(8-fluoroisochroman-1-yl)-N,N-dimethylmethanamine hydrochloride salt as a white solid. (ESI) m/z: 210 [M+H]$^+$. $^1$H-NMR (400 MHz, methanol-d$_4$) δ 7.35-7.30 (dd, J=8.0, 14.0 Hz, 1H), 7.11 (d, J=7.2 Hz, 1H), 7.05 (t, J=9.6 Hz, 1H), 5.44 (d, J=9.6 Hz, 1H), 4.23-4.17 (m, 1H), 3.92-3.86 (m, 1H), 3.69 (m, 1H), 3.57 (m, 1H), 3.07 (s, 3 H), 2.98 (m, 4 H), 2.90- 2.84 (m, 1H).

(b). (S)-1-(8-fluoroisochroman-1-yl)-N,N-dimethylmethanamine (84)

(S)-1-(8-fluoroisochroman-1-yl)-N,N-dimethylmethanamine (84) was synthesized similarly to (R)-1-(8-fluoroisochroman-1-yl)-N,N-dimethylmethanamine (85) starting from (S)-1-(8-fluoroisochroman-1-yl)-N,N-dimethylmethanamine. (ESI) m/z=210 [M+H]$^+$. $^1$H NMR (400 MHz, methanol-d$_4$) δ 7.35-7.30 (dd, J=8.0, 14.0 Hz, 1H), 7.11 (d, J=7.2 Hz, 1 H), 7.05 (t, J=9.6 Hz, 1H), 5.44 (d, J=9.6 Hz, 1H), 4.23-4.17 (m, 1H), 3.92-3.86 (m, 1H), 3.69 (m, 1H), 3.57 (m, 1H), 3.07 (s, 3 H), 2.98 (m, 4 H), 2.90-2.84 (m, 1H).

General Procedure L 12.1 Preparation of (R)-1-(2,2-difluoro-6,9-dihydro-7H-[1,3]dioxolo[4,5-h]sochromen-9-yl)-N-methylmethanamine (101) and (S)-1-(2,2-difluoro-6,9-dihydro-7H-[1,3]dioxolo[4,5-h]sochromen-9-yl)-N-methylmethanamine (102), order unknown (a). tert-butyl (2-(5-bromo-2,2-difitiorobenzo[d][1,3]dioxo1-4-yl)-2-hydroxyethyl) (methyl)carbamate

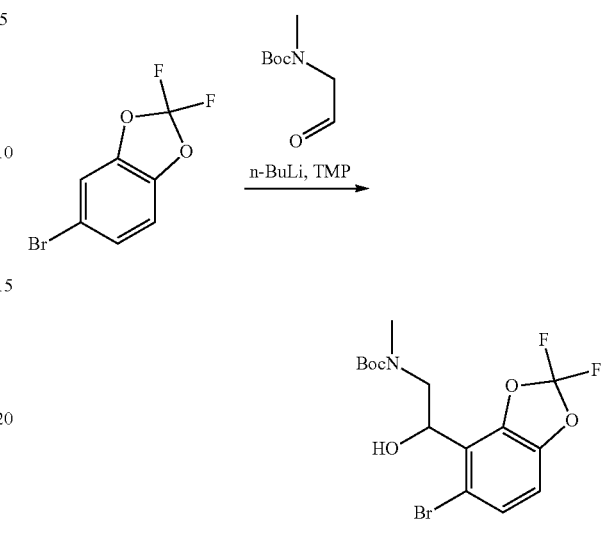

To a solution of 2,2,6,6-tetramethylpiperidine (TMP) (2.90 g, 20.6 mmol) in THF (30 mL) was added n-butyllithium (1.31 g, 20.6 mmol) at −78° C. This mixture was then added to a solution of 5-bromo-2,2-difluorobenzo[d][1,3]dioxole (4.9 g, 20.6 mmol) in THF (30 mL) followed by adding tert-butyl (2-oxoethyl)carbamate (3.27 g, 20.6 mmol). The reaction was stirred at −78° C. until the reaction was complete (~3 h). Saturated aqueous NH4Cl was added and the resulting biphasic mixture was washed with saturated aqueous NaCl, then dried over anhydrous Na$_2$SO$_4$, filtered and concentrated in vacuo. The resulting oil was purified by flash column chromatography (hexanes/EtOAc 90/10 to 60/40) to provide tert-butyl (2-(5-bromo -2,2-difluorobenzo[d][1,3]dioxo1-4-yl)-2-hy droxy ethyl)(methyl)carbamate (4.46 g, 10.8 mmol) as a colorless oil.

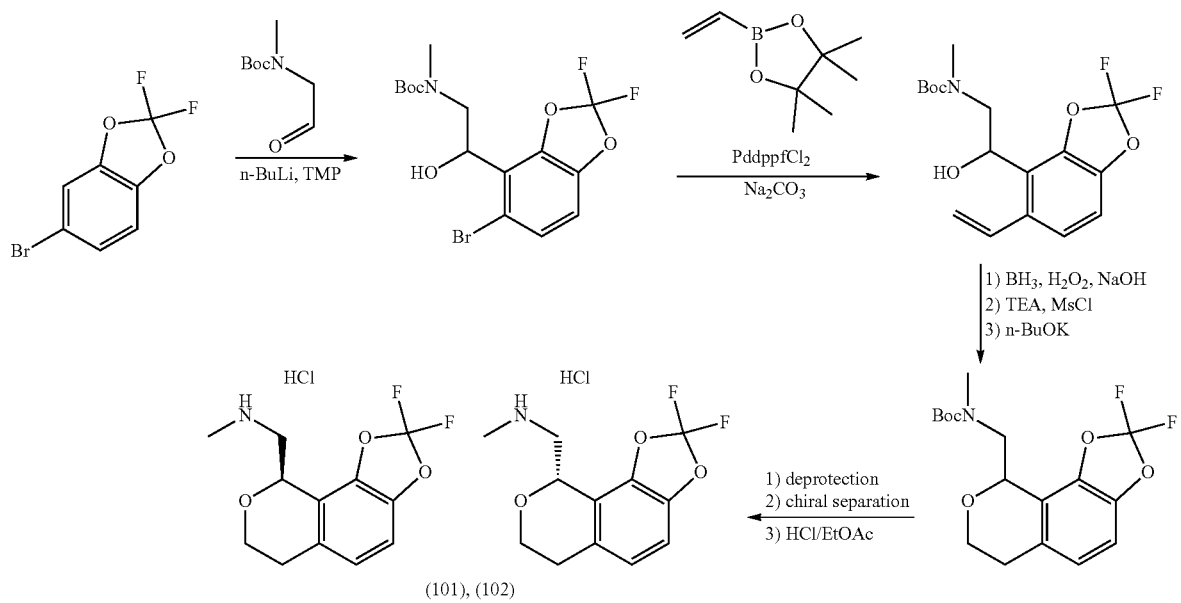

(101), (102)

(b). tert-butyl (2-(2,2-difitioro-5-vinylbenzo[d][1,3]dioxol-4-yl)-2-hydroxyethyl) (methyl)carbamate

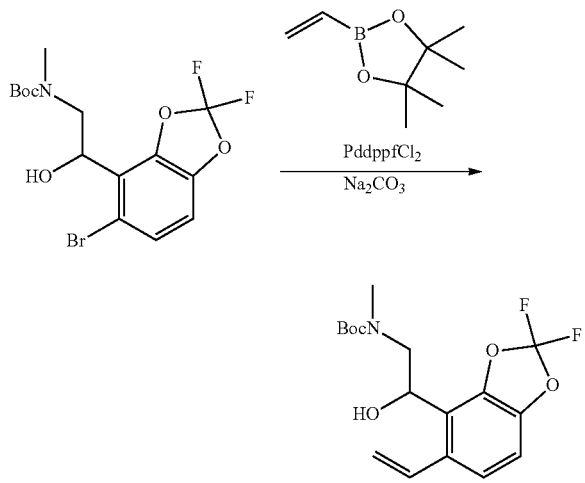

To a solution of tert-butyl (2-(5-bromo-2,2-difluorobenzo[d][1,3]dioxol-4-yl)-2-hydroxyethyl)(methyl)carbamate (4.8 g, 11.7 mmol) in 1,4-dioxane (20 mL) and water (2 mL) were added $Na_2CO_3$ (3.72 g, 35.1 mmol) and 3,3,4,4-tetramethyl-1-vinylborolane (5.26 g, 35.1 mmol). The reaction mixture was heated to 100° C. and stirred until the reaction was complete (~16 h). EtOAc was added and resulting mixture was washed with saturated aqueous NaCl. The combined organics were dried over anhydrous $Na_2SO_4$, filtered and concentrated. Purification by flash column chromatography (hexanes/EtOAc 95/5 to 70/30) provided tert-butyl(2-(2,2-difluoro-5-vinylbenzo[d][1,3]dioxol-4-yl)-2-hydroxyethyl)(methyl) carbamate (3.04 g, 8.50 mmol) as a yellow solid.

(c). tert-butyl ((2,2-difluoro-6,9-dihydro-7H-[1,3]dioxolo[4,5-h]isochromen-9-yl) methyl) (methyl)carbamate

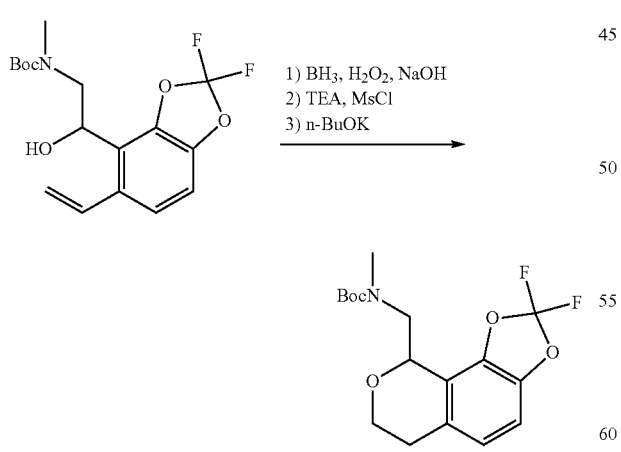

To a solution of tert-butyl (2-(2,2-difluoro-5-vinylbenzo[d][1,3]dioxol-4-yl)-2-hydroxyethyl)(methyl)carbamate (2.0 g, 5.59 mmol) in THF (15 mL) was added borane (77.3 mg, 5.59 mmol). The reaction was stirred at ambient temperature for 16 h. To the reaction solution was added sodium hydroxide (22.3 mg, 559 μmol, in 10 mL water) and hydrogen peroxide (568 mg, 16.7 mmol). The reaction was stirred at ambient temperature for 1 h, then EtOAc (250 mL) was added, then the reaction mixture was washed with saturated aqueous NaCl. The combined organics were dried over anhydrous $Na_2SO_4$, filtered and concentrated in vacuo. The resulting suspension was purified by column chromatography (hexanes/EtOAc 95/5 to 70/30) to provide tert-butyl (2-(2,2-difluoro-5-(2-hydroxyethyl)benzo[d][1,3]dioxol-4-yl)-2-hydroxy-ethyl)(methyl)carbamate (1.04 g, 2.78 mmol) as a yellow solid.

To a solution of ter t-butyl (2-(2,2-difluoro-5-(2-hydroxyethyl)benzo[d][1,3]dioxol-4-yl)-2-hydroxyethyl)(methyl) carbamate (1.0 g, 2.66 mmol) in $CH_2Cl_2$ (10 mL) was added methanesulfonyl chloride (334 mg, 2.92 mmol) and TEA (806 mg, 7.98 mmol). The reaction was stirred at ambient temperature until the reaction was complete (~16 h), then the reaction mixture was concentrated and purified by flash column chromatography (Hexanes/EtOAc 95/5 to 70/30) to provide 2-(4-(2-((tert-butoxycarbonyl)(methyDamino)-1-hydroxyethyl)-2,2-difluorobenzo[d][1,3]dioxo1-5-yl)ethyl methanesulfonate (960 mg, 2.11 mmol) as a yellow solid.

To a solution of 2-(4-(2-((tert-butoxycarbonyl)(methyDamino)-1-hydroxyethyl)-2,2-difluorobenzo[d][1,3]dioxo1-5-yl)ethyl methanesulfonate (900 mg, 1.98 mmol) in THF (5 mL) was added potassium butan-1-olate (444 mg, 3.96 mmol). The reaction was stirred at ambient temperature until the reaction was complete (~3 h), then EtOAc (200 mL) was added and the reaction mixture was washed with saturated aqueous NaCl. The combined organics were dried over anhydrous $Na_2SO_4$, filtered and concentrated in vacuo. The resulting solid was purified by flash column chromatography (Hexanes/EtOAc 90/10 to 80/20) to provide tert-butyl ((2,2-difluoro-7,9-dihydro-6H-[1,3]dioxolo[4,5-h]isochromen-9-yl)methyl)(methyl)carbamate (624 mg, 1.74 mmol) as a colorless oil.

(d). Deprotection, chiral separation, and salt formation.

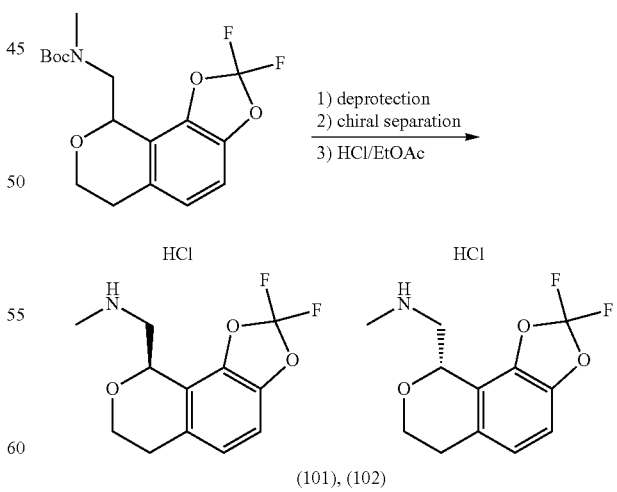

(101), (102)

To a solution of tert-butyl (2,2-difluoro-7,9-dihydro-6H-[1,3]dioxolo[4,5-h]isochromen-9-yl)methyl(methyl)carbamate (650 mg, 2.88 mmol) in 3 M HCl/EtOAc (20 mL) was stirred at room temperature for 12 h. The mixture was concentrated in vacuo to get the crude, washed with EtOAc (15 mL), dried in vacuo to yield the desired product (468 mg, yield: 100%). MS (ESI): m/z 257 [M+H]+.

1-(2,2-difluoro-7,9-dihydro-6H-[1,3]dioxolo[4,5-h]isochromen-9-yl)-N-methylmethanamine(468 mg) was separated into (R)-1-(2,2-difluoro-7,9-dihydro-6H-[1,3]dioxolo[4,5-h]isochromen-9-yl)-N-methylmethanamine and (S)-1-(2,2-difluoro-7,9-dihydro-6H-[1,3]dioxolo[4,5-h]isochromen-9-yl)-N-methylmethanamine by using Column: AY-H (250×4.6 mm, 5 um) Mobile Phase: n-Hexane (0.1% DEA):EtOH (0.1% DEA)=90:10 Temperature: 40° C. Inject Volume: 15 uL. Chiral HPLC for ee determination: Column AY-H (150*4.6 mm, 5 um; Mobile Phase: n -Hexane (0.1% DEA):EtOH (0.1% DEA)=90:10; Temp=40° C.; Flow rate=1.0 mL/min.

Compound 101 hydrochloride salt: Ret Time=7.21 min; Enantiopurity: 100% ee. MS (ESI): m/z 258 [M +H]+. $^1$H-NMR (400 MHz, methanol-$d_4$): δ 7.17 (d, J=8.4 Hz, 1H), 7.07 (d, J=8.4 Hz, 1H), 5.24 (d, J=8.8 Hz, 1H), 4.27-4.22 (m, 1H), 3.92-3.86 (m, 1H), 3.67-3.63 (m, 1H), 3.47-3.41 (m, 1H), 3.02-2.98 (m, 1H), 2.84 (t, J=4.0 Hz, 1H), 2.80 (s, 3H).

Compound 102 hydrochloride salt: Ret Time=4.997 min; Enantiopurity: 100% ee. MS (ESI): m/z 258 [M +H]+. $^1$H-NMR (400 MHz, methanol-$d_4$): 6: δ 7.17 (d, J=8.0 Hz, 1H), 7.07 (d, J=8.4 Hz, 1H), 5.24 (d, J=9.2 Hz, 1H), 4.27-4.22 (m, 1H), 3.92-3.86 (m, 1H), 3.67-3.63 (m, 1H), 3.47-3.41 (m, 1H), 3.02-2.98 (m, 1H), 2.84 (t, J=3.6 Hz, 1H), 2.81 (s, 3H).

General Procedure M 13.1 Preparation of (6S,9R)-9-((methylamino)methyl)-6,9-dihydro-7H-[1,3]dioxolo[4,5-h]isochromen-6-ol (111), (6R, 9S)-9-((methylamino)methyl)-6,9-dihydro-7H-[1,3]dioxolo[4,5-h]sochromen-6-ol (112), (6S,9S)-9-((methylamino)methyl)-6,9-dihydro-7H-[1,3]dioxolo[4,5-h]isochromen-6-ol (113) and (6R,9R)-9-((methylamino)methyl)-6,9-dihydro-7H-[1,3]dioxolo[4,5-h]sochromen-6-ol (114).

(a). tert-butyl (2-((tert-butyldimethylsilyl)oxy)-2-(5-vinylbenzo[d][1,3]dioxol-4-yl) ethyl)(methyl)carbamate

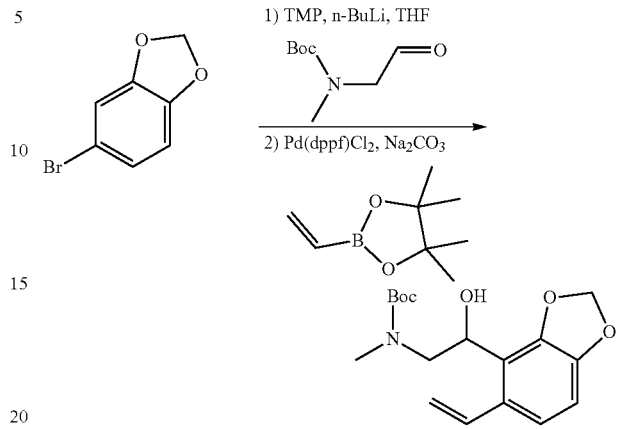

To a solution of 2,2,6,6-tetramethylpiperidine (TMP) (4.60 g, 32.6 mmol) in THF (50 mL) was added n-BuLi (2.5 N) (1.92 g, 30.1 mmol) dropwise at −78 ° C. under nitrogen. After stirring for 1 h, a solution of 5-bromobenzo[d][1,3]dioxole (5.06 g, 25.1 mmol) in THF(10 mL) was added and stirred at this temperature for another 2 h, then a solution of tert-butyl methyl(2-oxoethyl)carbamate (5.21 g, 30.1 mmol) in THF (10 mL) was added. The mixture was stirred at this temperature for 2 h. The mixture was quenched with water, extracted with EtOAc, dried and concentrated in vacuo. Purification by silica gel chromatography (petroleum ether: EtOAc 10:1) provided tert-butyl (2-(5-bromobenzo[d][1,3]dioxol-4-yl)-2-hydroxyethyl)(methyl)carbamate. MS(ESI) m/z: 300[M-56-17]+, purity: 78%, 214 nm; 8.0 g yellow oil obtained, yield: 66.4%.

To a solution of tert-butyl (2-(5-bromobenzo[d][1,3]dioxol-4-yl)-2-hydroxyethyl) (methyl)carbamate (800 mg, 2.13 mmol) in dioxane/water=4/1 (10 mL) was added 4,4,5,5-tetramethyl-2-vinyl-1,3,2-dioxaborolane (589 mg, 3.83 mmol), Pd(dppf)Cl$_2$ (155 mg, 213 μmol) and Na$_2$CO$_3$ (563

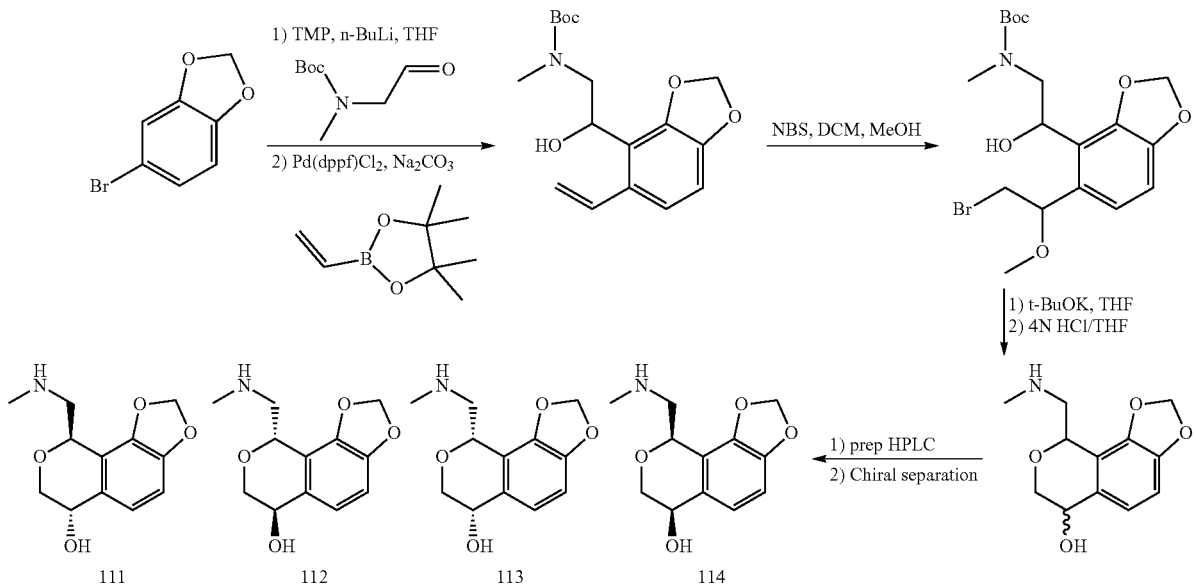

mg, 5.32 mmol) under nitrogen. The mixture was heated to 105° C. with stirring for overnight. The mixture was evaporated in vacuo to get the residue, diluted in water, extracted with DCM, dried and concentrated in vacuo. Purification by silica gel chromatography (petroleum ether:EtOAc=5:1) provided tert-butyl 2-hydroxy-2-(5-vinylbenzo[d][1,3]dioxol-4-yl)ethyl(methyl) carbamate (500 mg, yield: 67%; purity: 92%) as a light yellow oil. MS(ESI): m/z 248 [M-56-17]+.

(b).tert-butyl-2-(5-(2-bromo-1-metharyethyl)benzo[d][1,3]dioxol-4-yl)-2-hydroxyethyl(methyl)carbamate

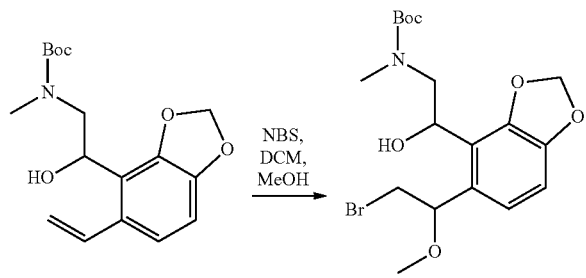 [SMILES: C=Cc1ccc2c(c1C(O)CN(C)C(=O)OC(C)(C)C)OCO2 ; COC(CBr)c1ccc2c(c1C(O)CN(C)C(=O)OC(C)(C)C)OCO2]

To a solution of tert-butyl (2-hydroxy-2-(5-vinylbenzo[d][1,3]dioxol-4-yl)ethyl) (methyl)carbamate (1.8 g, 5.6 mmol) in MeCN/MeOH=1:1 (20 mL) was added NBS (1.09 g, 6.16 mmol) at 0° C. The mixture was then allowed to warm to room temperature and stirred for 2 h. The mixture was quenched with water, evaporated in vacuo to get the residue, extracted with DCM, dried and concentrated under reduced pressure to get tert-butyl 2-(5-(2-bromo-1-methoxyethyl)benzo[d][1,3]dioxol-4-yl)-2-hydroxyethyl(methyl) carbamate (1.2 g, yield: 42%, purity: 86%) as a yellow oil. MS(ESI): m/z 300, 302 [M-31-100]+.

(c). 9-((methylamino)methyl)-6,9-dihydro-7H-[1,3]dioxolo[4,5-h]isochromen-6-ol

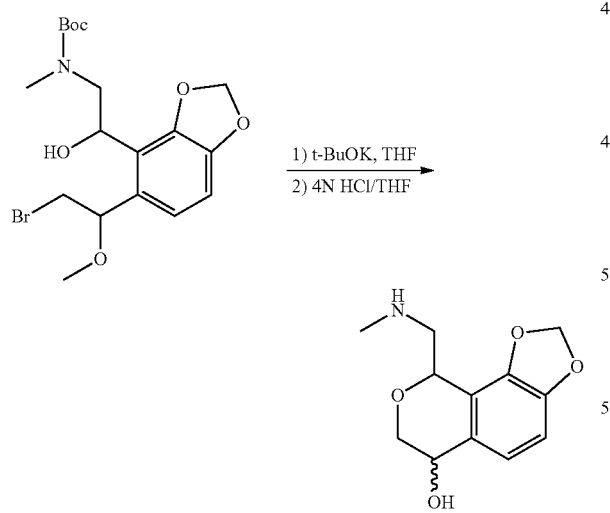

To a solution of tert-butyl (2-(5-(2-bromo-1-methoxyethyl)benzo[d][1,3]dioxol-4-yl)-2-hydroxyethyl)(methyl) carbamate (1.2 g, 2.77 mmol) in THF (15 mL) was added t-BuOK (620 mg, 5.54 mmol) at 0° C. The mixture was then allowed to warm to room temperature and stirred overnight. The mixture was quenched with water, evaporated in vacuo to get the residue, extracted with DCM, dried and concentrated under reduced pressure. Purification by silica gel chromatography (petroleum ether:EtOAc 3:1) provided tert-butyl (6-methoxy-7,9-dihydro-6H-[1,3]dioxolo[4,5-h]isochromen-9-yl) methyl(methyl)carbamate (600 mg; yield: 53%; purity: 86%) as a yellow solid. MS(ESI): m/z 374 [M+Na]+.

To a solution of tert-butyl ((6-methoxy-7,9-dihydro-6H-[1,3]dioxolo[4,5-h]isochromen-9-yl)methyl)(methyl)carbamate (540 mg, 1.53 mmol) in THF (6 mL) was added HCl (6.0 N aq, 2.55 mL, 15.3 mmol) at room temperature. The mixture was stirred at room temperature overnight. The mixture was filtered, then the filtration was basified with 2 N aq. NaOH, extracted with DCM/MeOH, dried and concentrated in vacuo to provide crude 9-((methylamino)methyl)-6,9-dihydro-7H-[1,3]dioxolo[4,5-h]isochromen-6-ol as a light brown oil (500 mg; yield: 69%; purity: 50%). MS(ESI): m/z 238 [M+H]+.

(d). Trans isomers (6S,9R)-9-((methylamino)methyl)-6,9-dihydro-7H-[1,3]dioxolo[4,5-h]isochromen-6-ol and (6R,9S)-9-((methylamino)methyl)-6,9-dihydro-7H-[1,3]dioxolo[4,5-h]isochromen-6-ol (111 and 112), Cis isomers (6S,9S)-9-((methylamino)methyl)-6,9-dihydro-7H-[1,3]dioxololisochromen-6-ol and (6R,9R)-9-((methylamino)methyl)-6, 9-dihydro-7H-[1,3]dioxolo[4,5-h]isochromen-6-ol (113 and 114).

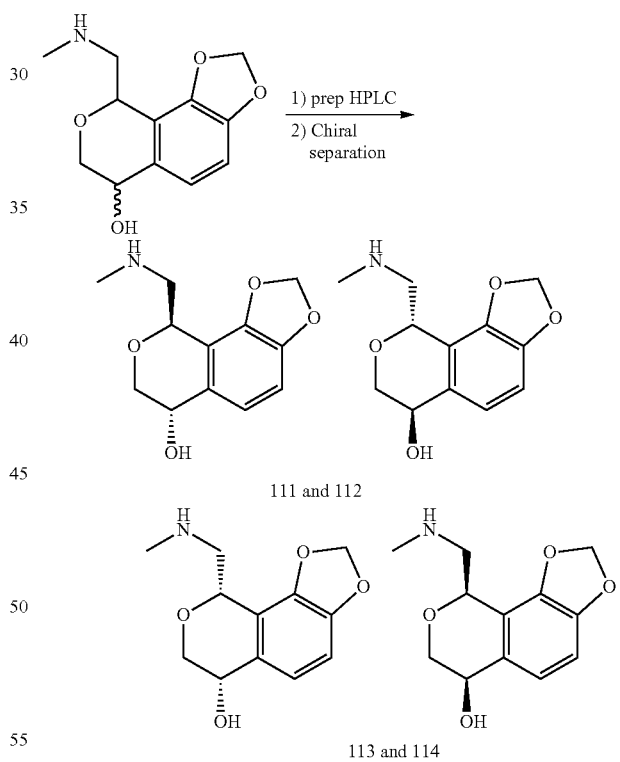

111 and 112

113 and 114

The mixture of four isomers was separated into racemic mixtures of the cis and trans isomers by prep-HPLC in 0.01% aq. NH$_4$HCO$_3$. The mixture was separately freeze-dried to dryness. MS(ESI): m/z 238 [M+H]+. P1, purity: 98%, 214 nm; 75 mg white solid obtained, yield: 14.7%. P2, purity: 93%, 214 nm; 140 mg white solid obtained, Yield: 26%.

The racemic mixture of trans isomers (111 and 112) was purified by chiral separation using Instrument: Gilson-281, Column: OZ 20×250, 10 um, Mobile Phase: n -Hex(0.1%

DEA):EtOH(0.1% DEA)=8:2 and Run time per injection: 10 mins to get the two isomers. The mixture was separately evaporated in vacuo to get the two desired products. MS(ESI): m/z 238 [M+H]+.

Trans isomer Peak 1 Compound 111: Retention time 8.70 min. Purity: 99%, ee%: 99%, 90 mg white solid obtained, Yield: 30%. $^1$H-NMR (400 MHz, CDCl$_3$): δ 6.90 (d, J=8.0 Hz, 1H), 6.79 (d, J=7.6 Hz, 1H), 6.03 (s, 1H), 5.94 (s, 1H), 5.02 (t, J=3.6 Hz, 1H), 4.45 (s, 1H), 4.15 (dd, J=2.0/11.6 Hz, 1H), 3.77 (d, J=11.6 Hz, 1H), 3.16-3.05 (m, 2H), 2.75 (brs, 2H), 2.37 (s, 3H).

Transisomer Peak 2 Compound 112: Retention time 11.03 min. Purity: 100%, ee%: 100%, 70 mg white solid obtained, Yield: 23%. $^1$H-NMR (400 MHz, CDCl$_3$): δ 6.91 (d, J=8.0 Hz, 1H), 6.80 (d, J=8.0 Hz, 1H), 6.04 (d, J=1.2 Hz, 1H), 5.95 (d, J=1.2 Hz, 1H), 5.02 (t, J=3.2 Hz, 1H), 4.45 (s, 1H), 4.15 (dd, J=2.0/11.6 Hz, 1H), 3.78 (d, J=11.2 Hz, 1H), 3.16-3.05 (m, 2H), 2.38 (s, 3H), 2.21 (brs, 2H).

The racemic mixture of cis isomers (113 and 114) was purified by chiral separation using Instrument: Gilson-281, Column: OZ 20×250, 10 um, Mobile Phase: n-Hexane (0.1% DEA):EtOH (0.1% DEA)=8:2 and Run time per injection: 10 mins to get the two isomers. The mixture was separately evaporated in vacuo to get the two desired products. MS(ESI): m/z 238 [M+H]+.

Cis isomer Peak 1 Compound 113: Retention time: 15.52 min. Purity: 100%, ee%: 100%, 320 mg white solid obtained, Yield: 67%. $^1$H-NMR (400 MHz, CDCl$_3$): δ 6.99 (d, J=8.0 Hz, 1H), 6.79 (d, J=8.0 Hz, 1H), 5.99 (d, J=1.2 Hz, 1H), 5.92 (d, J=1.2 Hz, 1H), 5.02 (dd, J=3.2, 8.8 Hz, 1H), 4.54 (t, J=4.0 Hz, 1H), 4.09 (dd, J=3.2, 11.6 Hz, 1H), 3.77 (dd, J =4.4, 12.0 Hz, 1H), 3.01-2.91 (m, 2H), 2.5 (s, 3H), 2.13 (brs, 2H).

Cis isomer Peak 2 Compound 114: Retention time: 21.12 min. Purity: 100%, ee%: 100%, 340 mg white solid obtained, yield: 71%. $^1$H-NMR (400 MHz, CDCl$_3$): δ 6.99 (d, J=8.0 Hz, 1H), 6.79 (d, J=8.0 Hz, 1H), 5.99 (d, J=1.2 Hz, 1H), 5.92 (d, J=1.2 Hz, 1H), 5.02 (dd, J=3.2, 8.8 Hz, 1H), 4.54 (t, J=4.0 Hz, 1H), 4.09 (dd, J=3.2, 11.6 Hz, 1H), 3.77 (dd, J =4.4, 12.0 Hz, 1H), 3.01-2.91 (m, 2H), 2.5 (s, 3H), 2.13 (brs, 2H).

General Procedure N 14.1 Preparation of (R)-9-((methylamino)methyl)-6,9-dihydro-7H-[1,3]dioxolo[4,5-h]sochromen-5-ol (103) and (S)-9-((methylamino)methyl)-6,9-dihydro-7H-[1,3]dioxolo[4,5-h]sochromen-5-ol (104)

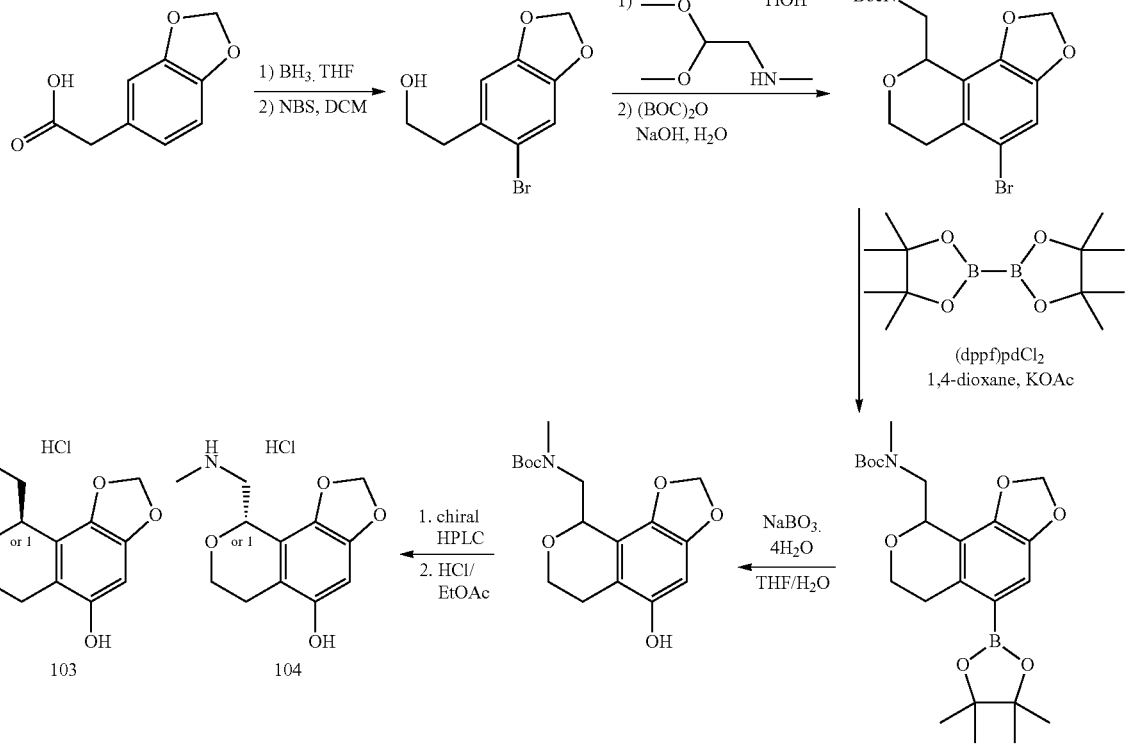

(a). 2-(6-bromobenzo[d][1,3]choxol-5-yl)ethan-1-ol

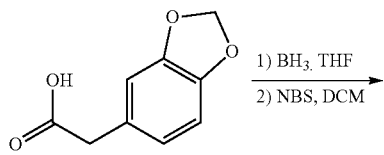

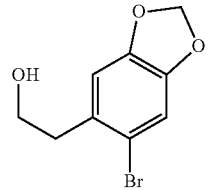

A solution of 2-(benzo[d][1,3]dioxol-5-yl)acetic acid (20 g, 111 mmol) in BH$_3$/THF (166 mL, 1.0 M, 166 mmol) was stirred at ambient temperature until the reaction was complete (~4h). The mixture was then poured into ice water and extracted with EtOAc, dried and concentrated. The crude was purified by silica gel (petroleum ether: EtOAc 20:1 to 10:1) to provide 2-(benzo[d][1,3]dioxol-5-yl)ethanol (16.5 g, yield=89.6%) as a colorless oil. MS (ESI): m/z 149 [M-18+1]+.

To a solution of 2-(benzo[d][1,3]dioxol-5-yl)ethanol (16.5 g, 99.2 mmol) in CH$_2$Cl$_2$ (200 mL) was added NBS (19.2 g, 109 mmol), and the reaction was stirred at ambient temperature until complete (~4 h). The mixture was then washed with NaHSO3 solution, brine and dried. The crude product was used in the next step without further purification. 21 g (yield: 100%). MS (ESI): m/z 227, 229[M-18+1]+.

(b). tert-butyl ((5-bromo-6,9-dihydro-7H-[1,3]clioxolo[4,5-h]isochromen-9-yl) methyl) (methyl)carbamate

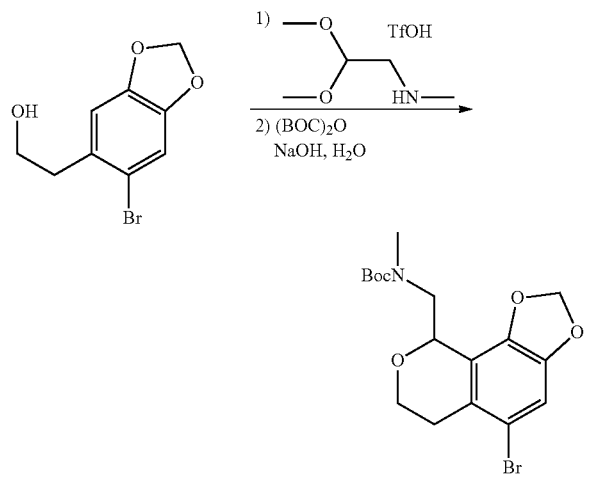

To a solution of 2-(6-bromobenzo[d][1,3]dioxol-5-yl) ethanol (8 g, 32.6 mmol) in CH$_2$Cl$_2$ (100 mL) was added 2,2-dimethoxy-N-methylethanamine (7.76 g, 65.2 mmol) and trifluoromethanesulfonic acid (14.6 g, 97.8 mmol) at 0° C. The reaction was then stirred at ambient temperature until complete (~16 h). The mixture was used in the next step without further purification.

To a solution of 1-(5-bromo-7,9-dihydro-6H-[1,3]dioxolo [4,5-h]isochromen-9-yl)-N-methylmethanamine (2 g, 6.66 mmol) in H$_2$O (50 mL) was added NaOH (2.12 g, 53.2 mmol) and di-tert-butyl dicarbonate (1.74 g, 7.99 mmol) at 0° C. The reaction was stirred at ambient temperature until complete (~16 h). EtOAc (100 mL) was added and the reaction was washed with saturated aqueous NH$_4$Cl, then dried over anhydrous Na$_2$SO$_4$, filtered and concentrated in vacuo. The residue was purified by silica chromatography, eluting with petroleum ether:EtOAc 5:1 to afford the title compound. MS (ESI): m/z 300, 302[M-100+H]+.

(c). tert-butyl methyl((5-(4,4,5,5-tetramethyl-1,3,2-dioxaborolan-2-yl)-6,9-dihydro-7H-[1,3]dioxolo[4,5-h]isochromen-9-yl)methyl)carbamate

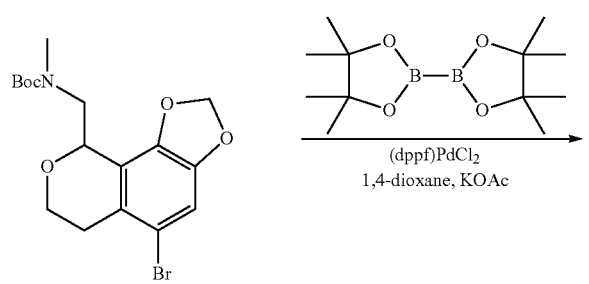

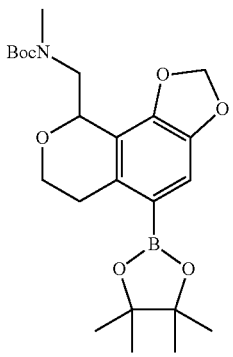

To a solution of tert-butyl ((5-bromo-6,9-dihydro-7H-[1, 3]dioxolo[4,5-h]isochromen-9-yl)methyl)(methyl)carbamate (12 g, 29.9 mmol) in 1,4-dioxane (150 mL) was added 4,4,4',4',5,5,5',5'-octamethyl-2,2'-bi(1,3,2-dioxaborolane) (7.59 g, 29.9 mmol), KOAc (5.86 g, 59.8 mmol) and Pd(dppf)Cl$_2$ (1.08 g, 1.49 mmol). The reaction mixture was stirred and heated to 100° C. until complete (~16 h). The reaction mixture was then concentrated, then water and EtOAc were added. The combined organics were dried over anhydrous Na$_2$SO$_4$, filtered and concentrated in vacuo. The residue was purified by silica chromatography, eluting with petroleum ether:EtOAc 20:1 to afford tert-butyl methyl((5-(4,4,5,5-tetramethyl-1,3,2-dioxaborolan-2-yl)-7,9-dihydro-6H-[1,3]dioxolo[4,5-h]isochromen-9-yl)methyl)carbamate, 10.0 g, yield=75.1%. MS (ESI): m/z 348 [M-100+H]+.

(d). tert-butyl ((5-hydroxy-6,9-dihydro-7H-[1,3]dioxolo[4, 5-h]isochromen-9-yl) methyl) (methyl)carbamate

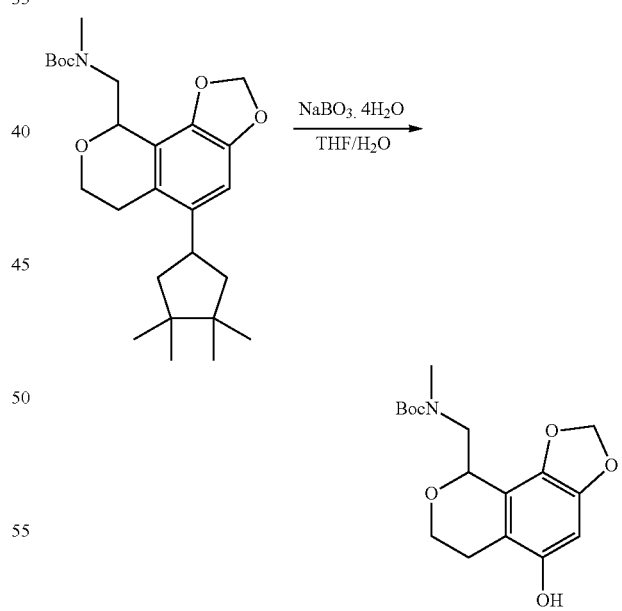

To a solution of tert-butylmethyl((5-(4,4,5,5-tetramethyl-1,3,2-dioxaborolan-2-yl)-7,9-dihydro-6H-[1,3]dioxolo[4,5-h]isochromen-9-yl)methyl)carbamate (8.0 g, 17.8 mmol) in THF/H$_2$O (100 mL/40 mL) was added NaBO$_3$·4H$_2$O (8.22 g, 53.4 mmol). The reaction was stirred at ambient temperature until complete (~3 h). The reaction was concentrated, then water and EtOAc were added. The layers were separated and the aqueous phase was washed with EtOAc. The combined organics were dried over anhydrous Na$_2$SO$_4$, filtered and concentrated in vacuo, purified by silica chromatography (petroleum ether:EtOAc 5:1) to provide tert-butyl((5-hydroxy-7,9-dihydro-6H-[1,3]dioxolo[4,5-h]isochromen-9-yl)methyl) (methyl)carbamate as a white solid (3.4 g, yield: 57%). MS (ESI): m/z 338 [M+H]+.

(e). (R)-9-((methylamino)methyl)-6,9-dihydro-7H-[1,3]dioxolo[4,5-h]isochromen-5-ol (103) and (S)-9-((methylamino)methyl)-6,9-dihydro-7H-[1,3]dioxolo[4,5-h]isochromen-5-ol (104)

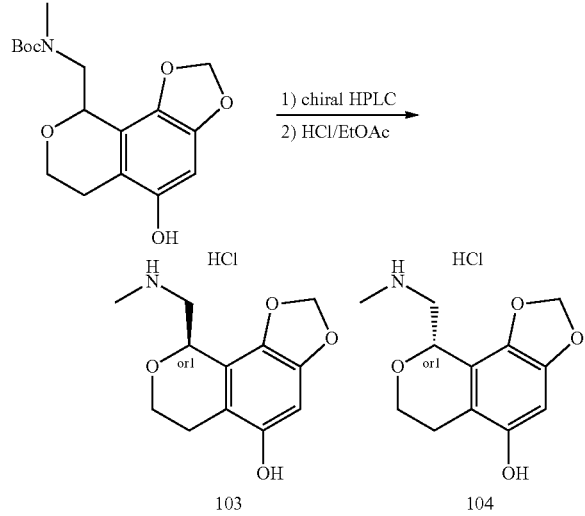

Tert-butyl((5-hydroxy-7,9-dihydro-6H-[1,3]dioxolo[4,5-h]isochromen-9-yl)methyl)(methyl)carbamate (1.5 g, 4.44 mmol) was separated into its enantiomers (R)-tert-butyl ((5-hydroxy-7,9-dihydro-6H-[1,3]dioxolo[4,5-h]isochromen-9-yl)methyl)(methyl)carbamate and (S)-tert-butyl ((5-hydroxy-7,9-dihydro-6H-[1,3]dioxolo[4,5-h]isochromen-9-yl)methyl)(methyl)carbamate by Gilson-281 using AY 20*250, 10 um and mobile phase Hexane(0.1% DEA):EtOH(0.1% DEA)=95:5. Flow rate=50mL/min. (R)-tert-butyl ((5-hydroxy-7,9-dihydro-6H-[1,3]dioxolo[4,5-h]isochromen-9-yl)methyl)(methyl)carbamate(0.6 g, Yield=40.2%) was obtained as white solid and (S)-tert-butyl ((5-hydroxy-7,9-dihydro-6H-[1,3]dioxolo[4,5-h]isochromen-9-yl) methyl)(methyl)carbamate (0.6 g, Yield=40.2%) was obtained as white solid.

To a solution of (R)-tert-butyl ((5-hydroxy-7,9-dihydro-6H-[1,3]dioxolo[4,5-h]isochromen-9-yl)methyl)(methyl) carbamate (0.32 g, 948 μmol) in EtOAc (10 mL) was added HCl/EtOAc (1.5 mL, 3.0 M, 4.73 mmol). The reaction was stirred at ambient temperature for 4 h. Filtration afforded compound 103 hydrochloride salt as a white solid (0.18 g, yield: 78.5%). Chiral HPLC: Column AY-H (250*4.6 mm, 5 um; Mobile Phase: n-Hexane (0.1% DEA):EtOH (0.1% DEA)=80:20; Temp=40° C.; Flow rate=1.0 mL/min; Ret Time=5.39 min; Enantiopurity: 100% ee. MS (ESI): m/z 238 [M+H]+. $^1$H-NMR (400 MHz, methanol -d$_4$): δ 6.4 (s, 1H), 5.92 (s, 1H), 5.87 (s, 1H), 5.07-5.04 (m, 1H), 4.22-4.17 (m, 1H), 3.82-3.76 (m, 1H), 3.66-3.63 (m, 1H), 3.42-3.37 (m, 1H), 2.75 (s, 3H), 2.68 (t, 2H).

To a solution of (S)-tert-butyl ((5-hydroxy-7,9-dihydro-6H-[1,3]dioxolo[4,5-h]isochromen-9-yl)methyl)(methyl) carbamate (0.35 g, 1.03 mmol) in EtOAc (5 mL) was added HCl/EtOAc (1.7 mL,3.0 M. 5.15 mmol). The reaction was stirred at ambient temperature for 4 h. Filtration afforded compound 104 hydrochloride salt as a white solid (0.19 g; yield: 76.2%). Chiral HPLC: Column AY-H (250*4.6 mm, 5 um; Mobile Phase: n-Hexane (0.1% DEA):EtOH (0.1% DEA)=80:20; Temp=40° C.; Flow rate=1.0 mL/min; Ret Time=6.05 min; Enantiopurity: 100% ee. MS (ESI): m/z 238 [M+H]+. $^1$H-NMR (400 MHz, methanol -d$_4$): δ 6.4 (s, 1H), 5.92 (s, 1H), 5.87 (s, 1H), 5.07-5.04 (m, 1H), 4.22-4.17 (m, 1H), 3.82-3.76 (m, 1H), 3.66-3.63 (m, 1H), 3.42-3.37 (m, 1H), 2.75 (s, 3H), 2.68 (t, 2H).

Example 115

Biological Assays

Neuropharmacological Assay (SmartCube™)

In order to demonstrate the utility of the provided compounds to treat neurological and psychiatric diseases and disorders, exemplary compounds were evaluated using the neuropharmacological screen described in S. L. Roberds et al., *Front. Neurosci.* 2011 Sep 9;5:103 (doi: 10.3389/fnins.2011.00103) ("Roberds"). As reported in Roberds, because psychiatric diseases generally result from disorders of cell-cell communication, circuitry, intact systems are useful in detecting improvement in disease-relevant endpoints. These endpoints are typically behavioral in nature, often requiring human observation and interpretation. To facilitate testing of multiple compounds for behavioral effects relevant to psychiatric disease, PsychoGenics, Inc. (Tarrytown, N.Y., "PGI") developed SmartCube™ an automated system in which behaviors of compound-treated mice are captured by digital video and analyzed with computer algorithms. (D. Brunner et al., *Drug Discov. Today* 2002, 7:S107-S112). PGI Analytical Systems uses data from SmartCube™ to compare the behavioral signature of a test compound to a database of behavioral signatures obtained using a large set of diverse reference compounds. (The composition of the database as well as validation of the method is further described in Roberds). In this way, the neuropharmacological effects of a test compound can be predicted by similarity to major classes of compounds, such as antipsychotics, anxiolytics and antidepressants.

The SmartCube™ system produces an activity signature indicating the probability that the activity of the test compound at the administered dose matches a given class of neuropharmacological agents. (See, e.g., Roberds, FIGS. 2 and 3). The test compound is simultaneously compared against multiple classes of agents; thus, a separate probability is generated for each behavioral effect measured (e.g., anxiolytic activity, analgesic activity, etc.). In the table below, these probabilities are reported for each behavioral effect measured as follows:

| LOQ≤ | + | <5% |
|---|---|---|
| 5%≤ | ++ | <25% |
| 25%≤ | +++ | <50% |
| 50%≤ | ++++ | | where LOQ is the limit of quantification.

Provided compounds were dissolved in a mixture of Pharmasolve™ (N-methyl-2-pyrrolidone), polyethylene glycol and propylene glycol, and were injected i.p. 15 min. before the behavioral test. For each compound, injections were administered at 3 different doses. For each behavioral effect measured, results for the most efficacious dose(s) are presented. In the table below, DP: anti-depressant; AX: anxiolytic; SD: sedative hypnotic; PS: anti-psychotic; MS: mood stabilizer; AD: ADHD; CE: cognitive enhancer; AG: analgesic; UN: uncharacterized CNS activity.

The potency of many of the compounds in the table was also determined in the SmartCube™ system. Test compounds were routinely examined at dose levels of 0.3, 1, 3 10 and 30 mg per kg (mpk), although the dose range was increased or decreased if necessary to obtain a full dose response curve. A compound's minimal effective dose (MED) is a measure of the compounds potency. The MED was defined as the dose (in mpk) having 50% or more total activity in SmartCube. The potencies of the compounds are shown in the table below, with potency values in mpk binned in the following manner:

| MED mpk range | BIN |
| --- | --- |
| ≤3 mpk | A |
| >3 to 10 mpk | B |
| >10 to ≤30 mpk | C |
| >30 mpk | D |

| Ex. | DP | AX | SD | PS | MS | AD | CE | AG | UN | POTENCY |
| --- | --- | --- | --- | --- | --- | --- | --- | --- | --- | --- |
| 1 | ++++ | ++ | ++ | ++ | + | + | + | + | + | A |
| 2 | +++ | ++ | + | ++ | ++ | + | ++ | ++ | +++ | A |
| 3 | +++ | ++ | + | + | + | ++ | + | ++ | + | C |
| 4 | ++++ | + | + | + | + | + | + | ++ | + | B |
| 5 | + | ++ | + | + | + | + | + | ++ | + | D |
| 6 | + | ++ | + | ++ | ++ | + | + | + | ++++ | C |
| 7 | ++ | +++ | + | ++ | ++ | ++ | ++ | +++ | ++ | A |
| 8 | ++ | ++ | + | ++ | + | + | ++ | ++ | +++ | B |
| 9 | +++ | ++ | ++ | ++ | ++ | + | + | ++ | +++ | B |
| 10 | ++ | ++ | + | ++ | + | + | ++ | + | +++ | C |
| 11 | ++++ | + | + | + | + | ++ | + | + | + | B |
| 12 | ++++ | + | ++ | ++ | + | + | + | ++ | ++ | B |
| 13 | ++ | ++ | ++ | + | + | + | + | ++ | +++ | C |
| 14 | ++++ | ++ | ++ | ++ | ++ | + | ++ | ++ | +++ | A |
| 15 | ++ | ++ | ++ | +++ | ++ | + | ++ | ++ | +++ | A |
| 16 | ++ | ++ | ++ | +++ | + | + | + | ++ | + | C |
| 17 | ++ | ++ | + | +++ | + | + | +++ | ++ | ++ | A |
| 18 | ++ | ++ | + | + | + | + | ++ | ++ | ++ | C |
| 19 | ++ | ++ | + | ++ | ++ | + | ++ | ++ | ++ | B |
| 20 | ++ | ++ | ++ | ++++ | + | + | ++ | + | ++++ | A |
| 21 | ++ | ++ | ++ | ++ | + | + | ++ | +++ | +++ | B |
| 22 | +++ | ++ | ++ | +++ | ++ | + | ++ | ++ | + | A |
| 23 | ++ | ++ | ++ | +++ | + | + | ++ | ++ | + | B |
| 24 | ++ | ++ | ++ | +++ | + | + | ++ | ++ | +++ | A |
| 25 | +++ | + | ++ | ++ | + | + | ++ | ++ | + | B |
| 26 | ++++ | ++ | ++ | ++ | + | + | ++ | ++ | +++ | A |
| 27 | ++ | ++ | + | + | + | + | ++ | ++ | +++ | C |
| 28 | ++ | ++ | ++ | +++ | + | + | ++ | ++ | +++ | A |
| 29 | ++++ | ++ | + | + | + | + | ++ | ++ | ++ | B |
| 30 | ++ | ++ | ++ | ++ | + | + | ++ | ++ | +++ | B |
| 31 | ++++ | ++ | + | + | + | + | ++ | ++ | + | A |
| 32 | ++ | ++ | + | ++ | + | + | ++ | + | + | C |
| 33 | ++++ | ++ | ++ | + | + | + | ++ | ++ | +++ | A |
| 34 | ++ | ++ | + | +++ | ++ | + | ++ | ++ | +++ | A |
| 35 | ++++ | ++ | ++ | ++ | + | ++ | ++ | ++ | ++++ | A |
| 36 | + | ++ | + | ++ | + | + | ++ | + | +++ | B |
| 37 | ++ | + | + | ++ | + | + | ++ | ++ | ++++ | A |
| 38 | ++ | ++ | ++ | ++ | + | + | + | ++ | +++ | A |
| 39 | ++++ | ++ | + | ++ | + | + | ++ | ++ | +++ | A |
| 40 | ++ | +++ | ++ | ++ | + | + | + | + | +++ | A |
| 41 | ++ | ++ | ++ | ++++ | + | + | + | ++ | ++++ | A |
| 42 | ++ | + | + | + | + | + | ++ | +++ | ++ | C |
| 43 | + | ++ | + | ++ | + | + | ++ | ++ | ++++ | C |
| 44 | + | ++ | + | ++ | + | + | ++ | ++ | +++ | B |
| 45 | + | ++ | + | ++ | + | + | ++ | ++ | ++++ | B |
| 46 | ++ | ++ | ++ | ++ | + | + | ++ | + | +++ | B |
| 47 | ++++ | ++ | ++ | ++ | + | + | + | + | ++ | B |
| 48 | + | ++ | + | ++ | + | + | ++ | ++ | ++++ | A |
| 49 | ++ | ++++ | + | ++ | + | + | ++ | ++ | +++ | A |
| 50 | + | ++ | + | + | + | + | + | ++ | ++++ | C |
| 51 | + | +++ | + | ++ | + | + | ++ | ++ | +++ | B |
| 52 | ++ | ++ | ++ | ++ | + | + | ++ | +++ | ++++ | B |
| 53 | ++++ | ++ | + | + | + | ++ | ++ | ++ | + | A |
| 54 | + | ++ | ++ | ++ | + | + | ++ | + | ++++ | B |
| 55 | ++ | ++ | + | + | + | + | + | ++ | ++++ | C |
| 56 | + | ++ | ++ | ++ | + | + | ++ | ++ | ++++ | A-B |
| 57 | + | ++ | + | + | + | + | ++ | ++ | +++ | D |
| 60 | ++ | ++ | ++++ | ++ | + | + | + | + | +++ | B |
| 61 | + | ++ | + | ++++ | + | + | + | + | +++ | B |
| 62 | + | ++++ | + | + | + | + | + | ++ | ++ | C |
| 63 | ++++ | ++ | ++ | + | + | ++ | + | + | ++++ | A-B |
| 64 | + | +++ | ++ | ++ | + | + | ++ | ++ | ++++ | A-B |
| 65 | ++ | ++ | ++ | ++ | + | + | + | ++ | ++++ | A-B |
| 66 | ++++ | ++ | + | + | + | + | + | + | + | A-B |
| 67 | ++++ | ++ | + | ++ | + | + | + | + | + | A-B |

-continued

| Ex. | DP | AX | SD | PS | MS | AD | CE | AG | UN | POTENCY |
|---|---|---|---|---|---|---|---|---|---|---|
| 93 | ++ | +++ | ++ | + | + | +++ | ++ | ++ | ++++ | A |
| 92 | ++ | ++ | ++ | + | + | + | ++ | ++ | +++ | C |
| 74 | + | ++ | ++ | + | + | + | + | + | +++ | C |
| 75 | ++ | ++ | + | ++ | + | + | ++ | ++ | ++++ | B |
| 71 | + | ++ | + | ++ | + | + | ++ | ++ | ++++ | A |
| 70 | ++ | ++ | ++ | +++ | + | + | ++ | ++ | +++ | B |
| 88 | ++ | ++ | ++ | ++ | + | + | ++ | ++ | ++ | B |
| 89 | ++ | ++ | + | ++ | + | + | +++ | ++ | ++++ | A |
| 79 | ++++ | + | ++ | + | + | ++ | + | + | + | A |
| 78 | ++ | ++ | + | + | + | + | + | ++ | ++++ | C |
| 98 | + | + | + | + | + | + | + | + | + | D |
| 99 | + | ++ | ++ | ++ | + | + | + | + | +++ | C |
| 86 | ++ | ++ | +++ | ++ | + | ++ | ++ | + | + | C |
| 87 | ++ | ++ | + | ++ | + | + | + | ++ | ++++ | A |
| 90 | ++ | ++ | +++ | ++ | + | + | ++ | ++ | +++ | A |
| 91 | + | + | + | ++ | + | + | + | ++ | ++++ | C |
| 96 | + | + | +++ | + | + | + | + | + | + | C |
| 97 | +++ | ++ | + | ++ | + | ++ | + | + | +++ | B |
| 85 | ++ | +++ | ++ | ++ | + | + | ++ | + | +++ | A |
| 84 | ++ | ++ | ++ | ++ | + | + | ++ | ++ | ++++ | A |
| 69 | ++ | ++ | + | ++ | ++ | ++ | + | +++ | ++++ | A |
| 68 | ++ | ++ | +++ | ++ | + | + | ++ | ++ | ++ | B |
| 81 | ++++ | ++ | + | + | + | ++ | + | + | ++ | A |
| 80 | ++ | ++ | + | +++ | + | + | ++ | + | + | C |
| 72 | ++ | ++ | + | + | + | + | + | + | +++ | B |
| 73 | +++ | ++ | ++ | + | + | + | ++ | + | ++++ | A |
| 101 | + | ++ | + | ++ | + | + | ++ | +++ | + | B |
| 102 | ++ | ++ | + | + | + | + | + | ++ | +++ | C |
| 103 | + | + | + | + | + | + | + | + | + | D |
| 104 | ++++ | +++ | ++ | + | + | + | ++ | + | ++ | A |
| 105 | ++ | ++ | +++ | ++ | + | + | + | + | + | A |
| 106 | ++ | ++ | ++ | ++ | + | + | +++ | + | + | C |
| 107 | ++ | ++ | ++ | ++ | + | + | + | + | +++ | B |
| 108 | ++ | + | + | ++ | + | + | + | + | ++++ | B |
| 109 | ++ | ++ | ++ | ++++ | + | + | + | + | ++ | B |
| 110 | ++ | ++ | +++ | ++ | + | ++ | + | + | + | B |
| 111 | ++++ | ++ | + | ++ | + | + | + | + | + | C |
| 112 | ++ | ++ | + | + | + | + | + | + | + | D |
| 113 | + | ++ | + | + | + | + | + | + | + | D |
| 114 | + | ++ | + | ++ | + | + | + | + | +++ | C |

Example 116

Additional Rodent Tests

Forced Swim Test Procedures

Figure 1B:
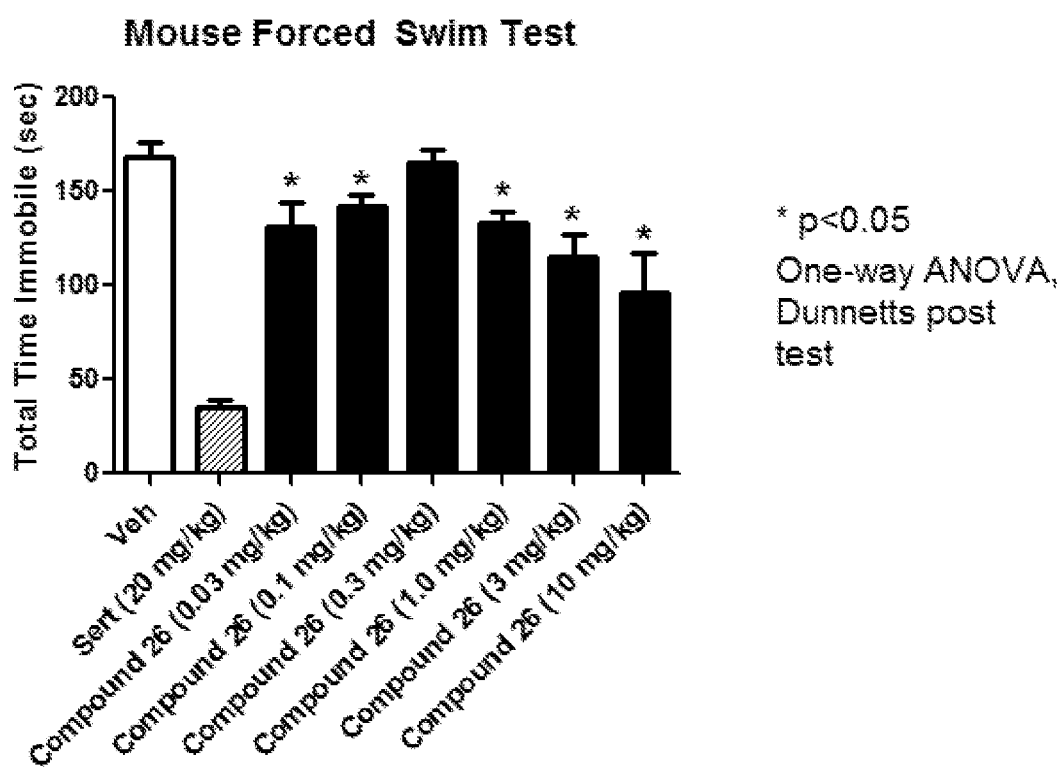

The Forced Swim test (FST) is an indicator of the antidepressant-like activity of a test compound. Male Balb/cJ mice (26-31 g) were given a 30 minute pretreatment with vehicle (sterile water), sertraline control or test compound. The FST consists of one 6 minute session of forced swimming in individual opaque cylinders containing water at a temperature of 23±2° C. The mouse will swim before "giving up" and becoming immobile, the time spent immobile was recorded over the 6 minute trial. A compound with antidepressant-like activity will decrease the time the mouse is immobile over the 6 minute trial. Data were analyzed by analysis of variance (ANOVA) followed by post-hoc comparisons with Fisher Tests when appropriate. Data is shown in FIGS. 1a and 1b.

Phencyclidine (PCP)-Induced Hyerlocomotion

Figure 2A:
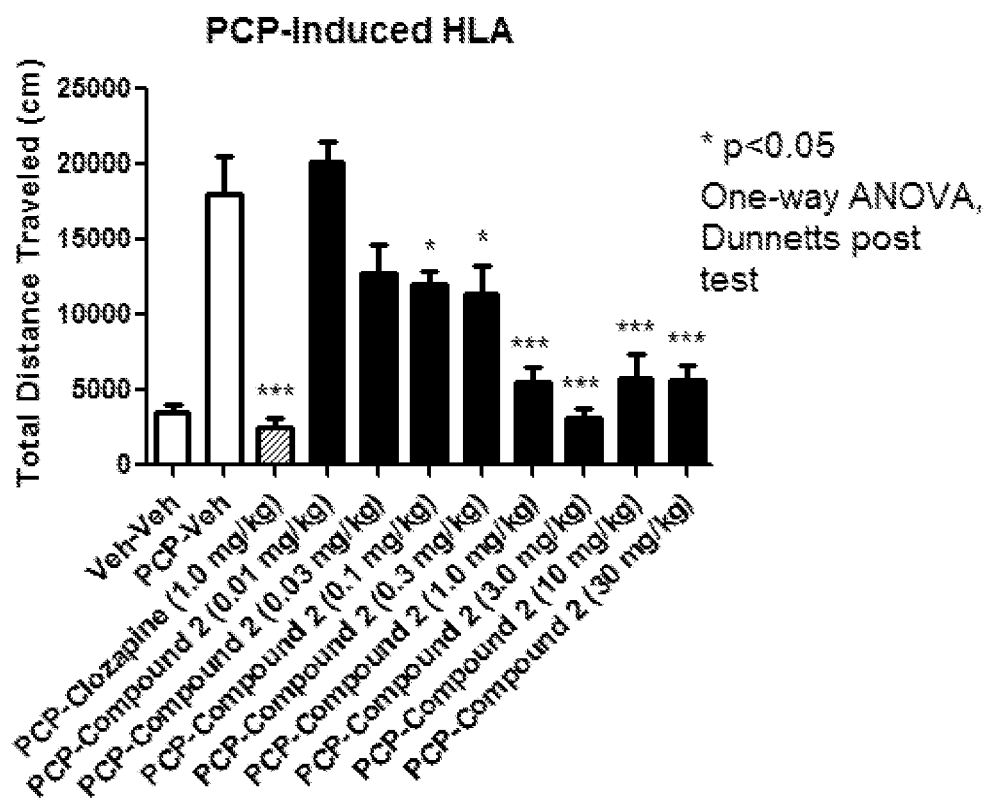
FIGS. 2a to 2b show the effect of representative compounds of the invention on inhibition of PCP-induced HLA.
Figure 2B:
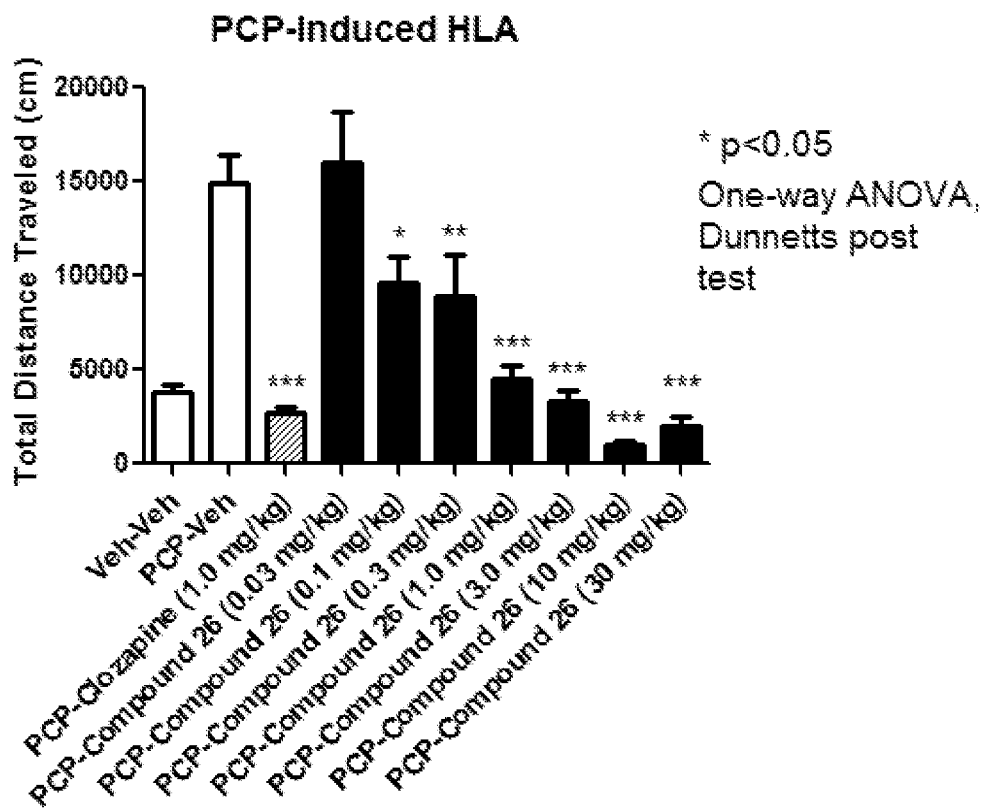
Figure 3A:
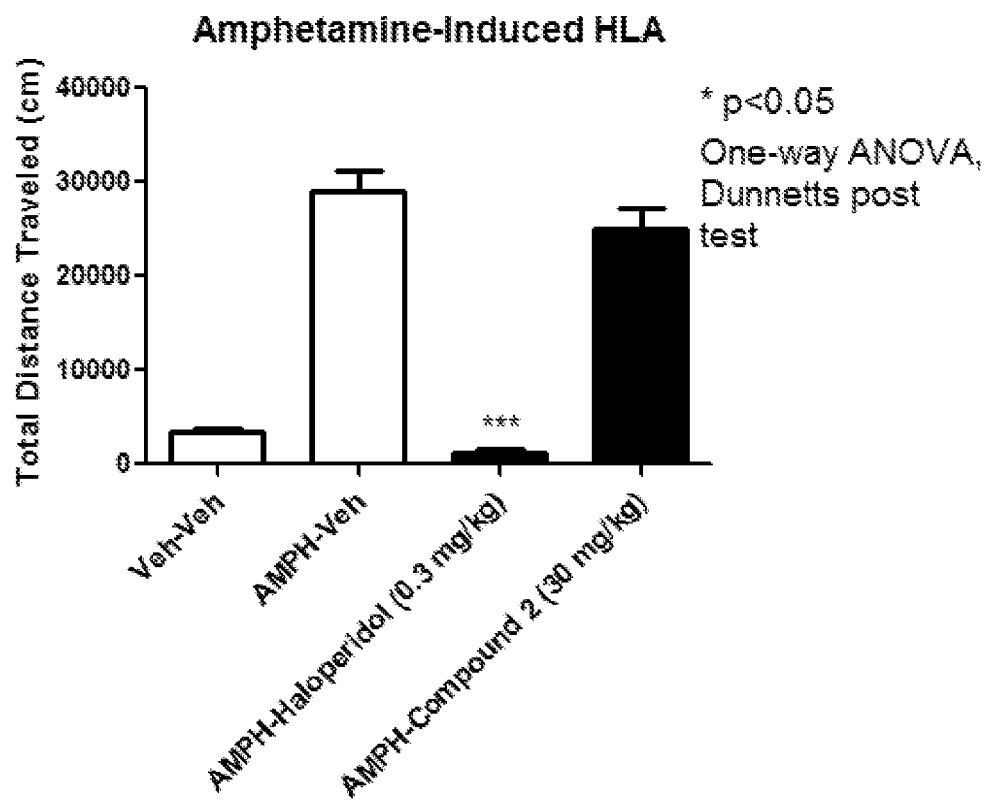
FIGS. 3a to 3d show the effect of representative compounds of the invention on mice in an amphetamine-induced hyperlocomotion assay.
Figure 3B:
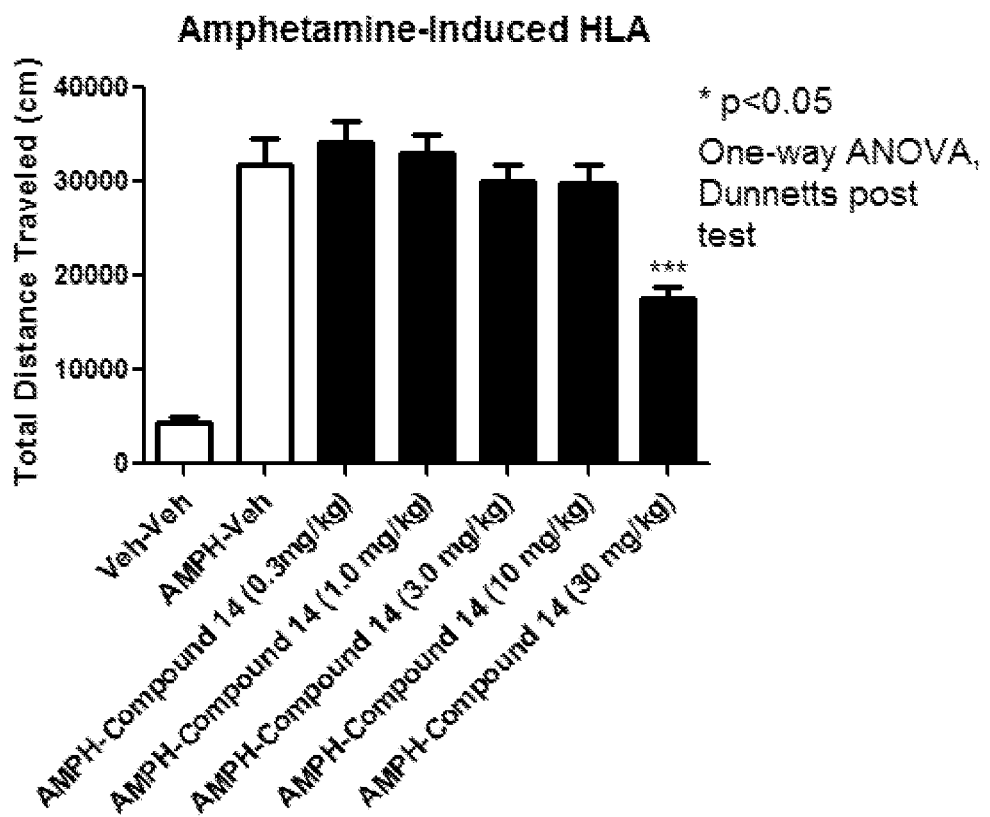
Figure 3C:
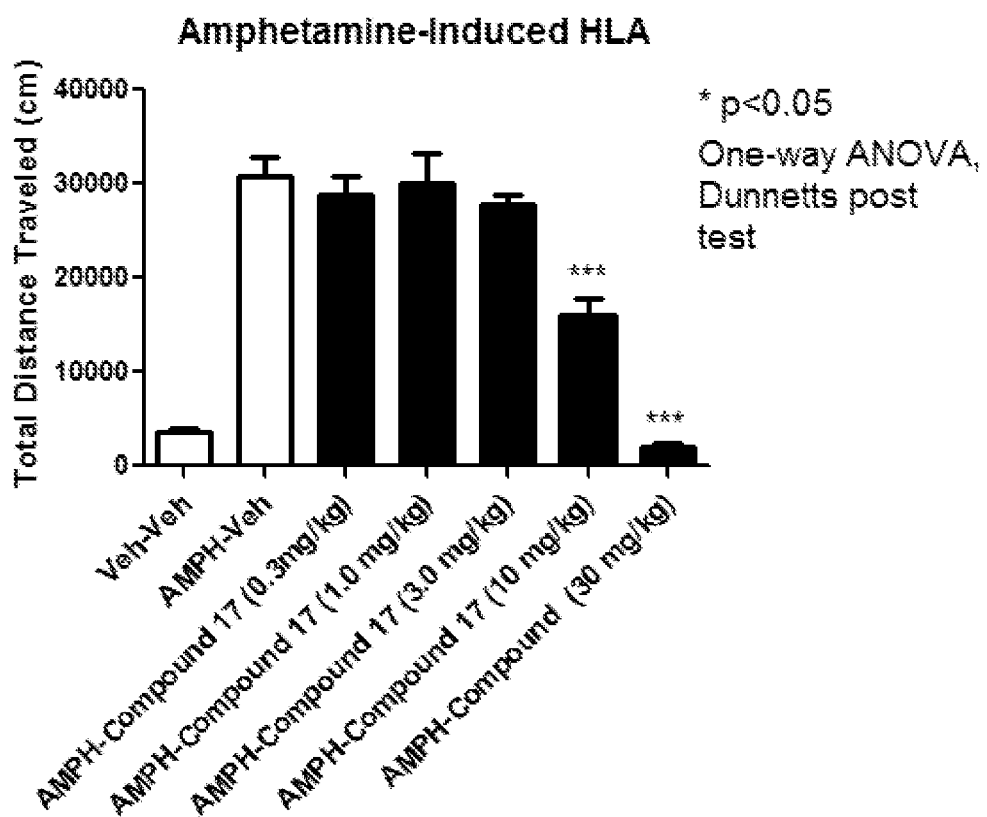
Figure 3D:
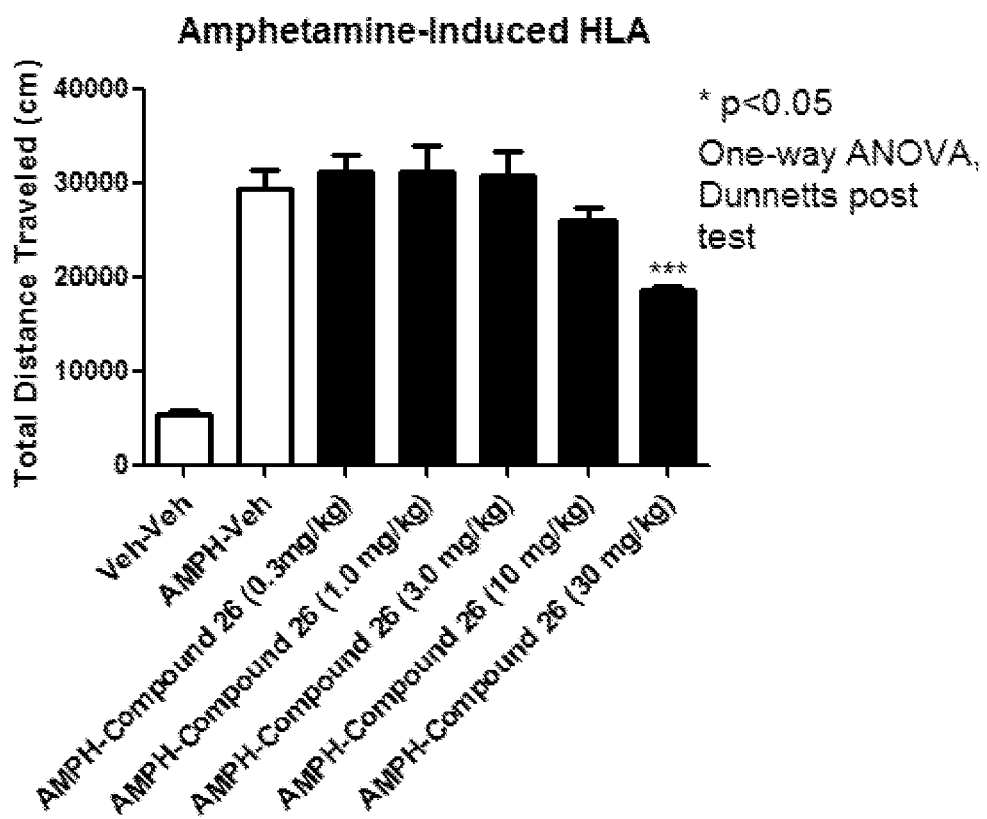

The PCP-induced hyperlocomotion assay is an indicator of antipsychotic-like activity. Male C57B1/6J mice (20-26 g) were administered vehicle or test compound and placed in holding cages for 30 minutes, after which they were placed in the locomotor activity chambers for 30 minutes of baseline capture. The test chambers are Plexiglas rectangular chambers (24×45 cm) that fit inside two steel frames (9.5×18 inches) and are fitted with two-dimensional 4×8 beam grids to monitor horizontal and vertical locomotor activity. Total distance traveled was measured from horizontal beam breaks as the animal traveled. Following the 30 minute baseline period, all rats were injected with saline or PCP (2.5 mg/kg, s.c.) and returned to the locomotor activity chambers for a 60 minute test session. A compound with antipsychotic-like activity will decrease the distance traveled following administration of PCP. Data were analyzed by analysis of variance (ANOVA) followed by post-hoc comparisons with Fisher Tests when appropriate. Data is shown in FIGS. 2a and 2b.

Amphetamine-Induced Hyperlocomotion Assay

Amphetamine (AMPH) is frequently used to induce or mimic a manic-like state. The antimanic-like effects of test compounds were evaluated in male C57B1/6J mice. Mice were acclimatized to the experimental room for at least 1 hour prior to testing. The mice (n=10 per group) were administered vehicle or test compound and placed in the open field (OF) chambers for 30 minutes of baseline activity measurement. The mice were then injected with either water or AMPH (4 mg/kg, ip) and placed back in the OF chambers for a 60-minute testing session during which, the effects of test compounds on stimulant-induced hyperactivity behaviors (total distance traveled, rearing and stereotypy) were measured. Data were analyzed by analysis of variance (ANOVA) followed by post-hoc comparisons with Fisher Tests when appropriate. Data is shown in FIGS. 3a to 3d.

Tail Suspension Test

The tail suspension test (TST) is a rodent screening test for potential (human) antidepressant drugs. It is based on the assumption that an animal will actively try to escape an aversive (stressful) stimulus. If escape is impossible, the animal will eventually stop trying ("give up"). In the TST, a mouse is suspended by the tail so that its body dangles in the air, head downward. Mice initially struggle to face upward and climb to a solid surface. When the animal stops struggling and hangs immobile it is considered to have "given up". Shorter periods of immobility are characteristic of antidepressant-like activity. Accordingly, longer periods of immobility are considered indicative of a depressive-like state. It has been shown that treatment with an antidepressant drug will decrease the time the animal spends immobile. See generally L. Steru et al., Psychopharmacology (Berl). 1985;85(3):367-70; B. Thierry et al., Psychopharmacology 1986;90:284-85.

Figure 4A:
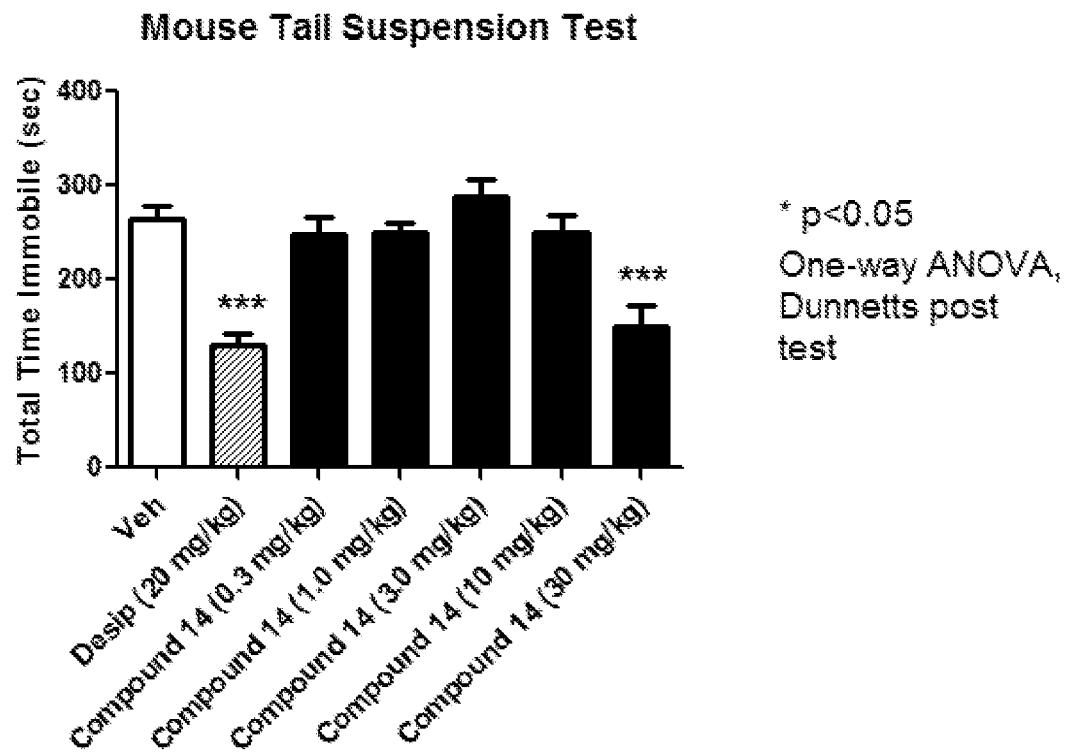
FIGS. 4a to 4c show the effect of representative compounds of the invention on mice in a mouse tail suspension test.
Figure 4B:
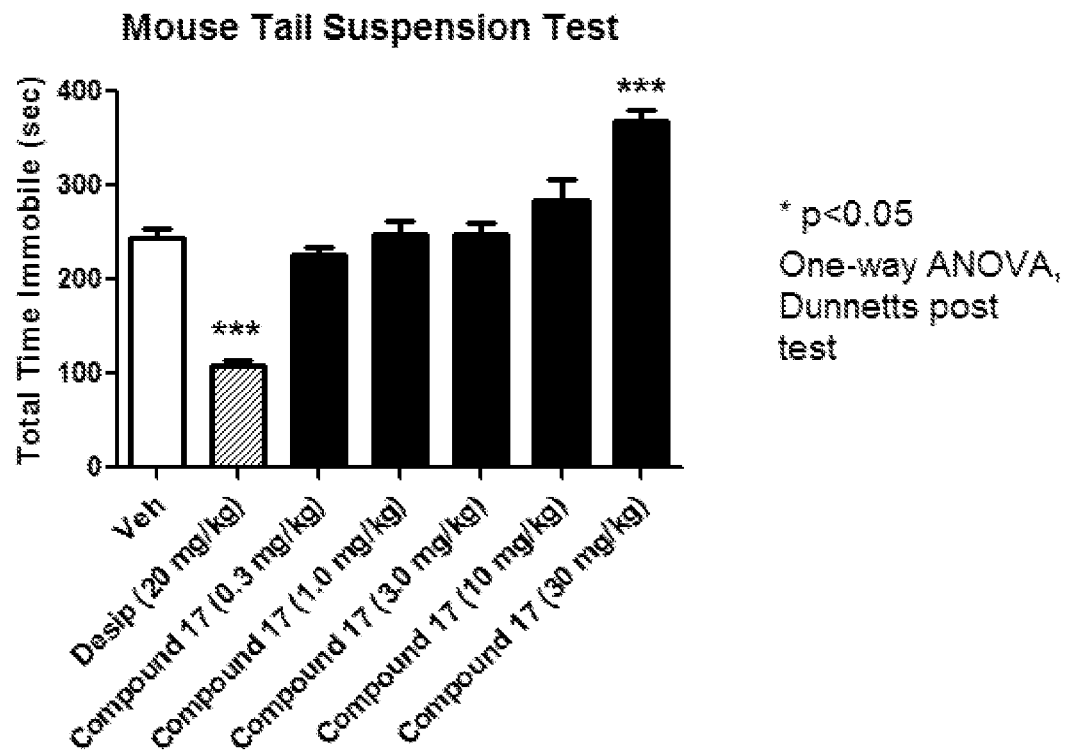
Figure 4C:
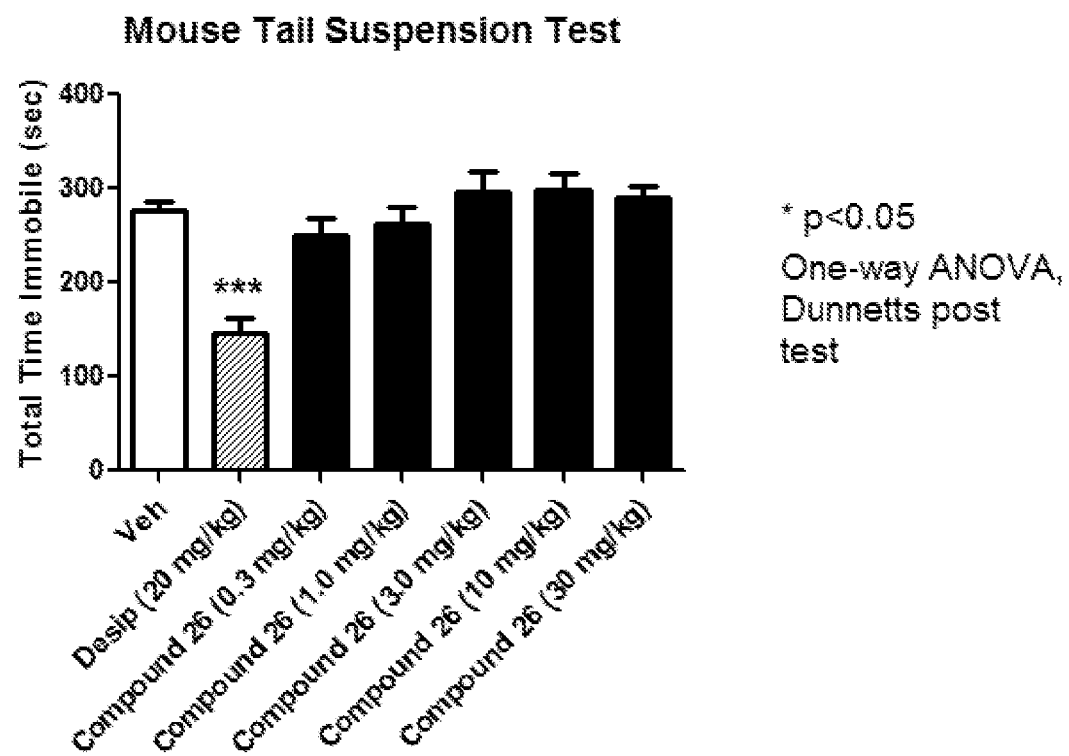

Procedure. Adult male AJ mice from Jackson Laboratories received vehicle (sterile water) or test compound orally by gavage, or the positive control desipramine (20 mg/kg, i.p.), in 10 mL/kg injection volumes, 30 min before being subjected to the Tail Suspension Test. In this test, mice are placed in the Tail Suspension chambers (white polyvinyl-chloride cubicles measuring 33×33×31.75 cm Med Associates, Inc. St. Albans, Vt.) by a piece of transparent (Scotch®) tape attached to the tail, from about the mid-tail, with approximately 2 cm of tape past the end of the tail for 10 min during which the time spent immobile is measured. A reduction in total time immobile relative to the vehicle condition indicates an antidepressant drug-like response. Data is shown in FIGS. 4a to 4c.

Additional data for the tests in Example 116 are shown below:

Data for additional rodent tests

| Compound Example No. | PCP | AMPH | TST | FST |
| --- | --- | --- | --- | --- |
| 2 | +++ | NE | ND | +++ |
| 14 | ND | + | + | ND |
| 17 | ND | ++ | NE | ND |
| 26 | +++ | + | NE | +++ |

Efficacious dose: +++ = <1.0 mg/kg, ++ = 1-10 mg/kg, + = 13-30 mg/kg, ND = not determined, NE = no effect It may be found upon examination that additional species and genera not presently excluded from the claims to pharmaceutical compositions and chemical compounds are not patentable to the inventors in this application. In that case, the subsequent exclusion of species and genera in applicants' claims are to be considered artifacts of patent prosecution and not reflective of the inventors' concept or description of their invention. The invention, in a composition aspect, is all compounds of formula I except those that are in the public's possession.

It is to be understood that the invention is not limited to the particular embodiments of the invention described above, as variations of the particular embodiments may be made and still fall within the scope of the appended claims.

The invention claimed is:

1. A process for preparing (R)-1-(8-fluoroisochroman-1-yl)-N-methylmethanamine, having the structure:

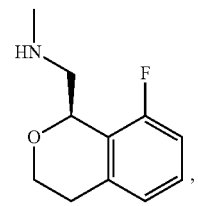

or a pharmaceutically acceptable salt thereof, comprising deprotecting tert-butyl ((8-fluoroisochroman-1-yl)methyl)(methyl)carbamate, having the structure:

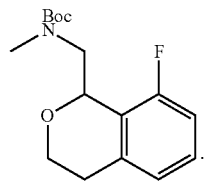 [SMILES: CN(CC1OCCc2cccc(F)c21)C(=O)OC(C)(C)C]

2. The process of claim 1, wherein the deprotecting comprises treating tert-butyl ((8-fluoroisochroman-1-yl)methyl)(methyl)carbamate with hydrochloric acid.

3. The process of claim 2, wherein the treating tert-butyl ((8-fluoroisochroman-1-yl)methyl)(methyl)carbamate with hydrochloric acid is carried out in the presence of ethyl acetate.

4. The process of claim 2, wherein the treating tert-butyl ((8-fluoroisochroman-1-yl)methyl)(methyl)carbamate with hydrochloric acid is carried out at ambient temperature.

5. The process of claim 2, wherein the treating tert-butyl ((8-fluoroisochroman-1-yl)methyl)(methyl)carbamate with hydrochloric acid is carried out for about 16 h.

6. The process of claim 1, further comprising separating (S)-1-(8-fluoroisochroman-1-yl)-N-methylmethanamine and (R)-1-(8-fluoroisochroman-1-yl)-N-methylmethanamine.

7. The process of claim 6, wherein the separating is performed by chiral HPLC.

8. The process of claim 1, wherein tert-butyl ((8-fluoroisochroman-1-yl)methyl)(methyl)carbamate is prepared by a process comprising converting tert-butyl ((5-bromo-8-fluoroisochroman-1-yl)methyl)(methyl)carbamate, having the structure:

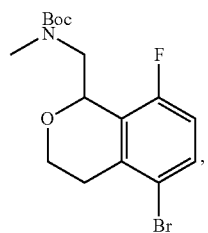 [SMILES: CN(CC1OCCc2c(Br)ccc(F)c21)C(=O)OC(C)(C)C]

to tert-butyl ((8-fluoroisochroman-1-yl)methyl)(methyl) carbamate.

9. The process of claim 8, wherein the converting tert-butyl ((5-bromo-8-fluoroisochroman-1-yl)methyl)(methyl) carbamate to tert-butyl ((8-fluoroisochroman-1-yl)methyl) (methyl)carbamate comprises treating tert-butyl ((5-bromo-8-fluoroisochroman-1-yl)methyl)(methyl)carbamate with Pd/C under an $H_2$ atmosphere.

10. The process of claim 9, wherein the treating tert-butyl ((5-bromo-8-fluoroisochroman-1-yl)methyl)(methyl)carbamate with Pd/C under an $H_2$ atmosphere is carried out in the presence of methanol.

11. The process of claim 9, wherein the treating tert-butyl ((5-bromo-8-fluoroisochroman-1-yl)methyl)(methyl)carbamate with Pd/C under H₂ atmosphere is carried out at ambient temperature.

12. The process of claim 9, wherein the treating tert-butyl ((5-bromo-8-fluoroisochroman-1-yl)methyl)(methyl)carbamate with Pd/C under H₂ atmosphere is carried out for about 4 h.

13. The process of claim 8, wherein tert-butyl ((5-bromo-8-fluoroisochroman-1-yl)methyl)(methyl)carbamate is prepared by a process comprising protecting 1-(5-bromo-8-fluoroisochroman-1-yl)-N-methylmethanamine, having the structure:

14. The process of claim 13, wherein the protecting 1-(5-bromo-8-fluoroisochroman-1-yl)-N-methylmethanamine comprises treating 1-(5-bromo-8-fluoroisochroman-1-yl)-N-methylmethanamine with di-tert-butyl dicarbonate.

15. The process of claim 14, wherein the treating 1-(5-bromo-8-fluoroisochroman-1-y1)-N-methylmethanamine with di-tert-butyl dicarbonate is carried out in the presence of water.

16. The process of claim 14, wherein the treating 1-(5-bromo-8-fluoroisochroman-1-y1)-N-methylmethanamine with di-tert-butyl dicarbonate is carried out at ambient temperature.

17. The process of claim 14, wherein the treating 1-(5-bromo-8-fluoroisochroman-1-y1)-N-methylmethanamine with di-tert-butyl dicarbonate is carried out for about 3 h.

18. The process of claim 13, wherein 1-(5-bromo-8-fluoroisochroman-1-yl)-N-methylmethanamine is prepared by a process comprising reacting 2-(2-bromo-5-fluorophenyl) ethanol, having the structure:

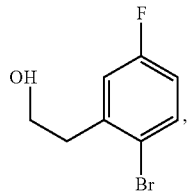 [SMILES: OCCc1cc(F)ccc1Br]

with 2,2-dimethoxy-N-methylethanamine, having the structure:

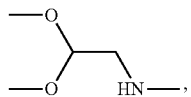

in the presence of an acid.

19. The process of claim 18, wherein the acid is trifluoromethanesulfonic acid.

20. The process of claim 18, wherein the acid is trimethylsilyl trifluoromethanesulfonate.

21. The process of claim 18, wherein the reacting of 2-(2-bromo-5-fluorophenyl) ethanol with 2,2-dimethoxy-N-methylethanamine is carried out in the presence of dichloromethane.

22. The process of claim 18, wherein the reacting of 2-(2-bromo-5-fluorophenyl) ethanol with 2,2-dimethoxy-N-methylethanamine is carried out at about 0° C.

23. The process of claim 18, wherein the reacting of 2-(2-bromo-5-fluorophenyl) ethanol with 2,2-dimethoxy-N-methylethanamine is carried out for about 16 h.

24. A process for preparing (R)-1-(8-fluoroisochroman-1-yl)-N-methylmethanamine, having the structure:

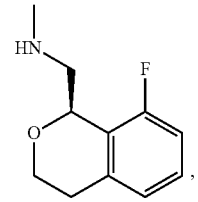

or a pharmaceutically acceptable salt thereof, comprising:
a) reacting 2-(2-bromo-5-fluorophenyl) ethanol, having the structure:

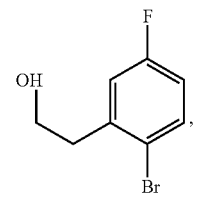

with 2,2-dimethoxy-N-methylethanamine, having the structure:

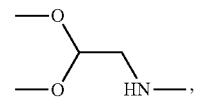

in the presence of an acid to provide 1-(5-bromo-8-fluoroisochroman-1-yl)-N-methylmethanamine, having the structure:

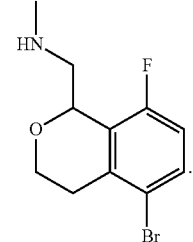

b) protecting 1-(5-bromo-8-fluoroisochroman-1-yl)-N-methylmethanamine to provide tert-butyl ((5-bromo-8-fluoroisochroman-1-yl)methyl)(methyl)carbamate, having the structure:

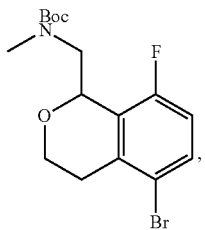 [SMILES: CN(CC1OCCc2c(Br)ccc(F)c21)C(=O)OC(C)(C)C]

c) converting tent-butyl ((5-bromo-8-fluoroisochroman-1-yl)methyl)(methyl)carbamate to tent-butyl ((8-fluoroisochroman-1-yl)methyl)(methyl)carbamate having the structure:

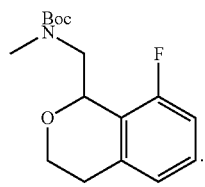 [SMILES: CN(CC1OCCc2cccc(F)c21)C(=O)OC(C)(C)C]

and
d) deprotecting tent-butyl ((8-fluoroisochroman-1-yl) methyl)(methyl)carbamate to provide (R)-1-(8-fluoroisochroman-1-yl)-N-methylmethanamine, or a pharmaceutically acceptable salt thereof.

25. A compound, which is (R)-1-(8-fluoroisochroman-1-yl)-N-methylmethanamine, or a pharmaceutically acceptable salt thereof, prepared by the process of claim 1.

26. A compound, which is (R)-1-(8-fluoroisochroman-1-yl)-N-methylmethanamine, or a pharmaceutically acceptable salt thereof, prepared by the process of claim 24.

* * * * *

UNITED STATES PATENT AND TRADEMARK OFFICE
CERTIFICATE OF CORRECTION

Page 1 of 1

PATENT NO. : 10,927,124 B2
APPLICATION NO. : 16/214985
DATED : February 23, 2021
INVENTOR(S) : Xie et al.

It is certified that error appears in the above-identified patent and that said Letters Patent is hereby corrected as shown below:

In the Claims

Column 136, Line 64: Claim 24, Delete "converting tent-butyl" and insert -- converting tert-butyl --

Column 136, Line 65: Claim 24, Delete "carbamate to tent-butyl" and insert -- carbamate to tert-butyl --

Column 137, Line 11: Claim 24, Delete "deprotecting tent-butyl" and insert -- deprotecting tert-butyl --

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*